US011513076B2

(12) United States Patent
Grabmayr et al.

(10) Patent No.: US 11,513,076 B2
(45) Date of Patent: *Nov. 29, 2022

(54) SINGLE MOLECULE DETECTION OR QUANTIFICATION USING DNA NANOTECHNOLOGY

(71) Applicant: LUDWIG-MAXIMILIANS-UNIVERSITÄT MÜNCHEN, Munich (DE)

(72) Inventors: Heinrich Grabmayr, Munich (DE); Johannes Benedikt Woehrstein, Munich (DE)

(73) Assignee: LUDWIG-MAXIMILIANS-UNIVERSITÄT MÜNCHEN, Munich (DE)

( * ) Notice: Subject to any disclaimer, the term of this patent is extended or adjusted under 35 U.S.C. 154(b) by 1017 days.

This patent is subject to a terminal disclaimer.

(21) Appl. No.: 16/310,322

(22) PCT Filed: Jun. 14, 2017

(86) PCT No.: PCT/EP2017/064634
§ 371 (c)(1),
(2) Date: Mar. 1, 2019

(87) PCT Pub. No.: WO2017/216270
PCT Pub. Date: Dec. 21, 2017

(65) Prior Publication Data
US 2019/0271647 A1    Sep. 5, 2019

(30) Foreign Application Priority Data

Jun. 15, 2016 (DE) .................. 102016007270.9

(51) Int. Cl.
| | |
|---|---|
| *G01N 21/64* | (2006.01) |
| *G01N 33/58* | (2006.01) |
| *B82Y 15/00* | (2011.01) |
| *B82Y 35/00* | (2011.01) |
| *C07H 21/04* | (2006.01) |
| *C12Q 1/682* | (2018.01) |

(52) U.S. Cl.
CPC ....... *G01N 21/6428* (2013.01); *G01N 33/587* (2013.01); *B82Y 15/00* (2013.01); *B82Y 35/00* (2013.01); *C07H 21/04* (2013.01); *C12Q 1/682* (2013.01)

(58) Field of Classification Search
CPC .. G01N 21/6428; G01N 33/587; B82Y 15/00; B82Y 35/00; C07H 21/04; C12Q 1/682; C12Q 2525/313; C12Q 2565/1025
See application file for complete search history.

(56) References Cited

U.S. PATENT DOCUMENTS

| | | |
|---|---|---|
| 4,599,315 A | 7/1986 | Terasaki et al. |
| 4,790,640 A | 12/1988 | Nason |
| 5,342,581 A | 8/1994 | Sanadi |
| 5,516,490 A | 5/1996 | Sanadi |
| 6,017,696 A | 1/2000 | Heller |
| 6,037,168 A | 3/2000 | Brown |
| 6,238,624 B1 | 5/2001 | Heller et al. |
| 6,303,315 B1 | 10/2001 | Skouv |
| 6,395,559 B1 | 5/2002 | Swenson |
| 6,538,810 B1 | 3/2003 | Karanfilov |
| 6,544,477 B1 | 4/2003 | Blumenfeld et al. |
| 6,610,470 B2 | 8/2003 | Blumenfeld et al. |
| 6,682,703 B2 | 1/2004 | Micklash, II et al. |
| 6,696,302 B1 | 2/2004 | Franzen |
| 6,733,729 B2 | 5/2004 | Blumenfeld et al. |
| 6,806,053 B1 | 10/2004 | Sportsman et al. |
| 6,902,703 B2 | 6/2005 | Marquiss et al. |
| 7,138,270 B2 | 11/2006 | Papkovsky et al. |
| 7,419,778 B2 | 9/2008 | Van Damme et al. |
| 7,560,273 B2 | 7/2009 | Sandell |
| 7,598,363 B2 | 10/2009 | Seeman et al. |

(Continued)

FOREIGN PATENT DOCUMENTS

| | | |
|---|---|---|
| CN | 1719253 | 1/2006 |
| CN | 100458443 | 2/2009 |

(Continued)

OTHER PUBLICATIONS

Prinz et al, DNA Origami Substrates for Highly Sensitive Surface-Enhanced Raman Scattering, 2013, J. Phys. Chem. Lett., 4, 4140-4145 (Year: 2013).*

International Search Report and Written Opinion for PCT Application No. PCT/EP2017/064634 dated Oct. 12, 2017.

Eiji Nakata et al.: "Zinc-Finger Proteins for Site-Specific Protein Positioning on DNA-Origami Structures" Angewandte Chemie International Edition, vol. 51, No. 10, Jan. 27, 2012 (Jan. 27, 2012), pp. 2421-2424.

Glasgow Ben J: "Conventional fluorescencemicroscopy below the diffraction limit with simultaneous capture of two fluorophores in DNA origami" Progress in Biomedical Optics and Imaging, SPIE—International Society for Optical Engineering, Bellingham, WA, US. vol. 9714, Feb. 29, 2016 (Feb. 29, 2016), pp. 971411-971411.

(Continued)

*Primary Examiner* — Narayan K Bhat
(74) *Attorney, Agent, or Firm* — Branch Partners PLLC; Bruce E. Black

(57) ABSTRACT

The present invention relates to a method and a DNA nanostructure for detecting a target structure. In particular, the present invention relates to a DNA nanostructure, which ensures a preferably linear dependence on the number of marker molecules and the measurement signal regardless of the physical arrangement of a plurality of such DNA nanostructures by virtue of the skilled selection of the shape of the DNA nanostructure and the placement of the marker molecules attached to it. The invention additionally relates to the use of said DNA nanostructures and other nanoreporters, preferably in combination with adapters which bind specifically to target molecules, in a method for quantifying a plurality of target molecules, preferably in a simultaneous manner, using a multiplex method.

19 Claims, 5 Drawing Sheets

Figure 1:
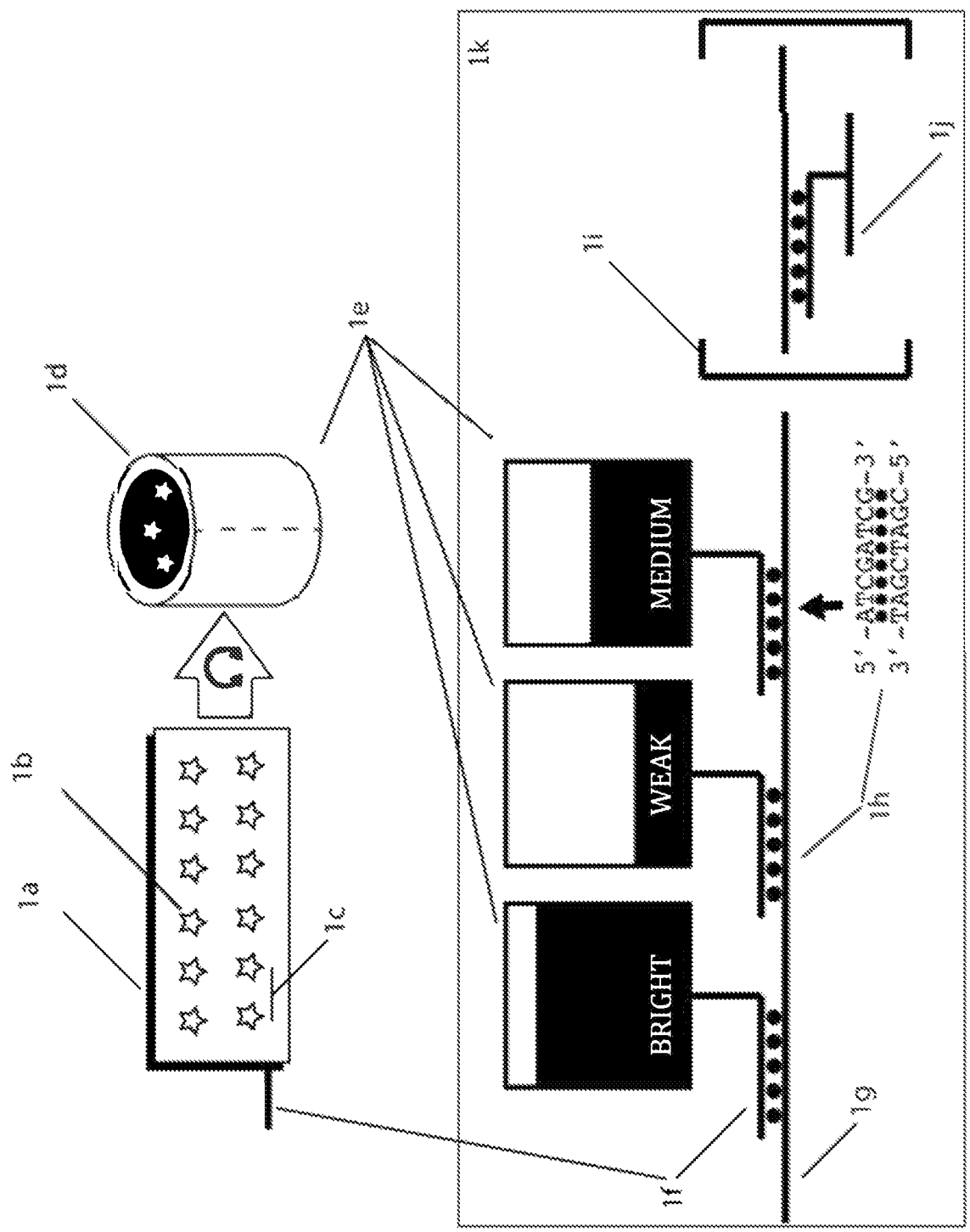

Specification includes a Sequence Listing.

(56) References Cited

U.S. PATENT DOCUMENTS

| | | |
|---|---|---|
| 7,682,565 B2 | 3/2010 | Linton et al. |
| 7,763,424 B2 | 7/2010 | Lee |
| 7,776,553 B2 | 8/2010 | Love et al. |
| 7,842,793 B2 | 11/2010 | Rothemund |
| 7,947,486 B2 | 5/2011 | Heller et al. |
| 7,951,596 B2 | 5/2011 | Shih et al. |
| 8,043,814 B2 | 10/2011 | Guilbeau |
| 8,222,048 B2 | 7/2012 | Fritchie et al. |
| 8,261,598 B2 | 9/2012 | Kim et al. |
| 8,445,193 B2 | 5/2013 | Muraguchi et al. |
| 8,501,412 B2 | 8/2013 | Guilbeau |
| 8,501,923 B2 | 8/2013 | Rothemund |
| 8,554,489 B2 | 10/2013 | Bathe et al. |
| 8,568,973 B2 | 10/2013 | Sportsman et al. |
| 8,609,337 B2 | 12/2013 | Pregibon et al. |
| 8,697,452 B2 | 4/2014 | Linton et al. |
| 8,772,049 B2 | 7/2014 | Love et al. |
| 8,815,507 B2 | 8/2014 | Zhang |
| 8,835,187 B2 | 9/2014 | Love et al. |
| 8,835,188 B2 | 9/2014 | Love et al. |
| 8,865,479 B2 | 10/2014 | Love et al. |
| 8,877,438 B2 | 11/2014 | Yin |
| 8,906,669 B2 | 12/2014 | Dimov et al. |
| 8,906,831 B2 | 12/2014 | Eid et al. |
| 8,986,986 B2 | 3/2015 | Hwang et al. |
| 9,061,282 B2 | 6/2015 | Icke et al. |
| 9,090,926 B2 | 7/2015 | Hoffmann |
| 9,102,520 B2 | 8/2015 | Han et al. |
| 9,188,586 B2 | 11/2015 | Fan et al. |
| 9,244,071 B2 | 1/2016 | Love et al. |
| 9,290,816 B2 | 3/2016 | Pregibon et al. |
| 9,291,628 B2 | 3/2016 | Leonard et al. |
| 9,329,194 B2 | 5/2016 | Fritchie et al. |
| 9,340,416 B2 | 5/2016 | Maune et al. |
| 9,371,552 B2 | 6/2016 | Shih et al. |
| 9,404,924 B2 | 8/2016 | Love et al. |
| 9,428,800 B2 | 8/2016 | Linton et al. |
| 9,463,431 B2 | 10/2016 | Love et al. |
| 9,476,101 B2 | 10/2016 | Pregibon et al. |
| 9,494,575 B2 | 11/2016 | Jin et al. |
| 9,506,917 B2 | 11/2016 | Fan et al. |
| 9,539,575 B2 | 1/2017 | Icke et al. |
| 9,598,690 B2 | 3/2017 | Sun et al. |
| 9,606,102 B2 | 3/2017 | Handlique et al. |
| 9,638,636 B2 | 5/2017 | Tibbe et al. |
| 9,645,143 B2 | 5/2017 | Holmes et al. |
| 9,717,685 B2 | 8/2017 | Shih et al. |
| 9,719,990 B2 | 8/2017 | Holmes et al. |
| 9,752,181 B2 | 9/2017 | Handlique et al. |
| 9,757,707 B2 | 9/2017 | Husain et al. |
| 9,796,748 B2 | 10/2017 | Schaus et al. |
| 9,796,749 B2 | 10/2017 | Yin et al. |
| 9,810,704 B2 | 11/2017 | Holmes et al. |
| 9,862,941 B2 | 1/2018 | Lee et al. |
| 9,863,930 B2 | 1/2018 | Sauder |
| 9,897,597 B2 | 2/2018 | Shih et al. |
| 9,909,162 B2 | 3/2018 | Yeh |
| 9,952,240 B2 | 4/2018 | Holmes et al. |
| 9,975,916 B2 | 5/2018 | Yin et al. |
| 9,977,017 B2 | 5/2018 | Jin et al. |
| 9,993,794 B2 | 6/2018 | Turner et al. |
| 10,018,643 B2 | 7/2018 | Holmes et al. |
| 10,024,796 B2 | 7/2018 | Lin et al. |
| 10,041,108 B2 | 8/2018 | Barish et al. |
| 10,099,195 B2 | 10/2018 | Tinnefeld et al. |
| 10,099,920 B2 | 10/2018 | Shen et al. |
| 10,137,426 B2 | 11/2018 | Love et al. |
| 10,189,874 B2 | 1/2019 | Han et al. |
| 10,247,656 B2 | 4/2019 | Kuypers et al. |
| 10,266,876 B2 | 4/2019 | Cai et al. |
| 10,267,795 B2 | 4/2019 | Herr et al. |
| 10,267,808 B2 | 4/2019 | Cai |
| 10,274,486 B2 | 4/2019 | Fan et al. |
| 10,350,570 B2 | 7/2019 | Gunderson et al. |
| 10,370,630 B2 | 8/2019 | Sivan et al. |
| 10,415,080 B2 | 9/2019 | Dunaway et al. |
| 10,471,430 B2 | 11/2019 | Le Berre et al. |
| 10,488,321 B2 | 11/2019 | Fathollahi et al. |
| 10,526,595 B2 | 1/2020 | Lee et al. |
| 10,534,009 B2 | 1/2020 | Holmes et al. |
| 10,549,277 B2 | 2/2020 | Lee et al. |
| 10,550,145 B2 | 2/2020 | Han et al. |
| 10,557,163 B2 | 2/2020 | Yeh |
| 10,557,863 B2 | 2/2020 | Holmes et al. |
| 10,604,543 B2 | 3/2020 | Yin et al. |
| 10,606,054 B2 | 3/2020 | Gerger et al. |
| 10,606,058 B2 | 3/2020 | Espensen |
| 10,627,418 B2 | 4/2020 | Wasson et al. |
| 10,633,693 B1 | 4/2020 | Handique et al. |
| 10,718,007 B2 | 7/2020 | Handique et al. |
| 10,774,107 B2 | 9/2020 | Han et al. |
| 2001/0048899 A1 | 12/2001 | Marouiss et al. |
| 2002/0006361 A1 | 1/2002 | Sanadi |
| 2002/0015995 A1 | 2/2002 | Blumenfeld et al. |
| 2002/0015996 A1 | 2/2002 | Blumenfeld et al. |
| 2003/0039974 A1 | 2/2003 | Skouv |
| 2003/0044324 A1 | 3/2003 | Micklash, II et al. |
| 2003/0180191 A1 | 9/2003 | Suzuki et al. |
| 2003/0232344 A1 | 12/2003 | Schleifer et al. |
| 2004/0018122 A1 | 1/2004 | Micklash, II et al. |
| 2004/0018610 A1 | 1/2004 | Sandell |
| 2004/0067171 A1 | 4/2004 | Icke et al. |
| 2004/0203000 A1 | 10/2004 | Sportsman et al. |
| 2004/0208792 A1 | 10/2004 | Linton et al. |
| 2004/0241783 A1 | 12/2004 | Papkovsky et al. |
| 2005/0019225 A1 | 1/2005 | Sanadi |
| 2005/0048571 A1 | 3/2005 | Danielson et al. |
| 2005/0079517 A1 | 4/2005 | Goncharko et al. |
| 2005/0106602 A1 | 5/2005 | Akhavan-Tafti |
| 2005/0136454 A1 | 6/2005 | Sportsman et al. |
| 2005/0136477 A1 | 6/2005 | Akhavan-Tafti |
| 2005/0208501 A1 | 9/2005 | Goldrick |
| 2005/0255445 A1 | 11/2005 | Van Damme et al. |
| 2006/0078910 A1 | 4/2006 | Seeman et al. |
| 2006/0134704 A1 | 6/2006 | Muraguchi et al. |
| 2006/0216744 A1 | 9/2006 | Chu |
| 2006/0252044 A1 | 11/2006 | Okumura et al. |
| 2007/0117109 A1 | 5/2007 | Rothemund |
| 2007/0190526 A1 | 8/2007 | Akhavan-Tafti et al. |
| 2008/0070250 A1 | 3/2008 | Lee |
| 2008/0287668 A1 | 11/2008 | Toth-Fejel |
| 2009/0036317 A1 | 2/2009 | Guilbeau |
| 2009/0062134 A1 | 3/2009 | Linton et al. |
| 2009/0062152 A1 | 3/2009 | Linton et al. |
| 2009/0117620 A1 | 5/2009 | Fritchie et al. |
| 2009/0181859 A1 | 7/2009 | Muraguchi et al. |
| 2009/0275117 A1 | 11/2009 | Sandell |
| 2009/0312198 A1 | 12/2009 | Goncharko et al. |
| 2010/0000304 A1 | 1/2010 | Kim et al. |
| 2010/0009872 A1 | 1/2010 | Eid et al. |
| 2010/0022416 A1 | 1/2010 | Flemming et al. |
| 2010/0047790 A1 | 2/2010 | Southern et al. |
| 2010/0048421 A1 | 2/2010 | Han et al. |
| 2010/0069621 A1 | 3/2010 | Maune et al. |
| 2010/0135860 A1 | 6/2010 | Halamis et al. |
| 2010/0151481 A1 | 6/2010 | Sportsman et al. |
| 2010/0152054 A1 | 6/2010 | Love et al. |
| 2010/0173792 A1 | 7/2010 | Heller et al. |
| 2010/0216978 A1 | 8/2010 | Shih |
| 2011/0046008 A1 | 2/2011 | Love et al. |
| 2011/0089944 A1 | 4/2011 | Shih et al. |
| 2011/0111981 A1 | 5/2011 | Love et al. |
| 2011/0237445 A1 | 9/2011 | Andersson Svahn et al. |
| 2011/0260105 A1 | 10/2011 | Shih et al. |
| 2011/0262906 A1 | 10/2011 | Dimov et al. |
| 2011/0281745 A1 | 11/2011 | Love et al. |
| 2011/0281764 A1 | 11/2011 | Love et al. |
| 2011/0294208 A1 | 12/2011 | Allbritton et al. |
| 2011/0294678 A1 | 12/2011 | Jin et al. |
| 2011/0306758 A1 | 12/2011 | Zhang |
| 2012/0004139 A1 | 1/2012 | Staker |
| 2012/0004140 A1 | 1/2012 | Staker |
| 2012/0009568 A1 | 1/2012 | Guilbeau |
| 2012/0022244 A1 | 1/2012 | Yin |

(56) References Cited

U.S. PATENT DOCUMENTS

| | | |
|---|---|---|
| 2012/0058467 A1 | 3/2012 | Thomas et al. |
| 2012/0065082 A1 | 3/2012 | Kuypers et al. |
| 2012/0107912 A1 | 5/2012 | Hwang et al. |
| 2012/0138221 A1 | 6/2012 | Icke et al. |
| 2012/0142014 A1 | 6/2012 | Cai |
| 2012/0149592 A1 | 6/2012 | Love et al. |
| 2012/0166152 A1 | 6/2012 | Bathe et al. |
| 2012/0245038 A1 | 9/2012 | Linton et al. |
| 2012/0251583 A1 | 10/2012 | Rothemund |
| 2012/0282684 A1 | 11/2012 | Fritchie et al. |
| 2012/0309651 A1 | 12/2012 | Pregibon et al. |
| 2012/0316082 A1 | 12/2012 | Pregibon et al. |
| 2013/0177903 A1 | 7/2013 | Thomas et al. |
| 2013/0190206 A1 | 7/2013 | Leonard et al. |
| 2013/0203120 A1 | 8/2013 | Hoffmann |
| 2013/0210653 A1 | 8/2013 | Pregibon et al. |
| 2013/0236377 A1 | 9/2013 | Kim et al. |
| 2013/0244895 A1 | 9/2013 | Voros et al. |
| 2013/0244909 A1 | 9/2013 | Windemuth et al. |
| 2013/0261019 A1 | 10/2013 | Lin et al. |
| 2013/0337500 A1 | 12/2013 | Tan et al. |
| 2013/0338030 A1 | 12/2013 | Love et al. |
| 2013/0338047 A1 | 12/2013 | Love et al. |
| 2014/0011709 A1 | 1/2014 | Love et al. |
| 2014/0031243 A1 | 1/2014 | Cai et al. |
| 2014/0179566 A1 | 1/2014 | Linton et al. |
| 2014/0057805 A1 | 2/2014 | Tinnefeld et al. |
| 2014/0066610 A1 | 3/2014 | Schaus et al. |
| 2014/0212881 A1 | 7/2014 | Handlique et al. |
| 2014/0213778 A1 | 7/2014 | Yin et al. |
| 2014/0220655 A1 | 8/2014 | Sun et al. |
| 2014/0296089 A1 | 10/2014 | Holmes et al. |
| 2014/0349867 A1 | 11/2014 | Handlique et al. |
| 2014/0371083 A1 | 12/2014 | Ahn et al. |
| 2015/0004193 A1 | 1/2015 | Chang et al. |
| 2015/0005198 A1 | 1/2015 | Pregibon et al. |
| 2015/0064233 A1 | 3/2015 | Shih et al. |
| 2015/0141266 A1 | 5/2015 | Turner et al. |
| 2015/0160135 A1 | 6/2015 | Tibbe et al. |
| 2015/0204862 A1 | 7/2015 | Fan et al. |
| 2015/0204864 A1 | 7/2015 | Fan et al. |
| 2015/0218204 A1 | 8/2015 | Yin et al. |
| 2015/0283545 A1 | 10/2015 | Icke et al. |
| 2015/0298090 A1 | 10/2015 | Tinnefeld et al. |
| 2015/0316547 A1 | 11/2015 | Herr et al. |
| 2015/0329584 A1 | 11/2015 | Yin et al. |
| 2015/0338428 A1 | 11/2015 | Holmes et al. |
| 2015/0368717 A1 | 12/2015 | Holmes et al. |
| 2016/0003823 A1 | 1/2016 | Holmes |
| 2016/0008809 A1 | 1/2016 | Li et al. |
| 2016/0011215 A1 | 1/2016 | Holmes |
| 2016/0024549 A1 | 1/2016 | Yeh |
| 2016/0025760 A1 | 1/2016 | Holmes |
| 2016/0025763 A1 | 1/2016 | Holmes |
| 2016/0033544 A1 | 2/2016 | Holmes et al. |
| 2016/0045884 A1 | 2/2016 | Husain et al. |
| 2016/0045885 A1 | 2/2016 | Love et al. |
| 2016/0060621 A1 | 3/2016 | Agresti et al. |
| 2016/0069921 A1 | 3/2016 | Holmes et al. |
| 2016/0082108 A1 | 3/2016 | Shih |
| 2016/0169880 A1 | 6/2016 | Holmes et al. |
| 2016/0169923 A1 | 6/2016 | Holmes et al. |
| 2016/0266088 A1 | 9/2016 | Sauder |
| 2016/0289669 A1 | 10/2016 | Fan et al. |
| 2016/0305936 A1 | 10/2016 | Leonard et al. |
| 2016/0312272 A1 | 10/2016 | Barish et al. |
| 2016/0320422 A1 | 11/2016 | Fritchie et al. |
| 2016/0333398 A1 | 11/2016 | Pregibon et al. |
| 2016/0348050 A1 | 12/2016 | Sivan et al. |
| 2016/0370396 A1 | 12/2016 | Wasson et al. |
| 2016/0377640 A1 | 12/2016 | Balwani et al. |
| 2017/0001166 A1 | 1/2017 | Love et al. |
| 2017/0009274 A1 | 1/2017 | Abate et al. |
| 2017/0015698 A1 | 1/2017 | Iinuma et al. |
| 2017/0023562 A1 | 1/2017 | Jin et al. |
| 2017/0038391 A1 | 2/2017 | Lara Gutierrez et al. |
| 2017/0038401 A1 | 2/2017 | Holmes et al. |
| 2017/0045506 A1 | 2/2017 | Shih et al. |
| 2017/0051338 A1 | 2/2017 | Manetto |
| 2017/0066796 A1 | 3/2017 | Han et al. |
| 2017/0067887 A1 | 3/2017 | Fan et al. |
| 2017/0073745 A1 | 3/2017 | Handlique et al. |
| 2017/0107507 A1 | 4/2017 | Lee et al. |
| 2017/0113221 A1 | 4/2017 | Hoffman et al. |
| 2017/0136458 A1 | 5/2017 | Duane et al. |
| 2017/0182493 A1 | 6/2017 | Perroud et al. |
| 2017/0190573 A1 | 7/2017 | Shen et al. |
| 2017/0209926 A1 | 7/2017 | Sun et al. |
| 2017/0307502 A1 | 10/2017 | Mason et al. |
| 2017/0320038 A1 | 11/2017 | Husain et al. |
| 2018/0010174 A1 | 1/2018 | Schaus et al. |
| 2018/0030515 A1 | 2/2018 | Regev et al. |
| 2018/0044372 A1 | 2/2018 | Han et al. |
| 2018/0067038 A1 | 3/2018 | Fathollahi et al. |
| 2018/0078940 A1 | 3/2018 | Lee et al. |
| 2018/0135043 A1 | 5/2018 | Wong et al. |
| 2018/0141020 A1 | 5/2018 | Gunderson et al. |
| 2018/0142286 A1 | 5/2018 | Dunaway et al. |
| 2018/0148760 A1 | 5/2018 | Yeh |
| 2018/0169657 A1 | 6/2018 | Kelly et al. |
| 2018/0214872 A1 | 8/2018 | Perroud et al. |
| 2018/0216160 A1 | 8/2018 | Abate et al. |
| 2018/0223344 A1 | 8/2018 | Chandrasekaran et al. |
| 2018/0224461 A1 | 8/2018 | Lara Gutierrez et al. |
| 2018/0230453 A1 | 8/2018 | Lee et al. |
| 2018/0250670 A1 | 9/2018 | Le Berre et al. |
| 2018/0250672 A1 | 9/2018 | Jamshidi et al. |
| 2018/0257075 A1 | 9/2018 | Yellen et al. |
| 2018/0258469 A1 | 9/2018 | Johnson-Buck et al. |
| 2018/0280918 A1 | 10/2018 | Tkachenko |
| 2018/0304257 A1 | 10/2018 | Misener et al. |
| 2018/0306783 A1 | 10/2018 | Shih et al. |
| 2018/0334706 A1 | 11/2018 | Handlique et al. |
| 2019/0003973 A1 | 1/2019 | Lin et al. |
| 2019/0018026 A1 | 1/2019 | Gerger et al. |
| 2019/0024165 A1 | 1/2019 | Wohrstein et al. |
| 2019/0046944 A1 | 2/2019 | Love et al. |
| 2019/0046985 A1 | 2/2019 | Kang et al. |
| 2019/0093103 A1 | 3/2019 | Vijayan et al. |
| 2019/0127682 A1 | 5/2019 | Aksimentiev et al. |
| 2019/0127782 A1 | 5/2019 | Regev et al. |
| 2019/0142882 A1 | 5/2019 | Sheperd et al. |
| 2019/0144491 A1 | 5/2019 | Han et al. |
| 2019/0144931 A1 | 5/2019 | Handlique et al. |
| 2019/0154679 A1 | 5/2019 | Doyle et al. |
| 2019/0156911 A1 | 5/2019 | Veneziano et al. |
| 2019/0194611 A1 | 6/2019 | Jo et al. |
| 2019/0201863 A1 | 7/2019 | Frank et al. |
| 2019/0203242 A1 | 7/2019 | Praetorius et al. |
| 2019/0210018 A1 | 7/2019 | Vijayan et al. |
| 2019/0212540 A1 | 7/2019 | Espensen |
| 2019/0218607 A1 | 7/2019 | Love et al. |
| 2019/0242887 A1 | 8/2019 | Jones et al. |
| 2019/0269728 A1 | 9/2019 | Foot et al. |
| 2019/0270991 A1 | 9/2019 | Foot et al. |
| 2019/0301986 A1 | 10/2019 | Olechno et al. |
| 2019/0324028 A1 | 10/2019 | Fan et al. |
| 2019/0344270 A1 | 11/2019 | Yoon et al. |
| 2019/0352640 A1 | 11/2019 | Shapiro et al. |
| 2019/0358629 A1 | 11/2019 | Vijayan et al. |
| 2019/0374923 A1 | 12/2019 | Gunderson et al. |
| 2019/0382764 A1 | 12/2019 | Easley et al. |
| 2019/0390258 A1 | 12/2019 | Dunaway et al. |
| 2020/0001295 A1 | 1/2020 | Vijayan et al. |
| 2020/0010789 A1 | 1/2020 | Doebler et al. |
| 2020/0025752 A1 | 1/2020 | Gopinath et al. |
| 2020/0047182 A1 | 2/2020 | Meldrum et al. |
| 2020/0109362 A1 | 4/2020 | Engelward et al. |

(56) References Cited

U.S. PATENT DOCUMENTS

| | | |
|---|---|---|
| 2020/0216840 A1 | 7/2020 | Tanno et al. |
| 2020/0256862 A1 | 8/2020 | Shalek et al. |

FOREIGN PATENT DOCUMENTS

| | | |
|---|---|---|
| CN | 102719357 | 10/2012 |
| CN | 103159170 | 6/2013 |
| CN | 103894248 | 7/2014 |
| CN | 103997404 | 8/2014 |
| CN | 104513787 | 4/2015 |
| CN | 105602949 | 5/2016 |
| CN | 105930586 | 9/2016 |
| CN | 106893722 | 6/2017 |
| CN | 107262170 | 10/2017 |
| CN | 107437003 | 12/2017 |
| CN | 107488661 | 12/2017 |
| CN | 107774347 | 3/2018 |
| CN | 107894411 | 4/2018 |
| CN | 108535145 | 9/2018 |
| CN | 108795939 | 11/2018 |
| CN | 110079633 | 8/2019 |
| CN | 110437992 | 11/2019 |
| CN | 110508335 | 11/2019 |
| CN | 110586209 | 12/2019 |
| CN | 110628567 | 12/2019 |
| CN | 111019941 | 4/2020 |
| CN | 111298129 | 6/2020 |
| DE | 102012107718 | 2/2014 |
| JP | 2017026516 | 2/2017 |
| KR | 20180108125 | 10/2018 |
| KR | 20200084406 | 7/2020 |
| WO | 9423839 | 10/1994 |
| WO | 9601836 | 1/1996 |
| WO | 9842874 | 10/1998 |
| WO | WO0075662 | 12/2000 |
| WO | WO0209868 | 2/2002 |
| WO | WO0225289 | 3/2002 |
| WO | WO0240158 | 5/2002 |
| WO | WO0242775 | 5/2002 |
| WO | WO03020426 | 3/2003 |
| WO | WO03059518 | 7/2003 |
| WO | WO03102578 | 12/2003 |
| WO | WO2004009239 | 1/2004 |
| WO | WO2004051266 | 6/2004 |
| WO | WO2004074818 | 9/2004 |
| WO | WO2004097415 | 11/2004 |
| WO | WO2005016841 | 2/2005 |
| WO | WO2005090984 | 9/2005 |
| WO | WO2006036243 | 4/2006 |
| WO | WO2006036246 | 4/2006 |
| WO | WO2006085921 | 8/2006 |
| WO | WO2007022026 | 2/2007 |
| WO | WO2007035633 | 3/2007 |
| WO | WO2007079229 | 7/2007 |
| WO | WO2007079250 | 7/2007 |
| WO | WO2007098379 | 8/2007 |
| WO | WO2007102785 | 9/2007 |
| WO | WO2007127020 | 11/2007 |
| WO | WO2008075086 | 6/2008 |
| WO | WO2008112739 | 9/2008 |
| WO | WO2008130585 | 10/2008 |
| WO | WO2009017226 | 2/2009 |
| WO | WO2009061641 | 5/2009 |
| WO | WO2009071665 | 6/2009 |
| WO | WO2009145818 | 12/2009 |
| WO | WO2010011939 | 1/2010 |
| WO | WO2010040831 | 4/2010 |
| WO | WO2010040851 | 4/2010 |
| WO | WO2010085275 | 7/2010 |
| WO | WO2010093766 | 8/2010 |
| WO | WO2011112634 | 9/2011 |
| WO | WO2011156432 | 12/2011 |
| WO | WO2011156434 | 12/2011 |
| WO | WO2012007537 | 1/2012 |
| WO | WO2012022482 | 2/2012 |
| WO | WO2012045669 | 4/2012 |
| WO | WO2012045670 | 4/2012 |
| WO | WO2012058638 | 5/2012 |
| WO | 2012/151328 | 11/2012 |
| WO | WO2012151328 | 11/2012 |
| WO | WO2013006411 | 1/2013 |
| WO | WO2013010134 | 1/2013 |
| WO | WO2013022694 | 2/2013 |
| WO | WO2013119676 | 8/2013 |
| WO | WO2013134633 | 9/2013 |
| WO | 2013148186 | 10/2013 |
| WO | 2013177953 | 12/2013 |
| WO | 2013180567 | 12/2013 |
| WO | 2014018675 | 1/2014 |
| WO | 2014031997 | 2/2014 |
| WO | 2014074597 | 5/2014 |
| WO | 2014/134338 | 9/2014 |
| WO | 2014/145620 | 9/2014 |
| WO | 2014138475 | 9/2014 |
| WO | 2014142786 | 9/2014 |
| WO | WO 2015/070080 | * 5/2015 |
| WO | 2015089506 | 6/2015 |
| WO | 2015118551 | 8/2015 |
| WO | 2015130805 | 9/2015 |
| WO | 2015138231 | 9/2015 |
| WO | 2015147004 | 10/2015 |
| WO | 2015164602 | 10/2015 |
| WO | 2015165643 | 11/2015 |
| WO | 2015187390 | 12/2015 |
| WO | 2015191916 | 12/2015 |
| WO | 2015200541 | 12/2015 |
| WO | 2016007819 | 1/2016 |
| WO | 2016040476 | 3/2016 |
| WO | 2016100196 | 6/2016 |
| WO | 2016118915 | 7/2016 |
| WO | 2016123419 | 8/2016 |
| WO | 2016126871 | 8/2016 |
| WO | 2016138231 | 9/2016 |
| WO | 2016144755 | 9/2016 |
| WO | 2016149639 | 9/2016 |
| WO | 2016196824 | 12/2016 |
| WO | 2017003950 | 1/2017 |
| WO | 2017027370 | 2/2017 |
| WO | 2017027549 | 2/2017 |
| WO | 2017042115 | 3/2017 |
| WO | 2017048975 | 3/2017 |
| WO | 2017066351 | 4/2017 |
| WO | 2017074815 | 5/2017 |
| WO | 2017074934 | 5/2017 |
| WO | 2017083817 | 5/2017 |
| WO | 2017087873 | 5/2017 |
| WO | 2017095917 | 6/2017 |
| WO | 2017100251 | 6/2017 |
| WO | 2017117105 | 7/2017 |
| WO | 2017123697 | 7/2017 |
| WO | 2017134303 | 8/2017 |
| WO | 2017184776 | 10/2017 |
| WO | 2017189870 | 11/2017 |
| WO | 2017222710 | 12/2017 |
| WO | 2017223254 | 12/2017 |
| WO | 2018054571 | 3/2018 |
| WO | 2018076025 | 4/2018 |
| WO | 2018085835 | 5/2018 |
| WO | 2018094385 | 5/2018 |
| WO | 2018129333 | 7/2018 |
| WO | 2018134825 | 7/2018 |
| WO | 2018140302 | 8/2018 |
| WO | 2018144723 | 8/2018 |
| WO | 2018165309 | 9/2018 |
| WO | 2018174899 | 9/2018 |
| WO | 2018175500 | 9/2018 |
| WO | 2018218646 | 12/2018 |
| WO | 2019012366 | 1/2019 |
| WO | 2019023627 | 1/2019 |
| WO | 2019051181 | 3/2019 |
| WO | 2019060830 | 3/2019 |
| WO | 2019060857 | 3/2019 |
| WO | 2019075321 | 4/2019 |
| WO | 2019084058 | 5/2019 |

(56) References Cited

FOREIGN PATENT DOCUMENTS

| WO | 2019094928 | 5/2019 |
|---|---|---|
| WO | 2019108954 | 6/2019 |
| WO | 2019113457 | 6/2019 |
| WO | 2019149932 | 8/2019 |
| WO | 2019157170 | 8/2019 |
| WO | 2019160739 | 8/2019 |
| WO | 2019166877 | 9/2019 |
| WO | 2019173238 | 9/2019 |
| WO | 2019173460 | 9/2019 |
| WO | 2019183554 | 9/2019 |
| WO | 2019211631 | 11/2019 |
| WO | 2020025909 | 2/2020 |
| WO | 2020036654 | 2/2020 |

OTHER PUBLICATIONS

Ke, Y., Meyer, T., Shih, W. et al. "Regulation at a distance of biomolecular interactions using a DNA origami nanoactuator." Nat Commun 7, 10935 (2016) doi:10.1038/ncomms10935.

Andersen, E., Dong, M., Nielsen, M. et al. "Self-assembly of a nanoscale DNA box with a controllable lid." Nature 459, 73-76 (2009) doi:10.1038/nature07971

\* cited by examiner

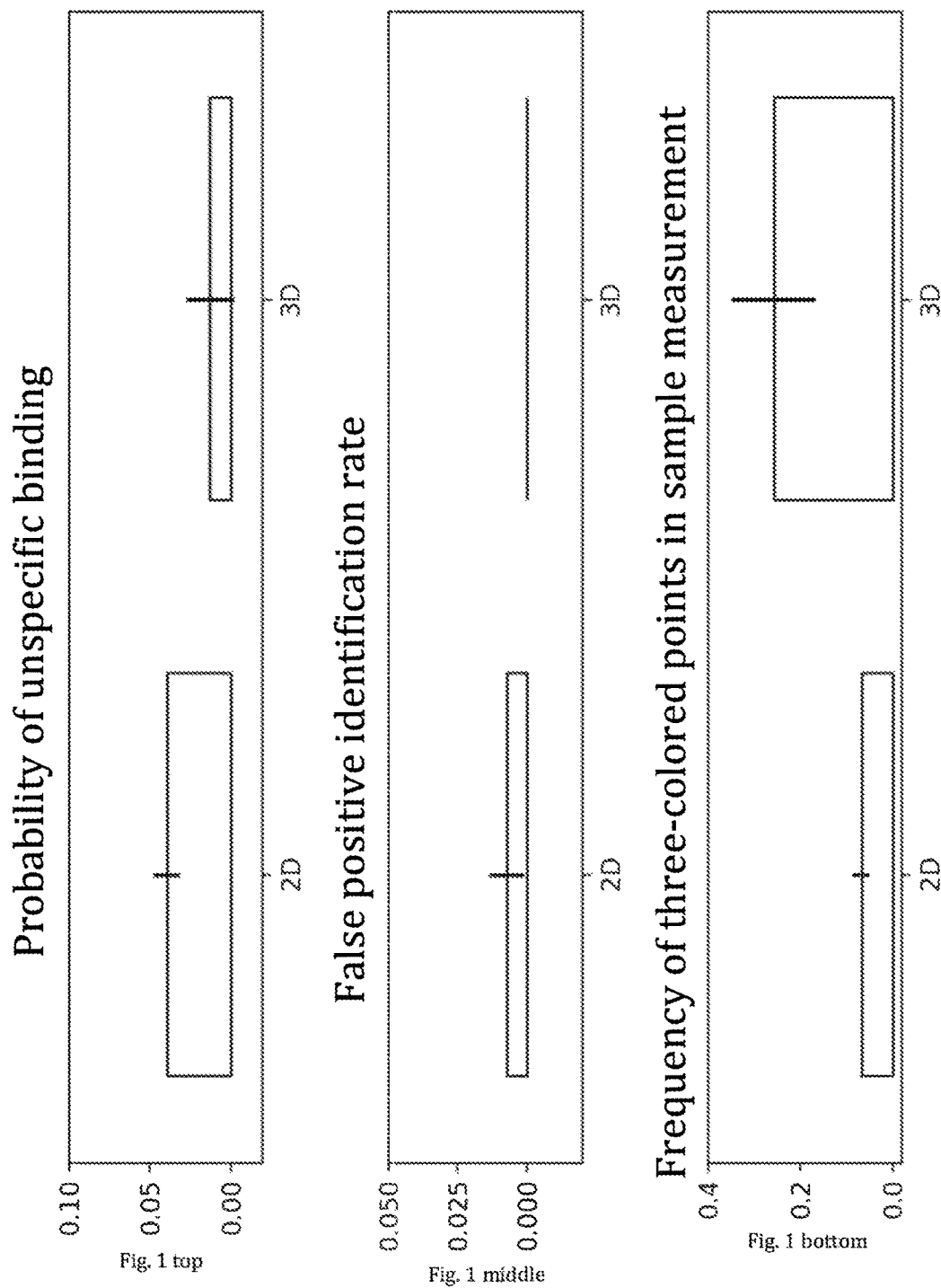

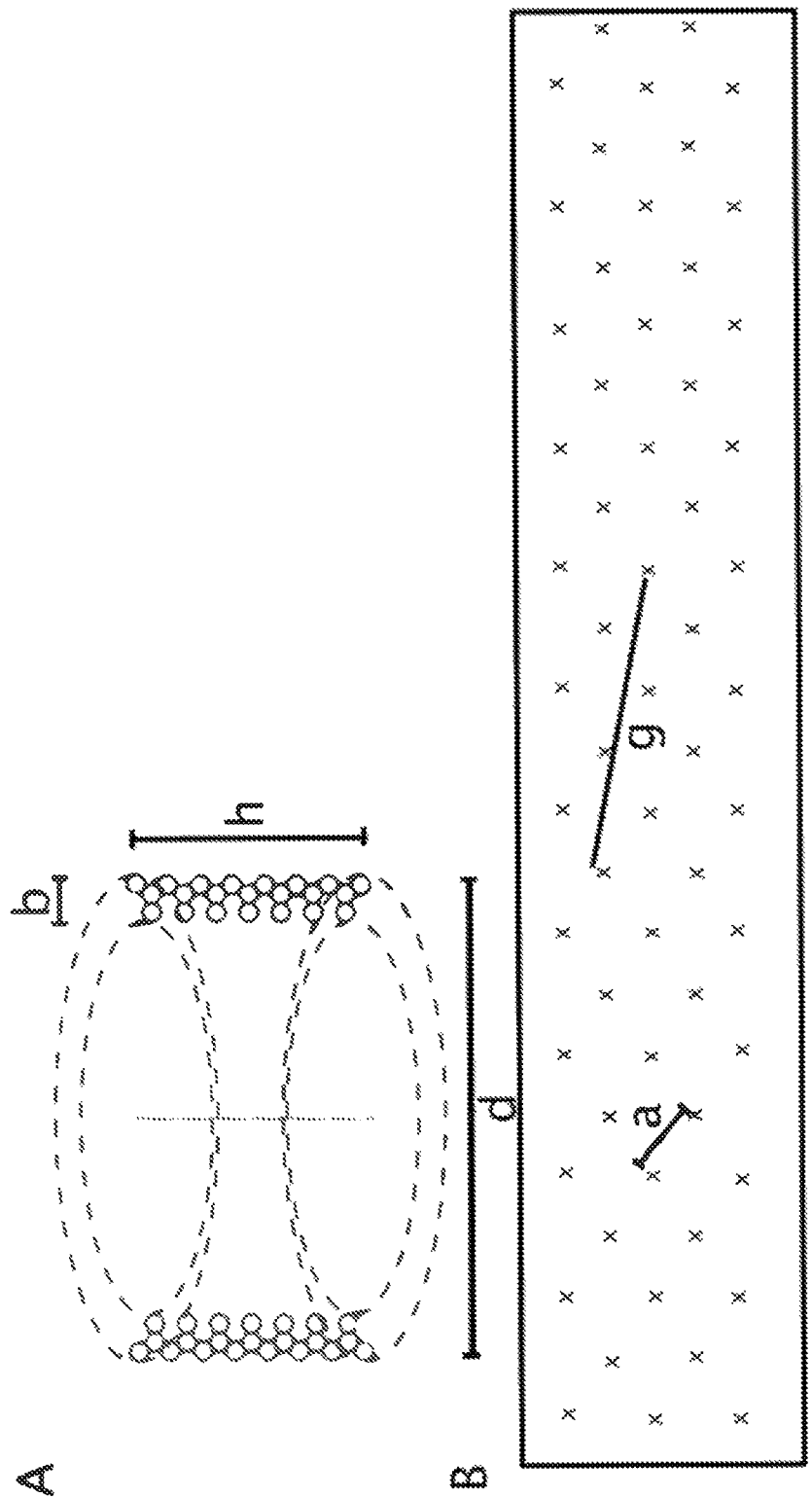

SEQUENCE LISTING

<160> NUMBER OF SEQ ID NOS: 1269

<210> SEQ ID NO 1
<211> LENGTH: 45
<212> TYPE: DNA
<213> ORGANISM: Artificial Sequence
<220> FEATURE:
<223> OTHER INFORMATION: Staple strand_0000 of the 3D DNA nanostructure.

<400> SEQUENCE: 1
agagtccact attttaatga acgctttcca gtcgggggtc gacgt          45

<210> SEQ ID NO 2
<211> LENGTH: 45
<212> TYPE: DNA
<213> ORGANISM: Artificial Sequence
<220> FEATURE:
<223> OTHER INFORMATION: Staple strand_0001 of the 3D DNA nanostructure.

<400> SEQUENCE: 2
tatctaaaat atcttttgaa tacctgaaag cgtaagagca ataca                45

<210> SEQ ID NO 3
<211> LENGTH: 45
<212> TYPE: DNA
<213> ORGANISM: Artificial Sequence
<220> FEATURE:
<223> OTHER INFORMATION: Staple strand_0002 of the 3D DNA nanostructure.

<400> SEQUENCE: 3
cagtacataa atcgcacgta aatggaaggg ttagaaagat taggt                45

<210> SEQ ID NO 4
<211> LENGTH: 45
<212> TYPE: DNA
<213> ORGANISM: Artificial Sequence
<220> FEATURE:
<223> OTHER INFORMATION: Staple strand_0003 of the 3D DNA nanostructure.

<400> SEQUENCE: 4
aacatgttca gctccgtgtg aatcttctga cctaaatgct tctaa                45

<210> SEQ ID NO 5
<211> LENGTH: 45
<212> TYPE: DNA
<213> ORGANISM: Artificial Sequence
<220> FEATURE:
<223> OTHER INFORMATION: Staple strand_0004 of the 3D DNA nanostructure.

<400> SEQUENCE: 5
gggtaattga gcgttaaatc atagcgaacc tcccgacaac aatac                45

<210> SEQ ID NO 6
<211> LENGTH: 45
<212> TYPE: DNA
<213> ORGANISM: Artificial Sequence
<220> FEATURE:
<223> OTHER INFORMATION: Staple strand_0005 of the 3D DNA nanostructure.

<400> SEQUENCE: 6
cgtcagactg tagaatagaa aaaagacacc acggaacaag aatga                45

<210> SEQ ID NO 7
<211> LENGTH: 45
<212> TYPE: DNA
<213> ORGANISM: Artificial Sequence
<220> FEATURE:
<223> OTHER INFORMATION: Staple strand_0006 of the 3D DNA nanostructure.

<400> SEQUENCE: 7
accgtactca ggagcgtcat atggaaagcg cagtctgtca tagag                45

<210> SEQ ID NO 8
<211> LENGTH: 45
<212> TYPE: DNA
<213> ORGANISM: Artificial Sequence
<220> FEATURE:
<223> OTHER INFORMATION: Staple strand_0007 of the 3D DNA nanostructure.

<400> SEQUENCE: 8
aacggctaca gagcgaataa tcggagtgag aatagaaacc gcctc                45

<210> SEQ ID NO 9
<211> LENGTH: 45
<212> TYPE: DNA

```
<213> ORGANISM: Artificial Sequence
<220> FEATURE:
<223> OTHER INFORMATION: Staple strand_0008 of the 3D DNA nanostructure.

<400> SEQUENCE: 9
aataaaacga actgtacaga cgaactgacc aactttcat gaggc                45

<210> SEQ ID NO 10
<211> LENGTH: 45
<212> TYPE: DNA
<213> ORGANISM: Artificial Sequence
<220> FEATURE:
<223> OTHER INFORMATION: Staple strand_0009 of the 3D DNA nanostructure.

<400> SEQUENCE: 10
tgttttaaat atgatgacca tcccctcaa atgctttaga aagtt                 45

<210> SEQ ID NO 11
<211> LENGTH: 45
<212> TYPE: DNA
<213> ORGANISM: Artificial Sequence
<220> FEATURE:
<223> OTHER INFORMATION: Staple strand_0010 of the 3D DNA nanostructure.

<400> SEQUENCE: 11
gtaatcgtaa aacgggagaa gtgtaccaaa acattagtt tcaca                 45

<210> SEQ ID NO 12
<211> LENGTH: 45
<212> TYPE: DNA
<213> ORGANISM: Artificial Sequence
<220> FEATURE:
<223> OTHER INFORMATION: Staple strand_0011 of the 3D DNA nanostructure.

<400> SEQUENCE: 12
aaaacgacgg ccacatcgta accgtaatgg gataggccgg ttgcg                45

<210> SEQ ID NO 13
<211> LENGTH: 45
<212> TYPE: DNA
<213> ORGANISM: Artificial Sequence
<220> FEATURE:
<223> OTHER INFORMATION: Staple strand_0012 of the 3D DNA nanostructure.

<400> SEQUENCE: 13
tcccttataa atccggtttg caagcctggg gtgcctcaag tccgg                45

<210> SEQ ID NO 14
<211> LENGTH: 45
<212> TYPE: DNA
<213> ORGANISM: Artificial Sequence
<220> FEATURE:
<223> OTHER INFORMATION: Staple strand_0013 of the 3D DNA nanostructure.

<400> SEQUENCE: 14
aaccctcaat caaaactgat acagtcacac gaccagtcac ttgaa                45

<210> SEQ ID NO 15
<211> LENGTH: 45
<212> TYPE: DNA
<213> ORGANISM: Artificial Sequence
<220> FEATURE:
<223> OTHER INFORMATION: Staple strand_0014 of the 3D DNA nanostructure.

<400> SEQUENCE: 15
caagaaaaca aaaagatttt catcagatga tggcaattga ggaca                45
```

```
<210> SEQ ID NO 16
<211> LENGTH: 45
<212> TYPE: DNA
<213> ORGANISM: Artificial Sequence
<220> FEATURE:
<223> OTHER INFORMATION: Staple strand_0015 of the 3D DNA nanostructure.

<400> SEQUENCE: 16
aagagaatat aaataaacac ctccaatcgc aagacaattt tccat            45

<210> SEQ ID NO 17
<211> LENGTH: 45
<212> TYPE: DNA
<213> ORGANISM: Artificial Sequence
<220> FEATURE:
<223> OTHER INFORMATION: Staple strand_0016 of the 3D DNA nanostructure.

<400> SEQUENCE: 17
ataaaaacag ggacagctac aatagcaagc aaatcaaata ataat            45

<210> SEQ ID NO 18
<211> LENGTH: 45
<212> TYPE: DNA
<213> ORGANISM: Artificial Sequence
<220> FEATURE:
<223> OTHER INFORMATION: Staple strand_0017 of the 3D DNA nanostructure.

<400> SEQUENCE: 18
caatgaaacc atcaaagaca agtatgttag caaacgagca agaac            45

<210> SEQ ID NO 19
<211> LENGTH: 45
<212> TYPE: DNA
<213> ORGANISM: Artificial Sequence
<220> FEATURE:
<223> OTHER INFORMATION: Staple strand_0018 of the 3D DNA nanostructure.

<400> SEQUENCE: 19
accaggcgga taagtgtact gcaggtcaga cgattgtctt ttcac            45

<210> SEQ ID NO 20
<211> LENGTH: 45
<212> TYPE: DNA
<213> ORGANISM: Artificial Sequence
<220> FEATURE:
<223> OTHER INFORMATION: Staple strand_0019 of the 3D DNA nanostructure.

<400> SEQUENCE: 20
ggccgctttt gcgccaaaaa aacgttagta aatgaaagag ccagt            45

<210> SEQ ID NO 21
<211> LENGTH: 45
<212> TYPE: DNA
<213> ORGANISM: Artificial Sequence
<220> FEATURE:
<223> OTHER INFORMATION: Staple strand_0020 of the 3D DNA nanostructure.

<400> SEQUENCE: 21
tgcgatttta agattcatca agacctgctc catgttaaat acgaa            45

<210> SEQ ID NO 22
<211> LENGTH: 45
<212> TYPE: DNA
<213> ORGANISM: Artificial Sequence
<220> FEATURE:
```

<223> OTHER INFORMATION: Staple strand_0021 of the 3D DNA nanostructure.

<400> SEQUENCE: 22
gaggtcattt ttgcctgact aaaatgttta gactggaata ccata         45

<210> SEQ ID NO 23
<211> LENGTH: 45
<212> TYPE: DNA
<213> ORGANISM: Artificial Sequence
<220> FEATURE:
<223> OTHER INFORMATION: Staple strand_0022 of the 3D DNA nanostructure.

<400> SEQUENCE: 23
ctacaaaggc tataaaattt taaggcaaag aattagcaat tctaa         45

<210> SEQ ID NO 24
<211> LENGTH: 45
<212> TYPE: DNA
<213> ORGANISM: Artificial Sequence
<220> FEATURE:
<223> OTHER INFORMATION: Staple strand_0023 of the 3D DNA nanostructure.

<400> SEQUENCE: 24
ggatgtgctg caaggacgac gttaaatgtg agcgagacag gaaat         45

<210> SEQ ID NO 25
<211> LENGTH: 45
<212> TYPE: DNA
<213> ORGANISM: Artificial Sequence
<220> FEATURE:
<223> OTHER INFORMATION: Staple strand_0024 of the 3D DNA nanostructure.

<400> SEQUENCE: 25
acgctggttt gccttctttt ctgaaattgt tatccggcta gtagc         45

<210> SEQ ID NO 26
<211> LENGTH: 45
<212> TYPE: DNA
<213> ORGANISM: Artificial Sequence
<220> FEATURE:
<223> OTHER INFORMATION: Staple strand_0025 of the 3D DNA nanostructure.

<400> SEQUENCE: 26
gctgagagcc agcaataccg aatacctaca ttttgatatc ggccc         45

<210> SEQ ID NO 27
<211> LENGTH: 45
<212> TYPE: DNA
<213> ORGANISM: Artificial Sequence
<220> FEATURE:
<223> OTHER INFORMATION: Staple strand_0026 of the 3D DNA nanostructure.

<400> SEQUENCE: 27
gcgcagaggc gaaacagtaa ccattttgcg gaacaaaaac aatac         45

<210> SEQ ID NO 28
<211> LENGTH: 45
<212> TYPE: DNA
<213> ORGANISM: Artificial Sequence
<220> FEATURE:
<223> OTHER INFORMATION: Staple strand_0027 of the 3D DNA nanostructure.

<400> SEQUENCE: 28
atcgccatat ttagcctgtt tccttttaa cctccggcga tagtc         45

```
<210> SEQ ID NO 29
<211> LENGTH: 45
<212> TYPE: DNA
<213> ORGANISM: Artificial Sequence
<220> FEATURE:
<223> OTHER INFORMATION: Staple strand_0028 of the 3D DNA nanostructure.

<400> SEQUENCE: 29
agaaacgatt tttcgctaac gctcatcgag aacaagtgta gaaga          45

<210> SEQ ID NO 30
<211> LENGTH: 45
<212> TYPE: DNA
<213> ORGANISM: Artificial Sequence
<220> FEATURE:
<223> OTHER INFORMATION: Staple strand_0029 of the 3D DNA nanostructure.

<400> SEQUENCE: 30
aattagagcc agcagggagg gacgcaataa taacggatct tacta          45

<210> SEQ ID NO 31
<211> LENGTH: 45
<212> TYPE: DNA
<213> ORGANISM: Artificial Sequence
<220> FEATURE:
<223> OTHER INFORMATION: Staple strand_0030 of the 3D DNA nanostructure.

<400> SEQUENCE: 31
agtattaaga ggcgtgcctt gcagagccgc caccagagag ccagg          45

<210> SEQ ID NO 32
<211> LENGTH: 45
<212> TYPE: DNA
<213> ORGANISM: Artificial Sequence
<220> FEATURE:
<223> OTHER INFORMATION: Staple strand_0031 of the 3D DNA nanostructure.

<400> SEQUENCE: 32
aacaaccatc gccattgtat cattccacag acagccgcaa gccaa          45

<210> SEQ ID NO 33
<211> LENGTH: 45
<212> TYPE: DNA
<213> ORGANISM: Artificial Sequence
<220> FEATURE:
<223> OTHER INFORMATION: Staple strand_0032 of the 3D DNA nanostructure.

<400> SEQUENCE: 33
gagtagtaaa ttgatattca tcgaaacaaa gtacaaaacc taaac          45

<210> SEQ ID NO 34
<211> LENGTH: 45
<212> TYPE: DNA
<213> ORGANISM: Artificial Sequence
<220> FEATURE:
<223> OTHER INFORMATION: Staple strand_0033 of the 3D DNA nanostructure.

<400> SEQUENCE: 34
ccggaagcaa actttgcatc aaaaaccaaa atagcgtaac gccac          45

<210> SEQ ID NO 35
<211> LENGTH: 45
<212> TYPE: DNA
<213> ORGANISM: Artificial Sequence
<220> FEATURE:
<223> OTHER INFORMATION: Staple strand_0034 of the 3D DNA nanostructure.
```

-continued

<400> SEQUENCE: 35
gatattcaac cgttgcaatg caaggtggca tcaattgacc attga            45

<210> SEQ ID NO 36
<211> LENGTH: 45
<212> TYPE: DNA
<213> ORGANISM: Artificial Sequence
<220> FEATURE:
<223> OTHER INFORMATION: Staple strand_0035 of the 3D DNA nanostructure.

<400> SEQUENCE: 36
aactgttggg aagcgcactc caggaacgcc atcaaaaatt gtaat            45

<210> SEQ ID NO 37
<211> LENGTH: 45
<212> TYPE: DNA
<213> ORGANISM: Artificial Sequence
<220> FEATURE:
<223> OTHER INFORMATION: Staple strand_0036 of the 3D DNA nanostructure.

<400> SEQUENCE: 37
ctggccaaca gaggattagt gatagggttg agtgtacgcg cggct            45

<210> SEQ ID NO 38
<211> LENGTH: 45
<212> TYPE: DNA
<213> ORGANISM: Artificial Sequence
<220> FEATURE:
<223> OTHER INFORMATION: Staple strand_0037 of the 3D DNA nanostructure.

<400> SEQUENCE: 38
tgattgtttg gataatagat caaatcaaca gttgaagtct ttatt            45

<210> SEQ ID NO 39
<211> LENGTH: 45
<212> TYPE: DNA
<213> ORGANISM: Artificial Sequence
<220> FEATURE:
<223> OTHER INFORMATION: Staple strand_0038 of the 3D DNA nanostructure.

<400> SEQUENCE: 39
tttttcaaat atagtcgcta aatttcattt gaattataaa gaacc            45

<210> SEQ ID NO 40
<211> LENGTH: 45
<212> TYPE: DNA
<213> ORGANISM: Artificial Sequence
<220> FEATURE:
<223> OTHER INFORMATION: Staple strand_0039 of the 3D DNA nanostructure.

<400> SEQUENCE: 40
ccggtattct aagtcctgaa aaagtaattc tgtccggcgt taaac            45

<210> SEQ ID NO 41
<211> LENGTH: 45
<212> TYPE: DNA
<213> ORGANISM: Artificial Sequence
<220> FEATURE:
<223> OTHER INFORMATION: Staple strand_0040 of the 3D DNA nanostructure.

<400> SEQUENCE: 41
aaaggtggca acaagcccaa agaattaact gaacattgct attat            45

<210> SEQ ID NO 42
<211> LENGTH: 45

```
<212> TYPE: DNA
<213> ORGANISM: Artificial Sequence
<220> FEATURE:
<223> OTHER INFORMATION: Staple strand_0041 of the 3D DNA nanostructure.

<400> SEQUENCE: 42
acaaataaat cctattagcg atcagtagcg acagatggtt tacat            45

<210> SEQ ID NO 43
<211> LENGTH: 45
<212> TYPE: DNA
<213> ORGANISM: Artificial Sequence
<220> FEATURE:
<223> OTHER INFORMATION: Staple strand_0042 of the 3D DNA nanostructure.

<400> SEQUENCE: 43
ttgctaaaca actgaaccgc ttgatataag tatagtttga tgaaa            45

<210> SEQ ID NO 44
<211> LENGTH: 45
<212> TYPE: DNA
<213> ORGANISM: Artificial Sequence
<220> FEATURE:
<223> OTHER INFORMATION: Staple strand_0043 of the 3D DNA nanostructure.

<400> SEQUENCE: 44
gcgcagacgg tcaccattaa gcagcgaaag acagctcacg ttgtt            45

<210> SEQ ID NO 45
<211> LENGTH: 45
<212> TYPE: DNA
<213> ORGANISM: Artificial Sequence
<220> FEATURE:
<223> OTHER INFORMATION: Staple strand_0044 of the 3D DNA nanostructure.

<400> SEQUENCE: 45
cggaatcgtc ataagttgag cagtcaggac gttggatagg ctgag            45

<210> SEQ ID NO 46
<211> LENGTH: 45
<212> TYPE: DNA
<213> ORGANISM: Artificial Sequence
<220> FEATURE:
<223> OTHER INFORMATION: Staple strand_0045 of the 3D DNA nanostructure.

<400> SEQUENCE: 46
agcctcagag cattaacagt ttaattgctg aatataaatc aggtg            45

<210> SEQ ID NO 47
<211> LENGTH: 45
<212> TYPE: DNA
<213> ORGANISM: Artificial Sequence
<220> FEATURE:
<223> OTHER INFORMATION: Staple strand_0046 of the 3D DNA nanostructure.

<400> SEQUENCE: 47
tctccgtggg aacgaaaagc gagtctggag caaacttcaa cgcaa            45

<210> SEQ ID NO 48
<211> LENGTH: 45
<212> TYPE: DNA
<213> ORGANISM: Artificial Sequence
<220> FEATURE:
<223> OTHER INFORMATION: Staple strand_0047 of the 3D DNA nanostructure.

<400> SEQUENCE: 48
```
cacattaatt gcgctttgat taacgccagg gtttttctgc cagat         45

<210> SEQ ID NO 49
<211> LENGTH: 45
<212> TYPE: DNA
<213> ORGANISM: Artificial Sequence
<220> FEATURE:
<223> OTHER INFORMATION: Staple strand_0048 of the 3D DNA nanostructure.

<400> SEQUENCE: 49
atggattatt tacagaagaa cctgtttgat ggtgggcgcc aggca         45

<210> SEQ ID NO 50
<211> LENGTH: 45
<212> TYPE: DNA
<213> ORGANISM: Artificial Sequence
<220> FEATURE:
<223> OTHER INFORMATION: Staple strand_0049 of the 3D DNA nanostructure.

<400> SEQUENCE: 50
agcggaatta tcagtattag taaagcatca ccttgaacat cgcaa         45

<210> SEQ ID NO 51
<211> LENGTH: 45
<212> TYPE: DNA
<213> ORGANISM: Artificial Sequence
<220> FEATURE:
<223> OTHER INFORMATION: Staple strand_0050 of the 3D DNA nanostructure.

<400> SEQUENCE: 51
ataactatat gtatccttga acctgagcaa aagaaacgtc agagg         45

<210> SEQ ID NO 52
<211> LENGTH: 45
<212> TYPE: DNA
<213> ORGANISM: Artificial Sequence
<220> FEATURE:
<223> OTHER INFORMATION: Staple strand_0051 of the 3D DNA nanostructure.

<400> SEQUENCE: 52
tcatcgtagg aatctaattt aatttaggca gaggctaatt actat         45

<210> SEQ ID NO 53
<211> LENGTH: 45
<212> TYPE: DNA
<213> ORGANISM: Artificial Sequence
<220> FEATURE:
<223> OTHER INFORMATION: Staple strand_0052 of the 3D DNA nanostructure.

<400> SEQUENCE: 53
ggcatgatta agaaaatagc atgaaaatag cagcccctga atctt         45

<210> SEQ ID NO 54
<211> LENGTH: 45
<212> TYPE: DNA
<213> ORGANISM: Artificial Sequence
<220> FEATURE:
<223> OTHER INFORMATION: Staple strand_0053 of the 3D DNA nanostructure.

<400> SEQUENCE: 54
gccgccagca ttgaaatcac accattacca ttagcacatt caact         45

<210> SEQ ID NO 55
<211> LENGTH: 45
<212> TYPE: DNA
<213> ORGANISM: Artificial Sequence

```
<220> FEATURE:
<223> OTHER INFORMATION: Staple strand_0054 of the 3D DNA nanostructure.

<400> SEQUENCE: 55
cgatctaaag tttcattttc gaaggattag gattagtttt aaccc            45

<210> SEQ ID NO 56
<211> LENGTH: 45
<212> TYPE: DNA
<213> ORGANISM: Artificial Sequence
<220> FEATURE:
<223> OTHER INFORMATION: Staple strand_0055 of the 3D DNA nanostructure.

<400> SEQUENCE: 56
cgcctgataa attactacga tattcggtcg ctgagcaaaa ggaaa            45

<210> SEQ ID NO 57
<211> LENGTH: 45
<212> TYPE: DNA
<213> ORGANISM: Artificial Sequence
<220> FEATURE:
<223> OTHER INFORMATION: Staple strand_0056 of the 3D DNA nanostructure.

<400> SEQUENCE: 57
gaagttttgc cagctaatgc aatttcaact ttaatcttga caaat            45

<210> SEQ ID NO 58
<211> LENGTH: 45
<212> TYPE: DNA
<213> ORGANISM: Artificial Sequence
<220> FEATURE:
<223> OTHER INFORMATION: Staple strand_0057 of the 3D DNA nanostructure.

<400> SEQUENCE: 58
cattaacatc caaagtagat tagagagtac ctttacagaa gcaaa            45

<210> SEQ ID NO 59
<211> LENGTH: 45
<212> TYPE: DNA
<213> ORGANISM: Artificial Sequence
<220> FEATURE:
<223> OTHER INFORMATION: Staple strand_0058 of the 3D DNA nanostructure.

<400> SEQUENCE: 59
ccttcctgta gcctaagcaa aatgccggag agggtctcat ataag            45

<210> SEQ ID NO 60
<211> LENGTH: 45
<212> TYPE: DNA
<213> ORGANISM: Artificial Sequence
<220> FEATURE:
<223> OTHER INFORMATION: Staple strand_0059 of the 3D DNA nanostructure.

<400> SEQUENCE: 60
acatacgagc cggaccgtat cctcttcgct attaccggcc tcagg            45

<210> SEQ ID NO 61
<211> LENGTH: 45
<212> TYPE: DNA
<213> ORGANISM: Artificial Sequence
<220> FEATURE:
<223> OTHER INFORMATION: Staple strand_0060 of the 3D DNA nanostructure.

<400> SEQUENCE: 61
attgcaacag gaagtaatat cctggccctg agagaagacg ggccg            45
```

<210> SEQ ID NO 62
<211> LENGTH: 45
<212> TYPE: DNA
<213> ORGANISM: Artificial Sequence
<220> FEATURE:
<223> OTHER INFORMATION: Staple strand_0061 of the 3D DNA nanostructure.

<400> SEQUENCE: 62
taattttaaa agtctcgtat gtcagtatta acaccaccag cagcc          45

<210> SEQ ID NO 63
<211> LENGTH: 45
<212> TYPE: DNA
<213> ORGANISM: Artificial Sequence
<220> FEATURE:
<223> OTHER INFORMATION: Staple strand_0062 of the 3D DNA nanostructure.

<400> SEQUENCE: 63
tatcaaaatc atataagacg cctgattgct ttgaatttac atcat          45

<210> SEQ ID NO 64
<211> LENGTH: 45
<212> TYPE: DNA
<213> ORGANISM: Artificial Sequence
<220> FEATURE:
<223> OTHER INFORMATION: Staple strand_0063 of the 3D DNA nanostructure.

<400> SEQUENCE: 64
agaacgggta ttaaataatc agccaacgct caacatatgc gtttt          45

<210> SEQ ID NO 65
<211> LENGTH: 45
<212> TYPE: DNA
<213> ORGANISM: Artificial Sequence
<220> FEATURE:
<223> OTHER INFORMATION: Staple strand_0064 of the 3D DNA nanostructure.

<400> SEQUENCE: 65
caaagttacc agactttta aaacagccat attatttcca gagca          45

<210> SEQ ID NO 66
<211> LENGTH: 45
<212> TYPE: DNA
<213> ORGANISM: Artificial Sequence
<220> FEATURE:
<223> OTHER INFORMATION: Staple strand_0065 of the 3D DNA nanostructure.

<400> SEQUENCE: 66
aaccgccacc ctcaaccgcc attatcaccg tcaccatatt gacaa          45

<210> SEQ ID NO 67
<211> LENGTH: 45
<212> TYPE: DNA
<213> ORGANISM: Artificial Sequence
<220> FEATURE:
<223> OTHER INFORMATION: Staple strand_0066 of the 3D DNA nanostructure.

<400> SEQUENCE: 67
accagtacaa actaacccat ctatttcgga acctagtgcc cgtag          45

<210> SEQ ID NO 68
<211> LENGTH: 45
<212> TYPE: DNA
<213> ORGANISM: Artificial Sequence
<220> FEATURE:
<223> OTHER INFORMATION: Staple strand_0067 of the 3D DNA nanostructure.

<400> SEQUENCE: 68
tttgaccccc agcgaggcaa agcttgatac cgatacagct tgctc    45

<210> SEQ ID NO 69
<211> LENGTH: 45
<212> TYPE: DNA
<213> ORGANISM: Artificial Sequence
<220> FEATURE:
<223> OTHER INFORMATION: Staple strand_0068 of the 3D DNA nanostructure.

<400> SEQUENCE: 69
ataaccctcg tttattacga ataaggcttg ccctgatcaa cgttc    45

<210> SEQ ID NO 70
<211> LENGTH: 45
<212> TYPE: DNA
<213> ORGANISM: Artificial Sequence
<220> FEATURE:
<223> OTHER INFORMATION: Staple strand_0069 of the 3D DNA nanostructure.

<400> SEQUENCE: 70
atattttcat tgtttcgca gcgttttaat tcgagtaaga ggatc    45

<210> SEQ ID NO 71
<211> LENGTH: 45
<212> TYPE: DNA
<213> ORGANISM: Artificial Sequence
<220> FEATURE:
<223> OTHER INFORMATION: Staple strand_0070 of the 3D DNA nanostructure.

<400> SEQUENCE: 71
gttaaatcag ctcatatttt aaggccggag acagtatgtg tagct    45

<210> SEQ ID NO 72
<211> LENGTH: 45
<212> TYPE: DNA
<213> ORGANISM: Artificial Sequence
<220> FEATURE:
<223> OTHER INFORMATION: Staple strand_0071 of the 3D DNA nanostructure.

<400> SEQUENCE: 72
taatcatggt cataaggatc aggcaaagcg ccattttcc ggctt    45

<210> SEQ ID NO 73
<211> LENGTH: 42
<212> TYPE: DNA
<213> ORGANISM: Artificial Sequence
<220> FEATURE:
<223> OTHER INFORMATION: Staple strand_0072 of the 3D DNA nanostructure.

<400> SEQUENCE: 73
acgtggacgg gactgcgcga gggtaggacc agctgcaaaa ga    42

<210> SEQ ID NO 74
<211> LENGTH: 40
<212> TYPE: DNA
<213> ORGANISM: Artificial Sequence
<220> FEATURE:
<223> OTHER INFORMATION: Staple strand_0073 of the 3D DNA nanostructure.

<400> SEQUENCE: 74
gtggcacagt gggcacactc gagaactccc gttgtaatac    40

<210> SEQ ID NO 75

```
<211> LENGTH: 42
<212> TYPE: DNA
<213> ORGANISM: Artificial Sequence
<220> FEATURE:
<223> OTHER INFORMATION: Staple strand_0074 of the 3D DNA nanostructure.

<400> SEQUENCE: 75
gagcactaac gggcccgaat tgagggcaag acaatatttt ag                    42

<210> SEQ ID NO 76
<211> LENGTH: 40
<212> TYPE: DNA
<213> ORGANISM: Artificial Sequence
<220> FEATURE:
<223> OTHER INFORMATION: Staple strand_0075 of the 3D DNA nanostructure.

<400> SEQUENCE: 76
catatcactg aggatatgag acgatgacaa ctaatcctac                       40

<210> SEQ ID NO 77
<211> LENGTH: 42
<212> TYPE: DNA
<213> ORGANISM: Artificial Sequence
<220> FEATURE:
<223> OTHER INFORMATION: Staple strand_0076 of the 3D DNA nanostructure.

<400> SEQUENCE: 77
atgtgagtcc agtcgccccc cgcagttgaa attatttaat at                    42

<210> SEQ ID NO 78
<211> LENGTH: 40
<212> TYPE: DNA
<213> ORGANISM: Artificial Sequence
<220> FEATURE:
<223> OTHER INFORMATION: Staple strand_0077 of the 3D DNA nanostructure.

<400> SEQUENCE: 78
tggtttgatc tgggtagcag cggtaggaat aaccttttaa                       40

<210> SEQ ID NO 79
<211> LENGTH: 42
<212> TYPE: DNA
<213> ORGANISM: Artificial Sequence
<220> FEATURE:
<223> OTHER INFORMATION: Staple strand_0078 of the 3D DNA nanostructure.

<400> SEQUENCE: 79
agaacgcgtt gcccacgagt gcggtgataa ataccgaaat gc                    42

<210> SEQ ID NO 80
<211> LENGTH: 40
<212> TYPE: DNA
<213> ORGANISM: Artificial Sequence
<220> FEATURE:
<223> OTHER INFORMATION: Staple strand_0079 of the 3D DNA nanostructure.

<400> SEQUENCE: 80
gggaggtatc ccggaccaca tatatccctg tttatcttgc                       40

<210> SEQ ID NO 81
<211> LENGTH: 42
<212> TYPE: DNA
<213> ORGANISM: Artificial Sequence
<220> FEATURE:
<223> OTHER INFORMATION: Staple strand_0080 of the 3D DNA nanostructure.

<400> SEQUENCE: 81
```
atcagagact gtgggccgcg caccgcccct tgaagcccta at    42

<210> SEQ ID NO 82
<211> LENGTH: 40
<212> TYPE: DNA
<213> ORGANISM: Artificial Sequence
<220> FEATURE:
<223> OTHER INFORMATION: Staple strand_0081 of the 3D DNA nanostructure.

<400> SEQUENCE: 82
ttattttgag gcgacggcta ttgaccgata acccataagt    40

<210> SEQ ID NO 83
<211> LENGTH: 42
<212> TYPE: DNA
<213> ORGANISM: Artificial Sequence
<220> FEATURE:
<223> OTHER INFORMATION: Staple strand_0082 of the 3D DNA nanostructure.

<400> SEQUENCE: 83
tttcatcgct agcggttcta agtcgggtgt cacaatccgc gt    42

<210> SEQ ID NO 84
<211> LENGTH: 40
<212> TYPE: DNA
<213> ORGANISM: Artificial Sequence
<220> FEATURE:
<223> OTHER INFORMATION: Staple strand_0083 of the 3D DNA nanostructure.

<400> SEQUENCE: 84
tttaccgtgt aaatgcgcgg ccgagggcat tttcgctgaa    40

<210> SEQ ID NO 85
<211> LENGTH: 42
<212> TYPE: DNA
<213> ORGANISM: Artificial Sequence
<220> FEATURE:
<223> OTHER INFORMATION: Staple strand_0084 of the 3D DNA nanostructure.

<400> SEQUENCE: 85
agtaccgctg ctggaccgtg gaccaaggtt ccagtaaggt tt    42

<210> SEQ ID NO 86
<211> LENGTH: 40
<212> TYPE: DNA
<213> ORGANISM: Artificial Sequence
<220> FEATURE:
<223> OTHER INFORMATION: Staple strand_0085 of the 3D DNA nanostructure.

<400> SEQUENCE: 86
acaactatga gggtacggga ccatggcacc ctcagaagga    40

<210> SEQ ID NO 87
<211> LENGTH: 42
<212> TYPE: DNA
<213> ORGANISM: Artificial Sequence
<220> FEATURE:
<223> OTHER INFORMATION: Staple strand_0086 of the 3D DNA nanostructure.

<400> SEQUENCE: 87
gaggactagg agttgtgcca atggcgagaa ggaattggct tt    42

<210> SEQ ID NO 88
<211> LENGTH: 40
<212> TYPE: DNA

<213> ORGANISM: Artificial Sequence
<220> FEATURE:
<223> OTHER INFORMATION: Staple strand_0087 of the 3D DNA nanostructure.

<400> SEQUENCE: 88
aggacaggca ctgggcgcct tgttcaaaga cttttgaaag                                    40

<210> SEQ ID NO 89
<211> LENGTH: 42
<212> TYPE: DNA
<213> ORGANISM: Artificial Sequence
<220> FEATURE:
<223> OTHER INFORMATION: Staple strand_0088 of the 3D DNA nanostructure.

<400> SEQUENCE: 89
aacaacatgc tctagtcgga cgtcgactat gaacggtaac gg                                 42

<210> SEQ ID NO 90
<211> LENGTH: 40
<212> TYPE: DNA
<213> ORGANISM: Artificial Sequence
<220> FEATURE:
<223> OTHER INFORMATION: Staple strand_0089 of the 3D DNA nanostructure.

<400> SEQUENCE: 90
agttcagcgc aacgggacgc acagcatatt acaggtaaac                                    40

<210> SEQ ID NO 91
<211> LENGTH: 42
<212> TYPE: DNA
<213> ORGANISM: Artificial Sequence
<220> FEATURE:
<223> OTHER INFORMATION: Staple strand_0090 of the 3D DNA nanostructure.

<400> SEQUENCE: 91
aaagtacgcg agggtagggc ctaactcaaa acgagacaa ct                                  42

<210> SEQ ID NO 92
<211> LENGTH: 40
<212> TYPE: DNA
<213> ORGANISM: Artificial Sequence
<220> FEATURE:
<223> OTHER INFORMATION: Staple strand_0091 of the 3D DNA nanostructure.

<400> SEQUENCE: 92
cctgtaagcg tctagggact cggcacgtgt ctggaatgac                                    40

<210> SEQ ID NO 93
<211> LENGTH: 42
<212> TYPE: DNA
<213> ORGANISM: Artificial Sequence
<220> FEATURE:
<223> OTHER INFORMATION: Staple strand_0092 of the 3D DNA nanostructure.

<400> SEQUENCE: 93
tgtcaatcgc ggtggccgta ctggcccata cttttgctag ca                                 42

<210> SEQ ID NO 94
<211> LENGTH: 40
<212> TYPE: DNA
<213> ORGANISM: Artificial Sequence
<220> FEATURE:
<223> OTHER INFORMATION: Staple strand_0093 of the 3D DNA nanostructure.

<400> SEQUENCE: 94
ttggtgttaa tctgtggata atccgaatat gtacctcacg                                    40

<210> SEQ ID NO 95
<211> LENGTH: 42
<212> TYPE: DNA
<213> ORGANISM: Artificial Sequence
<220> FEATURE:
<223> OTHER INFORMATION: Staple strand_0094 of the 3D DNA nanostructure.

<400> SEQUENCE: 95
aagcttgccg gctcaaggcc tcgcgccaag atgggcggtg cc     42

<210> SEQ ID NO 96
<211> LENGTH: 40
<212> TYPE: DNA
<213> ORGANISM: Artificial Sequence
<220> FEATURE:
<223> OTHER INFORMATION: Staple strand_0095 of the 3D DNA nanostructure.

<400> SEQUENCE: 96
tgtcgtgggc caagacgtag cgcatgatgc ctgcaaaacc     40

<210> SEQ ID NO 97
<211> LENGTH: 42
<212> TYPE: DNA
<213> ORGANISM: Artificial Sequence
<220> FEATURE:
<223> OTHER INFORMATION: Staple strand_0096 of the 3D DNA nanostructure.

<400> SEQUENCE: 97
cagtttggcc ggagacccag ggataagccc tcggccatgt tc     42

<210> SEQ ID NO 98
<211> LENGTH: 40
<212> TYPE: DNA
<213> ORGANISM: Artificial Sequence
<220> FEATURE:
<223> OTHER INFORMATION: Staple strand_0097 of the 3D DNA nanostructure.

<400> SEQUENCE: 98
acccttcgag gttgagggcg cagatgaact tctttataga     40

<210> SEQ ID NO 99
<211> LENGTH: 42
<212> TYPE: DNA
<213> ORGANISM: Artificial Sequence
<220> FEATURE:
<223> OTHER INFORMATION: Staple strand_0098 of the 3D DNA nanostructure.

<400> SEQUENCE: 99
attgaggagc ggctgcgtac gttcgagctg gctattaag ga     42

<210> SEQ ID NO 100
<211> LENGTH: 40
<212> TYPE: DNA
<213> ORGANISM: Artificial Sequence
<220> FEATURE:
<223> OTHER INFORMATION: Staple strand_0099 of the 3D DNA nanostructure.

<400> SEQUENCE: 100
ttctgaaatg ccgcttctcc agtgttagag ccgtctatac     40

<210> SEQ ID NO 101
<211> LENGTH: 42
<212> TYPE: DNA
<213> ORGANISM: Artificial Sequence
<220> FEATURE:

<223> OTHER INFORMATION: Staple strand_0100 of the 3D DNA nanostructure.

<400> SEQUENCE: 101
ttttaatgta ctacccgagg acggagctta aacagaaacc tt                          42

<210> SEQ ID NO 102
<211> LENGTH: 40
<212> TYPE: DNA
<213> ORGANISM: Artificial Sequence
<220> FEATURE:
<223> OTHER INFORMATION: Staple strand_0101 of the 3D DNA nanostructure.

<400> SEQUENCE: 102
gttaattcgc tgttccctgc gcgcttgagt aaatcttta                              40

<210> SEQ ID NO 103
<211> LENGTH: 42
<212> TYPE: DNA
<213> ORGANISM: Artificial Sequence
<220> FEATURE:
<223> OTHER INFORMATION: Staple strand_0102 of the 3D DNA nanostructure.

<400> SEQUENCE: 103
acgacaatca cacacacggc gaattatgtc taaataaaga cg                          42

<210> SEQ ID NO 104
<211> LENGTH: 40
<212> TYPE: DNA
<213> ORGANISM: Artificial Sequence
<220> FEATURE:
<223> OTHER INFORMATION: Staple strand_0103 of the 3D DNA nanostructure.

<400> SEQUENCE: 104
gaggcgttgt ggcgtcgtgc gatggcaaag ataagaacgc                             40

<210> SEQ ID NO 105
<211> LENGTH: 42
<212> TYPE: DNA
<213> ORGANISM: Artificial Sequence
<220> FEATURE:
<223> OTHER INFORMATION: Staple strand_0104 of the 3D DNA nanostructure.

<400> SEQUENCE: 105
aacaaagtgt ttcgaggagg ccgttcgttt agattagccc tg                          42

<210> SEQ ID NO 106
<211> LENGTH: 40
<212> TYPE: DNA
<213> ORGANISM: Artificial Sequence
<220> FEATURE:
<223> OTHER INFORMATION: Staple strand_0105 of the 3D DNA nanostructure.

<400> SEQUENCE: 106
aagaaacgtt acatccccct cacaagcatg agttatataa                             40

<210> SEQ ID NO 107
<211> LENGTH: 42
<212> TYPE: DNA
<213> ORGANISM: Artificial Sequence
<220> FEATURE:
<223> OTHER INFORMATION: Staple strand_0106 of the 3D DNA nanostructure.

<400> SEQUENCE: 107
gtttgcctca gtgcgtgcgc cacgtggtgc attcataatc aa                          42

```
<210> SEQ ID NO 108
<211> LENGTH: 40
<212> TYPE: DNA
<213> ORGANISM: Artificial Sequence
<220> FEATURE:
<223> OTHER INFORMATION: Staple strand_0107 of the 3D DNA nanostructure.

<400> SEQUENCE: 108
aagccagtac ctcccaggct cctacattcc cccttcatta                                40

<210> SEQ ID NO 109
<211> LENGTH: 42
<212> TYPE: DNA
<213> ORGANISM: Artificial Sequence
<220> FEATURE:
<223> OTHER INFORMATION: Staple strand_0108 of the 3D DNA nanostructure.

<400> SEQUENCE: 109
aataggtgga ggccggtcac cctagctgaa catggctccc gg                            42

<210> SEQ ID NO 110
<211> LENGTH: 40
<212> TYPE: DNA
<213> ORGANISM: Artificial Sequence
<220> FEATURE:
<223> OTHER INFORMATION: Staple strand_0109 of the 3D DNA nanostructure.

<400> SEQUENCE: 110
cagtttctgg caagggctga gggcagtaac cctcattcaa                                40

<210> SEQ ID NO 111
<211> LENGTH: 42
<212> TYPE: DNA
<213> ORGANISM: Artificial Sequence
<220> FEATURE:
<223> OTHER INFORMATION: Staple strand_0110 of the 3D DNA nanostructure.

<400> SEQUENCE: 111
aacgagggga actcgctgtg cgggtctgag aattttatc gg                             42

<210> SEQ ID NO 112
<211> LENGTH: 40
<212> TYPE: DNA
<213> ORGANISM: Artificial Sequence
<220> FEATURE:
<223> OTHER INFORMATION: Staple strand_0111 of the 3D DNA nanostructure.

<400> SEQUENCE: 112
aagggaacac gttgcgcatg aagccataga agtttatcat                                40

<210> SEQ ID NO 113
<211> LENGTH: 42
<212> TYPE: DNA
<213> ORGANISM: Artificial Sequence
<220> FEATURE:
<223> OTHER INFORMATION: Staple strand_0112 of the 3D DNA nanostructure.

<400> SEQUENCE: 113
aaaatctagg tgaccgttgg cgtaccgtcc caggcgcgaa ga                            42

<210> SEQ ID NO 114
<211> LENGTH: 40
<212> TYPE: DNA
<213> ORGANISM: Artificial Sequence
<220> FEATURE:
<223> OTHER INFORMATION: Staple strand_0113 of the 3D DNA nanostructure.
```

<400> SEQUENCE: 114
tcattgaagg ttggccgctg acttctcgat tcatcaatat                              40

<210> SEQ ID NO 115
<211> LENGTH: 42
<212> TYPE: DNA
<213> ORGANISM: Artificial Sequence
<220> FEATURE:
<223> OTHER INFORMATION: Staple strand_0114 of the 3D DNA nanostructure.

<400> SEQUENCE: 115
tgtagctcat tcgccgtgga cgcctttgat aaatcaaaat gc                           42

<210> SEQ ID NO 116
<211> LENGTH: 40
<212> TYPE: DNA
<213> ORGANISM: Artificial Sequence
<220> FEATURE:
<223> OTHER INFORMATION: Staple strand_0115 of the 3D DNA nanostructure.

<400> SEQUENCE: 116
taaatcgcct atgcgcgtag acgcagaatt ccataaaagc                              40

<210> SEQ ID NO 117
<211> LENGTH: 42
<212> TYPE: DNA
<213> ORGANISM: Artificial Sequence
<220> FEATURE:
<223> OTHER INFORMATION: Staple strand_0116 of the 3D DNA nanostructure.

<400> SEQUENCE: 117
aatcgatgcg cagcccgcca gcacactcgt cctttataag ag                           42

<210> SEQ ID NO 118
<211> LENGTH: 40
<212> TYPE: DNA
<213> ORGANISM: Artificial Sequence
<220> FEATURE:
<223> OTHER INFORMATION: Staple strand_0117 of the 3D DNA nanostructure.

<400> SEQUENCE: 118
gcggattgct tcctgagatt cttactaaat aatcaaaacg                              40

<210> SEQ ID NO 119
<211> LENGTH: 42
<212> TYPE: DNA
<213> ORGANISM: Artificial Sequence
<220> FEATURE:
<223> OTHER INFORMATION: Staple strand_0118 of the 3D DNA nanostructure.

<400> SEQUENCE: 119
tcacgacgcg gccaaggatt tactgctcga ccgtgcaccc ag                           42

<210> SEQ ID NO 120
<211> LENGTH: 40
<212> TYPE: DNA
<213> ORGANISM: Artificial Sequence
<220> FEATURE:
<223> OTHER INFORMATION: Staple strand_0119 of the 3D DNA nanostructure.

<400> SEQUENCE: 120
ctcactgtgc tctgctccgc tgcggttttc tagacttgcg                              40

<210> SEQ ID NO 121
<211> LENGTH: 42

<212> TYPE: DNA
<213> ORGANISM: Artificial Sequence
<220> FEATURE:
<223> OTHER INFORMATION: Staple strand_0120 of the 3D DNA nanostructure.

<400> SEQUENCE: 121
aatagcccaa acgacgaggg gcacgaaaaa ggagaggaaa ag                42

<210> SEQ ID NO 122
<211> LENGTH: 40
<212> TYPE: DNA
<213> ORGANISM: Artificial Sequence
<220> FEATURE:
<223> OTHER INFORMATION: Staple strand_0121 of the 3D DNA nanostructure.

<400> SEQUENCE: 122
aaagggaggc agcactgcaa gaacgggaaa taacataata                  40

<210> SEQ ID NO 123
<211> LENGTH: 42
<212> TYPE: DNA
<213> ORGANISM: Artificial Sequence
<220> FEATURE:
<223> OTHER INFORMATION: Staple strand_0122 of the 3D DNA nanostructure.

<400> SEQUENCE: 123
ggtcagttat cagggagtca ccgcctctca atgcgcgtat ct               42

<210> SEQ ID NO 124
<211> LENGTH: 40
<212> TYPE: DNA
<213> ORGANISM: Artificial Sequence
<220> FEATURE:
<223> OTHER INFORMATION: Staple strand_0123 of the 3D DNA nanostructure.

<400> SEQUENCE: 124
caatatagcc cgcctgaaag acgcctggaa tacatttcat                  40

<210> SEQ ID NO 125
<211> LENGTH: 42
<212> TYPE: DNA
<213> ORGANISM: Artificial Sequence
<220> FEATURE:
<223> OTHER INFORMATION: Staple strand_0124 of the 3D DNA nanostructure.

<400> SEQUENCE: 125
tacatttact ggcgtccccc tgagtcccat attgcgttta at               42

<210> SEQ ID NO 126
<211> LENGTH: 40
<212> TYPE: DNA
<213> ORGANISM: Artificial Sequence
<220> FEATURE:
<223> OTHER INFORMATION: Staple strand_0125 of the 3D DNA nanostructure.

<400> SEQUENCE: 126
cgcgagatat cactcgtgag cccagtactt aattaaagaa                  40

<210> SEQ ID NO 127
<211> LENGTH: 42
<212> TYPE: DNA
<213> ORGANISM: Artificial Sequence
<220> FEATURE:
<223> OTHER INFORMATION: Staple strand_0126 of the 3D DNA nanostructure.

<400> SEQUENCE: 127
gacaaaagct aagccgaagc ggaaagccaa ataagaagta cc          42

<210> SEQ ID NO 128
<211> LENGTH: 40
<212> TYPE: DNA
<213> ORGANISM: Artificial Sequence
<220> FEATURE:
<223> OTHER INFORMATION: Staple strand_0127 of the 3D DNA nanostructure.

<400> SEQUENCE: 128
agaaggcggc accacacgag aaggacgtca agaaagatat             40

<210> SEQ ID NO 129
<211> LENGTH: 42
<212> TYPE: DNA
<213> ORGANISM: Artificial Sequence
<220> FEATURE:
<223> OTHER INFORMATION: Staple strand_0128 of the 3D DNA nanostructure.

<400> SEQUENCE: 129
attagacgcg tggctcgcaa gggcagcgtt ttgcaccagc gc          42

<210> SEQ ID NO 130
<211> LENGTH: 40
<212> TYPE: DNA
<213> ORGANISM: Artificial Sequence
<220> FEATURE:
<223> OTHER INFORMATION: Staple strand_0129 of the 3D DNA nanostructure.

<400> SEQUENCE: 130
aatacattgc tgttggttac acgccgggta ataagtagaa             40

<210> SEQ ID NO 131
<211> LENGTH: 42
<212> TYPE: DNA
<213> ORGANISM: Artificial Sequence
<220> FEATURE:
<223> OTHER INFORMATION: Staple strand_0130 of the 3D DNA nanostructure.

<400> SEQUENCE: 131
cagcaccgtg ctgccgcaag cgagaaaaac cagcgccgat ag          42

<210> SEQ ID NO 132
<211> LENGTH: 40
<212> TYPE: DNA
<213> ORGANISM: Artificial Sequence
<220> FEATURE:
<223> OTHER INFORMATION: Staple strand_0131 of the 3D DNA nanostructure.

<400> SEQUENCE: 132
gatattccaa gatggtaggt ccttgatatt tgccagcctt             40

<210> SEQ ID NO 133
<211> LENGTH: 42
<212> TYPE: DNA
<213> ORGANISM: Artificial Sequence
<220> FEATURE:
<223> OTHER INFORMATION: Staple strand_0132 of the 3D DNA nanostructure.

<400> SEQUENCE: 133
gtcgagagca actggagtgg cgaccggtac tacaggagtg cc          42

<210> SEQ ID NO 134
<211> LENGTH: 40
<212> TYPE: DNA
<213> ORGANISM: Artificial Sequence

```
<220> FEATURE:
<223> OTHER INFORMATION: Staple strand_0133 of the 3D DNA nanostructure.

<400> SEQUENCE: 134
tgtatgggtg cgcgagaccg ttctagggca ccctcttttc                              40

<210> SEQ ID NO 135
<211> LENGTH: 42
<212> TYPE: DNA
<213> ORGANISM: Artificial Sequence
<220> FEATURE:
<223> OTHER INFORMATION: Staple strand_0134 of the 3D DNA nanostructure.

<400> SEQUENCE: 135
gtcacccttc aaagcacgcc caccgtgtga aaaatctgga tc                           42

<210> SEQ ID NO 136
<211> LENGTH: 40
<212> TYPE: DNA
<213> ORGANISM: Artificial Sequence
<220> FEATURE:
<223> OTHER INFORMATION: Staple strand_0135 of the 3D DNA nanostructure.

<400> SEQUENCE: 136
gccggaacca cgcagtgtca gtcggacaac gggtaactta                              40

<210> SEQ ID NO 137
<211> LENGTH: 42
<212> TYPE: DNA
<213> ORGANISM: Artificial Sequence
<220> FEATURE:
<223> OTHER INFORMATION: Staple strand_0136 of the 3D DNA nanostructure.

<400> SEQUENCE: 137
ctcattatca acgggcacag cccatcggcg gctgaccact gg                           42

<210> SEQ ID NO 138
<211> LENGTH: 40
<212> TYPE: DNA
<213> ORGANISM: Artificial Sequence
<220> FEATURE:
<223> OTHER INFORMATION: Staple strand_0137 of the 3D DNA nanostructure.

<400> SEQUENCE: 138
gtccaatcgc aaggttctcc gactcaacat ttaggatagc                              40

<210> SEQ ID NO 139
<211> LENGTH: 42
<212> TYPE: DNA
<213> ORGANISM: Artificial Sequence
<220> FEATURE:
<223> OTHER INFORMATION: Staple strand_0138 of the 3D DNA nanostructure.

<400> SEQUENCE: 139
ggcttagacg tccctgcgca ataggccgac tctttaccgg at                           42

<210> SEQ ID NO 140
<211> LENGTH: 40
<212> TYPE: DNA
<213> ORGANISM: Artificial Sequence
<220> FEATURE:
<223> OTHER INFORMATION: Staple strand_0139 of the 3D DNA nanostructure.

<400> SEQUENCE: 140
ttaagcagag tgctgtgttt cgacgggctg attcccaaaa                              40
```

<210> SEQ ID NO 141
<211> LENGTH: 42
<212> TYPE: DNA
<213> ORGANISM: Artificial Sequence
<220> FEATURE:
<223> OTHER INFORMATION: Staple strand_0140 of the 3D DNA nanostructure.

<400> SEQUENCE: 141
cattgcctga gagtcgtggt acgatgtgat aaggatacag gt            42

<210> SEQ ID NO 142
<211> LENGTH: 40
<212> TYPE: DNA
<213> ORGANISM: Artificial Sequence
<220> FEATURE:
<223> OTHER INFORMATION: Staple strand_0141 of the 3D DNA nanostructure.

<400> SEQUENCE: 142
acccgtcaga taggctggct ccgtgtgacc caaaataaca                40

<210> SEQ ID NO 143
<211> LENGTH: 42
<212> TYPE: DNA
<213> ORGANISM: Artificial Sequence
<220> FEATURE:
<223> OTHER INFORMATION: Staple strand_0142 of the 3D DNA nanostructure.

<400> SEQUENCE: 143
ttaagttgca aggctgttcc gcaacggggg tttgaggggc ga            42

<210> SEQ ID NO 144
<211> LENGTH: 40
<212> TYPE: DNA
<213> ORGANISM: Artificial Sequence
<220> FEATURE:
<223> OTHER INFORMATION: Staple strand_0143 of the 3D DNA nanostructure.

<400> SEQUENCE: 144
gtgagctgga ctgtgagcga ccggtcggag cgaggaatga                40

<210> SEQ ID NO 145
<211> LENGTH: 42
<212> TYPE: DNA
<213> ORGANISM: Artificial Sequence
<220> FEATURE:
<223> OTHER INFORMATION: Staple strand_0144 of the 3D DNA nanostructure.

<400> SEQUENCE: 145
aaatcggcca gcattcccta gcctcccgta gtattggttc cg            42

<210> SEQ ID NO 146
<211> LENGTH: 40
<212> TYPE: DNA
<213> ORGANISM: Artificial Sequence
<220> FEATURE:
<223> OTHER INFORMATION: Staple strand_0145 of the 3D DNA nanostructure.

<400> SEQUENCE: 146
cagattcggg aacaccacca ctgatgaacc tgagtattgg                40

<210> SEQ ID NO 147
<211> LENGTH: 42
<212> TYPE: DNA
<213> ORGANISM: Artificial Sequence
<220> FEATURE:
<223> OTHER INFORMATION: Staple strand_0146 of the 3D DNA nanostructure.

<400> SEQUENCE: 147
cctcaaatgg acttgcaagg cggcgaaaac gccctaactg aa    42

<210> SEQ ID NO 148
<211> LENGTH: 40
<212> TYPE: DNA
<213> ORGANISM: Artificial Sequence
<220> FEATURE:
<223> OTHER INFORMATION: Staple strand_0147 of the 3D DNA nanostructure.

<400> SEQUENCE: 148
ttcctgaggc ttcttgcggc atgatgattt tagaatcata    40

<210> SEQ ID NO 149
<211> LENGTH: 42
<212> TYPE: DNA
<213> ORGANISM: Artificial Sequence
<220> FEATURE:
<223> OTHER INFORMATION: Staple strand_0148 of the 3D DNA nanostructure.

<400> SEQUENCE: 149
tgaaacaagg tcccgacagc ttcgcgtatt aggtttagat ga    42

<210> SEQ ID NO 150
<211> LENGTH: 40
<212> TYPE: DNA
<213> ORGANISM: Artificial Sequence
<220> FEATURE:
<223> OTHER INFORMATION: Staple strand_0149 of the 3D DNA nanostructure.

<400> SEQUENCE: 150
tgatgcaaag cacggagcat tgccgtacct tagaaaatgc    40

<210> SEQ ID NO 151
<211> LENGTH: 42
<212> TYPE: DNA
<213> ORGANISM: Artificial Sequence
<220> FEATURE:
<223> OTHER INFORMATION: Staple strand_0150 of the 3D DNA nanostructure.

<400> SEQUENCE: 151
cgagccagtg ccgcgactcg aaggtaacaa ggaatcaatt tt    42

<210> SEQ ID NO 152
<211> LENGTH: 40
<212> TYPE: DNA
<213> ORGANISM: Artificial Sequence
<220> FEATURE:
<223> OTHER INFORMATION: Staple strand_0151 of the 3D DNA nanostructure.

<400> SEQUENCE: 152
ccgcgcccgg gagcagacgt gtggtgtatc ccatccatta    40

<210> SEQ ID NO 153
<211> LENGTH: 42
<212> TYPE: DNA
<213> ORGANISM: Artificial Sequence
<220> FEATURE:
<223> OTHER INFORMATION: Staple strand_0152 of the 3D DNA nanostructure.

<400> SEQUENCE: 153
agagagaaga acgaacgagc gggattcaca attttatttt ac    42

<210> SEQ ID NO 154

```
<211> LENGTH: 40
<212> TYPE: DNA
<213> ORGANISM: Artificial Sequence
<220> FEATURE:
<223> OTHER INFORMATION: Staple strand_0153 of the 3D DNA nanostructure.

<400> SEQUENCE: 154
tattacgaca ttcccattag ccgggataaa caatgctcct                            40

<210> SEQ ID NO 155
<211> LENGTH: 42
<212> TYPE: DNA
<213> ORGANISM: Artificial Sequence
<220> FEATURE:
<223> OTHER INFORMATION: Staple strand_0154 of the 3D DNA nanostructure.

<400> SEQUENCE: 155
cggaaacgcg acgatttgca gcgcttctca aagggcgaag gc                         42

<210> SEQ ID NO 156
<211> LENGTH: 40
<212> TYPE: DNA
<213> ORGANISM: Artificial Sequence
<220> FEATURE:
<223> OTHER INFORMATION: Staple strand_0155 of the 3D DNA nanostructure.

<400> SEQUENCE: 156
aggttgaacg agcagaccgg cacgggtcat aatcaacagg                            40

<210> SEQ ID NO 157
<211> LENGTH: 42
<212> TYPE: DNA
<213> ORGANISM: Artificial Sequence
<220> FEATURE:
<223> OTHER INFORMATION: Staple strand_0156 of the 3D DNA nanostructure.

<400> SEQUENCE: 157
gttttgctgt gcgtcgaggc gactaactgg gtaataagcg gg                         42

<210> SEQ ID NO 158
<211> LENGTH: 40
<212> TYPE: DNA
<213> ORGANISM: Artificial Sequence
<220> FEATURE:
<223> OTHER INFORMATION: Staple strand_0157 of the 3D DNA nanostructure.

<400> SEQUENCE: 158
tctttcctag ttgggccggt cccgtccacc acccttgtcg                            40

<210> SEQ ID NO 159
<211> LENGTH: 42
<212> TYPE: DNA
<213> ORGANISM: Artificial Sequence
<220> FEATURE:
<223> OTHER INFORMATION: Staple strand_0158 of the 3D DNA nanostructure.

<400> SEQUENCE: 159
cagggagtcg ggatgccttc tgcttctcag aaggctcgct tg                         42

<210> SEQ ID NO 160
<211> LENGTH: 40
<212> TYPE: DNA
<213> ORGANISM: Artificial Sequence
<220> FEATURE:
<223> OTHER INFORMATION: Staple strand_0159 of the 3D DNA nanostructure.

<400> SEQUENCE: 160
```
gaaatccggt gcgaactgtg gccgactata atgccgtgtc                                   40

<210> SEQ ID NO 161
<211> LENGTH: 42
<212> TYPE: DNA
<213> ORGANISM: Artificial Sequence
<220> FEATURE:
<223> OTHER INFORMATION: Staple strand_0160 of the 3D DNA nanostructure.

<400> SEQUENCE: 161
tgaattacgg gagtctgccg agaatggcgc gagtaatcat tg                                42

<210> SEQ ID NO 162
<211> LENGTH: 40
<212> TYPE: DNA
<213> ORGANISM: Artificial Sequence
<220> FEATURE:
<223> OTHER INFORMATION: Staple strand_0161 of the 3D DNA nanostructure.

<400> SEQUENCE: 162
gtaatagcgt gcttttccat gtcggtctca ttcaaagggg                                   40

<210> SEQ ID NO 163
<211> LENGTH: 42
<212> TYPE: DNA
<213> ORGANISM: Artificial Sequence
<220> FEATURE:
<223> OTHER INFORMATION: Staple strand_0162 of the 3D DNA nanostructure.

<400> SEQUENCE: 163
tccttttgct acctgggcca ctgcacgcta ttatagtatt gc                                42

<210> SEQ ID NO 164
<211> LENGTH: 40
<212> TYPE: DNA
<213> ORGANISM: Artificial Sequence
<220> FEATURE:
<223> OTHER INFORMATION: Staple strand_0163 of the 3D DNA nanostructure.

<400> SEQUENCE: 164
catacagacg cattacctgg aacgacatgc gaacgtaaat                                   40

<210> SEQ ID NO 165
<211> LENGTH: 42
<212> TYPE: DNA
<213> ORGANISM: Artificial Sequence
<220> FEATURE:
<223> OTHER INFORMATION: Staple strand_0164 of the 3D DNA nanostructure.

<400> SEQUENCE: 165
tttttgagct cacaccgcag tagcccgagc tagaaccagc ta                                42

<210> SEQ ID NO 166
<211> LENGTH: 40
<212> TYPE: DNA
<213> ORGANISM: Artificial Sequence
<220> FEATURE:
<223> OTHER INFORMATION: Staple strand_0165 of the 3D DNA nanostructure.

<400> SEQUENCE: 166
tcatcaacct acgtagaccg cacgatagga ttgtaagctt                                   40

<210> SEQ ID NO 167
<211> LENGTH: 42
<212> TYPE: DNA

```
<213> ORGANISM: Artificial Sequence
<220> FEATURE:
<223> OTHER INFORMATION: Staple strand_0166 of the 3D DNA nanostructure.

<400> SEQUENCE: 167
ctggcgaagt agtgccgcga cgctgatgca acagtatgcc ag                    42

<210> SEQ ID NO 168
<211> LENGTH: 40
<212> TYPE: DNA
<213> ORGANISM: Artificial Sequence
<220> FEATURE:
<223> OTHER INFORMATION: Staple strand_0167 of the 3D DNA nanostructure.

<400> SEQUENCE: 168
taaagtgcgt cccttcggac ccacgtaggc tagcgaagca                       40

<210> SEQ ID NO 169
<211> LENGTH: 42
<212> TYPE: DNA
<213> ORGANISM: Artificial Sequence
<220> FEATURE:
<223> OTHER INFORMATION: Staple strand_0168 of the 3D DNA nanostructure.

<400> SEQUENCE: 169
aggcgaaaac ggtggtcacc ggtgcgtgca gtggtttcca gc                    42

<210> SEQ ID NO 170
<211> LENGTH: 40
<212> TYPE: DNA
<213> ORGANISM: Artificial Sequence
<220> FEATURE:
<223> OTHER INFORMATION: Staple strand_0169 of the 3D DNA nanostructure.

<400> SEQUENCE: 170
aatcgtcccg actgccggat ggttcgatct caaaccgctc                       40

<210> SEQ ID NO 171
<211> LENGTH: 42
<212> TYPE: DNA
<213> ORGANISM: Artificial Sequence
<220> FEATURE:
<223> OTHER INFORMATION: Staple strand_0170 of the 3D DNA nanostructure.

<400> SEQUENCE: 171
atgaaaaact ttccttctag cttatggctg cattaaaagc aa                    42

<210> SEQ ID NO 172
<211> LENGTH: 40
<212> TYPE: DNA
<213> ORGANISM: Artificial Sequence
<220> FEATURE:
<223> OTHER INFORMATION: Staple strand_0171 of the 3D DNA nanostructure.

<400> SEQUENCE: 172
ccaccagcct agggcgcccg gtgagatcac tttacagaaa                       40

<210> SEQ ID NO 173
<211> LENGTH: 42
<212> TYPE: DNA
<213> ORGANISM: Artificial Sequence
<220> FEATURE:
<223> OTHER INFORMATION: Staple strand_0172 of the 3D DNA nanostructure.

<400> SEQUENCE: 173
catttcaagc attgaggccc tcggaaggaa tgaatattta tt                    42
```

-continued

<210> SEQ ID NO 174
<211> LENGTH: 40
<212> TYPE: DNA
<213> ORGANISM: Artificial Sequence
<220> FEATURE:
<223> OTHER INFORMATION: Staple strand_0173 of the 3D DNA nanostructure.

<400> SEQUENCE: 174
ggttggggca tggacccagg tgaagattaa acatagctta                                40

<210> SEQ ID NO 175
<211> LENGTH: 42
<212> TYPE: DNA
<213> ORGANISM: Artificial Sequence
<220> FEATURE:
<223> OTHER INFORMATION: Staple strand_0174 of the 3D DNA nanostructure.

<400> SEQUENCE: 175
gccaacatgt cagctgctct ccgtccggtt agaaaaaaca ac                             42

<210> SEQ ID NO 176
<211> LENGTH: 40
<212> TYPE: DNA
<213> ORGANISM: Artificial Sequence
<220> FEATURE:
<223> OTHER INFORMATION: Staple strand_0175 of the 3D DNA nanostructure.

<400> SEQUENCE: 176 cgttttttcga ggcacacgtc taggttgtac gagcacaagc                               40

<210> SEQ ID NO 177
<211> LENGTH: 42
<212> TYPE: DNA
<213> ORGANISM: Artificial Sequence
<220> FEATURE:
<223> OTHER INFORMATION: Staple strand_0176 of the 3D DNA nanostructure.

<400> SEQUENCE: 177
aacgtcaacg ctctgttcgc gcactaccat ttaccaatgt tt                             42

<210> SEQ ID NO 178
<211> LENGTH: 40
<212> TYPE: DNA
<213> ORGANISM: Artificial Sequence
<220> FEATURE:
<223> OTHER INFORMATION: Staple strand_0177 of the 3D DNA nanostructure.

<400> SEQUENCE: 178
ccaaaagccg cgttcggcga aacgggaaaa tagctaatac                                40

<210> SEQ ID NO 179
<211> LENGTH: 42
<212> TYPE: DNA
<213> ORGANISM: Artificial Sequence
<220> FEATURE:
<223> OTHER INFORMATION: Staple strand_0178 of the 3D DNA nanostructure.

<400> SEQUENCE: 179
caccagtagg ccggaagttg tttatccaaa ccgattgaaa at                             42

<210> SEQ ID NO 180
<211> LENGTH: 40
<212> TYPE: DNA
<213> ORGANISM: Artificial Sequence
<220> FEATURE:

```
<223> OTHER INFORMATION: Staple strand_0179 of the 3D DNA nanostructure.

<400> SEQUENCE: 180
ccaccagtac aggcatgagt gcggcggccg gaaccaacca                                40

<210> SEQ ID NO 181
<211> LENGTH: 42
<212> TYPE: DNA
<213> ORGANISM: Artificial Sequence
<220> FEATURE:
<223> OTHER INFORMATION: Staple strand_0180 of the 3D DNA nanostructure.

<400> SEQUENCE: 181
ctcctcaaga cgtaaatgac taaacccgag ggggtcatga ga                             42

<210> SEQ ID NO 182
<211> LENGTH: 40
<212> TYPE: DNA
<213> ORGANISM: Artificial Sequence
<220> FEATURE:
<223> OTHER INFORMATION: Staple strand_0181 of the 3D DNA nanostructure.

<400> SEQUENCE: 182
agttagcatg gataccggcg gctggcgaag ggatactcat                                40

<210> SEQ ID NO 183
<211> LENGTH: 42
<212> TYPE: DNA
<213> ORGANISM: Artificial Sequence
<220> FEATURE:
<223> OTHER INFORMATION: Staple strand_0182 of the 3D DNA nanostructure.

<400> SEQUENCE: 183
ataaccgatg ccgctgctgt gctcgcaggt gcctttacac gc                             42

<210> SEQ ID NO 184
<211> LENGTH: 40
<212> TYPE: DNA
<213> ORGANISM: Artificial Sequence
<220> FEATURE:
<223> OTHER INFORMATION: Staple strand_0183 of the 3D DNA nanostructure.

<400> SEQUENCE: 184
atttgtacct ggcccaaaac tggagataag gcacccggag                                40

<210> SEQ ID NO 185
<211> LENGTH: 42
<212> TYPE: DNA
<213> ORGANISM: Artificial Sequence
<220> FEATURE:
<223> OTHER INFORMATION: Staple strand_0184 of the 3D DNA nanostructure.

<400> SEQUENCE: 185
gagatggttc gcatatgcgg atcccaactc gaaccggggc tt                             42

<210> SEQ ID NO 186
<211> LENGTH: 40
<212> TYPE: DNA
<213> ORGANISM: Artificial Sequence
<220> FEATURE:
<223> OTHER INFORMATION: Staple strand_0185 of the 3D DNA nanostructure.

<400> SEQUENCE: 186
cttttgcttc gcgcgttgga gtcgatttag atacaagagg                                40
```

```
<210> SEQ ID NO 187
<211> LENGTH: 42
<212> TYPE: DNA
<213> ORGANISM: Artificial Sequence
<220> FEATURE:
<223> OTHER INFORMATION: Staple strand_0186 of the 3D DNA nanostructure.

<400> SEQUENCE: 187
aggtcagggg ctagtgccag cccgtcctaa aagcggacca ac                42

<210> SEQ ID NO 188
<211> LENGTH: 40
<212> TYPE: DNA
<213> ORGANISM: Artificial Sequence
<220> FEATURE:
<223> OTHER INFORMATION: Staple strand_0187 of the 3D DNA nanostructure.

<400> SEQUENCE: 188
aatagtagcc tacagtttgt ggccgaattt agtttctact                   40

<210> SEQ ID NO 189
<211> LENGTH: 42
<212> TYPE: DNA
<213> ORGANISM: Artificial Sequence
<220> FEATURE:
<223> OTHER INFORMATION: Staple strand_0188 of the 3D DNA nanostructure.

<400> SEQUENCE: 189
ctgataaagc gcgagcagtc gatagcgcgt ttttaaatct ag                42

<210> SEQ ID NO 190
<211> LENGTH: 40
<212> TYPE: DNA
<213> ORGANISM: Artificial Sequence
<220> FEATURE:
<223> OTHER INFORMATION: Staple strand_0189 of the 3D DNA nanostructure.

<400> SEQUENCE: 190
ttcgcgtact cgaggctagg ttcaacttat atttaaataa                   40

<210> SEQ ID NO 191
<211> LENGTH: 42
<212> TYPE: DNA
<213> ORGANISM: Artificial Sequence
<220> FEATURE:
<223> OTHER INFORMATION: Staple strand_0190 of the 3D DNA nanostructure.

<400> SEQUENCE: 191
tcggtgcggc ggaattgacg tcaatgccct ggaagatggc ga                42

<210> SEQ ID NO 192
<211> LENGTH: 40
<212> TYPE: DNA
<213> ORGANISM: Artificial Sequence
<220> FEATURE:
<223> OTHER INFORMATION: Staple strand_0191 of the 3D DNA nanostructure.

<400> SEQUENCE: 192
aattccagtt gttgttctct ctccgcggac gcatgctcac                   40

<210> SEQ ID NO 193
<211> LENGTH: 42
<212> TYPE: DNA
<213> ORGANISM: Artificial Sequence
<220> FEATURE:
<223> OTHER INFORMATION: Staple strand_0192 of the 3D DNA nanostructure.
```

<400> SEQUENCE: 193
agcaagcgct tcacgttaag cactgcgctg accagtggtt gc        42

<210> SEQ ID NO 194
<211> LENGTH: 40
<212> TYPE: DNA
<213> ORGANISM: Artificial Sequence
<220> FEATURE:
<223> OTHER INFORMATION: Staple strand_0193 of the 3D DNA nanostructure.

<400> SEQUENCE: 194
ctcatggacc ctgtaggcct ccctcggtct tgctgaaacg        40

<210> SEQ ID NO 195
<211> LENGTH: 42
<212> TYPE: DNA
<213> ORGANISM: Artificial Sequence
<220> FEATURE:
<223> OTHER INFORMATION: Staple strand_0194 of the 3D DNA nanostructure.

<400> SEQUENCE: 195
caacagtgcg gacccggctg tggagctaaa acgaaccgcc tg        42

<210> SEQ ID NO 196
<211> LENGTH: 40
<212> TYPE: DNA
<213> ORGANISM: Artificial Sequence
<220> FEATURE:
<223> OTHER INFORMATION: Staple strand_0195 of the 3D DNA nanostructure.

<400> SEQUENCE: 196
taacattgga ggcctctgca tctgcacctc gacaattgag        40

<210> SEQ ID NO 197
<211> LENGTH: 42
<212> TYPE: DNA
<213> ORGANISM: Artificial Sequence
<220> FEATURE:
<223> OTHER INFORMATION: Staple strand_0196 of the 3D DNA nanostructure.

<400> SEQUENCE: 197
agttacaaag accgcgtagg accgctgaat agtaccttac ca        42

<210> SEQ ID NO 198
<211> LENGTH: 40
<212> TYPE: DNA
<213> ORGANISM: Artificial Sequence
<220> FEATURE:
<223> OTHER INFORMATION: Staple strand_0197 of the 3D DNA nanostructure.

<400> SEQUENCE: 198
gagagacgat gagtacgcat cgtccaaact tagatggtct        40

<210> SEQ ID NO 199
<211> LENGTH: 42
<212> TYPE: DNA
<213> ORGANISM: Artificial Sequence
<220> FEATURE:
<223> OTHER INFORMATION: Staple strand_0198 of the 3D DNA nanostructure.

<400> SEQUENCE: 199
gcttaattgt aggccggcac tggcacggta agtatcagta gg        42

<210> SEQ ID NO 200
<211> LENGTH: 40

-continued

```
<212> TYPE: DNA
<213> ORGANISM: Artificial Sequence
<220> FEATURE:
<223> OTHER INFORMATION: Staple strand_0199 of the 3D DNA nanostructure.

<400> SEQUENCE: 200
agtaccgtgt cgcaggccac aggtgagaac caatcaacca                                 40

<210> SEQ ID NO 201
<211> LENGTH: 42
<212> TYPE: DNA
<213> ORGANISM: Artificial Sequence
<220> FEATURE:
<223> OTHER INFORMATION: Staple strand_0200 of the 3D DNA nanostructure.

<400> SEQUENCE: 201
ccaatccaca aaccgttcca gcccacatca agcgtcttta tc                              42

<210> SEQ ID NO 202
<211> LENGTH: 40
<212> TYPE: DNA
<213> ORGANISM: Artificial Sequence
<220> FEATURE:
<223> OTHER INFORMATION: Staple strand_0201 of the 3D DNA nanostructure.

<400> SEQUENCE: 202
accgaggaca tcgggtggtg ccctagaacg aagccaggaa                                 40

<210> SEQ ID NO 203
<211> LENGTH: 42
<212> TYPE: DNA
<213> ORGANISM: Artificial Sequence
<220> FEATURE:
<223> OTHER INFORMATION: Staple strand_0202 of the 3D DNA nanostructure.

<400> SEQUENCE: 203
gagccattag ggcgacgcac gtcataacaa aaggtaagac tt                              42

<210> SEQ ID NO 204
<211> LENGTH: 40
<212> TYPE: DNA
<213> ORGANISM: Artificial Sequence
<220> FEATURE:
<223> OTHER INFORMATION: Staple strand_0203 of the 3D DNA nanostructure.

<400> SEQUENCE: 204
caccacctct gtatgctagg tgctcgtgcc accggagagc                                 40

<210> SEQ ID NO 205
<211> LENGTH: 42
<212> TYPE: DNA
<213> ORGANISM: Artificial Sequence
<220> FEATURE:
<223> OTHER INFORMATION: Staple strand_0204 of the 3D DNA nanostructure.

<400> SEQUENCE: 205
ctgaaacagc ggccctgcca agctgcccct agtaacatta tt                              42

<210> SEQ ID NO 206
<211> LENGTH: 40
<212> TYPE: DNA
<213> ORGANISM: Artificial Sequence
<220> FEATURE:
<223> OTHER INFORMATION: Staple strand_0205 of the 3D DNA nanostructure.

<400> SEQUENCE: 206
```
gcctgtaatc gggcgtccct aacttctgca ataggacaac                    40

<210> SEQ ID NO 207
<211> LENGTH: 42
<212> TYPE: DNA
<213> ORGANISM: Artificial Sequence
<220> FEATURE:
<223> OTHER INFORMATION: Staple strand_0206 of the 3D DNA nanostructure.

<400> SEQUENCE: 207
gccgacaacg gcatggcgaa caaggacagc ggtttatgtt gc                 42

<210> SEQ ID NO 208
<211> LENGTH: 40
<212> TYPE: DNA
<213> ORGANISM: Artificial Sequence
<220> FEATURE:
<223> OTHER INFORMATION: Staple strand_0207 of the 3D DNA nanostructure.

<400> SEQUENCE: 208
taccaagtct cgccaccctc accttgtgaa cgaaagatta                    40

<210> SEQ ID NO 209
<211> LENGTH: 42
<212> TYPE: DNA
<213> ORGANISM: Artificial Sequence
<220> FEATURE:
<223> OTHER INFORMATION: Staple strand_0208 of the 3D DNA nanostructure.

<400> SEQUENCE: 209
aaacaccaca ccttctgcac tgtcgtcacg tacccaaacg ag                 42

<210> SEQ ID NO 210
<211> LENGTH: 40
<212> TYPE: DNA
<213> ORGANISM: Artificial Sequence
<220> FEATURE:
<223> OTHER INFORMATION: Staple strand_0209 of the 3D DNA nanostructure.

<400> SEQUENCE: 210
acgacgagct tcacagaccc taccgcgaaa aaggaaccag                    40

<210> SEQ ID NO 211
<211> LENGTH: 42
<212> TYPE: DNA
<213> ORGANISM: Artificial Sequence
<220> FEATURE:
<223> OTHER INFORMATION: Staple strand_0210 of the 3D DNA nanostructure.

<400> SEQUENCE: 211
aagcgaacaa cacctccgta ctccaccta aaaagatctt ca                  42

<210> SEQ ID NO 212
<211> LENGTH: 40
<212> TYPE: DNA
<213> ORGANISM: Artificial Sequence
<220> FEATURE:
<223> OTHER INFORMATION: Staple strand_0211 of the 3D DNA nanostructure.

<400> SEQUENCE: 212
cgagctgttg cgcaaaaggc gcgaagcaag atacagggcg                    40

<210> SEQ ID NO 213
<211> LENGTH: 42
<212> TYPE: DNA
<213> ORGANISM: Artificial Sequence

```
<220> FEATURE:
<223> OTHER INFORMATION: Staple strand_0212 of the 3D DNA nanostructure.

<400> SEQUENCE: 213
caccatcatg ttgagtccgc tgccatgaaa ctgagtacaa at                           42

<210> SEQ ID NO 214
<211> LENGTH: 40
<212> TYPE: DNA
<213> ORGANISM: Artificial Sequence
<220> FEATURE:
<223> OTHER INFORMATION: Staple strand_0213 of the 3D DNA nanostructure.

<400> SEQUENCE: 214
ttaaccactc cgaggtcgcc ggagggataa cgttaatttt                              40

<210> SEQ ID NO 215
<211> LENGTH: 42
<212> TYPE: DNA
<213> ORGANISM: Artificial Sequence
<220> FEATURE:
<223> OTHER INFORMATION: Staple strand_0214 of the 3D DNA nanostructure.

<400> SEQUENCE: 215
ttcaggctca cgcaacactc ccgtctagat agccagccgc ca                           42

<210> SEQ ID NO 216
<211> LENGTH: 40
<212> TYPE: DNA
<213> ORGANISM: Artificial Sequence
<220> FEATURE:
<223> OTHER INFORMATION: Staple strand_0215 of the 3D DNA nanostructure.

<400> SEQUENCE: 216
tttcctgact cgaaccgcac cctgcagccc cgtatagctg                              40

<210> SEQ ID NO 217
<211> LENGTH: 42
<212> TYPE: DNA
<213> ORGANISM: Artificial Sequence
<220> FEATURE:
<223> OTHER INFORMATION: Staple strand_0216 of the 3D DNA nanostructure.

<400> SEQUENCE: 217
cccttcactg tgcaccgccc ggatggtgtt aacagctgat tg                           42

<210> SEQ ID NO 218
<211> LENGTH: 40
<212> TYPE: DNA
<213> ORGANISM: Artificial Sequence
<220> FEATURE:
<223> OTHER INFORMATION: Staple strand_0217 of the 3D DNA nanostructure.

<400> SEQUENCE: 218
taccgccaag acaacagcgc caggctcgcc agaacaatat                              40

<210> SEQ ID NO 219
<211> LENGTH: 42
<212> TYPE: DNA
<213> ORGANISM: Artificial Sequence
<220> FEATURE:
<223> OTHER INFORMATION: Staple strand_0218 of the 3D DNA nanostructure.

<400> SEQUENCE: 219
aggtgagggt atagcgccat cgggcataag aagataaaac ag                           42
```

<210> SEQ ID NO 220
<211> LENGTH: 40
<212> TYPE: DNA
<213> ORGANISM: Artificial Sequence
<220> FEATURE:
<223> OTHER INFORMATION: Staple strand_0219 of the 3D DNA nanostructure.

<400> SEQUENCE: 220
ccgaacggga cccagccgag agccgacgta aatcctttgc                                40

<210> SEQ ID NO 221
<211> LENGTH: 42
<212> TYPE: DNA
<213> ORGANISM: Artificial Sequence
<220> FEATURE:
<223> OTHER INFORMATION: Staple strand_0220 of the 3D DNA nanostructure.

<400> SEQUENCE: 221
aacggattaa ctgcgtgagt gaaggaactt gggagaaaca at                            42

<210> SEQ ID NO 222
<211> LENGTH: 40
<212> TYPE: DNA
<213> ORGANISM: Artificial Sequence
<220> FEATURE:
<223> OTHER INFORMATION: Staple strand_0221 of the 3D DNA nanostructure.

<400> SEQUENCE: 222
aatagtgaca ggtgtaggat cgggcgcgct gagaagagtc                                40

<210> SEQ ID NO 223
<211> LENGTH: 42
<212> TYPE: DNA
<213> ORGANISM: Artificial Sequence
<220> FEATURE:
<223> OTHER INFORMATION: Staple strand_0222 of the 3D DNA nanostructure.

<400> SEQUENCE: 223
accagtatgg catcaactgt ggtgacggaa atacaaattc tt                            42

<210> SEQ ID NO 224
<211> LENGTH: 40
<212> TYPE: DNA
<213> ORGANISM: Artificial Sequence
<220> FEATURE:
<223> OTHER INFORMATION: Staple strand_0223 of the 3D DNA nanostructure.

<400> SEQUENCE: 224
ttatcataga cctctgcttg tgccacaagg ctgtctttcc                                40

<210> SEQ ID NO 225
<211> LENGTH: 42
<212> TYPE: DNA
<213> ORGANISM: Artificial Sequence
<220> FEATURE:
<223> OTHER INFORMATION: Staple strand_0224 of the 3D DNA nanostructure.

<400> SEQUENCE: 225
gttacaaagc gccagcgact gggcgtcctc cctaatttgc ca                            42

<210> SEQ ID NO 226
<211> LENGTH: 40
<212> TYPE: DNA
<213> ORGANISM: Artificial Sequence
<220> FEATURE:
<223> OTHER INFORMATION: Staple strand_0225 of the 3D DNA nanostructure.

<400> SEQUENCE: 226
agatagctct gctcaacact caccgcatag aaaagtaagc 40

<210> SEQ ID NO 227
<211> LENGTH: 42
<212> TYPE: DNA
<213> ORGANISM: Artificial Sequence
<220> FEATURE:
<223> OTHER INFORMATION: Staple strand_0226 of the 3D DNA nanostructure.

<400> SEQUENCE: 227
ttaaaggtag tccgccctac agaagttccg ggaaattatt ca 42

<210> SEQ ID NO 228
<211> LENGTH: 40
<212> TYPE: DNA
<213> ORGANISM: Artificial Sequence
<220> FEATURE:
<223> OTHER INFORMATION: Staple strand_0227 of the 3D DNA nanostructure.

<400> SEQUENCE: 228
gccacccccc ggtcgaaaga gcaaacgatc cctcagagcc 40

<210> SEQ ID NO 229
<211> LENGTH: 42
<212> TYPE: DNA
<213> ORGANISM: Artificial Sequence
<220> FEATURE:
<223> OTHER INFORMATION: Staple strand_0228 of the 3D DNA nanostructure.

<400> SEQUENCE: 229
tgccccctag cagcccgtcc gtgatgagtc ataaacagtt aa 42

<210> SEQ ID NO 230
<211> LENGTH: 40
<212> TYPE: DNA
<213> ORGANISM: Artificial Sequence
<220> FEATURE:
<223> OTHER INFORMATION: Staple strand_0229 of the 3D DNA nanostructure.

<400> SEQUENCE: 230
tgagtttagg ccagagtcga gtgcatgcgt accgtaacac 40

<210> SEQ ID NO 231
<211> LENGTH: 42
<212> TYPE: DNA
<213> ORGANISM: Artificial Sequence
<220> FEATURE:
<223> OTHER INFORMATION: Staple strand_0230 of the 3D DNA nanostructure.

<400> SEQUENCE: 231
tttcttaaat ccgggcattt gggaagcccg tttcgaggtg aa 42

<210> SEQ ID NO 232
<211> LENGTH: 40
<212> TYPE: DNA
<213> ORGANISM: Artificial Sequence
<220> FEATURE:
<223> OTHER INFORMATION: Staple strand_0231 of the 3D DNA nanostructure.

<400> SEQUENCE: 232
aaacactggc cggcgtctta gttacgacaa gaatacacta 40

<210> SEQ ID NO 233

```
<211> LENGTH: 42
<212> TYPE: DNA
<213> ORGANISM: Artificial Sequence
<220> FEATURE:
<223> OTHER INFORMATION: Staple strand_0232 of the 3D DNA nanostructure.

<400> SEQUENCE: 233
cattcagtcc gggccgcgca tacggaccca aacaaagctg ct                              42

<210> SEQ ID NO 234
<211> LENGTH: 40
<212> TYPE: DNA
<213> ORGANISM: Artificial Sequence
<220> FEATURE:
<223> OTHER INFORMATION: Staple strand_0233 of the 3D DNA nanostructure.

<400> SEQUENCE: 234
gcaacactga ctgggcagtg gttgctgagg catagtaaga                                 40

<210> SEQ ID NO 235
<211> LENGTH: 42
<212> TYPE: DNA
<213> ORGANISM: Artificial Sequence
<220> FEATURE:
<223> OTHER INFORMATION: Staple strand_0234 of the 3D DNA nanostructure.

<400> SEQUENCE: 235
ttcaaatatc gtcgcgcgtg tagcatatta agcccgaaag ac                              42

<210> SEQ ID NO 236
<211> LENGTH: 40
<212> TYPE: DNA
<213> ORGANISM: Artificial Sequence
<220> FEATURE:
<223> OTHER INFORMATION: Staple strand_0235 of the 3D DNA nanostructure.

<400> SEQUENCE: 236
cctgtttgtt cgttcgatga ttgtcgtcaa tggtcaataa                                 40

<210> SEQ ID NO 237
<211> LENGTH: 42
<212> TYPE: DNA
<213> ORGANISM: Artificial Sequence
<220> FEATURE:
<223> OTHER INFORMATION: Staple strand_0236 of the 3D DNA nanostructure.

<400> SEQUENCE: 237
aagggtgaac cctgtcgggc cacatggtag gtaaagattc aa                              42

<210> SEQ ID NO 238
<211> LENGTH: 40
<212> TYPE: DNA
<213> ORGANISM: Artificial Sequence
<220> FEATURE:
<223> OTHER INFORMATION: Staple strand_0237 of the 3D DNA nanostructure.

<400> SEQUENCE: 238
attaaatctt acgtgggcgt cgagaagagt taaaattcgc                                 40

<210> SEQ ID NO 239
<211> LENGTH: 42
<212> TYPE: DNA
<213> ORGANISM: Artificial Sequence
<220> FEATURE:
<223> OTHER INFORMATION: Staple strand_0238 of the 3D DNA nanostructure.

<400> SEQUENCE: 239
```
gccggaaact tgttgtgtca cctcggagtt accgcttctg gt                      42

<210> SEQ ID NO 240
<211> LENGTH: 40
<212> TYPE: DNA
<213> ORGANISM: Artificial Sequence
<220> FEATURE:
<223> OTHER INFORMATION: Staple strand_0239 of the 3D DNA nanostructure.

<400> SEQUENCE: 240
gctcgaagcc cgaagaggac gtgtgccccc cgggtaccga                        40

<210> SEQ ID NO 241
<211> LENGTH: 39
<212> TYPE: DNA
<213> ORGANISM: Artificial Sequence
<220> FEATURE:
<223> OTHER INFORMATION: Staple strand_0240 of the 3D DNA nanostructure.

<400> SEQUENCE: 241
tcgggcccgt catcgtctca tatcctcagc aactgcggg                         39

<210> SEQ ID NO 242
<211> LENGTH: 39
<212> TYPE: DNA
<213> ORGANISM: Artificial Sequence
<220> FEATURE:
<223> OTHER INFORMATION: Staple strand_0241 of the 3D DNA nanostructure.

<400> SEQUENCE: 242
gggcgactgg ctaccgctgc tacccagata tcaccgcac                         39

<210> SEQ ID NO 243
<211> LENGTH: 39
<212> TYPE: DNA
<213> ORGANISM: Artificial Sequence
<220> FEATURE:
<223> OTHER INFORMATION: Staple strand_0242 of the 3D DNA nanostructure.

<400> SEQUENCE: 243
tcgtgggcaa gatatatgtg gtccgggatg ggcggtgcg                         39

<210> SEQ ID NO 244
<211> LENGTH: 39
<212> TYPE: DNA
<213> ORGANISM: Artificial Sequence
<220> FEATURE:
<223> OTHER INFORMATION: Staple strand_0243 of the 3D DNA nanostructure.

<400> SEQUENCE: 244
cggcccacag ggtcaatagc cgtcgcctca cccgactta                         39

<210> SEQ ID NO 245
<211> LENGTH: 39
<212> TYPE: DNA
<213> ORGANISM: Artificial Sequence
<220> FEATURE:
<223> OTHER INFORMATION: Staple strand_0244 of the 3D DNA nanostructure.

<400> SEQUENCE: 245
gaaccgctag cctcggccgc gcatttacac cttggtcca                         39

<210> SEQ ID NO 246
<211> LENGTH: 39
<212> TYPE: DNA

```
<213> ORGANISM: Artificial Sequence
<220> FEATURE:
<223> OTHER INFORMATION: Staple strand_0245 of the 3D DNA nanostructure.

<400> SEQUENCE: 246
cggtccagca ccatggtccc gtaccctcac tcgccattg                             39

<210> SEQ ID NO 247
<211> LENGTH: 39
<212> TYPE: DNA
<213> ORGANISM: Artificial Sequence
<220> FEATURE:
<223> OTHER INFORMATION: Staple strand_0246 of the 3D DNA nanostructure.

<400> SEQUENCE: 247
gcacaactcc tgaacaaggc gcccagtgca gtcgacgtc                             39

<210> SEQ ID NO 248
<211> LENGTH: 39
<212> TYPE: DNA
<213> ORGANISM: Artificial Sequence
<220> FEATURE:
<223> OTHER INFORMATION: Staple strand_0247 of the 3D DNA nanostructure.

<400> SEQUENCE: 248
cgactagagc tgctgtgcgt cccgttgcgt gagttaggc                             39

<210> SEQ ID NO 249
<211> LENGTH: 39
<212> TYPE: DNA
<213> ORGANISM: Artificial Sequence
<220> FEATURE:
<223> OTHER INFORMATION: Staple strand_0248 of the 3D DNA nanostructure.

<400> SEQUENCE: 249
cctaccctcg gtgccgagtc cctagacgct gggccagta                             39

<210> SEQ ID NO 250
<211> LENGTH: 39
<212> TYPE: DNA
<213> ORGANISM: Artificial Sequence
<220> FEATURE:
<223> OTHER INFORMATION: Staple strand_0249 of the 3D DNA nanostructure.

<400> SEQUENCE: 250
cggccaccgc tcggattatc cacagattat ggcgcgagg                             39

<210> SEQ ID NO 251
<211> LENGTH: 39
<212> TYPE: DNA
<213> ORGANISM: Artificial Sequence
<220> FEATURE:
<223> OTHER INFORMATION: Staple strand_0250 of the 3D DNA nanostructure.

<400> SEQUENCE: 251
ccttgagccg catgcgctac gtcttggcct cctaccctc                             39

<210> SEQ ID NO 252
<211> LENGTH: 39
<212> TYPE: DNA
<213> ORGANISM: Artificial Sequence
<220> FEATURE:
<223> OTHER INFORMATION: Staple strand_0251 of the 3D DNA nanostructure.

<400> SEQUENCE: 252
gcgcagtccc gttctcgagt gtgcccactt gccctcaat                             39
```

<210> SEQ ID NO 253
<211> LENGTH: 60
<212> TYPE: DNA
<213> ORGANISM: Artificial Sequence
<220> FEATURE:
<223> OTHER INFORMATION: Staple strand_0252 of the 3D DNA nanostructure.

<400> SEQUENCE: 253
actccctgat aggcgtcttt caggcgggcg ggactcaggt tcctctacca cctacatcac    60

<210> SEQ ID NO 254
<211> LENGTH: 60
<212> TYPE: DNA
<213> ORGANISM: Artificial Sequence
<220> FEATURE:
<223> OTHER INFORMATION: Staple strand_0253 of the 3D DNA nanostructure.

<400> SEQUENCE: 254
gggacgccag actgggctca cgagtgatag gctttccgct tcctctacca cctacatcac    60

<210> SEQ ID NO 255
<211> LENGTH: 60
<212> TYPE: DNA
<213> ORGANISM: Artificial Sequence
<220> FEATURE:
<223> OTHER INFORMATION: Staple strand_0254 of the 3D DNA nanostructure.

<400> SEQUENCE: 255
ttcggcttag gtccttctcg tgtggtgccc gctgcccttt tcctctacca cctacatcac    60

<210> SEQ ID NO 256
<211> LENGTH: 60
<212> TYPE: DNA
<213> ORGANISM: Artificial Sequence
<220> FEATURE:
<223> OTHER INFORMATION: Staple strand_0255 of the 3D DNA nanostructure.

<400> SEQUENCE: 256
gcgagccacg cggcgtgtaa ccaacagcat tttctcgctt tcctctacca cctacatcac    60

<210> SEQ ID NO 257
<211> LENGTH: 60
<212> TYPE: DNA
<213> ORGANISM: Artificial Sequence
<220> FEATURE:
<223> OTHER INFORMATION: Staple strand_0256 of the 3D DNA nanostructure.

<400> SEQUENCE: 257
tgcggcagca tcaaggacct accatcttga ccggtcgcct tcctctacca cctacatcac    60

<210> SEQ ID NO 258
<211> LENGTH: 60
<212> TYPE: DNA
<213> ORGANISM: Artificial Sequence
<220> FEATURE:
<223> OTHER INFORMATION: Staple strand_0257 of the 3D DNA nanostructure.

<400> SEQUENCE: 258
actccagttg ctagaacggt ctcgcgcaca cacggtgggt tcctctacca cctacatcac    60

<210> SEQ ID NO 259
<211> LENGTH: 60
<212> TYPE: DNA
<213> ORGANISM: Artificial Sequence
<220> FEATURE:

-continued

<223> OTHER INFORMATION: Staple strand_0258 of the 3D DNA nanostructure.

<400> SEQUENCE: 259
cgtgctttga tccgactgac actgcgtggc cgatgggctt tcctctacca cctacatcac    60

<210> SEQ ID NO 260
<211> LENGTH: 60
<212> TYPE: DNA
<213> ORGANISM: Artificial Sequence
<220> FEATURE:
<223> OTHER INFORMATION: Staple strand_0259 of the 3D DNA nanostructure.

<400> SEQUENCE: 260
gtgcccgttg tgagtcggag aaccttgcgc ggcctattgt tcctctacca cctacatcac    60

<210> SEQ ID NO 261
<211> LENGTH: 60
<212> TYPE: DNA
<213> ORGANISM: Artificial Sequence
<220> FEATURE:
<223> OTHER INFORMATION: Staple strand_0260 of the 3D DNA nanostructure.

<400> SEQUENCE: 261
cgcagggacg ccgtcgaaac acagcactcc acatcgtact tcctctacca cctacatcac    60

<210> SEQ ID NO 262
<211> LENGTH: 60
<212> TYPE: DNA
<213> ORGANISM: Artificial Sequence
<220> FEATURE:
<223> OTHER INFORMATION: Staple strand_0261 of the 3D DNA nanostructure.

<400> SEQUENCE: 262
cacgactctc acacggagcc agcctatctc ccgttgcggt tcctctacca cctacatcac    60

<210> SEQ ID NO 263
<211> LENGTH: 60
<212> TYPE: DNA
<213> ORGANISM: Artificial Sequence
<220> FEATURE:
<223> OTHER INFORMATION: Staple strand_0262 of the 3D DNA nanostructure.

<400> SEQUENCE: 263
aacagccttg gaccggtcgc tcacagtcct ttcgtgccct tcctctacca cctacatcac    60

<210> SEQ ID NO 264
<211> LENGTH: 60
<212> TYPE: DNA
<213> ORGANISM: Artificial Sequence
<220> FEATURE:
<223> OTHER INFORMATION: Staple strand_0263 of the 3D DNA nanostructure.

<400> SEQUENCE: 264
ctcgtcgttt ccgttcttgc agtgctgcca gaggcggtgt tcctctacca cctacatcac    60

<210> SEQ ID NO 265
<211> LENGTH: 60
<212> TYPE: DNA
<213> ORGANISM: Artificial Sequence
<220> FEATURE:
<223> OTHER INFORMATION: Staple strand_0264 of the 3D DNA nanostructure.

<400> SEQUENCE: 265
agaaggaaag tctcaccggg cgccctaggc cttccgaggt tcctctacca cctacatcac    60

<210> SEQ ID NO 266
<211> LENGTH: 60
<212> TYPE: DNA
<213> ORGANISM: Artificial Sequence
<220> FEATURE:
<223> OTHER INFORMATION: Staple strand_0265 of the 3D DNA nanostructure.

<400> SEQUENCE: 266
gcctcaatgc tcttcacctg ggtccatgcc cggacggagt tcctctacca cctacatcac    60

<210> SEQ ID NO 267
<211> LENGTH: 60
<212> TYPE: DNA
<213> ORGANISM: Artificial Sequence
<220> FEATURE:
<223> OTHER INFORMATION: Staple strand_0266 of the 3D DNA nanostructure.

<400> SEQUENCE: 267
agcagctgac aacctagacg tgtgcctcgg gtagtgcgct tcctctacca cctacatcac    60

<210> SEQ ID NO 268
<211> LENGTH: 60
<212> TYPE: DNA
<213> ORGANISM: Artificial Sequence
<220> FEATURE:
<223> OTHER INFORMATION: Staple strand_0267 of the 3D DNA nanostructure.

<400> SEQUENCE: 268
gaacagagcg cccgtttcgc cgaacgcggt ggataaacat tcctctacca cctacatcac    60

<210> SEQ ID NO 269
<211> LENGTH: 60
<212> TYPE: DNA
<213> ORGANISM: Artificial Sequence
<220> FEATURE:
<223> OTHER INFORMATION: Staple strand_0268 of the 3D DNA nanostructure.

<400> SEQUENCE: 269
acttccggcc cgccgcactc atgcctgtac gggtttagtt tcctctacca cctacatcac    60

<210> SEQ ID NO 270
<211> LENGTH: 60
<212> TYPE: DNA
<213> ORGANISM: Artificial Sequence
<220> FEATURE:
<223> OTHER INFORMATION: Staple strand_0269 of the 3D DNA nanostructure.

<400> SEQUENCE: 270
catttacgtc gccagccgcc ggtatccatc tgcgagcact tcctctacca cctacatcac    60

<210> SEQ ID NO 271
<211> LENGTH: 60
<212> TYPE: DNA
<213> ORGANISM: Artificial Sequence
<220> FEATURE:
<223> OTHER INFORMATION: Staple strand_0270 of the 3D DNA nanostructure.

<400> SEQUENCE: 271
agcagcggca tctccagttt tgggccaggg ttgggatcct tcctctacca cctacatcac    60

<210> SEQ ID NO 272
<211> LENGTH: 60
<212> TYPE: DNA
<213> ORGANISM: Artificial Sequence
<220> FEATURE:
<223> OTHER INFORMATION: Staple strand_0271 of the 3D DNA nanostructure.

<400> SEQUENCE: 272
gcatatgcga atcgactcca acgcgcgaaa ggacgggctt tcctctacca cctacatcac    60

<210> SEQ ID NO 273
<211> LENGTH: 60
<212> TYPE: DNA
<213> ORGANISM: Artificial Sequence
<220> FEATURE:
<223> OTHER INFORMATION: Staple strand_0272 of the 3D DNA nanostructure.

<400> SEQUENCE: 273
ggcactagcc tcggccacaa actgtaggcg cgctatcgat tcctctacca cctacatcac    60

<210> SEQ ID NO 274
<211> LENGTH: 60
<212> TYPE: DNA
<213> ORGANISM: Artificial Sequence
<220> FEATURE:
<223> OTHER INFORMATION: Staple strand_0273 of the 3D DNA nanostructure.

<400> SEQUENCE: 274
ctgctcgcgc gttgaaccta gcctcgagtg gcattgacgt tcctctacca cctacatcac    60

<210> SEQ ID NO 275
<211> LENGTH: 60
<212> TYPE: DNA
<213> ORGANISM: Artificial Sequence
<220> FEATURE:
<223> OTHER INFORMATION: Staple strand_0274 of the 3D DNA nanostructure.

<400> SEQUENCE: 275
tcaattccgc gcggagagag aacaacaacc acgcaccggt tcctctacca cctacatcac    60

<210> SEQ ID NO 276
<211> LENGTH: 60
<212> TYPE: DNA
<213> ORGANISM: Artificial Sequence
<220> FEATURE:
<223> OTHER INFORMATION: Staple strand_0275 of the 3D DNA nanostructure.

<400> SEQUENCE: 276
tgaccaccgt cgaaccatcc ggcagtcggg ccataagctt tcctctacca cctacatcac    60

<210> SEQ ID NO 277
<211> LENGTH: 39
<212> TYPE: DNA
<213> ORGANISM: Artificial Sequence
<220> FEATURE:
<223> OTHER INFORMATION: Staple strand_0276 of the 3D DNA nanostructure.

<400> SEQUENCE: 277
ggcgctatac tcggctctcg gctgggtccg ttccttcac    39

<210> SEQ ID NO 278
<211> LENGTH: 39
<212> TYPE: DNA
<213> ORGANISM: Artificial Sequence
<220> FEATURE:
<223> OTHER INFORMATION: Staple strand_0277 of the 3D DNA nanostructure.

<400> SEQUENCE: 278
tcacgcagtt cgcccgatcc tacacctgtc cgtcaccac    39

<210> SEQ ID NO 279
<211> LENGTH: 39

```
<212> TYPE: DNA
<213> ORGANISM: Artificial Sequence
<220> FEATURE:
<223> OTHER INFORMATION: Staple strand_0278 of the 3D DNA nanostructure.

<400> SEQUENCE: 279
agttgatgcc gtggcacaag cagaggtctg gacgcccag                    39

<210> SEQ ID NO 280
<211> LENGTH: 39
<212> TYPE: DNA
<213> ORGANISM: Artificial Sequence
<220> FEATURE:
<223> OTHER INFORMATION: Staple strand_0279 of the 3D DNA nanostructure.

<400> SEQUENCE: 280
tcgctggcgc gcggtgagtg ttgagcagag aacttctgt                    39

<210> SEQ ID NO 281
<211> LENGTH: 39
<212> TYPE: DNA
<213> ORGANISM: Artificial Sequence
<220> FEATURE:
<223> OTHER INFORMATION: Staple strand_0280 of the 3D DNA nanostructure.

<400> SEQUENCE: 281
agggcggact gtttgctctt tcgaccgggc tcatcacgg                    39

<210> SEQ ID NO 282
<211> LENGTH: 39
<212> TYPE: DNA
<213> ORGANISM: Artificial Sequence
<220> FEATURE:
<223> OTHER INFORMATION: Staple strand_0281 of the 3D DNA nanostructure.

<400> SEQUENCE: 282
acgggctgct atgcactcga ctctggcctg gcttcccaa                    39

<210> SEQ ID NO 283
<211> LENGTH: 39
<212> TYPE: DNA
<213> ORGANISM: Artificial Sequence
<220> FEATURE:
<223> OTHER INFORMATION: Staple strand_0282 of the 3D DNA nanostructure.

<400> SEQUENCE: 283
atgcccggat cgtaactaag acgccggccg gtccgtatg                    39

<210> SEQ ID NO 284
<211> LENGTH: 39
<212> TYPE: DNA
<213> ORGANISM: Artificial Sequence
<220> FEATURE:
<223> OTHER INFORMATION: Staple strand_0283 of the 3D DNA nanostructure.

<400> SEQUENCE: 284
cgcggcccgg agcaaccact gcccagtcaa tatgctaca                    39

<210> SEQ ID NO 285
<211> LENGTH: 39
<212> TYPE: DNA
<213> ORGANISM: Artificial Sequence
<220> FEATURE:
<223> OTHER INFORMATION: Staple strand_0284 of the 3D DNA nanostructure.

<400> SEQUENCE: 285
```

```
cgcgcgacga cgacaatcat cgaacgaaca ccatgtggc                                  39

<210> SEQ ID NO 286
<211> LENGTH: 39
<212> TYPE: DNA
<213> ORGANISM: Artificial Sequence
<220> FEATURE:
<223> OTHER INFORMATION: Staple strand_0285 of the 3D DNA nanostructure.

<400> SEQUENCE: 286
ccgacagggt ttctcgacgc ccacgtaagc tccgaggtg                                  39

<210> SEQ ID NO 287
<211> LENGTH: 39
<212> TYPE: DNA
<213> ORGANISM: Artificial Sequence
<220> FEATURE:
<223> OTHER INFORMATION: Staple strand_0286 of the 3D DNA nanostructure.

<400> SEQUENCE: 287
acacaacaag gcacacgtcc tcttcgggcc accatccgg                                  39

<210> SEQ ID NO 288
<211> LENGTH: 39
<212> TYPE: DNA
<213> ORGANISM: Artificial Sequence
<220> FEATURE:
<223> OTHER INFORMATION: Staple strand_0287 of the 3D DNA nanostructure.

<400> SEQUENCE: 288
gcggtgcaca agcctggcgc tgttgtcttt atgcccgat                                  39

<210> SEQ ID NO 289
<211> LENGTH: 60
<212> TYPE: DNA
<213> ORGANISM: Artificial Sequence
<220> FEATURE:
<223> OTHER INFORMATION: Staple strand_0288 of the 3D DNA nanostructure.

<400> SEQUENCE: 289
cctcaacctc gctcgaacgt acgcagccgc aacactggat tcctctacca cctacatcac          60

<210> SEQ ID NO 290
<211> LENGTH: 60
<212> TYPE: DNA
<213> ORGANISM: Artificial Sequence
<220> FEATURE:
<223> OTHER INFORMATION: Staple strand_0289 of the 3D DNA nanostructure.

<400> SEQUENCE: 290
gaagcggcat agctccgtcc tcgggtagta aagcgcgcat tcctctacca cctacatcac          60

<210> SEQ ID NO 291
<211> LENGTH: 60
<212> TYPE: DNA
<213> ORGANISM: Artificial Sequence
<220> FEATURE:
<223> OTHER INFORMATION: Staple strand_0290 of the 3D DNA nanostructure.

<400> SEQUENCE: 291
gggaacagcg cataattcgc cgtgtgtgtg gccatcgcat tcctctacca cctacatcac          60

<210> SEQ ID NO 292
<211> LENGTH: 60
<212> TYPE: DNA
<213> ORGANISM: Artificial Sequence
```

```
<220> FEATURE:
<223> OTHER INFORMATION: Staple strand_0291 of the 3D DNA nanostructure.

<400> SEQUENCE: 292
cgacgccaca acgaacggcc tcctcgaaac cttgtgaggt tcctctacca cctacatcac      60

<210> SEQ ID NO 293
<211> LENGTH: 60
<212> TYPE: DNA
<213> ORGANISM: Artificial Sequence
<220> FEATURE:
<223> OTHER INFORMATION: Staple strand_0292 of the 3D DNA nanostructure.

<400> SEQUENCE: 293
gggatgtaac accacgtggc gcacgcactg tgtaggagct tcctctacca cctacatcac      60

<210> SEQ ID NO 294
<211> LENGTH: 60
<212> TYPE: DNA
<213> ORGANISM: Artificial Sequence
<220> FEATURE:
<223> OTHER INFORMATION: Staple strand_0293 of the 3D DNA nanostructure.

<400> SEQUENCE: 294
ctgggaggta cagctagggt gaccggcctc ctgccctcat tcctctacca cctacatcac      60

<210> SEQ ID NO 295
<211> LENGTH: 60
<212> TYPE: DNA
<213> ORGANISM: Artificial Sequence
<220> FEATURE:
<223> OTHER INFORMATION: Staple strand_0294 of the 3D DNA nanostructure.

<400> SEQUENCE: 295
gcccttgcca cagacccgca cagcgagttc tggcttcatt tcctctacca cctacatcac      60

<210> SEQ ID NO 296
<211> LENGTH: 60
<212> TYPE: DNA
<213> ORGANISM: Artificial Sequence
<220> FEATURE:
<223> OTHER INFORMATION: Staple strand_0295 of the 3D DNA nanostructure.

<400> SEQUENCE: 296
gcgcaacgtg acggtacgcc aacggtcacc agaagtcagt tcctctacca cctacatcac      60

<210> SEQ ID NO 297
<211> LENGTH: 60
<212> TYPE: DNA
<213> ORGANISM: Artificial Sequence
<220> FEATURE:
<223> OTHER INFORMATION: Staple strand_0296 of the 3D DNA nanostructure.

<400> SEQUENCE: 297
cggccaacct caaaggcgtc cacggcgaat ctgcgtctat tcctctacca cctacatcac      60

<210> SEQ ID NO 298
<211> LENGTH: 60
<212> TYPE: DNA
<213> ORGANISM: Artificial Sequence
<220> FEATURE:
<223> OTHER INFORMATION: Staple strand_0297 of the 3D DNA nanostructure.

<400> SEQUENCE: 298
cgcgcatagg gagtgtgctg gcgggctgcg agtaagaatt tcctctacca cctacatcac      60
```

<210> SEQ ID NO 299
<211> LENGTH: 60
<212> TYPE: DNA
<213> ORGANISM: Artificial Sequence
<220> FEATURE:
<223> OTHER INFORMATION: Staple strand_0298 of the 3D DNA nanostructure.

<400> SEQUENCE: 299
ctcaggaagc gagcagtaaa tccttggccg accgcagcgt tcctctacca cctacatcac    60

<210> SEQ ID NO 300
<211> LENGTH: 60
<212> TYPE: DNA
<213> ORGANISM: Artificial Sequence
<220> FEATURE:
<223> OTHER INFORMATION: Staple strand_0299 of the 3D DNA nanostructure.

<400> SEQUENCE: 300
gagcagagca gcttatccct gggtctccgg catctgcgct tcctctacca cctacatcac    60

<210> SEQ ID NO 301
<211> LENGTH: 60
<212> TYPE: DNA
<213> ORGANISM: Artificial Sequence
<220> FEATURE:
<223> OTHER INFORMATION: Staple strand_0300 of the 3D DNA nanostructure.

<400> SEQUENCE: 301
tggtgttccc tttcgccgcc ttgcaagtcc catcatgcct tcctctacca cctacatcac    60

<210> SEQ ID NO 302
<211> LENGTH: 60
<212> TYPE: DNA
<213> ORGANISM: Artificial Sequence
<220> FEATURE:
<223> OTHER INFORMATION: Staple strand_0301 of the 3D DNA nanostructure.

<400> SEQUENCE: 302
gcaagaagcc tacgcgaagc tgtcgggacc acggcaatgt tcctctacca cctacatcac    60

<210> SEQ ID NO 303
<211> LENGTH: 60
<212> TYPE: DNA
<213> ORGANISM: Artificial Sequence
<220> FEATURE:
<223> OTHER INFORMATION: Staple strand_0302 of the 3D DNA nanostructure.

<400> SEQUENCE: 303
ctccgtgctt gttaccttcg agtcgcggca caccacacgt tcctctacca cctacatcac    60

<210> SEQ ID NO 304
<211> LENGTH: 60
<212> TYPE: DNA
<213> ORGANISM: Artificial Sequence
<220> FEATURE:
<223> OTHER INFORMATION: Staple strand_0303 of the 3D DNA nanostructure.

<400> SEQUENCE: 304
tctgctcccg tgaatcccgc tcgttcgttc tcccggctat tcctctacca cctacatcac    60

<210> SEQ ID NO 305
<211> LENGTH: 60
<212> TYPE: DNA
<213> ORGANISM: Artificial Sequence
<220> FEATURE:
<223> OTHER INFORMATION: Staple strand_0304 of the 3D DNA nanostructure.

<400> SEQUENCE: 305
atgggaatgt agaagcgctg caaatcgtcg cccgtgccgt tcctctacca cctacatcac    60

<210> SEQ ID NO 306
<211> LENGTH: 60
<212> TYPE: DNA
<213> ORGANISM: Artificial Sequence
<220> FEATURE:
<223> OTHER INFORMATION: Staple strand_0305 of the 3D DNA nanostructure.

<400> SEQUENCE: 306
gtctgctcgt agttagtcgc ctcgacgcac gacgggacct tcctctacca cctacatcac    60

<210> SEQ ID NO 307
<211> LENGTH: 60
<212> TYPE: DNA
<213> ORGANISM: Artificial Sequence
<220> FEATURE:
<223> OTHER INFORMATION: Staple strand_0306 of the 3D DNA nanostructure.

<400> SEQUENCE: 307
ggcccaacta gagaagcaga aggcatcccg gtcggccact tcctctacca cctacatcac    60

<210> SEQ ID NO 308
<211> LENGTH: 60
<212> TYPE: DNA
<213> ORGANISM: Artificial Sequence
<220> FEATURE:
<223> OTHER INFORMATION: Staple strand_0307 of the 3D DNA nanostructure.

<400> SEQUENCE: 308
agttcgcacc gccattctcg gcagactccc accgacatgt tcctctacca cctacatcac    60

<210> SEQ ID NO 309
<211> LENGTH: 60
<212> TYPE: DNA
<213> ORGANISM: Artificial Sequence
<220> FEATURE:
<223> OTHER INFORMATION: Staple strand_0308 of the 3D DNA nanostructure.

<400> SEQUENCE: 309
gaaaagcacg gcgtgcagtg gcccaggtag gtcgttccat tcctctacca cctacatcac    60

<210> SEQ ID NO 310
<211> LENGTH: 60
<212> TYPE: DNA
<213> ORGANISM: Artificial Sequence
<220> FEATURE:
<223> OTHER INFORMATION: Staple strand_0309 of the 3D DNA nanostructure.

<400> SEQUENCE: 310
ggtaatgcgt tcgggctact gcggtgtgag atcgtgcggt tcctctacca cctacatcac    60

<210> SEQ ID NO 311
<211> LENGTH: 60
<212> TYPE: DNA
<213> ORGANISM: Artificial Sequence
<220> FEATURE:
<223> OTHER INFORMATION: Staple strand_0310 of the 3D DNA nanostructure.

<400> SEQUENCE: 311
tctacgtagg catcagcgtc gcggcactac acgtgggtct tcctctacca cctacatcac    60

<210> SEQ ID NO 312

```
<211> LENGTH: 60
<212> TYPE: DNA
<213> ORGANISM: Artificial Sequence
<220> FEATURE:
<223> OTHER INFORMATION: Staple strand_0311 of the 3D DNA nanostructure.

<400> SEQUENCE: 312
cgaagggacg cgggaggcta gggaatgctg catcagtggt tcctctacca cctacatcac       60

<210> SEQ ID NO 313
<211> LENGTH: 39
<212> TYPE: DNA
<213> ORGANISM: Artificial Sequence
<220> FEATURE:
<223> OTHER INFORMATION: Staple strand_0312 of the 3D DNA nanostructure.

<400> SEQUENCE: 313
cctacagggt tagctccaca gccgggtccg tgcagatgc                              39

<210> SEQ ID NO 314
<211> LENGTH: 39
<212> TYPE: DNA
<213> ORGANISM: Artificial Sequence
<220> FEATURE:
<223> OTHER INFORMATION: Staple strand_0313 of the 3D DNA nanostructure.

<400> SEQUENCE: 314
agaggcctcc tcagcggtcc tacgcggtct tggacgatg                              39

<210> SEQ ID NO 315
<211> LENGTH: 39
<212> TYPE: DNA
<213> ORGANISM: Artificial Sequence
<220> FEATURE:
<223> OTHER INFORMATION: Staple strand_0314 of the 3D DNA nanostructure.

<400> SEQUENCE: 315
cgtactcatc ccgtgccagt gccggcctac tcacctgtg                              39

<210> SEQ ID NO 316
<211> LENGTH: 39
<212> TYPE: DNA
<213> ORGANISM: Artificial Sequence
<220> FEATURE:
<223> OTHER INFORMATION: Staple strand_0315 of the 3D DNA nanostructure.

<400> SEQUENCE: 316
gcctgcgaca atgtgggctg aacggtttg ctagggcac                               39

<210> SEQ ID NO 317
<211> LENGTH: 39
<212> TYPE: DNA
<213> ORGANISM: Artificial Sequence
<220> FEATURE:
<223> OTHER INFORMATION: Staple strand_0316 of the 3D DNA nanostructure.

<400> SEQUENCE: 317
cacccgatgt gttatgacgt gcgtcgccct cgagcacct                              39

<210> SEQ ID NO 318
<211> LENGTH: 39
<212> TYPE: DNA
<213> ORGANISM: Artificial Sequence
<220> FEATURE:
<223> OTHER INFORMATION: Staple strand_0317 of the 3D DNA nanostructure.

<400> SEQUENCE: 318
```
agcatacaga gggcagcttg gcagggccgc gaagttagg            39

<210> SEQ ID NO 319
<211> LENGTH: 39
<212> TYPE: DNA
<213> ORGANISM: Artificial Sequence
<220> FEATURE:
<223> OTHER INFORMATION: Staple strand_0318 of the 3D DNA nanostructure.

<400> SEQUENCE: 319
gacgcccgat tgtccttgtt cgccatgccg caaggtgag            39

<210> SEQ ID NO 320
<211> LENGTH: 39
<212> TYPE: DNA
<213> ORGANISM: Artificial Sequence
<220> FEATURE:
<223> OTHER INFORMATION: Staple strand_0319 of the 3D DNA nanostructure.

<400> SEQUENCE: 320
ggtggcgaga tgacgacagt gcagaaggtg gcggtaggg            39

<210> SEQ ID NO 321
<211> LENGTH: 39
<212> TYPE: DNA
<213> ORGANISM: Artificial Sequence
<220> FEATURE:
<223> OTHER INFORMATION: Staple strand_0320 of the 3D DNA nanostructure.

<400> SEQUENCE: 321
tctgtgaagc gggtggagta cggaggtgtt cttcgcgcc            39

<210> SEQ ID NO 322
<211> LENGTH: 39
<212> TYPE: DNA
<213> ORGANISM: Artificial Sequence
<220> FEATURE:
<223> OTHER INFORMATION: Staple strand_0321 of the 3D DNA nanostructure.

<400> SEQUENCE: 322
ttttgcgcaa tcatggcagc ggactcaaca ccctccggc            39

<210> SEQ ID NO 323
<211> LENGTH: 39
<212> TYPE: DNA
<213> ORGANISM: Artificial Sequence
<220> FEATURE:
<223> OTHER INFORMATION: Staple strand_0322 of the 3D DNA nanostructure.

<400> SEQUENCE: 323
gacctcggag ctagacggga gtgttgcgtg tgcagggtg            39

<210> SEQ ID NO 324
<211> LENGTH: 39
<212> TYPE: DNA
<213> ORGANISM: Artificial Sequence
<220> FEATURE:
<223> OTHER INFORMATION: Staple strand_0323 of the 3D DNA nanostructure.

<400> SEQUENCE: 324
cggttcgagt gcgcagtgct taacgtgaag cgagggagg            39

<210> SEQ ID NO 325
<211> LENGTH: 60
<212> TYPE: DNA

```
<213> ORGANISM: Artificial Sequence
<220> FEATURE:
<223> OTHER INFORMATION: Staple strand_0324 of the 3D DNA nanostructure.

<400> SEQUENCE: 325
actccctgat aggcgtcttt caggcgggcg ggactcaggt aacattccta acttctcata    60

<210> SEQ ID NO 326
<211> LENGTH: 60
<212> TYPE: DNA
<213> ORGANISM: Artificial Sequence
<220> FEATURE:
<223> OTHER INFORMATION: Staple strand_0325 of the 3D DNA nanostructure.

<400> SEQUENCE: 326
gggacgccag actgggctca cgagtgatag gctttccgct aacattccta acttctcata    60

<210> SEQ ID NO 327
<211> LENGTH: 60
<212> TYPE: DNA
<213> ORGANISM: Artificial Sequence
<220> FEATURE:
<223> OTHER INFORMATION: Staple strand_0326 of the 3D DNA nanostructure.

<400> SEQUENCE: 327
ttcggcttag gtccttctcg tgtggtgccc gctgcccttt aacattccta acttctcata    60

<210> SEQ ID NO 328
<211> LENGTH: 60
<212> TYPE: DNA
<213> ORGANISM: Artificial Sequence
<220> FEATURE:
<223> OTHER INFORMATION: Staple strand_0327 of the 3D DNA nanostructure.

<400> SEQUENCE: 328
gcgagccacg cggcgtgtaa ccaacagcat tttctcgctt aacattccta acttctcata    60

<210> SEQ ID NO 329
<211> LENGTH: 60
<212> TYPE: DNA
<213> ORGANISM: Artificial Sequence
<220> FEATURE:
<223> OTHER INFORMATION: Staple strand_0328 of the 3D DNA nanostructure.

<400> SEQUENCE: 329
tgcggcagca tcaaggacct accatcttga ccggtcgcct aacattccta acttctcata    60

<210> SEQ ID NO 330
<211> LENGTH: 60
<212> TYPE: DNA
<213> ORGANISM: Artificial Sequence
<220> FEATURE:
<223> OTHER INFORMATION: Staple strand_0329 of the 3D DNA nanostructure.

<400> SEQUENCE: 330
actccagttg ctagaacggt ctcgcgcaca cacggtgggt aacattccta acttctcata    60

<210> SEQ ID NO 331
<211> LENGTH: 60
<212> TYPE: DNA
<213> ORGANISM: Artificial Sequence
<220> FEATURE:
<223> OTHER INFORMATION: Staple strand_0330 of the 3D DNA nanostructure.

<400> SEQUENCE: 331
cgtgctttga tccgactgac actgcgtggc cgatgggctt aacattccta acttctcata    60
```

<210> SEQ ID NO 332
<211> LENGTH: 60
<212> TYPE: DNA
<213> ORGANISM: Artificial Sequence
<220> FEATURE:
<223> OTHER INFORMATION: Staple strand_0331 of the 3D DNA nanostructure.

<400> SEQUENCE: 332
gtgcccgttg tgagtcggag aaccttgcgc ggcctattgt aacattccta acttctcata    60

<210> SEQ ID NO 333
<211> LENGTH: 60
<212> TYPE: DNA
<213> ORGANISM: Artificial Sequence
<220> FEATURE:
<223> OTHER INFORMATION: Staple strand_0332 of the 3D DNA nanostructure.

<400> SEQUENCE: 333
cgcagggacg ccgtcgaaac acagcactcc acatcgtact aacattccta acttctcata    60

<210> SEQ ID NO 334
<211> LENGTH: 60
<212> TYPE: DNA
<213> ORGANISM: Artificial Sequence
<220> FEATURE:
<223> OTHER INFORMATION: Staple strand_0333 of the 3D DNA nanostructure.

<400> SEQUENCE: 334
cacgactctc acacggagcc agcctatctc ccgttgcggt aacattccta acttctcata    60

<210> SEQ ID NO 335
<211> LENGTH: 60
<212> TYPE: DNA
<213> ORGANISM: Artificial Sequence
<220> FEATURE:
<223> OTHER INFORMATION: Staple strand_0334 of the 3D DNA nanostructure.

<400> SEQUENCE: 335
aacagccttg gaccggtcgc tcacagtcct ttcgtgccct aacattccta acttctcata    60

<210> SEQ ID NO 336
<211> LENGTH: 60
<212> TYPE: DNA
<213> ORGANISM: Artificial Sequence
<220> FEATURE:
<223> OTHER INFORMATION: Staple strand_0335 of the 3D DNA nanostructure.

<400> SEQUENCE: 336
ctcgtcgttt ccgttcttgc agtgctgcca gaggcggtgt aacattccta acttctcata    60

<210> SEQ ID NO 337
<211> LENGTH: 60
<212> TYPE: DNA
<213> ORGANISM: Artificial Sequence
<220> FEATURE:
<223> OTHER INFORMATION: Staple strand_0336 of the 3D DNA nanostructure.

<400> SEQUENCE: 337
agaaggaaag tctcaccggg cgccctaggc cttccgaggt aacattccta acttctcata    60

<210> SEQ ID NO 338
<211> LENGTH: 60
<212> TYPE: DNA
<213> ORGANISM: Artificial Sequence
<220> FEATURE:

<223> OTHER INFORMATION: Staple strand_0337 of the 3D DNA nanostructure.

<400> SEQUENCE: 338
gcctcaatgc tcttcacctg ggtccatgcc cggacggagt aacattccta acttctcata    60

<210> SEQ ID NO 339
<211> LENGTH: 60
<212> TYPE: DNA
<213> ORGANISM: Artificial Sequence
<220> FEATURE:
<223> OTHER INFORMATION: Staple strand_0338 of the 3D DNA nanostructure.

<400> SEQUENCE: 339
agcagctgac aacctagacg tgtgcctcgg gtagtgcgct aacattccta acttctcata    60

<210> SEQ ID NO 340
<211> LENGTH: 60
<212> TYPE: DNA
<213> ORGANISM: Artificial Sequence
<220> FEATURE:
<223> OTHER INFORMATION: Staple strand_0339 of the 3D DNA nanostructure.

<400> SEQUENCE: 340
gaacagagcg cccgtttcgc cgaacgcggt ggataaacat aacattccta acttctcata    60

<210> SEQ ID NO 341
<211> LENGTH: 60
<212> TYPE: DNA
<213> ORGANISM: Artificial Sequence
<220> FEATURE:
<223> OTHER INFORMATION: Staple strand_0340 of the 3D DNA nanostructure.

<400> SEQUENCE: 341
acttccggcc cgccgcactc atgcctgtac gggtttagtt aacattccta acttctcata    60

<210> SEQ ID NO 342
<211> LENGTH: 60
<212> TYPE: DNA
<213> ORGANISM: Artificial Sequence
<220> FEATURE:
<223> OTHER INFORMATION: Staple strand_0341 of the 3D DNA nanostructure.

<400> SEQUENCE: 342
catttacgtc gccagccgcc ggtatccatc tgcgagcact aacattccta acttctcata    60

<210> SEQ ID NO 343
<211> LENGTH: 60
<212> TYPE: DNA
<213> ORGANISM: Artificial Sequence
<220> FEATURE:
<223> OTHER INFORMATION: Staple strand_0342 of the 3D DNA nanostructure.

<400> SEQUENCE: 343
agcagcggca tctccagttt tgggccaggg ttgggatcct aacattccta acttctcata    60

<210> SEQ ID NO 344
<211> LENGTH: 60
<212> TYPE: DNA
<213> ORGANISM: Artificial Sequence
<220> FEATURE:
<223> OTHER INFORMATION: Staple strand_0343 of the 3D DNA nanostructure.

<400> SEQUENCE: 344
gcatatgcga atcgactcca acgcgcgaaa ggacgggctt aacattccta acttctcata    60

```
<210> SEQ ID NO 345
<211> LENGTH: 60
<212> TYPE: DNA
<213> ORGANISM: Artificial Sequence
<220> FEATURE:
<223> OTHER INFORMATION: Staple strand_0344 of the 3D DNA nanostructure.

<400> SEQUENCE: 345
ggcactagcc tcggccacaa actgtaggcg cgctatcgat aacattccta acttctcata      60

<210> SEQ ID NO 346
<211> LENGTH: 60
<212> TYPE: DNA
<213> ORGANISM: Artificial Sequence
<220> FEATURE:
<223> OTHER INFORMATION: Staple strand_0345 of the 3D DNA nanostructure.

<400> SEQUENCE: 346
ctgctcgcgc gttgaaccta gcctcgagtg gcattgacgt aacattccta acttctcata      60

<210> SEQ ID NO 347
<211> LENGTH: 60
<212> TYPE: DNA
<213> ORGANISM: Artificial Sequence
<220> FEATURE:
<223> OTHER INFORMATION: Staple strand_0346 of the 3D DNA nanostructure.

<400> SEQUENCE: 347
tcaattccgc gcggagagag aacaacaacc acgcaccggt aacattccta acttctcata      60

<210> SEQ ID NO 348
<211> LENGTH: 60
<212> TYPE: DNA
<213> ORGANISM: Artificial Sequence
<220> FEATURE:
<223> OTHER INFORMATION: Staple strand_0347 of the 3D DNA nanostructure.

<400> SEQUENCE: 348
tgaccaccgt cgaaccatcc ggcagtcggg ccataagctt aacattccta acttctcata      60

<210> SEQ ID NO 349
<211> LENGTH: 60
<212> TYPE: DNA
<213> ORGANISM: Artificial Sequence
<220> FEATURE:
<223> OTHER INFORMATION: Staple strand_0348 of the 3D DNA nanostructure.

<400> SEQUENCE: 349
cctcaacctc gctcgaacgt acgcagccgc aacactggat aacattccta acttctcata      60

<210> SEQ ID NO 350
<211> LENGTH: 60
<212> TYPE: DNA
<213> ORGANISM: Artificial Sequence
<220> FEATURE:
<223> OTHER INFORMATION: Staple strand_0349 of the 3D DNA nanostructure.

<400> SEQUENCE: 350
gaagcggcat agctccgtcc tcgggtagta aagcgcgcat aacattccta acttctcata      60

<210> SEQ ID NO 351
<211> LENGTH: 60
<212> TYPE: DNA
<213> ORGANISM: Artificial Sequence
<220> FEATURE:
<223> OTHER INFORMATION: Staple strand_0350 of the 3D DNA nanostructure.
```

<400> SEQUENCE: 351
gggaacagcg cataattcgc cgtgtgtgtg gccatcgcat aacattccta acttctcata    60

<210> SEQ ID NO 352
<211> LENGTH: 60
<212> TYPE: DNA
<213> ORGANISM: Artificial Sequence
<220> FEATURE:
<223> OTHER INFORMATION: Staple strand_0351 of the 3D DNA nanostructure.

<400> SEQUENCE: 352
cgacgccaca acgaacggcc tcctcgaaac cttgtgaggt aacattccta acttctcata    60

<210> SEQ ID NO 353
<211> LENGTH: 60
<212> TYPE: DNA
<213> ORGANISM: Artificial Sequence
<220> FEATURE:
<223> OTHER INFORMATION: Staple strand_0352 of the 3D DNA nanostructure.

<400> SEQUENCE: 353
gggatgtaac accacgtggc gcacgcactg tgtaggagct aacattccta acttctcata    60

<210> SEQ ID NO 354
<211> LENGTH: 60
<212> TYPE: DNA
<213> ORGANISM: Artificial Sequence
<220> FEATURE:
<223> OTHER INFORMATION: Staple strand_0353 of the 3D DNA nanostructure.

<400> SEQUENCE: 354
ctgggaggta cagctagggt gaccggcctc ctgccctcat aacattccta acttctcata    60

<210> SEQ ID NO 355
<211> LENGTH: 60
<212> TYPE: DNA
<213> ORGANISM: Artificial Sequence
<220> FEATURE:
<223> OTHER INFORMATION: Staple strand_0354 of the 3D DNA nanostructure.

<400> SEQUENCE: 355
gcccttgcca cagacccgca cagcgagttc tggcttcatt aacattccta acttctcata    60

<210> SEQ ID NO 356
<211> LENGTH: 60
<212> TYPE: DNA
<213> ORGANISM: Artificial Sequence
<220> FEATURE:
<223> OTHER INFORMATION: Staple strand_0355 of the 3D DNA nanostructure.

<400> SEQUENCE: 356
gcgcaacgtg acggtacgcc aacggtcacc agaagtcagt aacattccta acttctcata    60

<210> SEQ ID NO 357
<211> LENGTH: 60
<212> TYPE: DNA
<213> ORGANISM: Artificial Sequence
<220> FEATURE:
<223> OTHER INFORMATION: Staple strand_0356 of the 3D DNA nanostructure.

<400> SEQUENCE: 357
cggccaacct caaaggcgtc cacggcgaat ctgcgtctat aacattccta acttctcata    60

<210> SEQ ID NO 358
<211> LENGTH: 60

-continued

<210> SEQ ID NO 358
<211> LENGTH: 60
<212> TYPE: DNA
<213> ORGANISM: Artificial Sequence
<220> FEATURE:
<223> OTHER INFORMATION: Staple strand_0357 of the 3D DNA nanostructure.

<400> SEQUENCE: 358
cgcgcatagg gagtgtgctg gcgggctgcg agtaagaatt aacattccta acttctcata    60

<210> SEQ ID NO 359
<211> LENGTH: 60
<212> TYPE: DNA
<213> ORGANISM: Artificial Sequence
<220> FEATURE:
<223> OTHER INFORMATION: Staple strand_0358 of the 3D DNA nanostructure.

<400> SEQUENCE: 359
ctcaggaagc gagcagtaaa tccttggccg accgcagcgt aacattccta acttctcata    60

<210> SEQ ID NO 360
<211> LENGTH: 60
<212> TYPE: DNA
<213> ORGANISM: Artificial Sequence
<220> FEATURE:
<223> OTHER INFORMATION: Staple strand_0359 of the 3D DNA nanostructure.

<400> SEQUENCE: 360
gagcagagca gcttatccct gggtctccgg catctgcgct aacattccta acttctcata    60

<210> SEQ ID NO 361
<211> LENGTH: 60
<212> TYPE: DNA
<213> ORGANISM: Artificial Sequence
<220> FEATURE:
<223> OTHER INFORMATION: Staple strand_0360 of the 3D DNA nanostructure.

<400> SEQUENCE: 361
tggtgttccc tttcgccgcc ttgcaagtcc catcatgcct aacattccta acttctcata    60

<210> SEQ ID NO 362
<211> LENGTH: 60
<212> TYPE: DNA
<213> ORGANISM: Artificial Sequence
<220> FEATURE:
<223> OTHER INFORMATION: Staple strand_0361 of the 3D DNA nanostructure.

<400> SEQUENCE: 362
gcaagaagcc tacgcgaagc tgtcgggacc acggcaatgt aacattccta acttctcata    60

<210> SEQ ID NO 363
<211> LENGTH: 60
<212> TYPE: DNA
<213> ORGANISM: Artificial Sequence
<220> FEATURE:
<223> OTHER INFORMATION: Staple strand_0362 of the 3D DNA nanostructure.

<400> SEQUENCE: 363
ctccgtgctt gttaccttcg agtcgcggca caccacacgt aacattccta acttctcata    60

<210> SEQ ID NO 364
<211> LENGTH: 60
<212> TYPE: DNA
<213> ORGANISM: Artificial Sequence
<220> FEATURE:
<223> OTHER INFORMATION: Staple strand_0363 of the 3D DNA nanostructure.

<400> SEQUENCE: 364
tctgctcccg tgaatcccgc tcgttcgttc tcccggctat aacattccta acttctcata        60

<210> SEQ ID NO 365
<211> LENGTH: 60
<212> TYPE: DNA
<213> ORGANISM: Artificial Sequence
<220> FEATURE:
<223> OTHER INFORMATION: Staple strand_0364 of the 3D DNA nanostructure.

<400> SEQUENCE: 365
atgggaatgt agaagcgctg caaatcgtcg cccgtgccgt aacattccta acttctcata        60

<210> SEQ ID NO 366
<211> LENGTH: 60
<212> TYPE: DNA
<213> ORGANISM: Artificial Sequence
<220> FEATURE:
<223> OTHER INFORMATION: Staple strand_0365 of the 3D DNA nanostructure.

<400> SEQUENCE: 366
gtctgctcgt agttagtcgc ctcgacgcac gacgggacct aacattccta acttctcata        60

<210> SEQ ID NO 367
<211> LENGTH: 60
<212> TYPE: DNA
<213> ORGANISM: Artificial Sequence
<220> FEATURE:
<223> OTHER INFORMATION: Staple strand_0366 of the 3D DNA nanostructure.

<400> SEQUENCE: 367
ggcccaacta gagaagcaga aggcatcccg gtcggccact aacattccta acttctcata        60

<210> SEQ ID NO 368
<211> LENGTH: 60
<212> TYPE: DNA
<213> ORGANISM: Artificial Sequence
<220> FEATURE:
<223> OTHER INFORMATION: Staple strand_0367 of the 3D DNA nanostructure.

<400> SEQUENCE: 368
agttcgcacc gccattctcg gcagactccc accgacatgt aacattccta acttctcata        60

<210> SEQ ID NO 369
<211> LENGTH: 60
<212> TYPE: DNA
<213> ORGANISM: Artificial Sequence
<220> FEATURE:
<223> OTHER INFORMATION: Staple strand_0368 of the 3D DNA nanostructure.

<400> SEQUENCE: 369
gaaaagcacg gcgtgcagtg gcccaggtag gtcgttccat aacattccta acttctcata        60

<210> SEQ ID NO 370
<211> LENGTH: 60
<212> TYPE: DNA
<213> ORGANISM: Artificial Sequence
<220> FEATURE:
<223> OTHER INFORMATION: Staple strand_0369 of the 3D DNA nanostructure.

<400> SEQUENCE: 370
ggtaatgcgt tcgggctact gcggtgtgag atcgtgcggt aacattccta acttctcata        60

<210> SEQ ID NO 371
<211> LENGTH: 60
<212> TYPE: DNA
<213> ORGANISM: Artificial Sequence

```
<220> FEATURE:
<223> OTHER INFORMATION: Staple strand_0370 of the 3D DNA nanostructure.

<400> SEQUENCE: 371
tctacgtagg catcagcgtc gcggcactac acgtgggtct aacattccta acttctcata    60

<210> SEQ ID NO 372
<211> LENGTH: 60
<212> TYPE: DNA
<213> ORGANISM: Artificial Sequence
<220> FEATURE:
<223> OTHER INFORMATION: Staple strand_0371 of the 3D DNA nanostructure.

<400> SEQUENCE: 372
cgaagggacg cgggaggcta gggaatgctg catcagtggt aacattccta acttctcata    60

<210> SEQ ID NO 373
<211> LENGTH: 60
<212> TYPE: DNA
<213> ORGANISM: Artificial Sequence
<220> FEATURE:
<223> OTHER INFORMATION: Staple strand_0372 of the 3D DNA nanostructure.

<400> SEQUENCE: 373
actccctgat aggcgtcttt caggcgggcg ggactcaggt taccatctct cctaaactcg    60

<210> SEQ ID NO 374
<211> LENGTH: 60
<212> TYPE: DNA
<213> ORGANISM: Artificial Sequence
<220> FEATURE:
<223> OTHER INFORMATION: Staple strand_0373 of the 3D DNA nanostructure.

<400> SEQUENCE: 374
gggacgccag actgggctca cgagtgatag gctttccgct taccatctct cctaaactcg    60

<210> SEQ ID NO 375
<211> LENGTH: 60
<212> TYPE: DNA
<213> ORGANISM: Artificial Sequence
<220> FEATURE:
<223> OTHER INFORMATION: Staple strand_0374 of the 3D DNA nanostructure.

<400> SEQUENCE: 375
ttcggcttag gtccttctcg tgtggtgccc gctgcccttt taccatctct cctaaactcg    60

<210> SEQ ID NO 376
<211> LENGTH: 60
<212> TYPE: DNA
<213> ORGANISM: Artificial Sequence
<220> FEATURE:
<223> OTHER INFORMATION: Staple strand_0375 of the 3D DNA nanostructure.

<400> SEQUENCE: 376
gcgagccacg cggcgtgtaa ccaacagcat tttctcgctt taccatctct cctaaactcg    60

<210> SEQ ID NO 377
<211> LENGTH: 60
<212> TYPE: DNA
<213> ORGANISM: Artificial Sequence
<220> FEATURE:
<223> OTHER INFORMATION: Staple strand_0376 of the 3D DNA nanostructure.

<400> SEQUENCE: 377
tgcggcagca tcaaggacct accatcttga ccggtcgcct taccatctct cctaaactcg    60
```

<210> SEQ ID NO 378
<211> LENGTH: 60
<212> TYPE: DNA
<213> ORGANISM: Artificial Sequence
<220> FEATURE:
<223> OTHER INFORMATION: Staple strand_0377 of the 3D DNA nanostructure.

<400> SEQUENCE: 378
actccagttg ctagaacggt ctcgcgcaca cacggtgggt taccatctct cctaaactcg    60

<210> SEQ ID NO 379
<211> LENGTH: 60
<212> TYPE: DNA
<213> ORGANISM: Artificial Sequence
<220> FEATURE:
<223> OTHER INFORMATION: Staple strand_0378 of the 3D DNA nanostructure.

<400> SEQUENCE: 379
cgtgctttga tccgactgac actgcgtggc cgatgggctt taccatctct cctaaactcg    60

<210> SEQ ID NO 380
<211> LENGTH: 60
<212> TYPE: DNA
<213> ORGANISM: Artificial Sequence
<220> FEATURE:
<223> OTHER INFORMATION: Staple strand_0379 of the 3D DNA nanostructure.

<400> SEQUENCE: 380
gtgcccgttg tgagtcggag aaccttgcgc ggcctattgt taccatctct cctaaactcg    60

<210> SEQ ID NO 381
<211> LENGTH: 60
<212> TYPE: DNA
<213> ORGANISM: Artificial Sequence
<220> FEATURE:
<223> OTHER INFORMATION: Staple strand_0380 of the 3D DNA nanostructure.

<400> SEQUENCE: 381
cgcagggacg ccgtcgaaac acagcactcc acatcgtact taccatctct cctaaactcg    60

<210> SEQ ID NO 382
<211> LENGTH: 60
<212> TYPE: DNA
<213> ORGANISM: Artificial Sequence
<220> FEATURE:
<223> OTHER INFORMATION: Staple strand_0381 of the 3D DNA nanostructure.

<400> SEQUENCE: 382
cacgactctc acacggagcc agcctatctc ccgttgcggt taccatctct cctaaactcg    60

<210> SEQ ID NO 383
<211> LENGTH: 60
<212> TYPE: DNA
<213> ORGANISM: Artificial Sequence
<220> FEATURE:
<223> OTHER INFORMATION: Staple strand_0382 of the 3D DNA nanostructure.

<400> SEQUENCE: 383
aacagccttg gaccggtcgc tcacagtcct ttcgtgccct taccatctct cctaaactcg    60

<210> SEQ ID NO 384
<211> LENGTH: 60
<212> TYPE: DNA
<213> ORGANISM: Artificial Sequence
<220> FEATURE:
<223> OTHER INFORMATION: Staple strand_0383 of the 3D DNA nanostructure.

<400> SEQUENCE: 384
ctcgtcgttt ccgttcttgc agtgctgcca gaggcggtgt taccatctct cctaaactcg    60

<210> SEQ ID NO 385
<211> LENGTH: 60
<212> TYPE: DNA
<213> ORGANISM: Artificial Sequence
<220> FEATURE:
<223> OTHER INFORMATION: Staple strand_0384 of the 3D DNA nanostructure.

<400> SEQUENCE: 385
agaaggaaag tctcaccggg cgccctaggc cttccgaggt taccatctct cctaaactcg    60

<210> SEQ ID NO 386
<211> LENGTH: 60
<212> TYPE: DNA
<213> ORGANISM: Artificial Sequence
<220> FEATURE:
<223> OTHER INFORMATION: Staple strand_0385 of the 3D DNA nanostructure.

<400> SEQUENCE: 386
gcctcaatgc tcttcacctg ggtccatgcc cggacggagt taccatctct cctaaactcg    60

<210> SEQ ID NO 387
<211> LENGTH: 60
<212> TYPE: DNA
<213> ORGANISM: Artificial Sequence
<220> FEATURE:
<223> OTHER INFORMATION: Staple strand_0386 of the 3D DNA nanostructure.

<400> SEQUENCE: 387
agcagctgac aacctagacg tgtgcctcgg gtagtgcgct taccatctct cctaaactcg    60

<210> SEQ ID NO 388
<211> LENGTH: 60
<212> TYPE: DNA
<213> ORGANISM: Artificial Sequence
<220> FEATURE:
<223> OTHER INFORMATION: Staple strand_0387 of the 3D DNA nanostructure.

<400> SEQUENCE: 388
gaacagagcg cccgtttcgc cgaacgcggt ggataaacat taccatctct cctaaactcg    60

<210> SEQ ID NO 389
<211> LENGTH: 60
<212> TYPE: DNA
<213> ORGANISM: Artificial Sequence
<220> FEATURE:
<223> OTHER INFORMATION: Staple strand_0388 of the 3D DNA nanostructure.

<400> SEQUENCE: 389
acttccggcc cgccgcactc atgcctgtac gggtttagtt taccatctct cctaaactcg    60

<210> SEQ ID NO 390
<211> LENGTH: 60
<212> TYPE: DNA
<213> ORGANISM: Artificial Sequence
<220> FEATURE:
<223> OTHER INFORMATION: Staple strand_0389 of the 3D DNA nanostructure.

<400> SEQUENCE: 390
catttacgtc gccagccgcc ggtatccatc tgcgagcact taccatctct cctaaactcg    60

<210> SEQ ID NO 391

```
<211> LENGTH: 60
<212> TYPE: DNA
<213> ORGANISM: Artificial Sequence
<220> FEATURE:
<223> OTHER INFORMATION: Staple strand_0390 of the 3D DNA nanostructure.

<400> SEQUENCE: 391
agcagcggca tctccagttt tgggccaggg ttgggatcct taccatctct cctaaactcg    60

<210> SEQ ID NO 392
<211> LENGTH: 60
<212> TYPE: DNA
<213> ORGANISM: Artificial Sequence
<220> FEATURE:
<223> OTHER INFORMATION: Staple strand_0391 of the 3D DNA nanostructure.

<400> SEQUENCE: 392
gcatatgcga atcgactcca acgcgcgaaa ggacgggctt taccatctct cctaaactcg    60

<210> SEQ ID NO 393
<211> LENGTH: 60
<212> TYPE: DNA
<213> ORGANISM: Artificial Sequence
<220> FEATURE:
<223> OTHER INFORMATION: Staple strand_0392 of the 3D DNA nanostructure.

<400> SEQUENCE: 393
ggcactagcc tcggccacaa actgtaggcg cgctatcgat taccatctct cctaaactcg    60

<210> SEQ ID NO 394
<211> LENGTH: 60
<212> TYPE: DNA
<213> ORGANISM: Artificial Sequence
<220> FEATURE:
<223> OTHER INFORMATION: Staple strand_0393 of the 3D DNA nanostructure.

<400> SEQUENCE: 394
ctgctcgcgc gttgaaccta gcctcgagtg gcattgacgt taccatctct cctaaactcg    60

<210> SEQ ID NO 395
<211> LENGTH: 60
<212> TYPE: DNA
<213> ORGANISM: Artificial Sequence
<220> FEATURE:
<223> OTHER INFORMATION: Staple strand_0394 of the 3D DNA nanostructure.

<400> SEQUENCE: 395
tcaattccgc gcggagagag aacaacaacc acgcaccggt taccatctct cctaaactcg    60

<210> SEQ ID NO 396
<211> LENGTH: 60
<212> TYPE: DNA
<213> ORGANISM: Artificial Sequence
<220> FEATURE:
<223> OTHER INFORMATION: Staple strand_0395 of the 3D DNA nanostructure.

<400> SEQUENCE: 396
tgaccaccgt cgaaccatcc ggcagtcggg ccataagctt taccatctct cctaaactcg    60

<210> SEQ ID NO 397
<211> LENGTH: 60
<212> TYPE: DNA
<213> ORGANISM: Artificial Sequence
<220> FEATURE:
<223> OTHER INFORMATION: Staple strand_0396 of the 3D DNA nanostructure.

<400> SEQUENCE: 397
```

```
cctcaacctc gctcgaacgt acgcagccgc aacactggat taccatctct cctaaactcg    60

<210> SEQ ID NO 398
<211> LENGTH: 60
<212> TYPE: DNA
<213> ORGANISM: Artificial Sequence
<220> FEATURE:
<223> OTHER INFORMATION: Staple strand_0397 of the 3D DNA nanostructure.

<400> SEQUENCE: 398
gaagcggcat agctccgtcc tcgggtagta aagcgcgcat taccatctct cctaaactcg    60

<210> SEQ ID NO 399
<211> LENGTH: 60
<212> TYPE: DNA
<213> ORGANISM: Artificial Sequence
<220> FEATURE:
<223> OTHER INFORMATION: Staple strand_0398 of the 3D DNA nanostructure.

<400> SEQUENCE: 399
gggaacagcg cataattcgc cgtgtgtgtg gccatcgcat taccatctct cctaaactcg    60

<210> SEQ ID NO 400
<211> LENGTH: 60
<212> TYPE: DNA
<213> ORGANISM: Artificial Sequence
<220> FEATURE:
<223> OTHER INFORMATION: Staple strand_0399 of the 3D DNA nanostructure.

<400> SEQUENCE: 400
cgacgccaca acgaacggcc tcctcgaaac cttgtgaggt taccatctct cctaaactcg    60

<210> SEQ ID NO 401
<211> LENGTH: 60
<212> TYPE: DNA
<213> ORGANISM: Artificial Sequence
<220> FEATURE:
<223> OTHER INFORMATION: Staple strand_0400 of the 3D DNA nanostructure.

<400> SEQUENCE: 401
gggatgtaac accacgtggc gcacgcactg tgtaggagct taccatctct cctaaactcg    60

<210> SEQ ID NO 402
<211> LENGTH: 60
<212> TYPE: DNA
<213> ORGANISM: Artificial Sequence
<220> FEATURE:
<223> OTHER INFORMATION: Staple strand_0401 of the 3D DNA nanostructure.

<400> SEQUENCE: 402
ctgggaggta cagctagggt gaccggcctc ctgccctcat taccatctct cctaaactcg    60

<210> SEQ ID NO 403
<211> LENGTH: 60
<212> TYPE: DNA
<213> ORGANISM: Artificial Sequence
<220> FEATURE:
<223> OTHER INFORMATION: Staple strand_0402 of the 3D DNA nanostructure.

<400> SEQUENCE: 403
gcccttgcca cagacccgca cagcgagttc tggcttcatt taccatctct cctaaactcg    60

<210> SEQ ID NO 404
<211> LENGTH: 60
<212> TYPE: DNA
```

```
<213> ORGANISM: Artificial Sequence
<220> FEATURE:
<223> OTHER INFORMATION: Staple strand_0403 of the 3D DNA nanostructure.

<400> SEQUENCE: 404
gcgcaacgtg acggtacgcc aacggtcacc agaagtcagt taccatctct cctaaactcg    60

<210> SEQ ID NO 405
<211> LENGTH: 60
<212> TYPE: DNA
<213> ORGANISM: Artificial Sequence
<220> FEATURE:
<223> OTHER INFORMATION: Staple strand_0404 of the 3D DNA nanostructure.

<400> SEQUENCE: 405
cggccaacct caaaggcgtc cacggcgaat ctgcgtctat taccatctct cctaaactcg    60

<210> SEQ ID NO 406
<211> LENGTH: 60
<212> TYPE: DNA
<213> ORGANISM: Artificial Sequence
<220> FEATURE:
<223> OTHER INFORMATION: Staple strand_0405 of the 3D DNA nanostructure.

<400> SEQUENCE: 406
cgcgcatagg gagtgtgctg gcgggctgcg agtaagaatt taccatctct cctaaactcg    60

<210> SEQ ID NO 407
<211> LENGTH: 60
<212> TYPE: DNA
<213> ORGANISM: Artificial Sequence
<220> FEATURE:
<223> OTHER INFORMATION: Staple strand_0406 of the 3D DNA nanostructure.

<400> SEQUENCE: 407
ctcaggaagc gagcagtaaa tccttggccg accgcagcgt taccatctct cctaaactcg    60

<210> SEQ ID NO 408
<211> LENGTH: 60
<212> TYPE: DNA
<213> ORGANISM: Artificial Sequence
<220> FEATURE:
<223> OTHER INFORMATION: Staple strand_0407 of the 3D DNA nanostructure.

<400> SEQUENCE: 408
gagcagagca gcttatccct gggtctccgg catctgcgct taccatctct cctaaactcg    60

<210> SEQ ID NO 409
<211> LENGTH: 60
<212> TYPE: DNA
<213> ORGANISM: Artificial Sequence
<220> FEATURE:
<223> OTHER INFORMATION: Staple strand_0408 of the 3D DNA nanostructure.

<400> SEQUENCE: 409
tggtgttccc tttcgccgcc ttgcaagtcc catcatgcct taccatctct cctaaactcg    60

<210> SEQ ID NO 410
<211> LENGTH: 60
<212> TYPE: DNA
<213> ORGANISM: Artificial Sequence
<220> FEATURE:
<223> OTHER INFORMATION: Staple strand_0409 of the 3D DNA nanostructure.

<400> SEQUENCE: 410
gcaagaagcc tacgcgaagc tgtcgggacc acggcaatgt taccatctct cctaaactcg    60
```

<210> SEQ ID NO 411
<211> LENGTH: 60
<212> TYPE: DNA
<213> ORGANISM: Artificial Sequence
<220> FEATURE:
<223> OTHER INFORMATION: Staple strand_0410 of the 3D DNA nanostructure.

<400> SEQUENCE: 411
ctccgtgctt gttaccttcg agtcgcggca caccacacgt taccatctct cctaaactcg    60

<210> SEQ ID NO 412
<211> LENGTH: 60
<212> TYPE: DNA
<213> ORGANISM: Artificial Sequence
<220> FEATURE:
<223> OTHER INFORMATION: Staple strand_0411 of the 3D DNA nanostructure.

<400> SEQUENCE: 412
tctgctcccg tgaatcccgc tcgttcgttc tcccggctat taccatctct cctaaactcg    60

<210> SEQ ID NO 413
<211> LENGTH: 60
<212> TYPE: DNA
<213> ORGANISM: Artificial Sequence
<220> FEATURE:
<223> OTHER INFORMATION: Staple strand_0412 of the 3D DNA nanostructure.

<400> SEQUENCE: 413
atgggaatgt agaagcgctg caaatcgtcg cccgtgccgt taccatctct cctaaactcg    60

<210> SEQ ID NO 414
<211> LENGTH: 60
<212> TYPE: DNA
<213> ORGANISM: Artificial Sequence
<220> FEATURE:
<223> OTHER INFORMATION: Staple strand_0413 of the 3D DNA nanostructure.

<400> SEQUENCE: 414
gtctgctcgt agttagtcgc ctcgacgcac gacgggacct taccatctct cctaaactcg    60

<210> SEQ ID NO 415
<211> LENGTH: 60
<212> TYPE: DNA
<213> ORGANISM: Artificial Sequence
<220> FEATURE:
<223> OTHER INFORMATION: Staple strand_0414 of the 3D DNA nanostructure.

<400> SEQUENCE: 415
ggcccaacta gagaagcaga aggcatcccg gtcggccact taccatctct cctaaactcg    60

<210> SEQ ID NO 416
<211> LENGTH: 60
<212> TYPE: DNA
<213> ORGANISM: Artificial Sequence
<220> FEATURE:
<223> OTHER INFORMATION: Staple strand_0415 of the 3D DNA nanostructure.

<400> SEQUENCE: 416
agttcgcacc gccattctcg gcagactccc accgacatgt taccatctct cctaaactcg    60

<210> SEQ ID NO 417
<211> LENGTH: 60
<212> TYPE: DNA
<213> ORGANISM: Artificial Sequence
<220> FEATURE:

-continued

<223> OTHER INFORMATION: Staple strand_0416 of the 3D DNA nanostructure.

<400> SEQUENCE: 417
gaaaagcacg gcgtgcagtg gcccaggtag gtcgttccat taccatctct cctaaactcg    60

<210> SEQ ID NO 418
<211> LENGTH: 60
<212> TYPE: DNA
<213> ORGANISM: Artificial Sequence
<220> FEATURE:
<223> OTHER INFORMATION: Staple strand_0417 of the 3D DNA nanostructure.

<400> SEQUENCE: 418
ggtaatgcgt tcgggctact gcggtgtgag atcgtgcggt taccatctct cctaaactcg    60

<210> SEQ ID NO 419
<211> LENGTH: 60
<212> TYPE: DNA
<213> ORGANISM: Artificial Sequence
<220> FEATURE:
<223> OTHER INFORMATION: Staple strand_0418 of the 3D DNA nanostructure.

<400> SEQUENCE: 419
tctacgtagg catcagcgtc gcggcactac acgtgggtct taccatctct cctaaactcg    60

<210> SEQ ID NO 420
<211> LENGTH: 60
<212> TYPE: DNA
<213> ORGANISM: Artificial Sequence
<220> FEATURE:
<223> OTHER INFORMATION: Staple strand_0419 of the 3D DNA nanostructure.

<400> SEQUENCE: 420
cgaagggacg cgggaggcta gggaatgctg catcagtggt taccatctct cctaaactcg    60

<210> SEQ ID NO 421
<211> LENGTH: 39
<212> TYPE: DNA
<213> ORGANISM: Artificial Sequence
<220> FEATURE:
<223> OTHER INFORMATION: Staple strand_0420 of the 3D DNA nanostructure.

<400> SEQUENCE: 421
actccctgat aggcgtcttt caggcgggcg ggactcagg                           39

<210> SEQ ID NO 422
<211> LENGTH: 39
<212> TYPE: DNA
<213> ORGANISM: Artificial Sequence
<220> FEATURE:
<223> OTHER INFORMATION: Staple strand_0421 of the 3D DNA nanostructure.

<400> SEQUENCE: 422
gggacgccag actgggctca cgagtgatag gctttccgc                           39

<210> SEQ ID NO 423
<211> LENGTH: 39
<212> TYPE: DNA
<213> ORGANISM: Artificial Sequence
<220> FEATURE:
<223> OTHER INFORMATION: Staple strand_0422 of the 3D DNA nanostructure.

<400> SEQUENCE: 423
ttcggcttag gtccttctcg tgtggtgccc gctgccctt                           39

```
<210> SEQ ID NO 424
<211> LENGTH: 39
<212> TYPE: DNA
<213> ORGANISM: Artificial Sequence
<220> FEATURE:
<223> OTHER INFORMATION: Staple strand_0423 of the 3D DNA nanostructure.

<400> SEQUENCE: 424
gcgagccacg cggcgtgtaa ccaacagcat tttctcgct                             39

<210> SEQ ID NO 425
<211> LENGTH: 39
<212> TYPE: DNA
<213> ORGANISM: Artificial Sequence
<220> FEATURE:
<223> OTHER INFORMATION: Staple strand_0424 of the 3D DNA nanostructure.

<400> SEQUENCE: 425
tgcggcagca tcaaggacct accatcttga ccggtcgcc                             39

<210> SEQ ID NO 426
<211> LENGTH: 39
<212> TYPE: DNA
<213> ORGANISM: Artificial Sequence
<220> FEATURE:
<223> OTHER INFORMATION: Staple strand_0425 of the 3D DNA nanostructure.

<400> SEQUENCE: 426
actccagttg ctagaacggt ctcgcgcaca cacggtggg                             39

<210> SEQ ID NO 427
<211> LENGTH: 39
<212> TYPE: DNA
<213> ORGANISM: Artificial Sequence
<220> FEATURE:
<223> OTHER INFORMATION: Staple strand_0426 of the 3D DNA nanostructure.

<400> SEQUENCE: 427
cgtgctttga tccgactgac actgcgtggc cgatgggct                             39

<210> SEQ ID NO 428
<211> LENGTH: 39
<212> TYPE: DNA
<213> ORGANISM: Artificial Sequence
<220> FEATURE:
<223> OTHER INFORMATION: Staple strand_0427 of the 3D DNA nanostructure.

<400> SEQUENCE: 428
gtgcccgttg tgagtcggag aaccttgcgc ggcctattg                             39

<210> SEQ ID NO 429
<211> LENGTH: 39
<212> TYPE: DNA
<213> ORGANISM: Artificial Sequence
<220> FEATURE:
<223> OTHER INFORMATION: Staple strand_0428 of the 3D DNA nanostructure.

<400> SEQUENCE: 429
cgcagggacg ccgtcgaaac acagcactcc acatcgtac                             39

<210> SEQ ID NO 430
<211> LENGTH: 39
<212> TYPE: DNA
<213> ORGANISM: Artificial Sequence
<220> FEATURE:
<223> OTHER INFORMATION: Staple strand_0429 of the 3D DNA nanostructure.
```

<400> SEQUENCE: 430
cacgactctc acacggagcc agcctatctc ccgttgcgg                    39

<210> SEQ ID NO 431
<211> LENGTH: 39
<212> TYPE: DNA
<213> ORGANISM: Artificial Sequence
<220> FEATURE:
<223> OTHER INFORMATION: Staple strand_0430 of the 3D DNA nanostructure.

<400> SEQUENCE: 431
aacagccttg gaccggtcgc tcacagtcct ttcgtgccc                    39

<210> SEQ ID NO 432
<211> LENGTH: 39
<212> TYPE: DNA
<213> ORGANISM: Artificial Sequence
<220> FEATURE:
<223> OTHER INFORMATION: Staple strand_0431 of the 3D DNA nanostructure.

<400> SEQUENCE: 432
ctcgtcgttt ccgttcttgc agtgctgcca gaggcggtg                    39

<210> SEQ ID NO 433
<211> LENGTH: 39
<212> TYPE: DNA
<213> ORGANISM: Artificial Sequence
<220> FEATURE:
<223> OTHER INFORMATION: Staple strand_0432 of the 3D DNA nanostructure.

<400> SEQUENCE: 433
agaaggaaag tctcaccggg cgccctaggc cttccgagg                    39

<210> SEQ ID NO 434
<211> LENGTH: 39
<212> TYPE: DNA
<213> ORGANISM: Artificial Sequence
<220> FEATURE:
<223> OTHER INFORMATION: Staple strand_0433 of the 3D DNA nanostructure.

<400> SEQUENCE: 434
gcctcaatgc tcttcacctg ggtccatgcc cggacggag                    39

<210> SEQ ID NO 435
<211> LENGTH: 39
<212> TYPE: DNA
<213> ORGANISM: Artificial Sequence
<220> FEATURE:
<223> OTHER INFORMATION: Staple strand_0434 of the 3D DNA nanostructure.

<400> SEQUENCE: 435
agcagctgac aacctagacg tgtgcctcgg gtagtgcgc                    39

<210> SEQ ID NO 436
<211> LENGTH: 39
<212> TYPE: DNA
<213> ORGANISM: Artificial Sequence
<220> FEATURE:
<223> OTHER INFORMATION: Staple strand_0435 of the 3D DNA nanostructure.

<400> SEQUENCE: 436
gaacagagcg cccgtttcgc cgaacgcggt ggataaaca                    39

<210> SEQ ID NO 437
<211> LENGTH: 39

```
<212> TYPE: DNA
<213> ORGANISM: Artificial Sequence
<220> FEATURE:
<223> OTHER INFORMATION: Staple strand_0436 of the 3D DNA nanostructure.

<400> SEQUENCE: 437
acttccggcc cgccgcactc atgcctgtac gggtttagt                          39

<210> SEQ ID NO 438
<211> LENGTH: 39
<212> TYPE: DNA
<213> ORGANISM: Artificial Sequence
<220> FEATURE:
<223> OTHER INFORMATION: Staple strand_0437 of the 3D DNA nanostructure.

<400> SEQUENCE: 438
catttacgtc gccagccgcc ggtatccatc tgcgagcac                          39

<210> SEQ ID NO 439
<211> LENGTH: 39
<212> TYPE: DNA
<213> ORGANISM: Artificial Sequence
<220> FEATURE:
<223> OTHER INFORMATION: Staple strand_0438 of the 3D DNA nanostructure.

<400> SEQUENCE: 439
agcagcggca tctccagttt tgggccaggg ttgggatcc                          39

<210> SEQ ID NO 440
<211> LENGTH: 39
<212> TYPE: DNA
<213> ORGANISM: Artificial Sequence
<220> FEATURE:
<223> OTHER INFORMATION: Staple strand_0439 of the 3D DNA nanostructure.

<400> SEQUENCE: 440
gcatatgcga atcgactcca acgcgcgaaa ggacgggct                          39

<210> SEQ ID NO 441
<211> LENGTH: 39
<212> TYPE: DNA
<213> ORGANISM: Artificial Sequence
<220> FEATURE:
<223> OTHER INFORMATION: Staple strand_0440 of the 3D DNA nanostructure.

<400> SEQUENCE: 441
ggcactagcc tcggccacaa actgtaggcg cgctatcga                          39

<210> SEQ ID NO 442
<211> LENGTH: 39
<212> TYPE: DNA
<213> ORGANISM: Artificial Sequence
<220> FEATURE:
<223> OTHER INFORMATION: Staple strand_0441 of the 3D DNA nanostructure.

<400> SEQUENCE: 442
ctgctcgcgc gttgaaccta gcctcgagtg gcattgacg                          39

<210> SEQ ID NO 443
<211> LENGTH: 39
<212> TYPE: DNA
<213> ORGANISM: Artificial Sequence
<220> FEATURE:
<223> OTHER INFORMATION: Staple strand_0442 of the 3D DNA nanostructure.

<400> SEQUENCE: 443
```
tcaattccgc gcggagagag aacaacaacc acgcaccgg      39

<210> SEQ ID NO 444
<211> LENGTH: 39
<212> TYPE: DNA
<213> ORGANISM: Artificial Sequence
<220> FEATURE:
<223> OTHER INFORMATION: Staple strand_0443 of the 3D DNA nanostructure.

<400> SEQUENCE: 444
tgaccaccgt cgaaccatcc ggcagtcggg ccataagct      39

<210> SEQ ID NO 445
<211> LENGTH: 39
<212> TYPE: DNA
<213> ORGANISM: Artificial Sequence
<220> FEATURE:
<223> OTHER INFORMATION: Staple strand_0444 of the 3D DNA nanostructure.

<400> SEQUENCE: 445
cctcaacctc gctcgaacgt acgcagccgc aacactgga      39

<210> SEQ ID NO 446
<211> LENGTH: 39
<212> TYPE: DNA
<213> ORGANISM: Artificial Sequence
<220> FEATURE:
<223> OTHER INFORMATION: Staple strand_0445 of the 3D DNA nanostructure.

<400> SEQUENCE: 446
gaagcggcat agctccgtcc tcgggtagta aagcgcgca      39

<210> SEQ ID NO 447
<211> LENGTH: 39
<212> TYPE: DNA
<213> ORGANISM: Artificial Sequence
<220> FEATURE:
<223> OTHER INFORMATION: Staple strand_0446 of the 3D DNA nanostructure.

<400> SEQUENCE: 447
gggaacagcg cataattcgc cgtgtgtgtg gccatcgca      39

<210> SEQ ID NO 448
<211> LENGTH: 39
<212> TYPE: DNA
<213> ORGANISM: Artificial Sequence
<220> FEATURE:
<223> OTHER INFORMATION: Staple strand_0447 of the 3D DNA nanostructure.

<400> SEQUENCE: 448
cgacgccaca acgaacggcc tcctcgaaac cttgtgagg      39

<210> SEQ ID NO 449
<211> LENGTH: 39
<212> TYPE: DNA
<213> ORGANISM: Artificial Sequence
<220> FEATURE:
<223> OTHER INFORMATION: Staple strand_0448 of the 3D DNA nanostructure.

<400> SEQUENCE: 449
gggatgtaac accacgtggc gcacgcactg tgtaggagc      39

<210> SEQ ID NO 450
<211> LENGTH: 39
<212> TYPE: DNA
<213> ORGANISM: Artificial Sequence

```
<220> FEATURE:
<223> OTHER INFORMATION: Staple strand_0449 of the 3D DNA nanostructure.

<400> SEQUENCE: 450
ctgggaggta cagctagggt gaccggcctc ctgccctca                               39

<210> SEQ ID NO 451
<211> LENGTH: 39
<212> TYPE: DNA
<213> ORGANISM: Artificial Sequence
<220> FEATURE:
<223> OTHER INFORMATION: Staple strand_0450 of the 3D DNA nanostructure.

<400> SEQUENCE: 451
gcccttgcca cagacccgca cagcgagttc tggcttcat                               39

<210> SEQ ID NO 452
<211> LENGTH: 39
<212> TYPE: DNA
<213> ORGANISM: Artificial Sequence
<220> FEATURE:
<223> OTHER INFORMATION: Staple strand_0451 of the 3D DNA nanostructure.

<400> SEQUENCE: 452
gcgcaacgtg acggtacgcc aacggtcacc agaagtcag                               39

<210> SEQ ID NO 453
<211> LENGTH: 39
<212> TYPE: DNA
<213> ORGANISM: Artificial Sequence
<220> FEATURE:
<223> OTHER INFORMATION: Staple strand_0452 of the 3D DNA nanostructure.

<400> SEQUENCE: 453
cggccaacct caaaggcgtc cacggcgaat ctgcgtcta                               39

<210> SEQ ID NO 454
<211> LENGTH: 39
<212> TYPE: DNA
<213> ORGANISM: Artificial Sequence
<220> FEATURE:
<223> OTHER INFORMATION: Staple strand_0453 of the 3D DNA nanostructure.

<400> SEQUENCE: 454
cgcgcatagg gagtgtgctg gcgggctgcg agtaagaat                               39

<210> SEQ ID NO 455
<211> LENGTH: 39
<212> TYPE: DNA
<213> ORGANISM: Artificial Sequence
<220> FEATURE:
<223> OTHER INFORMATION: Staple strand_0454 of the 3D DNA nanostructure.

<400> SEQUENCE: 455
ctcaggaagc gagcagtaaa tccttggccg accgcagcg                               39

<210> SEQ ID NO 456
<211> LENGTH: 39
<212> TYPE: DNA
<213> ORGANISM: Artificial Sequence
<220> FEATURE:
<223> OTHER INFORMATION: Staple strand_0455 of the 3D DNA nanostructure.

<400> SEQUENCE: 456
gagcagagca gcttatccct gggtctccgg catctgcgc                               39
```

<210> SEQ ID NO 457
<211> LENGTH: 39
<212> TYPE: DNA
<213> ORGANISM: Artificial Sequence
<220> FEATURE:
<223> OTHER INFORMATION: Staple strand_0456 of the 3D DNA nanostructure.

<400> SEQUENCE: 457
tggtgttccc tttcgccgcc ttgcaagtcc catcatgcc                                39

<210> SEQ ID NO 458
<211> LENGTH: 39
<212> TYPE: DNA
<213> ORGANISM: Artificial Sequence
<220> FEATURE:
<223> OTHER INFORMATION: Staple strand_0457 of the 3D DNA nanostructure.

<400> SEQUENCE: 458
gcaagaagcc tacgcgaagc tgtcgggacc acggcaatg                                39

<210> SEQ ID NO 459
<211> LENGTH: 39
<212> TYPE: DNA
<213> ORGANISM: Artificial Sequence
<220> FEATURE:
<223> OTHER INFORMATION: Staple strand_0458 of the 3D DNA nanostructure.

<400> SEQUENCE: 459
ctccgtgctt gttaccttcg agtcgcggca caccacacg                                39

<210> SEQ ID NO 460
<211> LENGTH: 39
<212> TYPE: DNA
<213> ORGANISM: Artificial Sequence
<220> FEATURE:
<223> OTHER INFORMATION: Staple strand_0459 of the 3D DNA nanostructure.

<400> SEQUENCE: 460
tctgctcccg tgaatcccgc tcgttcgttc tcccggcta                                39

<210> SEQ ID NO 461
<211> LENGTH: 39
<212> TYPE: DNA
<213> ORGANISM: Artificial Sequence
<220> FEATURE:
<223> OTHER INFORMATION: Staple strand_0460 of the 3D DNA nanostructure.

<400> SEQUENCE: 461
atgggaatgt agaagcgctg caaatcgtcg cccgtgccg                                39

<210> SEQ ID NO 462
<211> LENGTH: 39
<212> TYPE: DNA
<213> ORGANISM: Artificial Sequence
<220> FEATURE:
<223> OTHER INFORMATION: Staple strand_0461 of the 3D DNA nanostructure.

<400> SEQUENCE: 462
gtctgctcgt agttagtcgc ctcgacgcac gacgggacc                                39

<210> SEQ ID NO 463
<211> LENGTH: 39
<212> TYPE: DNA
<213> ORGANISM: Artificial Sequence
<220> FEATURE:
<223> OTHER INFORMATION: Staple strand_0462 of the 3D DNA nanostructure.

```
<400> SEQUENCE: 463
ggcccaacta gagaagcaga aggcatcccg gtcggccac                                39

<210> SEQ ID NO 464
<211> LENGTH: 39
<212> TYPE: DNA
<213> ORGANISM: Artificial Sequence
<220> FEATURE:
<223> OTHER INFORMATION: Staple strand_0463 of the 3D DNA nanostructure.

<400> SEQUENCE: 464
agttcgcacc gccattctcg gcagactccc accgacatg                                39

<210> SEQ ID NO 465
<211> LENGTH: 39
<212> TYPE: DNA
<213> ORGANISM: Artificial Sequence
<220> FEATURE:
<223> OTHER INFORMATION: Staple strand_0464 of the 3D DNA nanostructure.

<400> SEQUENCE: 465
gaaaagcacg gcgtgcagtg gcccaggtag gtcgttcca                                39

<210> SEQ ID NO 466
<211> LENGTH: 39
<212> TYPE: DNA
<213> ORGANISM: Artificial Sequence
<220> FEATURE:
<223> OTHER INFORMATION: Staple strand_0465 of the 3D DNA nanostructure.

<400> SEQUENCE: 466
ggtaatgcgt tcgggctact gcggtgtgag atcgtgcgg                                39

<210> SEQ ID NO 467
<211> LENGTH: 39
<212> TYPE: DNA
<213> ORGANISM: Artificial Sequence
<220> FEATURE:
<223> OTHER INFORMATION: Staple strand_0466 of the 3D DNA nanostructure.

<400> SEQUENCE: 467
tctacgtagg catcagcgtc gcggcactac acgtgggtc                                39

<210> SEQ ID NO 468
<211> LENGTH: 39
<212> TYPE: DNA
<213> ORGANISM: Artificial Sequence
<220> FEATURE:
<223> OTHER INFORMATION: Staple strand_0467 of the 3D DNA nanostructure.

<400> SEQUENCE: 468
cgaagggacg cgggaggcta gggaatgctg catcagtgg                                39

<210> SEQ ID NO 469
<211> LENGTH: 60
<212> TYPE: DNA
<213> ORGANISM: Artificial Sequence
<220> FEATURE:
<223> OTHER INFORMATION: Staple strand_0468 of the 3D DNA nanostructure.

<400> SEQUENCE: 469
cctacagggt tagctccaca gccgggtccg tgcagatgct tcctctacca cctacatcac         60

<210> SEQ ID NO 470
```

```
<211> LENGTH: 60
<212> TYPE: DNA
<213> ORGANISM: Artificial Sequence
<220> FEATURE:
<223> OTHER INFORMATION: Staple strand_0469 of the 3D DNA nanostructure.

<400> SEQUENCE: 470
agaggcctcc tcagcggtcc tacgcggtct tggacgatgt tcctctacca cctacatcac    60

<210> SEQ ID NO 471
<211> LENGTH: 60
<212> TYPE: DNA
<213> ORGANISM: Artificial Sequence
<220> FEATURE:
<223> OTHER INFORMATION: Staple strand_0470 of the 3D DNA nanostructure.

<400> SEQUENCE: 471
cgtactcatc ccgtgccagt gccggcctac tcacctgtgt tcctctacca cctacatcac    60

<210> SEQ ID NO 472
<211> LENGTH: 60
<212> TYPE: DNA
<213> ORGANISM: Artificial Sequence
<220> FEATURE:
<223> OTHER INFORMATION: Staple strand_0471 of the 3D DNA nanostructure.

<400> SEQUENCE: 472
gcctgcgaca atgtgggctg gaacggtttg ctagggcact tcctctacca cctacatcac    60

<210> SEQ ID NO 473
<211> LENGTH: 60
<212> TYPE: DNA
<213> ORGANISM: Artificial Sequence
<220> FEATURE:
<223> OTHER INFORMATION: Staple strand_0472 of the 3D DNA nanostructure.

<400> SEQUENCE: 473
cacccgatgt gttatgacgt gcgtcgccct cgagcacctt tcctctacca cctacatcac    60

<210> SEQ ID NO 474
<211> LENGTH: 60
<212> TYPE: DNA
<213> ORGANISM: Artificial Sequence
<220> FEATURE:
<223> OTHER INFORMATION: Staple strand_0473 of the 3D DNA nanostructure.

<400> SEQUENCE: 474
agcatacaga gggcagcttg gcagggccgc gaagttaggt tcctctacca cctacatcac    60

<210> SEQ ID NO 475
<211> LENGTH: 60
<212> TYPE: DNA
<213> ORGANISM: Artificial Sequence
<220> FEATURE:
<223> OTHER INFORMATION: Staple strand_0474 of the 3D DNA nanostructure.

<400> SEQUENCE: 475
gacgcccgat tgtccttgtt cgccatgccg caaggtgagt tcctctacca cctacatcac    60

<210> SEQ ID NO 476
<211> LENGTH: 60
<212> TYPE: DNA
<213> ORGANISM: Artificial Sequence
<220> FEATURE:
<223> OTHER INFORMATION: Staple strand_0475 of the 3D DNA nanostructure.

<400> SEQUENCE: 476
```
ggtggcgaga tgacgacagt gcagaaggtg gcggtagggt tcctctacca cctacatcac    60

<210> SEQ ID NO 477
<211> LENGTH: 60
<212> TYPE: DNA
<213> ORGANISM: Artificial Sequence
<220> FEATURE:
<223> OTHER INFORMATION: Staple strand_0476 of the 3D DNA nanostructure.

<400> SEQUENCE: 477
tctgtgaagc gggtggagta cggaggtgtt cttcgcgcct tcctctacca cctacatcac    60

<210> SEQ ID NO 478
<211> LENGTH: 60
<212> TYPE: DNA
<213> ORGANISM: Artificial Sequence
<220> FEATURE:
<223> OTHER INFORMATION: Staple strand_0477 of the 3D DNA nanostructure.

<400> SEQUENCE: 478
ttttgcgcaa tcatggcagc ggactcaaca ccctccggct tcctctacca cctacatcac    60

<210> SEQ ID NO 479
<211> LENGTH: 60
<212> TYPE: DNA
<213> ORGANISM: Artificial Sequence
<220> FEATURE:
<223> OTHER INFORMATION: Staple strand_0478 of the 3D DNA nanostructure.

<400> SEQUENCE: 479
gacctcggag ctagacggga gtgttgcgtg tgcagggtgt tcctctacca cctacatcac    60

<210> SEQ ID NO 480
<211> LENGTH: 60
<212> TYPE: DNA
<213> ORGANISM: Artificial Sequence
<220> FEATURE:
<223> OTHER INFORMATION: Staple strand_0479 of the 3D DNA nanostructure.

<400> SEQUENCE: 480
cggttcgagt gcgcagtgct taacgtgaag cgagggaggt tcctctacca cctacatcac    60

<210> SEQ ID NO 481
<211> LENGTH: 60
<212> TYPE: DNA
<213> ORGANISM: Artificial Sequence
<220> FEATURE:
<223> OTHER INFORMATION: Staple strand_0480 of the 3D DNA nanostructure.

<400> SEQUENCE: 481
cctacagggt tagctccaca gccgggtccg tgcagatgct aacattccta acttctcata    60

<210> SEQ ID NO 482
<211> LENGTH: 60
<212> TYPE: DNA
<213> ORGANISM: Artificial Sequence
<220> FEATURE:
<223> OTHER INFORMATION: Staple strand_0481 of the 3D DNA nanostructure.

<400> SEQUENCE: 482
agaggcctcc tcagcggtcc tacgcggtct tggacgatgt aacattccta acttctcata    60

<210> SEQ ID NO 483
<211> LENGTH: 60
<212> TYPE: DNA

```
<213> ORGANISM: Artificial Sequence
<220> FEATURE:
<223> OTHER INFORMATION: Staple strand_0482 of the 3D DNA nanostructure.

<400> SEQUENCE: 483
cgtactcatc ccgtgccagt gccggcctac tcacctgtgt aacattccta acttctcata    60

<210> SEQ ID NO 484
<211> LENGTH: 60
<212> TYPE: DNA
<213> ORGANISM: Artificial Sequence
<220> FEATURE:
<223> OTHER INFORMATION: Staple strand_0483 of the 3D DNA nanostructure.

<400> SEQUENCE: 484
gcctgcgaca atgtgggctg gaacggtttg ctagggcact aacattccta acttctcata    60

<210> SEQ ID NO 485
<211> LENGTH: 60
<212> TYPE: DNA
<213> ORGANISM: Artificial Sequence
<220> FEATURE:
<223> OTHER INFORMATION: Staple strand_0484 of the 3D DNA nanostructure.

<400> SEQUENCE: 485
cacccgatgt gttatgacgt gcgtcgccct cgagcacctt aacattccta acttctcata    60

<210> SEQ ID NO 486
<211> LENGTH: 60
<212> TYPE: DNA
<213> ORGANISM: Artificial Sequence
<220> FEATURE:
<223> OTHER INFORMATION: Staple strand_0485 of the 3D DNA nanostructure.

<400> SEQUENCE: 486
agcatacaga gggcagcttg gcagggccgc gaagttaggt aacattccta acttctcata    60

<210> SEQ ID NO 487
<211> LENGTH: 60
<212> TYPE: DNA
<213> ORGANISM: Artificial Sequence
<220> FEATURE:
<223> OTHER INFORMATION: Staple strand_0486 of the 3D DNA nanostructure.

<400> SEQUENCE: 487
gacgcccgat tgtccttgtt cgccatgccg caaggtgagt aacattccta acttctcata    60

<210> SEQ ID NO 488
<211> LENGTH: 60
<212> TYPE: DNA
<213> ORGANISM: Artificial Sequence
<220> FEATURE:
<223> OTHER INFORMATION: Staple strand_0487 of the 3D DNA nanostructure.

<400> SEQUENCE: 488
ggtggcgaga tgacgacagt gcagaaggtg gcggtagggt aacattccta acttctcata    60

<210> SEQ ID NO 489
<211> LENGTH: 60
<212> TYPE: DNA
<213> ORGANISM: Artificial Sequence
<220> FEATURE:
<223> OTHER INFORMATION: Staple strand_0488 of the 3D DNA nanostructure.

<400> SEQUENCE: 489
tctgtgaagc gggtggagta cggaggtgtt cttcgcgcct aacattccta acttctcata    60
```

<210> SEQ ID NO 490
<211> LENGTH: 60
<212> TYPE: DNA
<213> ORGANISM: Artificial Sequence
<220> FEATURE:
<223> OTHER INFORMATION: Staple strand_0489 of the 3D DNA nanostructure.

<400> SEQUENCE: 490
ttttgcgcaa tcatggcagc ggactcaaca ccctccggct aacattccta acttctcata    60

<210> SEQ ID NO 491
<211> LENGTH: 60
<212> TYPE: DNA
<213> ORGANISM: Artificial Sequence
<220> FEATURE:
<223> OTHER INFORMATION: Staple strand_0490 of the 3D DNA nanostructure.

<400> SEQUENCE: 491
gacctcggag ctagacggga gtgttgcgtg tgcagggtgt aacattccta acttctcata    60

<210> SEQ ID NO 492
<211> LENGTH: 60
<212> TYPE: DNA
<213> ORGANISM: Artificial Sequence
<220> FEATURE:
<223> OTHER INFORMATION: Staple strand_0491 of the 3D DNA nanostructure.

<400> SEQUENCE: 492
cggttcgagt gcgcagtgct taacgtgaag cgagggaggt aacattccta acttctcata    60

<210> SEQ ID NO 493
<211> LENGTH: 60
<212> TYPE: DNA
<213> ORGANISM: Artificial Sequence
<220> FEATURE:
<223> OTHER INFORMATION: Staple strand_0492 of the 3D DNA nanostructure.

<400> SEQUENCE: 493
cctacagggt tagctccaca gccgggtccg tgcagatgct taccatctct cctaaactcg    60

<210> SEQ ID NO 494
<211> LENGTH: 60
<212> TYPE: DNA
<213> ORGANISM: Artificial Sequence
<220> FEATURE:
<223> OTHER INFORMATION: Staple strand_0493 of the 3D DNA nanostructure.

<400> SEQUENCE: 494
agaggcctcc tcagcggtcc tacgcggtct tggacgatgt taccatctct cctaaactcg    60

<210> SEQ ID NO 495
<211> LENGTH: 60
<212> TYPE: DNA
<213> ORGANISM: Artificial Sequence
<220> FEATURE:
<223> OTHER INFORMATION: Staple strand_0494 of the 3D DNA nanostructure.

<400> SEQUENCE: 495
cgtactcatc ccgtgccagt gccggcctac tcacctgtgt taccatctct cctaaactcg    60

<210> SEQ ID NO 496
<211> LENGTH: 60
<212> TYPE: DNA
<213> ORGANISM: Artificial Sequence
<220> FEATURE:

<223> OTHER INFORMATION: Staple strand_0495 of the 3D DNA nanostructure.

<400> SEQUENCE: 496
gcctgcgaca atgtgggctg aacggtttg ctagggcact taccatctct cctaaactcg         60

<210> SEQ ID NO 497
<211> LENGTH: 60
<212> TYPE: DNA
<213> ORGANISM: Artificial Sequence
<220> FEATURE:
<223> OTHER INFORMATION: Staple strand_0496 of the 3D DNA nanostructure.

<400> SEQUENCE: 497
cacccgatgt gttatgacgt gcgtcgccct cgagcacctt taccatctct cctaaactcg         60

<210> SEQ ID NO 498
<211> LENGTH: 60
<212> TYPE: DNA
<213> ORGANISM: Artificial Sequence
<220> FEATURE:
<223> OTHER INFORMATION: Staple strand_0497 of the 3D DNA nanostructure.

<400> SEQUENCE: 498
agcatacaga gggcagcttg gcagggccgc gaagttaggt taccatctct cctaaactcg         60

<210> SEQ ID NO 499
<211> LENGTH: 60
<212> TYPE: DNA
<213> ORGANISM: Artificial Sequence
<220> FEATURE:
<223> OTHER INFORMATION: Staple strand_0498 of the 3D DNA nanostructure.

<400> SEQUENCE: 499
gacgcccgat tgtccttgtt cgccatgccg caaggtgagt taccatctct cctaaactcg         60

<210> SEQ ID NO 500
<211> LENGTH: 60
<212> TYPE: DNA
<213> ORGANISM: Artificial Sequence
<220> FEATURE:
<223> OTHER INFORMATION: Staple strand_0499 of the 3D DNA nanostructure.

<400> SEQUENCE: 500
ggtggcgaga tgacgacagt gcagaaggtg gcggtagggt taccatctct cctaaactcg         60

<210> SEQ ID NO 501
<211> LENGTH: 60
<212> TYPE: DNA
<213> ORGANISM: Artificial Sequence
<220> FEATURE:
<223> OTHER INFORMATION: Staple strand_0500 of the 3D DNA nanostructure.

<400> SEQUENCE: 501
tctgtgaagc gggtggagta cggaggtgtt cttcgcgcct taccatctct cctaaactcg         60

<210> SEQ ID NO 502
<211> LENGTH: 60
<212> TYPE: DNA
<213> ORGANISM: Artificial Sequence
<220> FEATURE:
<223> OTHER INFORMATION: Staple strand_0501 of the 3D DNA nanostructure.

<400> SEQUENCE: 502
ttttgcgcaa tcatggcagc ggactcaaca ccctccggct taccatctct cctaaactcg         60

-continued

```
<210> SEQ ID NO 503
<211> LENGTH: 60
<212> TYPE: DNA
<213> ORGANISM: Artificial Sequence
<220> FEATURE:
<223> OTHER INFORMATION: Staple strand_0502 of the 3D DNA nanostructure.

<400> SEQUENCE: 503
gacctcggag ctagacggga gtgttgcgtg tgcagggtgt taccatctct cctaaactcg      60

<210> SEQ ID NO 504
<211> LENGTH: 60
<212> TYPE: DNA
<213> ORGANISM: Artificial Sequence
<220> FEATURE:
<223> OTHER INFORMATION: Staple strand_0503 of the 3D DNA nanostructure.

<400> SEQUENCE: 504
cggttcgagt gcgcagtgct taacgtgaag cgagggaggt taccatctct cctaaactcg      60

<210> SEQ ID NO 505
<211> LENGTH: 31
<212> TYPE: DNA
<213> ORGANISM: Artificial Sequence
<220> FEATURE:
<223> OTHER INFORMATION: Staple strand_0504 of the 2D DNA nanostructure.

<400> SEQUENCE: 505
agaaaggaac aactaaagga attcaaaaaa a                                     31

<210> SEQ ID NO 506
<211> LENGTH: 30
<212> TYPE: DNA
<213> ORGANISM: Artificial Sequence
<220> FEATURE:
<223> OTHER INFORMATION: Staple strand_0505 of the 2D DNA nanostructure.

<400> SEQUENCE: 506
aggctccaga ggctttgagg acacgggtaa                                       30

<210> SEQ ID NO 507
<211> LENGTH: 32
<212> TYPE: DNA
<213> ORGANISM: Artificial Sequence
<220> FEATURE:
<223> OTHER INFORMATION: Staple strand_0506 of the 2D DNA nanostructure.

<400> SEQUENCE: 507
acggctacaa aaggagcctt taatgtgaga at                                    32

<210> SEQ ID NO 508
<211> LENGTH: 30
<212> TYPE: DNA
<213> ORGANISM: Artificial Sequence
<220> FEATURE:
<223> OTHER INFORMATION: Staple strand_0507 of the 2D DNA nanostructure.

<400> SEQUENCE: 508
aatacgtttg aaagaggaca gactgacctt                                       30

<210> SEQ ID NO 509
<211> LENGTH: 32
<212> TYPE: DNA
<213> ORGANISM: Artificial Sequence
<220> FEATURE:
<223> OTHER INFORMATION: Staple strand_0508 of the 2D DNA nanostructure.
```

<400> SEQUENCE: 509
gaccaactaa tgccactacg aagggggtag ca                                      32

<210> SEQ ID NO 510
<211> LENGTH: 30
<212> TYPE: DNA
<213> ORGANISM: Artificial Sequence
<220> FEATURE:
<223> OTHER INFORMATION: Staple strand_0509 of the 2D DNA nanostructure.

<400> SEQUENCE: 510
catcaagtaa aacgaactaa cgagttgaga                                         30

<210> SEQ ID NO 511
<211> LENGTH: 32
<212> TYPE: DNA
<213> ORGANISM: Artificial Sequence
<220> FEATURE:
<223> OTHER INFORMATION: Staple strand_0510 of the 2D DNA nanostructure.

<400> SEQUENCE: 511
tacgttaaag taatcttgac aagaaccgaa ct                                      32

<210> SEQ ID NO 512
<211> LENGTH: 30
<212> TYPE: DNA
<213> ORGANISM: Artificial Sequence
<220> FEATURE:
<223> OTHER INFORMATION: Staple strand_0511 of the 2D DNA nanostructure.

<400> SEQUENCE: 512
tttaggacaa atgcttaaa caatcaggtc                                          30

<210> SEQ ID NO 513
<211> LENGTH: 32
<212> TYPE: DNA
<213> ORGANISM: Artificial Sequence
<220> FEATURE:
<223> OTHER INFORMATION: Staple strand_0512 of the 2D DNA nanostructure.

<400> SEQUENCE: 513 atcccctat accacattca actagaaaaa tc                                       32

<210> SEQ ID NO 514
<211> LENGTH: 30
<212> TYPE: DNA
<213> ORGANISM: Artificial Sequence
<220> FEATURE:
<223> OTHER INFORMATION: Staple strand_0513 of the 2D DNA nanostructure.

<400> SEQUENCE: 514
tttaccccaa catgttttaa atttccatat                                         30

<210> SEQ ID NO 515
<211> LENGTH: 32
<212> TYPE: DNA
<213> ORGANISM: Artificial Sequence
<220> FEATURE:
<223> OTHER INFORMATION: Staple strand_0514 of the 2D DNA nanostructure.

<400> SEQUENCE: 515
ctgtagcttg actattatag tcagttcatt ga                                      32

<210> SEQ ID NO 516
<211> LENGTH: 30

-continued

<212> TYPE: DNA
<213> ORGANISM: Artificial Sequence
<220> FEATURE:
<223> OTHER INFORMATION: Staple strand_0515 of the 2D DNA nanostructure.

<400> SEQUENCE: 516
aacagttttg taccaaaaac attttatttc                                    30

<210> SEQ ID NO 517
<211> LENGTH: 32
<212> TYPE: DNA
<213> ORGANISM: Artificial Sequence
<220> FEATURE:
<223> OTHER INFORMATION: Staple strand_0516 of the 2D DNA nanostructure.

<400> SEQUENCE: 517
acaactttca acagtttcag cggatgtatc gg                                 32

<210> SEQ ID NO 518
<211> LENGTH: 32
<212> TYPE: DNA
<213> ORGANISM: Artificial Sequence
<220> FEATURE:
<223> OTHER INFORMATION: Staple strand_0517 of the 2D DNA nanostructure.

<400> SEQUENCE: 518
tttatcagga cagcatcgga acgacaccaa cc                                 32

<210> SEQ ID NO 519
<211> LENGTH: 30
<212> TYPE: DNA
<213> ORGANISM: Artificial Sequence
<220> FEATURE:
<223> OTHER INFORMATION: Staple strand_0518 of the 2D DNA nanostructure.

<400> SEQUENCE: 519
cagcgaaact tgctttcgag gtgttgctaa                                    30

<210> SEQ ID NO 520
<211> LENGTH: 32
<212> TYPE: DNA
<213> ORGANISM: Artificial Sequence
<220> FEATURE:
<223> OTHER INFORMATION: Staple strand_0519 of the 2D DNA nanostructure.

<400> SEQUENCE: 520
taaaacgagg tcaatcataa gggaaccgga ta                                 32

<210> SEQ ID NO 521
<211> LENGTH: 30
<212> TYPE: DNA
<213> ORGANISM: Artificial Sequence
<220> FEATURE:
<223> OTHER INFORMATION: Staple strand_0520 of the 2D DNA nanostructure.

<400> SEQUENCE: 521
gcgcagacaa gaggcaaaag aatccctcag                                    30

<210> SEQ ID NO 522
<211> LENGTH: 32
<212> TYPE: DNA
<213> ORGANISM: Artificial Sequence
<220> FEATURE:
<223> OTHER INFORMATION: Staple strand_0521 of the 2D DNA nanostructure.

<400> SEQUENCE: 522
ttcattacgt caggacgttg ggaaatgcag at         32

<210> SEQ ID NO 523
<211> LENGTH: 30
<212> TYPE: DNA
<213> ORGANISM: Artificial Sequence
<220> FEATURE:
<223> OTHER INFORMATION: Staple strand_0522 of the 2D DNA nanostructure.

<400> SEQUENCE: 523
ttataccacc aaatcaacgt aacgaacgag         30

<210> SEQ ID NO 524
<211> LENGTH: 32
<212> TYPE: DNA
<213> ORGANISM: Artificial Sequence
<220> FEATURE:
<223> OTHER INFORMATION: Staple strand_0523 of the 2D DNA nanostructure.

<400> SEQUENCE: 524
acataacggg aatcgtcata aataaagcaa ag         32

<210> SEQ ID NO 525
<211> LENGTH: 30
<212> TYPE: DNA
<213> ORGANISM: Artificial Sequence
<220> FEATURE:
<223> OTHER INFORMATION: Staple strand_0524 of the 2D DNA nanostructure.

<400> SEQUENCE: 525
aatactgccc aaaggaatt acgtggctca         30

<210> SEQ ID NO 526
<211> LENGTH: 32
<212> TYPE: DNA
<213> ORGANISM: Artificial Sequence
<220> FEATURE:
<223> OTHER INFORMATION: Staple strand_0525 of the 2D DNA nanostructure.

<400> SEQUENCE: 526
cggattgcag agcttaattg ctgaaacgag ta         32

<210> SEQ ID NO 527
<211> LENGTH: 30
<212> TYPE: DNA
<213> ORGANISM: Artificial Sequence
<220> FEATURE:
<223> OTHER INFORMATION: Staple strand_0526 of the 2D DNA nanostructure.

<400> SEQUENCE: 527
gatggcttat caaaaagatt aagagcgtcc         30

<210> SEQ ID NO 528
<211> LENGTH: 32
<212> TYPE: DNA
<213> ORGANISM: Artificial Sequence
<220> FEATURE:
<223> OTHER INFORMATION: Staple strand_0527 of the 2D DNA nanostructure.

<400> SEQUENCE: 528
gatttagtca ataaagcctc agagaaccct ca         32

<210> SEQ ID NO 529
<211> LENGTH: 32
<212> TYPE: DNA
<213> ORGANISM: Artificial Sequence

```
<220> FEATURE:
<223> OTHER INFORMATION: Staple strand_0528 of the 2D DNA nanostructure.

<400> SEQUENCE: 529
taaatgaatt ttctgtatgg gattaatttc tt                                32

<210> SEQ ID NO 530
<211> LENGTH: 32
<212> TYPE: DNA
<213> ORGANISM: Artificial Sequence
<220> FEATURE:
<223> OTHER INFORMATION: Staple strand_0529 of the 2D DNA nanostructure.

<400> SEQUENCE: 530
aaacagcttt ttgcgggatc gtcaacacta aa                                32

<210> SEQ ID NO 531
<211> LENGTH: 32
<212> TYPE: DNA
<213> ORGANISM: Artificial Sequence
<220> FEATURE:
<223> OTHER INFORMATION: Staple strand_0530 of the 2D DNA nanostructure.

<400> SEQUENCE: 531
aaggccgctg ataccgatag ttgcgacgtt ag                                32

<210> SEQ ID NO 532
<211> LENGTH: 32
<212> TYPE: DNA
<213> ORGANISM: Artificial Sequence
<220> FEATURE:
<223> OTHER INFORMATION: Staple strand_0531 of the 2D DNA nanostructure.

<400> SEQUENCE: 532
acactcatcc atgttactta gccgaaagct gc                                32

<210> SEQ ID NO 533
<211> LENGTH: 32
<212> TYPE: DNA
<213> ORGANISM: Artificial Sequence
<220> FEATURE:
<223> OTHER INFORMATION: Staple strand_0532 of the 2D DNA nanostructure.

<400> SEQUENCE: 533
gacctgctct ttgaccccca gcgagggagt ta                                32

<210> SEQ ID NO 534
<211> LENGTH: 32
<212> TYPE: DNA
<213> ORGANISM: Artificial Sequence
<220> FEATURE:
<223> OTHER INFORMATION: Staple strand_0533 of the 2D DNA nanostructure.

<400> SEQUENCE: 534
tcattcagat gcgatttaa gaacaggcat ag                                 32

<210> SEQ ID NO 535
<211> LENGTH: 32
<212> TYPE: DNA
<213> ORGANISM: Artificial Sequence
<220> FEATURE:
<223> OTHER INFORMATION: Staple strand_0534 of the 2D DNA nanostructure.

<400> SEQUENCE: 535
attacctttg aataaggctt gcccaaatcc gc                                32
```

```
<210> SEQ ID NO 536
<211> LENGTH: 32
<212> TYPE: DNA
<213> ORGANISM: Artificial Sequence
<220> FEATURE:
<223> OTHER INFORMATION: Staple strand_0535 of the 2D DNA nanostructure.

<400> SEQUENCE: 536
taagagcaaa tgtttagact ggataggaag cc                                    32

<210> SEQ ID NO 537
<211> LENGTH: 32
<212> TYPE: DNA
<213> ORGANISM: Artificial Sequence
<220> FEATURE:
<223> OTHER INFORMATION: Staple strand_0536 of the 2D DNA nanostructure.

<400> SEQUENCE: 537
aatagtaaac actatcataa ccctcattgt ga                                    32

<210> SEQ ID NO 538
<211> LENGTH: 32
<212> TYPE: DNA
<213> ORGANISM: Artificial Sequence
<220> FEATURE:
<223> OTHER INFORMATION: Staple strand_0537 of the 2D DNA nanostructure.

<400> SEQUENCE: 538
cgaaagactt tgataagagg tcatatttcg ca                                    32

<210> SEQ ID NO 539
<211> LENGTH: 32
<212> TYPE: DNA
<213> ORGANISM: Artificial Sequence
<220> FEATURE:
<223> OTHER INFORMATION: Staple strand_0538 of the 2D DNA nanostructure.

<400> SEQUENCE: 539
ttgctccttt caaatatcgc gtttgagggg gt                                    32

<210> SEQ ID NO 540
<211> LENGTH: 32
<212> TYPE: DNA
<213> ORGANISM: Artificial Sequence
<220> FEATURE:
<223> OTHER INFORMATION: Staple strand_0539 of the 2D DNA nanostructure.

<400> SEQUENCE: 540
aatggtcaac aggcaaggca aagagtaatg tg                                    32

<210> SEQ ID NO 541
<211> LENGTH: 31
<212> TYPE: DNA
<213> ORGANISM: Artificial Sequence
<220> FEATURE:
<223> OTHER INFORMATION: Staple strand_0540 of the 2D DNA nanostructure.

<400> SEQUENCE: 541
tctaaagttt tgtcgtcttt ccagccgaca a                                     31

<210> SEQ ID NO 542
<211> LENGTH: 44
<212> TYPE: DNA
<213> ORGANISM: Artificial Sequence
<220> FEATURE:
<223> OTHER INFORMATION: Staple strand_0541 of the 2D DNA nanostructure.
```

-continued

<400> SEQUENCE: 542
tgacaactcg ctgaggcttg cattatacca agcgcgatga taaa    44

<210> SEQ ID NO 543
<211> LENGTH: 32
<212> TYPE: DNA
<213> ORGANISM: Artificial Sequence
<220> FEATURE:
<223> OTHER INFORMATION: Staple strand_0542 of the 2D DNA nanostructure.

<400> SEQUENCE: 543
atattcggaa ccatcgccca cgcagagaag ga    32

<210> SEQ ID NO 544
<211> LENGTH: 32
<212> TYPE: DNA
<213> ORGANISM: Artificial Sequence
<220> FEATURE:
<223> OTHER INFORMATION: Staple strand_0543 of the 2D DNA nanostructure.

<400> SEQUENCE: 544
tcatcgccaa caaagtacaa cggacgccag ca    32

<210> SEQ ID NO 545
<211> LENGTH: 32
<212> TYPE: DNA
<213> ORGANISM: Artificial Sequence
<220> FEATURE:
<223> OTHER INFORMATION: Staple strand_0544 of the 2D DNA nanostructure.

<400> SEQUENCE: 545
gatggtttga acgagtagta aatttaccat ta    32

<210> SEQ ID NO 546
<211> LENGTH: 38
<212> TYPE: DNA
<213> ORGANISM: Artificial Sequence
<220> FEATURE:
<223> OTHER INFORMATION: Staple strand_0545 of the 2D DNA nanostructure.

<400> SEQUENCE: 546
cgtttaccag acgacaaaga agttttgcca taattcga    38

<210> SEQ ID NO 547
<211> LENGTH: 32
<212> TYPE: DNA
<213> ORGANISM: Artificial Sequence
<220> FEATURE:
<223> OTHER INFORMATION: Staple strand_0546 of the 2D DNA nanostructure.

<400> SEQUENCE: 547
cttttgcaga taaaaccaa ataaagact cc    32

<210> SEQ ID NO 548
<211> LENGTH: 30
<212> TYPE: DNA
<213> ORGANISM: Artificial Sequence
<220> FEATURE:
<223> OTHER INFORMATION: Staple strand_0547 of the 2D DNA nanostructure.

<400> SEQUENCE: 548
gcttcaatca ggattagaga gttattttca    30

<210> SEQ ID NO 549

```
<211> LENGTH: 32
<212> TYPE: DNA
<213> ORGANISM: Artificial Sequence
<220> FEATURE:
<223> OTHER INFORMATION: Staple strand_0548 of the 2D DNA nanostructure.

<400> SEQUENCE: 549
ccaacaggag cgaaccagac cggagccttt ac                                        32

<210> SEQ ID NO 550
<211> LENGTH: 30
<212> TYPE: DNA
<213> ORGANISM: Artificial Sequence
<220> FEATURE:
<223> OTHER INFORMATION: Staple strand_0549 of the 2D DNA nanostructure.

<400> SEQUENCE: 550
tttggggata gtagtagcat taaaaggccg                                           30

<210> SEQ ID NO 551
<211> LENGTH: 32
<212> TYPE: DNA
<213> ORGANISM: Artificial Sequence
<220> FEATURE:
<223> OTHER INFORMATION: Staple strand_0550 of the 2D DNA nanostructure.

<400> SEQUENCE: 551
tccacagaca gccctcatag ttagcgtaac ga                                        32

<210> SEQ ID NO 552
<211> LENGTH: 32
<212> TYPE: DNA
<213> ORGANISM: Artificial Sequence
<220> FEATURE:
<223> OTHER INFORMATION: Staple strand_0551 of the 2D DNA nanostructure.

<400> SEQUENCE: 552
ttaggattgg ctgagactcc tcaataaccg at                                        32

<210> SEQ ID NO 553
<211> LENGTH: 30
<212> TYPE: DNA
<213> ORGANISM: Artificial Sequence
<220> FEATURE:
<223> OTHER INFORMATION: Staple strand_0552 of the 2D DNA nanostructure.

<400> SEQUENCE: 553
tattaagaag cggggttttg ctcgtagcat                                           30

<210> SEQ ID NO 554
<211> LENGTH: 32
<212> TYPE: DNA
<213> ORGANISM: Artificial Sequence
<220> FEATURE:
<223> OTHER INFORMATION: Staple strand_0553 of the 2D DNA nanostructure.

<400> SEQUENCE: 554
ttgacaggcc accaccagag ccgcgatttg ta                                        32

<210> SEQ ID NO 555
<211> LENGTH: 30
<212> TYPE: DNA
<213> ORGANISM: Artificial Sequence
<220> FEATURE:
<223> OTHER INFORMATION: Staple strand_0554 of the 2D DNA nanostructure.

<400> SEQUENCE: 555
```
caccagaaag gttgaggcag gtcatgaaag                                                    30

<210> SEQ ID NO 556
<211> LENGTH: 32
<212> TYPE: DNA
<213> ORGANISM: Artificial Sequence
<220> FEATURE:
<223> OTHER INFORMATION: Staple strand_0555 of the 2D DNA nanostructure.

<400> SEQUENCE: 556
gcaaggcctc accagtagca ccatgggctt ga                                                 32

<210> SEQ ID NO 557
<211> LENGTH: 30
<212> TYPE: DNA
<213> ORGANISM: Artificial Sequence
<220> FEATURE:
<223> OTHER INFORMATION: Staple strand_0556 of the 2D DNA nanostructure.

<400> SEQUENCE: 557
cagcaaaagg aaacgtcacc aatgagccgc                                                    30

<210> SEQ ID NO 558
<211> LENGTH: 32
<212> TYPE: DNA
<213> ORGANISM: Artificial Sequence
<220> FEATURE:
<223> OTHER INFORMATION: Staple strand_0557 of the 2D DNA nanostructure.

<400> SEQUENCE: 558
ttattacgaa gaactggcat gattgcgaga gg                                                 32

<210> SEQ ID NO 559
<211> LENGTH: 30
<212> TYPE: DNA
<213> ORGANISM: Artificial Sequence
<220> FEATURE:
<223> OTHER INFORMATION: Staple strand_0558 of the 2D DNA nanostructure.

<400> SEQUENCE: 559
atacccaaca gtatgttagc aaattagagc                                                    30

<210> SEQ ID NO 560
<211> LENGTH: 32
<212> TYPE: DNA
<213> ORGANISM: Artificial Sequence
<220> FEATURE:
<223> OTHER INFORMATION: Staple strand_0559 of the 2D DNA nanostructure.

<400> SEQUENCE: 560
agagagaaaa aaatgaaaat agcaagcaaa ct                                                 32

<210> SEQ ID NO 561
<211> LENGTH: 30
<212> TYPE: DNA
<213> ORGANISM: Artificial Sequence
<220> FEATURE:
<223> OTHER INFORMATION: Staple strand_0560 of the 2D DNA nanostructure.

<400> SEQUENCE: 561
ttaacgtcta acataaaaac aggtaacgga                                                    30

<210> SEQ ID NO 562
<211> LENGTH: 32
<212> TYPE: DNA

```
<213> ORGANISM: Artificial Sequence
<220> FEATURE:
<223> OTHER INFORMATION: Staple strand_0561 of the 2D DNA nanostructure.

<400> SEQUENCE: 562
ccaatagctc atcgtaggaa tcatggcatc aa                                    32

<210> SEQ ID NO 563
<211> LENGTH: 32
<212> TYPE: DNA
<213> ORGANISM: Artificial Sequence
<220> FEATURE:
<223> OTHER INFORMATION: Staple strand_0562 of the 2D DNA nanostructure.

<400> SEQUENCE: 563
tcaccagtac aaactacaac gcctagtacc ag                                    32

<210> SEQ ID NO 564
<211> LENGTH: 32
<212> TYPE: DNA
<213> ORGANISM: Artificial Sequence
<220> FEATURE:
<223> OTHER INFORMATION: Staple strand_0563 of the 2D DNA nanostructure.

<400> SEQUENCE: 564
gcggataacc tattattctg aaacagacga tt                                    32

<210> SEQ ID NO 565
<211> LENGTH: 32
<212> TYPE: DNA
<213> ORGANISM: Artificial Sequence
<220> FEATURE:
<223> OTHER INFORMATION: Staple strand_0564 of the 2D DNA nanostructure.

<400> SEQUENCE: 565
tttcggaagt gccgtcgaga gggtgagttt cg                                    32

<210> SEQ ID NO 566
<211> LENGTH: 32
<212> TYPE: DNA
<213> ORGANISM: Artificial Sequence
<220> FEATURE:
<223> OTHER INFORMATION: Staple strand_0565 of the 2D DNA nanostructure.

<400> SEQUENCE: 566
ggccttgaag agccaccacc ctcagaaacc at                                    32

<210> SEQ ID NO 567
<211> LENGTH: 32
<212> TYPE: DNA
<213> ORGANISM: Artificial Sequence
<220> FEATURE:
<223> OTHER INFORMATION: Staple strand_0566 of the 2D DNA nanostructure.

<400> SEQUENCE: 567
ccaccctcta ttcacaaaca aatacctgcc ta                                    32

<210> SEQ ID NO 568
<211> LENGTH: 32
<212> TYPE: DNA
<213> ORGANISM: Artificial Sequence
<220> FEATURE:
<223> OTHER INFORMATION: Staple strand_0567 of the 2D DNA nanostructure.

<400> SEQUENCE: 568
cgatagcatt gagccatttg ggaacgtaga aa                                    32
```

<210> SEQ ID NO 569
<211> LENGTH: 32
<212> TYPE: DNA
<213> ORGANISM: Artificial Sequence
<220> FEATURE:
<223> OTHER INFORMATION: Staple strand_0568 of the 2D DNA nanostructure.

<400> SEQUENCE: 569
tcaccgacgc accgtaatca gtagcagaac cg                                32

<210> SEQ ID NO 570
<211> LENGTH: 32
<212> TYPE: DNA
<213> ORGANISM: Artificial Sequence
<220> FEATURE:
<223> OTHER INFORMATION: Staple strand_0569 of the 2D DNA nanostructure.

<400> SEQUENCE: 570
atacataccg aggaaacgca ataagaagcg ca                                32

<210> SEQ ID NO 571
<211> LENGTH: 32
<212> TYPE: DNA
<213> ORGANISM: Artificial Sequence
<220> FEATURE:
<223> OTHER INFORMATION: Staple strand_0570 of the 2D DNA nanostructure.

<400> SEQUENCE: 571
aaggaaacat aaaggtggca acattatcac cg                                32

<210> SEQ ID NO 572
<211> LENGTH: 32
<212> TYPE: DNA
<213> ORGANISM: Artificial Sequence
<220> FEATURE:
<223> OTHER INFORMATION: Staple strand_0571 of the 2D DNA nanostructure.

<400> SEQUENCE: 572
ttagacggcc aaataagaaa cgatagaagg ct                                32

<210> SEQ ID NO 573
<211> LENGTH: 32
<212> TYPE: DNA
<213> ORGANISM: Artificial Sequence
<220> FEATURE:
<223> OTHER INFORMATION: Staple strand_0572 of the 2D DNA nanostructure.

<400> SEQUENCE: 573
atcccaatga gaattaactg aacagttacc ag                                32

<210> SEQ ID NO 574
<211> LENGTH: 32
<212> TYPE: DNA
<213> ORGANISM: Artificial Sequence
<220> FEATURE:
<223> OTHER INFORMATION: Staple strand_0573 of the 2D DNA nanostructure.

<400> SEQUENCE: 574
tatccggtct catcgagaac aagcgacaaa ag                                32

<210> SEQ ID NO 575
<211> LENGTH: 31
<212> TYPE: DNA
<213> ORGANISM: Artificial Sequence
<220> FEATURE:

<223> OTHER INFORMATION: Staple strand_0574 of the 2D DNA nanostructure.

<400> SEQUENCE: 575
aggaacccat gtaccgtaac acttgatata a        31

<210> SEQ ID NO 576
<211> LENGTH: 30
<212> TYPE: DNA
<213> ORGANISM: Artificial Sequence
<220> FEATURE:
<223> OTHER INFORMATION: Staple strand_0575 of the 2D DNA nanostructure.

<400> SEQUENCE: 576
gtatagcaaa cagttaatgc ccaatcctca        30

<210> SEQ ID NO 577
<211> LENGTH: 32
<212> TYPE: DNA
<213> ORGANISM: Artificial Sequence
<220> FEATURE:
<223> OTHER INFORMATION: Staple strand_0576 of the 2D DNA nanostructure.

<400> SEQUENCE: 577
gcccgtatcc ggaataggtg tatcagccca at        32

<210> SEQ ID NO 578
<211> LENGTH: 30
<212> TYPE: DNA
<213> ORGANISM: Artificial Sequence
<220> FEATURE:
<223> OTHER INFORMATION: Staple strand_0577 of the 2D DNA nanostructure.

<400> SEQUENCE: 578
ttaaagccag agccgccacc ctcgacagaa        30

<210> SEQ ID NO 579
<211> LENGTH: 32
<212> TYPE: DNA
<213> ORGANISM: Artificial Sequence
<220> FEATURE:
<223> OTHER INFORMATION: Staple strand_0578 of the 2D DNA nanostructure.

<400> SEQUENCE: 579
gcctccctca gaatggaaag cgcagtaaca gt        32

<210> SEQ ID NO 580
<211> LENGTH: 30
<212> TYPE: DNA
<213> ORGANISM: Artificial Sequence
<220> FEATURE:
<223> OTHER INFORMATION: Staple strand_0579 of the 2D DNA nanostructure.

<400> SEQUENCE: 580
tcaagtttca ttaaaggtga atataaaaga        30

<210> SEQ ID NO 581
<211> LENGTH: 32
<212> TYPE: DNA
<213> ORGANISM: Artificial Sequence
<220> FEATURE:
<223> OTHER INFORMATION: Staple strand_0580 of the 2D DNA nanostructure.

<400> SEQUENCE: 581
gaaattattg cctttagcgt cagaccggaa cc        32

```
<210> SEQ ID NO 582
<211> LENGTH: 30
<212> TYPE: DNA
<213> ORGANISM: Artificial Sequence
<220> FEATURE:
<223> OTHER INFORMATION: Staple strand_0581 of the 2D DNA nanostructure.

<400> SEQUENCE: 582
aacgcaaaga tagccgaaca aaccctgaac                                           30

<210> SEQ ID NO 583
<211> LENGTH: 32
<212> TYPE: DNA
<213> ORGANISM: Artificial Sequence
<220> FEATURE:
<223> OTHER INFORMATION: Staple strand_0582 of the 2D DNA nanostructure.

<400> SEQUENCE: 583
aagtaagcag acaccacgga ataatattga cg                                        32

<210> SEQ ID NO 584
<211> LENGTH: 30
<212> TYPE: DNA
<213> ORGANISM: Artificial Sequence
<220> FEATURE:
<223> OTHER INFORMATION: Staple strand_0583 of the 2D DNA nanostructure.

<400> SEQUENCE: 584
aaagtcacaa aataaacagc cagcgtttta                                           30

<210> SEQ ID NO 585
<211> LENGTH: 32
<212> TYPE: DNA
<213> ORGANISM: Artificial Sequence
<220> FEATURE:
<223> OTHER INFORMATION: Staple strand_0584 of the 2D DNA nanostructure.

<400> SEQUENCE: 585
gccagttaga gggtaattga gcgctttaag aa                                        32

<210> SEQ ID NO 586
<211> LENGTH: 30
<212> TYPE: DNA
<213> ORGANISM: Artificial Sequence
<220> FEATURE:
<223> OTHER INFORMATION: Staple strand_0585 of the 2D DNA nanostructure.

<400> SEQUENCE: 586
gcgaacctcc aagaacgggt atgacaataa                                           30

<210> SEQ ID NO 587
<211> LENGTH: 32
<212> TYPE: DNA
<213> ORGANISM: Artificial Sequence
<220> FEATURE:
<223> OTHER INFORMATION: Staple strand_0586 of the 2D DNA nanostructure.

<400> SEQUENCE: 587
ccaccctcat tttcagggat agcaaccgta ct                                        32

<210> SEQ ID NO 588
<211> LENGTH: 32
<212> TYPE: DNA
<213> ORGANISM: Artificial Sequence
<220> FEATURE:
<223> OTHER INFORMATION: Staple strand_0587 of the 2D DNA nanostructure.
```

<400> SEQUENCE: 588
caggaggtgg ggtcagtgcc ttgagtctct ga                                    32

<210> SEQ ID NO 589
<211> LENGTH: 30
<212> TYPE: DNA
<213> ORGANISM: Artificial Sequence
<220> FEATURE:
<223> OTHER INFORMATION: Staple strand_0588 of the 2D DNA nanostructure.

<400> SEQUENCE: 589
gttttaactt agtaccgcca cccagagcca                                       30

<210> SEQ ID NO 590
<211> LENGTH: 32
<212> TYPE: DNA
<213> ORGANISM: Artificial Sequence
<220> FEATURE:
<223> OTHER INFORMATION: Staple strand_0589 of the 2D DNA nanostructure.

<400> SEQUENCE: 590
atttaccggg aaccagagcc accactgtag cg                                    32

<210> SEQ ID NO 591
<211> LENGTH: 30
<212> TYPE: DNA
<213> ORGANISM: Artificial Sequence
<220> FEATURE:
<223> OTHER INFORMATION: Staple strand_0590 of the 2D DNA nanostructure.

<400> SEQUENCE: 591
aaatcacctt ccagtaagcg tcagtaataa                                       30

<210> SEQ ID NO 592
<211> LENGTH: 32
<212> TYPE: DNA
<213> ORGANISM: Artificial Sequence
<220> FEATURE:
<223> OTHER INFORMATION: Staple strand_0591 of the 2D DNA nanostructure.

<400> SEQUENCE: 592
cgttttcaag ggagggaagg taaagtttat tt                                    32

<210> SEQ ID NO 593
<211> LENGTH: 30
<212> TYPE: DNA
<213> ORGANISM: Artificial Sequence
<220> FEATURE:
<223> OTHER INFORMATION: Staple strand_0592 of the 2D DNA nanostructure.

<400> SEQUENCE: 593
accgattgtc ggcattttcg gtcataatca                                       30

<210> SEQ ID NO 594
<211> LENGTH: 32
<212> TYPE: DNA
<213> ORGANISM: Artificial Sequence
<220> FEATURE:
<223> OTHER INFORMATION: Staple strand_0593 of the 2D DNA nanostructure.

<400> SEQUENCE: 594
tgtcacaatc ttaccgaagc cctttaatat ca                                    32

<210> SEQ ID NO 595
<211> LENGTH: 30

```
<212> TYPE: DNA
<213> ORGANISM: Artificial Sequence
<220> FEATURE:
<223> OTHER INFORMATION: Staple strand_0594 of the 2D DNA nanostructure.

<400> SEQUENCE: 595
aatagctatc aatagaaaat tcaacattca                                    30

<210> SEQ ID NO 596
<211> LENGTH: 32
<212> TYPE: DNA
<213> ORGANISM: Artificial Sequence
<220> FEATURE:
<223> OTHER INFORMATION: Staple strand_0595 of the 2D DNA nanostructure.

<400> SEQUENCE: 596
gagagataga gcgtctttcc agaggttttg aa                                 32

<210> SEQ ID NO 597
<211> LENGTH: 30
<212> TYPE: DNA
<213> ORGANISM: Artificial Sequence
<220> FEATURE:
<223> OTHER INFORMATION: Staple strand_0596 of the 2D DNA nanostructure.

<400> SEQUENCE: 597
acgctaacac ccacaagaat tgaaaatagc                                    30

<210> SEQ ID NO 598
<211> LENGTH: 32
<212> TYPE: DNA
<213> ORGANISM: Artificial Sequence
<220> FEATURE:
<223> OTHER INFORMATION: Staple strand_0597 of the 2D DNA nanostructure.

<400> SEQUENCE: 598
gccttaaacc aatcaataat cggcacgcgc ct                                 32

<210> SEQ ID NO 599
<211> LENGTH: 32
<212> TYPE: DNA
<213> ORGANISM: Artificial Sequence
<220> FEATURE:
<223> OTHER INFORMATION: Staple strand_0598 of the 2D DNA nanostructure.

<400> SEQUENCE: 599
taaatcggga ttcccaattc tgcgatataa tg                                 32

<210> SEQ ID NO 600
<211> LENGTH: 30
<212> TYPE: DNA
<213> ORGANISM: Artificial Sequence
<220> FEATURE:
<223> OTHER INFORMATION: Staple strand_0599 of the 2D DNA nanostructure.

<400> SEQUENCE: 600
aacgcaaaat cgatgaacgg taccggttga                                    30

<210> SEQ ID NO 601
<211> LENGTH: 32
<212> TYPE: DNA
<213> ORGANISM: Artificial Sequence
<220> FEATURE:
<223> OTHER INFORMATION: Staple strand_0600 of the 2D DNA nanostructure.

<400> SEQUENCE: 601
```

```
aacaagaggg ataaaaattt ttagcataaa gc                                      32

<210> SEQ ID NO 602
<211> LENGTH: 30
<212> TYPE: DNA
<213> ORGANISM: Artificial Sequence
<220> FEATURE:
<223> OTHER INFORMATION: Staple strand_0601 of the 2D DNA nanostructure.

<400> SEQUENCE: 602
taatcagcgg attgaccgta atcgtaaccg                                         30

<210> SEQ ID NO 603
<211> LENGTH: 32
<212> TYPE: DNA
<213> ORGANISM: Artificial Sequence
<220> FEATURE:
<223> OTHER INFORMATION: Staple strand_0602 of the 2D DNA nanostructure.

<400> SEQUENCE: 603
acaaacggaa agcccccaaa aacactggag ca                                      32

<210> SEQ ID NO 604
<211> LENGTH: 30
<212> TYPE: DNA
<213> ORGANISM: Artificial Sequence
<220> FEATURE:
<223> OTHER INFORMATION: Staple strand_0603 of the 2D DNA nanostructure.

<400> SEQUENCE: 604
tgcatctttc ccagtcacga cggcctgcag                                         30

<210> SEQ ID NO 605
<211> LENGTH: 32
<212> TYPE: DNA
<213> ORGANISM: Artificial Sequence
<220> FEATURE:
<223> OTHER INFORMATION: Staple strand_0604 of the 2D DNA nanostructure.

<400> SEQUENCE: 605
ccagggttgc cagtttgagg ggacccgtgg ga                                      32

<210> SEQ ID NO 606
<211> LENGTH: 30
<212> TYPE: DNA
<213> ORGANISM: Artificial Sequence
<220> FEATURE:
<223> OTHER INFORMATION: Staple strand_0605 of the 2D DNA nanostructure.

<400> SEQUENCE: 606
gtcgacttcg gccaacgcgc ggggttttc                                          30

<210> SEQ ID NO 607
<211> LENGTH: 32
<212> TYPE: DNA
<213> ORGANISM: Artificial Sequence
<220> FEATURE:
<223> OTHER INFORMATION: Staple strand_0606 of the 2D DNA nanostructure.

<400> SEQUENCE: 607
ttaatgaact agaggatccc cgggggggtaa cg                                     32

<210> SEQ ID NO 608
<211> LENGTH: 30
<212> TYPE: DNA
<213> ORGANISM: Artificial Sequence
```

```
<220> FEATURE:
<223> OTHER INFORMATION: Staple strand_0607 of the 2D DNA nanostructure.

<400> SEQUENCE: 608
ttttcactca aagggcgaaa aaccatcacc                                          30

<210> SEQ ID NO 609
<211> LENGTH: 32
<212> TYPE: DNA
<213> ORGANISM: Artificial Sequence
<220> FEATURE:
<223> OTHER INFORMATION: Staple strand_0608 of the 2D DNA nanostructure.

<400> SEQUENCE: 609
ctccaacgca gtgagacggg caaccagctg ca                                       32

<210> SEQ ID NO 610
<211> LENGTH: 31
<212> TYPE: DNA
<213> ORGANISM: Artificial Sequence
<220> FEATURE:
<223> OTHER INFORMATION: Staple strand_0609 of the 2D DNA nanostructure.

<400> SEQUENCE: 610
caaatcaagt tttttggggt cgaaacgtgg a                                        31

<210> SEQ ID NO 611
<211> LENGTH: 30
<212> TYPE: DNA
<213> ORGANISM: Artificial Sequence
<220> FEATURE:
<223> OTHER INFORMATION: Staple strand_0610 of the 2D DNA nanostructure.

<400> SEQUENCE: 611
aaattaagtt gaccattaga tacttttgcg                                          30

<210> SEQ ID NO 612
<211> LENGTH: 32
<212> TYPE: DNA
<213> ORGANISM: Artificial Sequence
<220> FEATURE:
<223> OTHER INFORMATION: Staple strand_0611 of the 2D DNA nanostructure.

<400> SEQUENCE: 612
tatattttgt cattgcctga gagtggaaga tt                                       32

<210> SEQ ID NO 613
<211> LENGTH: 30
<212> TYPE: DNA
<213> ORGANISM: Artificial Sequence
<220> FEATURE:
<223> OTHER INFORMATION: Staple strand_0612 of the 2D DNA nanostructure.

<400> SEQUENCE: 613
gctatcagaa atgcaatgcc tgaattagca                                          30

<210> SEQ ID NO 614
<211> LENGTH: 32
<212> TYPE: DNA
<213> ORGANISM: Artificial Sequence
<220> FEATURE:
<223> OTHER INFORMATION: Staple strand_0613 of the 2D DNA nanostructure.

<400> SEQUENCE: 614
gtataagcca acccgtcgga ttctgacgac ag                                       32
```

<210> SEQ ID NO 615
<211> LENGTH: 30
<212> TYPE: DNA
<213> ORGANISM: Artificial Sequence
<220> FEATURE:
<223> OTHER INFORMATION: Staple strand_0614 of the 2D DNA nanostructure.

<400> SEQUENCE: 615
gcgagtaaaa atatttaaat tgttacaaag                                    30

<210> SEQ ID NO 616
<211> LENGTH: 32
<212> TYPE: DNA
<213> ORGANISM: Artificial Sequence
<220> FEATURE:
<223> OTHER INFORMATION: Staple strand_0615 of the 2D DNA nanostructure.

<400> SEQUENCE: 616
tatcggccgc aaggcgatta agtttaccga gc                                 32

<210> SEQ ID NO 617
<211> LENGTH: 30
<212> TYPE: DNA
<213> ORGANISM: Artificial Sequence
<220> FEATURE:
<223> OTHER INFORMATION: Staple strand_0616 of the 2D DNA nanostructure.

<400> SEQUENCE: 617
gatgtgcttc aggaagatcg cacaatgtga                                    30

<210> SEQ ID NO 618
<211> LENGTH: 32
<212> TYPE: DNA
<213> ORGANISM: Artificial Sequence
<220> FEATURE:
<223> OTHER INFORMATION: Staple strand_0617 of the 2D DNA nanostructure.

<400> SEQUENCE: 618
tcgaattcgg gaaacctgtc gtgcagctga tt                                 32

<210> SEQ ID NO 619
<211> LENGTH: 30
<212> TYPE: DNA
<213> ORGANISM: Artificial Sequence
<220> FEATURE:
<223> OTHER INFORMATION: Staple strand_0618 of the 2D DNA nanostructure.

<400> SEQUENCE: 619
ttccagtcgt aatcatggtc ataaaagggg                                    30

<210> SEQ ID NO 620
<211> LENGTH: 32
<212> TYPE: DNA
<213> ORGANISM: Artificial Sequence
<220> FEATURE:
<223> OTHER INFORMATION: Staple strand_0619 of the 2D DNA nanostructure.

<400> SEQUENCE: 620
gcccttcaga gtccactatt aaagggtgcc gt                                 32

<210> SEQ ID NO 621
<211> LENGTH: 30
<212> TYPE: DNA
<213> ORGANISM: Artificial Sequence
<220> FEATURE:
<223> OTHER INFORMATION: Staple strand_0620 of the 2D DNA nanostructure.

<400> SEQUENCE: 621
tggaacaacc gcctggccct gaggcccgct              30

<210> SEQ ID NO 622
<211> LENGTH: 30
<212> TYPE: DNA
<213> ORGANISM: Artificial Sequence
<220> FEATURE:
<223> OTHER INFORMATION: Staple strand_0621 of the 2D DNA nanostructure.

<400> SEQUENCE: 622
aaagcactaa atcggaaccc taatccagtt              30

<210> SEQ ID NO 623
<211> LENGTH: 32
<212> TYPE: DNA
<213> ORGANISM: Artificial Sequence
<220> FEATURE:
<223> OTHER INFORMATION: Staple strand_0622 of the 2D DNA nanostructure.

<400> SEQUENCE: 623
taaatcatat aacctgttta gctaaccttt aa              32

<210> SEQ ID NO 624
<211> LENGTH: 32
<212> TYPE: DNA
<213> ORGANISM: Artificial Sequence
<220> FEATURE:
<223> OTHER INFORMATION: Staple strand_0623 of the 2D DNA nanostructure.

<400> SEQUENCE: 624
taggtaaact atttttgaga gatcaaacgt ta              32

<210> SEQ ID NO 625
<211> LENGTH: 32
<212> TYPE: DNA
<213> ORGANISM: Artificial Sequence
<220> FEATURE:
<223> OTHER INFORMATION: Staple strand_0624 of the 2D DNA nanostructure.

<400> SEQUENCE: 625
gagggtagga ttcaaaaggg tgagacatcc aa              32

<210> SEQ ID NO 626
<211> LENGTH: 32
<212> TYPE: DNA
<213> ORGANISM: Artificial Sequence
<220> FEATURE:
<223> OTHER INFORMATION: Staple strand_0625 of the 2D DNA nanostructure.

<400> SEQUENCE: 626
atattttggc tttcatcaac attatccagc ca              32

<210> SEQ ID NO 627
<211> LENGTH: 32
<212> TYPE: DNA
<213> ORGANISM: Artificial Sequence
<220> FEATURE:
<223> OTHER INFORMATION: Staple strand_0626 of the 2D DNA nanostructure.

<400> SEQUENCE: 627
tgtagccatt aaaattcgca ttaaatgccg ga              32

<210> SEQ ID NO 628

```
<211> LENGTH: 32
<212> TYPE: DNA
<213> ORGANISM: Artificial Sequence
<220> FEATURE:
<223> OTHER INFORMATION: Staple strand_0627 of the 2D DNA nanostructure.

<400> SEQUENCE: 628
gctttccgat tacgccagct ggcggctgtt tc                                      32

<210> SEQ ID NO 629
<211> LENGTH: 32
<212> TYPE: DNA
<213> ORGANISM: Artificial Sequence
<220> FEATURE:
<223> OTHER INFORMATION: Staple strand_0628 of the 2D DNA nanostructure.

<400> SEQUENCE: 629
tcttcgctgc accgcttctg gtgcggcctt cc                                      32

<210> SEQ ID NO 630
<211> LENGTH: 32
<212> TYPE: DNA
<213> ORGANISM: Artificial Sequence
<220> FEATURE:
<223> OTHER INFORMATION: Staple strand_0629 of the 2D DNA nanostructure.

<400> SEQUENCE: 630
ctgtgtgatt gcgttgcgct cactagagtt gc                                      32

<210> SEQ ID NO 631
<211> LENGTH: 32
<212> TYPE: DNA
<213> ORGANISM: Artificial Sequence
<220> FEATURE:
<223> OTHER INFORMATION: Staple strand_0630 of the 2D DNA nanostructure.

<400> SEQUENCE: 631
cacattaaaa ttgttatccg ctcatgcggg cc                                      32

<210> SEQ ID NO 632
<211> LENGTH: 32
<212> TYPE: DNA
<213> ORGANISM: Artificial Sequence
<220> FEATURE:
<223> OTHER INFORMATION: Staple strand_0631 of the 2D DNA nanostructure.

<400> SEQUENCE: 632
agcaagcgta gggttgagtg ttgtagggag cc                                      32

<210> SEQ ID NO 633
<211> LENGTH: 32
<212> TYPE: DNA
<213> ORGANISM: Artificial Sequence
<220> FEATURE:
<223> OTHER INFORMATION: Staple strand_0632 of the 2D DNA nanostructure.

<400> SEQUENCE: 633
gcccgagagt ccacgctggt ttgcagctaa ct                                      32

<210> SEQ ID NO 634
<211> LENGTH: 32
<212> TYPE: DNA
<213> ORGANISM: Artificial Sequence
<220> FEATURE:
<223> OTHER INFORMATION: Staple strand_0633 of the 2D DNA nanostructure.

<400> SEQUENCE: 634
```
cccgatttag agcttgacgg ggaaaaagaa ta                                        32

<210> SEQ ID NO 635
<211> LENGTH: 32
<212> TYPE: DNA
<213> ORGANISM: Artificial Sequence
<220> FEATURE:
<223> OTHER INFORMATION: Staple strand_0634 of the 2D DNA nanostructure.

<400> SEQUENCE: 635
ttctactacg cgagctgaaa aggttaccgc gc                                        32

<210> SEQ ID NO 636
<211> LENGTH: 30
<212> TYPE: DNA
<213> ORGANISM: Artificial Sequence
<220> FEATURE:
<223> OTHER INFORMATION: Staple strand_0635 of the 2D DNA nanostructure.

<400> SEQUENCE: 636
gagacagcta gctgataaat taattttgt                                            30

<210> SEQ ID NO 637
<211> LENGTH: 32
<212> TYPE: DNA
<213> ORGANISM: Artificial Sequence
<220> FEATURE:
<223> OTHER INFORMATION: Staple strand_0636 of the 2D DNA nanostructure.

<400> SEQUENCE: 637
caaccgtttc aaatcaccat caattcgagc ca                                        32

<210> SEQ ID NO 638
<211> LENGTH: 44
<212> TYPE: DNA
<213> ORGANISM: Artificial Sequence
<220> FEATURE:
<223> OTHER INFORMATION: Staple strand_0637 of the 2D DNA nanostructure.

<400> SEQUENCE: 638
taaatcaaaa taattcgcgt ctcggaaacc aggcaaaggg aagg                           44

<210> SEQ ID NO 639
<211> LENGTH: 32
<212> TYPE: DNA
<213> ORGANISM: Artificial Sequence
<220> FEATURE:
<223> OTHER INFORMATION: Staple strand_0638 of the 2D DNA nanostructure.

<400> SEQUENCE: 639
gccatcaagc tcatttttta accacaaatc ca                                        32

<210> SEQ ID NO 640
<211> LENGTH: 32
<212> TYPE: DNA
<213> ORGANISM: Artificial Sequence
<220> FEATURE:
<223> OTHER INFORMATION: Staple strand_0639 of the 2D DNA nanostructure.

<400> SEQUENCE: 640
caactgttgc gccattcgcc attcaaacat ca                                        32

<210> SEQ ID NO 641
<211> LENGTH: 32
<212> TYPE: DNA

```
<213> ORGANISM: Artificial Sequence
<220> FEATURE:
<223> OTHER INFORMATION: Staple strand_0640 of the 2D DNA nanostructure.

<400> SEQUENCE: 641
aagcctggta cgagccggaa gcatagatga tg                                 32

<210> SEQ ID NO 642
<211> LENGTH: 38
<212> TYPE: DNA
<213> ORGANISM: Artificial Sequence
<220> FEATURE:
<223> OTHER INFORMATION: Staple strand_0641 of the 2D DNA nanostructure.

<400> SEQUENCE: 642
cccagcaggc gaaaaatccc ttataaatca agccggcg                           38

<210> SEQ ID NO 643
<211> LENGTH: 32
<212> TYPE: DNA
<213> ORGANISM: Artificial Sequence
<220> FEATURE:
<223> OTHER INFORMATION: Staple strand_0642 of the 2D DNA nanostructure.

<400> SEQUENCE: 643
tcggcaaatc ctgtttgatg gtggaccctc aa                                 32

<210> SEQ ID NO 644
<211> LENGTH: 31
<212> TYPE: DNA
<213> ORGANISM: Artificial Sequence
<220> FEATURE:
<223> OTHER INFORMATION: Staple strand_0643 of the 2D DNA nanostructure.

<400> SEQUENCE: 644
aacgtggcga gaaggaagg gaaaccagta a                                   31

<210> SEQ ID NO 645
<211> LENGTH: 30
<212> TYPE: DNA
<213> ORGANISM: Artificial Sequence
<220> FEATURE:
<223> OTHER INFORMATION: Staple strand_0644 of the 2D DNA nanostructure.

<400> SEQUENCE: 645
ttttatttaa gcaaatcaga tatttttgt                                     30

<210> SEQ ID NO 646
<211> LENGTH: 32
<212> TYPE: DNA
<213> ORGANISM: Artificial Sequence
<220> FEATURE:
<223> OTHER INFORMATION: Staple strand_0645 of the 2D DNA nanostructure.

<400> SEQUENCE: 646
gtaataagtt aggcagaggc atttatgata tt                                 32

<210> SEQ ID NO 647
<211> LENGTH: 30
<212> TYPE: DNA
<213> ORGANISM: Artificial Sequence
<220> FEATURE:
<223> OTHER INFORMATION: Staple strand_0646 of the 2D DNA nanostructure.

<400> SEQUENCE: 647
catgtaatag aatataaagt accaagccgt                                    30
```

<210> SEQ ID NO 648
<211> LENGTH: 32
<212> TYPE: DNA
<213> ORGANISM: Artificial Sequence
<220> FEATURE:
<223> OTHER INFORMATION: Staple strand_0647 of the 2D DNA nanostructure.

<400> SEQUENCE: 648
atcgcaagta tgtaaatgct gatgatagga ac         32

<210> SEQ ID NO 649
<211> LENGTH: 30
<212> TYPE: DNA
<213> ORGANISM: Artificial Sequence
<220> FEATURE:
<223> OTHER INFORMATION: Staple strand_0648 of the 2D DNA nanostructure.

<400> SEQUENCE: 649
tataactaac aaagaacgcg agaacgccaa            30

<210> SEQ ID NO 650
<211> LENGTH: 32
<212> TYPE: DNA
<213> ORGANISM: Artificial Sequence
<220> FEATURE:
<223> OTHER INFORMATION: Staple strand_0649 of the 2D DNA nanostructure.

<400> SEQUENCE: 650
agaaaacaaa gaagatgatg aaacaggctg cg         32

<210> SEQ ID NO 651
<211> LENGTH: 30
<212> TYPE: DNA
<213> ORGANISM: Artificial Sequence
<220> FEATURE:
<223> OTHER INFORMATION: Staple strand_0650 of the 2D DNA nanostructure.

<400> SEQUENCE: 651
ctgagcaaaa attaattaca ttttgggtta            30

<210> SEQ ID NO 652
<211> LENGTH: 32
<212> TYPE: DNA
<213> ORGANISM: Artificial Sequence
<220> FEATURE:
<223> OTHER INFORMATION: Staple strand_0651 of the 2D DNA nanostructure.

<400> SEQUENCE: 652
gcaattcaca tattcctgat tatcaaagtg ta         32

<210> SEQ ID NO 653
<211> LENGTH: 30
<212> TYPE: DNA
<213> ORGANISM: Artificial Sequence
<220> FEATURE:
<223> OTHER INFORMATION: Staple strand_0652 of the 2D DNA nanostructure.

<400> SEQUENCE: 653
attatcattc aatataatcc tgacaattac            30

<210> SEQ ID NO 654
<211> LENGTH: 32
<212> TYPE: DNA
<213> ORGANISM: Artificial Sequence
<220> FEATURE:

<223> OTHER INFORMATION: Staple strand_0653 of the 2D DNA nanostructure.

<400> SEQUENCE: 654
tcaatatcga acctcaaata tcaattccga aa                                      32

<210> SEQ ID NO 655
<211> LENGTH: 30
<212> TYPE: DNA
<213> ORGANISM: Artificial Sequence
<220> FEATURE:
<223> OTHER INFORMATION: Staple strand_0654 of the 2D DNA nanostructure.

<400> SEQUENCE: 655
accttgcttg gtcagttggc aaagagcgga                                         30

<210> SEQ ID NO 656
<211> LENGTH: 30
<212> TYPE: DNA
<213> ORGANISM: Artificial Sequence
<220> FEATURE:
<223> OTHER INFORMATION: Staple strand_0655 of the 2D DNA nanostructure.

<400> SEQUENCE: 656 taaagggac attctggcca acaaagcatc                                          30

<210> SEQ ID NO 657
<211> LENGTH: 32
<212> TYPE: DNA
<213> ORGANISM: Artificial Sequence
<220> FEATURE:
<223> OTHER INFORMATION: Staple strand_0656 of the 2D DNA nanostructure.

<400> SEQUENCE: 657
gtaccgcaat tctaagaacg cgagtattat tt                                      32

<210> SEQ ID NO 658
<211> LENGTH: 32
<212> TYPE: DNA
<213> ORGANISM: Artificial Sequence
<220> FEATURE:
<223> OTHER INFORMATION: Staple strand_0657 of the 2D DNA nanostructure.

<400> SEQUENCE: 658
gtaaagtaat cgccatattt aacaaaactt tt                                      32

<210> SEQ ID NO 659
<211> LENGTH: 32
<212> TYPE: DNA
<213> ORGANISM: Artificial Sequence
<220> FEATURE:
<223> OTHER INFORMATION: Staple strand_0658 of the 2D DNA nanostructure.

<400> SEQUENCE: 659
aattgagaat tctgtccaga cgactaaacc aa                                      32

<210> SEQ ID NO 660
<211> LENGTH: 32
<212> TYPE: DNA
<213> ORGANISM: Artificial Sequence
<220> FEATURE:
<223> OTHER INFORMATION: Staple strand_0659 of the 2D DNA nanostructure.

<400> SEQUENCE: 660
tcaaatataa cctccggctt aggtaacaat tt                                      32

```
<210> SEQ ID NO 661
<211> LENGTH: 32
<212> TYPE: DNA
<213> ORGANISM: Artificial Sequence
<220> FEATURE:
<223> OTHER INFORMATION: Staple strand_0660 of the 2D DNA nanostructure.

<400> SEQUENCE: 661 accttttat tttagttaat ttcatagggc tt                                      32

<210> SEQ ID NO 662
<211> LENGTH: 32
<212> TYPE: DNA
<213> ORGANISM: Artificial Sequence
<220> FEATURE:
<223> OTHER INFORMATION: Staple strand_0661 of the 2D DNA nanostructure.

<400> SEQUENCE: 662
catttgaagg cgaattattc atttttgttt gg                                     32

<210> SEQ ID NO 663
<211> LENGTH: 32
<212> TYPE: DNA
<213> ORGANISM: Artificial Sequence
<220> FEATURE:
<223> OTHER INFORMATION: Staple strand_0662 of the 2D DNA nanostructure.

<400> SEQUENCE: 663
cgcgcagatt acctttttta atgggagaga ct                                     32

<210> SEQ ID NO 664
<211> LENGTH: 32
<212> TYPE: DNA
<213> ORGANISM: Artificial Sequence
<220> FEATURE:
<223> OTHER INFORMATION: Staple strand_0663 of the 2D DNA nanostructure.

<400> SEQUENCE: 664
attatactaa gaaaccacca gaagtcaaca gt                                     32

<210> SEQ ID NO 665
<211> LENGTH: 32
<212> TYPE: DNA
<213> ORGANISM: Artificial Sequence
<220> FEATURE:
<223> OTHER INFORMATION: Staple strand_0664 of the 2D DNA nanostructure.

<400> SEQUENCE: 665
gcggaacatc tgaataatgg aaggtacaaa at                                     32

<210> SEQ ID NO 666
<211> LENGTH: 32
<212> TYPE: DNA
<213> ORGANISM: Artificial Sequence
<220> FEATURE:
<223> OTHER INFORMATION: Staple strand_0665 of the 2D DNA nanostructure.

<400> SEQUENCE: 666
tgaaaggagc aaatgaaaaa tctagagata ga                                     32

<210> SEQ ID NO 667
<211> LENGTH: 32
<212> TYPE: DNA
<213> ORGANISM: Artificial Sequence
<220> FEATURE:
<223> OTHER INFORMATION: Staple strand_0666 of the 2D DNA nanostructure.
```

<400> SEQUENCE: 667
agccagcaat tgaggaaggt tatcatcatt tt					32

<210> SEQ ID NO 668
<211> LENGTH: 32
<212> TYPE: DNA
<213> ORGANISM: Artificial Sequence
<220> FEATURE:
<223> OTHER INFORMATION: Staple strand_0667 of the 2D DNA nanostructure.

<400> SEQUENCE: 668
acccttctga cctgaaagcg taagacgctg ag					32

<210> SEQ ID NO 669
<211> LENGTH: 32
<212> TYPE: DNA
<213> ORGANISM: Artificial Sequence
<220> FEATURE:
<223> OTHER INFORMATION: Staple strand_0668 of the 2D DNA nanostructure.

<400> SEQUENCE: 669
cttatcattc ccgacttgcg ggagcctaat tt					32

<210> SEQ ID NO 670
<211> LENGTH: 30
<212> TYPE: DNA
<213> ORGANISM: Artificial Sequence
<220> FEATURE:
<223> OTHER INFORMATION: Staple strand_0669 of the 2D DNA nanostructure.

<400> SEQUENCE: 670
acaacatgcc aacgctcaac agtcttctga					30

<210> SEQ ID NO 671
<211> LENGTH: 32
<212> TYPE: DNA
<213> ORGANISM: Artificial Sequence
<220> FEATURE:
<223> OTHER INFORMATION: Staple strand_0670 of the 2D DNA nanostructure.

<400> SEQUENCE: 671
agtataaagt tcagctaatg cagatgtctt tc					32

<210> SEQ ID NO 672
<211> LENGTH: 30
<212> TYPE: DNA
<213> ORGANISM: Artificial Sequence
<220> FEATURE:
<223> OTHER INFORMATION: Staple strand_0671 of the 2D DNA nanostructure.

<400> SEQUENCE: 672
cctaaatcaa aatcataggt ctaaacagta					30

<210> SEQ ID NO 673
<211> LENGTH: 32
<212> TYPE: DNA
<213> ORGANISM: Artificial Sequence
<220> FEATURE:
<223> OTHER INFORMATION: Staple strand_0672 of the 2D DNA nanostructure.

<400> SEQUENCE: 673
gaatttattt aatggtttga aatattctta cc					32

<210> SEQ ID NO 674
<211> LENGTH: 30

```
<212> TYPE: DNA
<213> ORGANISM: Artificial Sequence
<220> FEATURE:
<223> OTHER INFORMATION: Staple strand_0673 of the 2D DNA nanostructure.

<400> SEQUENCE: 674
cataaatctt tgaataccaa gtgttagaac                                      30

<210> SEQ ID NO 675
<211> LENGTH: 32
<212> TYPE: DNA
<213> ORGANISM: Artificial Sequence
<220> FEATURE:
<223> OTHER INFORMATION: Staple strand_0674 of the 2D DNA nanostructure.

<400> SEQUENCE: 675
cctgattgca atatatgtga gtgatcaata gt                                   32

<210> SEQ ID NO 676
<211> LENGTH: 30
<212> TYPE: DNA
<213> ORGANISM: Artificial Sequence
<220> FEATURE:
<223> OTHER INFORMATION: Staple strand_0675 of the 2D DNA nanostructure.

<400> SEQUENCE: 676
ctaccatagt ttgagtaaca tttaaaatat                                      30

<210> SEQ ID NO 677
<211> LENGTH: 32
<212> TYPE: DNA
<213> ORGANISM: Artificial Sequence
<220> FEATURE:
<223> OTHER INFORMATION: Staple strand_0676 of the 2D DNA nanostructure.

<400> SEQUENCE: 677
attttaaaat caaaattatt tgcacggatt cg                                   32

<210> SEQ ID NO 678
<211> LENGTH: 30
<212> TYPE: DNA
<213> ORGANISM: Artificial Sequence
<220> FEATURE:
<223> OTHER INFORMATION: Staple strand_0677 of the 2D DNA nanostructure.

<400> SEQUENCE: 678
ctttagggcc tgcaacagtg ccaatacgtg                                      30

<210> SEQ ID NO 679
<211> LENGTH: 32
<212> TYPE: DNA
<213> ORGANISM: Artificial Sequence
<220> FEATURE:
<223> OTHER INFORMATION: Staple strand_0678 of the 2D DNA nanostructure.

<400> SEQUENCE: 679
ttaacaccag cactaacaac taatcgttat ta                                   32

<210> SEQ ID NO 680
<211> LENGTH: 31
<212> TYPE: DNA
<213> ORGANISM: Artificial Sequence
<220> FEATURE:
<223> OTHER INFORMATION: Staple strand_0679 of the 2D DNA nanostructure.

<400> SEQUENCE: 680
```

```
gcacagacaa tattttttgaa tggggtcagt a                              31

<210> SEQ ID NO 681
<211> LENGTH: 30
<212> TYPE: DNA
<213> ORGANISM: Artificial Sequence
<220> FEATURE:
<223> OTHER INFORMATION: Staple strand_0680 of the 2D DNA nanostructure.

<400> SEQUENCE: 681
tgtagaaatc aagattagtt gctcttacca                                 30

<210> SEQ ID NO 682
<211> LENGTH: 32
<212> TYPE: DNA
<213> ORGANISM: Artificial Sequence
<220> FEATURE:
<223> OTHER INFORMATION: Staple strand_0681 of the 2D DNA nanostructure.

<400> SEQUENCE: 682
gtttatcaat atgcgttata caaaccgacc gt                              32

<210> SEQ ID NO 683
<211> LENGTH: 30
<212> TYPE: DNA
<213> ORGANISM: Artificial Sequence
<220> FEATURE:
<223> OTHER INFORMATION: Staple strand_0682 of the 2D DNA nanostructure.

<400> SEQUENCE: 683
ttagtatcac aatagataag tccacgagca                                 30

<210> SEQ ID NO 684
<211> LENGTH: 32
<212> TYPE: DNA
<213> ORGANISM: Artificial Sequence
<220> FEATURE:
<223> OTHER INFORMATION: Staple strand_0683 of the 2D DNA nanostructure.

<400> SEQUENCE: 684
gtgataaaaa gacgctgaga agagataacc tt                              32

<210> SEQ ID NO 685
<211> LENGTH: 30
<212> TYPE: DNA
<213> ORGANISM: Artificial Sequence
<220> FEATURE:
<223> OTHER INFORMATION: Staple strand_0684 of the 2D DNA nanostructure.

<400> SEQUENCE: 685
cttagattta aggcgttaaa taaagcctgt                                 30

<210> SEQ ID NO 686
<211> LENGTH: 32
<212> TYPE: DNA
<213> ORGANISM: Artificial Sequence
<220> FEATURE:
<223> OTHER INFORMATION: Staple strand_0685 of the 2D DNA nanostructure.

<400> SEQUENCE: 686
gcttctgttc gggagaaaca ataacgtaaa ac                              32

<210> SEQ ID NO 687
<211> LENGTH: 30
<212> TYPE: DNA
<213> ORGANISM: Artificial Sequence
```

<220> FEATURE:
<223> OTHER INFORMATION: Staple strand_0686 of the 2D DNA nanostructure.

<400> SEQUENCE: 687
cttttacaaa atcgtcgcta ttagcgatag                                30

<210> SEQ ID NO 688
<211> LENGTH: 32
<212> TYPE: DNA
<213> ORGANISM: Artificial Sequence
<220> FEATURE:
<223> OTHER INFORMATION: Staple strand_0687 of the 2D DNA nanostructure.

<400> SEQUENCE: 688
agaaataaaa atcctttgcc cgaaagatta ga                             32

<210> SEQ ID NO 689
<211> LENGTH: 30
<212> TYPE: DNA
<213> ORGANISM: Artificial Sequence
<220> FEATURE:
<223> OTHER INFORMATION: Staple strand_0688 of the 2D DNA nanostructure.

<400> SEQUENCE: 689
ctcgtattag aaattgcgta gatacagtac                                30

<210> SEQ ID NO 690
<211> LENGTH: 32
<212> TYPE: DNA
<213> ORGANISM: Artificial Sequence
<220> FEATURE:
<223> OTHER INFORMATION: Staple strand_0689 of the 2D DNA nanostructure.

<400> SEQUENCE: 690
gccgtcaaaa aacagaggtg aggcctatta gt                             32

<210> SEQ ID NO 691
<211> LENGTH: 30
<212> TYPE: DNA
<213> ORGANISM: Artificial Sequence
<220> FEATURE:
<223> OTHER INFORMATION: Staple strand_0690 of the 2D DNA nanostructure.

<400> SEQUENCE: 691
cagaagatta gataatacat ttgtcgacaa                                30

<210> SEQ ID NO 692
<211> LENGTH: 30
<212> TYPE: DNA
<213> ORGANISM: Artificial Sequence
<220> FEATURE:
<223> OTHER INFORMATION: Staple strand_0691 of the 2D DNA nanostructure.

<400> SEQUENCE: 692
ctttaatgcg cgaactgata gccccaccag                                30

<210> SEQ ID NO 693
<211> LENGTH: 52
<212> TYPE: DNA
<213> ORGANISM: Artificial Sequence
<220> FEATURE:
<223> OTHER INFORMATION: Staple strand_0692 of the 2D DNA nanostructure.

<400> SEQUENCE: 693
agaaaggaac aactaaagga attcaaaaaa attcctctac cacctacatc ac       52

<210> SEQ ID NO 694
<211> LENGTH: 51
<212> TYPE: DNA
<213> ORGANISM: Artificial Sequence
<220> FEATURE:
<223> OTHER INFORMATION: Staple strand_0693 of the 2D DNA nanostructure.

<400> SEQUENCE: 694
aggctccaga ggctttgagg acacgggtaa ttcctctacc acctacatca c    51

<210> SEQ ID NO 695
<211> LENGTH: 53
<212> TYPE: DNA
<213> ORGANISM: Artificial Sequence
<220> FEATURE:
<223> OTHER INFORMATION: Staple strand_0694 of the 2D DNA nanostructure.

<400> SEQUENCE: 695
acggctacaa aaggagcctt taatgtgaga atttcctcta ccacctacat cac    53

<210> SEQ ID NO 696
<211> LENGTH: 51
<212> TYPE: DNA
<213> ORGANISM: Artificial Sequence
<220> FEATURE:
<223> OTHER INFORMATION: Staple strand_0695 of the 2D DNA nanostructure.

<400> SEQUENCE: 696
aatacgtttg aaagaggaca gactgacctt ttcctctacc acctacatca c    51

<210> SEQ ID NO 697
<211> LENGTH: 53
<212> TYPE: DNA
<213> ORGANISM: Artificial Sequence
<220> FEATURE:
<223> OTHER INFORMATION: Staple strand_0696 of the 2D DNA nanostructure.

<400> SEQUENCE: 697
gaccaactaa tgccactacg aaggggtag cattcctcta ccacctacat cac    53

<210> SEQ ID NO 698
<211> LENGTH: 51
<212> TYPE: DNA
<213> ORGANISM: Artificial Sequence
<220> FEATURE:
<223> OTHER INFORMATION: Staple strand_0697 of the 2D DNA nanostructure.

<400> SEQUENCE: 698
catcaagtaa aacgaactaa cgagttgaga ttcctctacc acctacatca c    51

<210> SEQ ID NO 699
<211> LENGTH: 53
<212> TYPE: DNA
<213> ORGANISM: Artificial Sequence
<220> FEATURE:
<223> OTHER INFORMATION: Staple strand_0698 of the 2D DNA nanostructure.

<400> SEQUENCE: 699
tacgttaaag taatcttgac aagaaccgaa ctttcctcta ccacctacat cac    53

<210> SEQ ID NO 700
<211> LENGTH: 51
<212> TYPE: DNA
<213> ORGANISM: Artificial Sequence
<220> FEATURE:
<223> OTHER INFORMATION: Staple strand_0699 of the 2D DNA nanostructure.

<400> SEQUENCE: 700
tttaggacaa atgctttaaa caatcaggtc ttcctctacc acctacatca c        51

<210> SEQ ID NO 701
<211> LENGTH: 53
<212> TYPE: DNA
<213> ORGANISM: Artificial Sequence
<220> FEATURE:
<223> OTHER INFORMATION: Staple strand_0700 of the 2D DNA nanostructure.

<400> SEQUENCE: 701 atcccctat accacattca actagaaaaa tcttcctcta ccacctacat cac        53

<210> SEQ ID NO 702
<211> LENGTH: 51
<212> TYPE: DNA
<213> ORGANISM: Artificial Sequence
<220> FEATURE:
<223> OTHER INFORMATION: Staple strand_0701 of the 2D DNA nanostructure.

<400> SEQUENCE: 702
tttaccccaa catgttttaa atttccatat ttcctctacc acctacatca c        51

<210> SEQ ID NO 703
<211> LENGTH: 53
<212> TYPE: DNA
<213> ORGANISM: Artificial Sequence
<220> FEATURE:
<223> OTHER INFORMATION: Staple strand_0702 of the 2D DNA nanostructure.

<400> SEQUENCE: 703
ctgtagcttg actattatag tcagttcatt gattcctcta ccacctacat cac        53

<210> SEQ ID NO 704
<211> LENGTH: 51
<212> TYPE: DNA
<213> ORGANISM: Artificial Sequence
<220> FEATURE:
<223> OTHER INFORMATION: Staple strand_0703 of the 2D DNA nanostructure.

<400> SEQUENCE: 704
aacagttttg taccaaaaac attttatttc ttcctctacc acctacatca c        51

<210> SEQ ID NO 705
<211> LENGTH: 53
<212> TYPE: DNA
<213> ORGANISM: Artificial Sequence
<220> FEATURE:
<223> OTHER INFORMATION: Staple strand_0704 of the 2D DNA nanostructure.

<400> SEQUENCE: 705
acaactttca acagtttcag cggatgtatc ggttcctcta ccacctacat cac        53

<210> SEQ ID NO 706
<211> LENGTH: 53
<212> TYPE: DNA
<213> ORGANISM: Artificial Sequence
<220> FEATURE:
<223> OTHER INFORMATION: Staple strand_0705 of the 2D DNA nanostructure.

<400> SEQUENCE: 706
tttatcagga cagcatcgga acgacaccaa ccttcctcta ccacctacat cac        53

<210> SEQ ID NO 707

```
<211> LENGTH: 51
<212> TYPE: DNA
<213> ORGANISM: Artificial Sequence
<220> FEATURE:
<223> OTHER INFORMATION: Staple strand_0706 of the 2D DNA nanostructure.

<400> SEQUENCE: 707
cagcgaaact tgctttcgag gtgttgctaa ttcctctacc acctacatca c          51

<210> SEQ ID NO 708
<211> LENGTH: 53
<212> TYPE: DNA
<213> ORGANISM: Artificial Sequence
<220> FEATURE:
<223> OTHER INFORMATION: Staple strand_0707 of the 2D DNA nanostructure.

<400> SEQUENCE: 708
taaaacgagg tcaatcataa gggaaccgga tattcctcta ccacctacat cac        53

<210> SEQ ID NO 709
<211> LENGTH: 51
<212> TYPE: DNA
<213> ORGANISM: Artificial Sequence
<220> FEATURE:
<223> OTHER INFORMATION: Staple strand_0708 of the 2D DNA nanostructure.

<400> SEQUENCE: 709
gcgcagacaa gaggcaaaag aatccctcag ttcctctacc acctacatca c          51

<210> SEQ ID NO 710
<211> LENGTH: 53
<212> TYPE: DNA
<213> ORGANISM: Artificial Sequence
<220> FEATURE:
<223> OTHER INFORMATION: Staple strand_0709 of the 2D DNA nanostructure.

<400> SEQUENCE: 710
ttcattacgt caggacgttg ggaaatgcag atttcctcta ccacctacat cac        53

<210> SEQ ID NO 711
<211> LENGTH: 51
<212> TYPE: DNA
<213> ORGANISM: Artificial Sequence
<220> FEATURE:
<223> OTHER INFORMATION: Staple strand_0710 of the 2D DNA nanostructure.

<400> SEQUENCE: 711
ttataccacc aaatcaacgt aacgaacgag ttcctctacc acctacatca c          51

<210> SEQ ID NO 712
<211> LENGTH: 53
<212> TYPE: DNA
<213> ORGANISM: Artificial Sequence
<220> FEATURE:
<223> OTHER INFORMATION: Staple strand_0711 of the 2D DNA nanostructure.

<400> SEQUENCE: 712
acataacggg aatcgtcata aataaagcaa agttcctcta ccacctacat cac        53

<210> SEQ ID NO 713
<211> LENGTH: 51
<212> TYPE: DNA
<213> ORGANISM: Artificial Sequence
<220> FEATURE:
<223> OTHER INFORMATION: Staple strand_0712 of the 2D DNA nanostructure.

<400> SEQUENCE: 713
```
aatactgccc aaaaggaatt acgtggctca ttcctctacc acctacatca c        51

<210> SEQ ID NO 714
<211> LENGTH: 53
<212> TYPE: DNA
<213> ORGANISM: Artificial Sequence
<220> FEATURE:
<223> OTHER INFORMATION: Staple strand_0713 of the 2D DNA nanostructure.

<400> SEQUENCE: 714
cggattgcag agcttaattg ctgaaacgag tattcctcta ccacctacat cac      53

<210> SEQ ID NO 715
<211> LENGTH: 51
<212> TYPE: DNA
<213> ORGANISM: Artificial Sequence
<220> FEATURE:
<223> OTHER INFORMATION: Staple strand_0714 of the 2D DNA nanostructure.

<400> SEQUENCE: 715
gatggcttat caaaaagatt aagagcgtcc ttcctctacc acctacatca c        51

<210> SEQ ID NO 716
<211> LENGTH: 53
<212> TYPE: DNA
<213> ORGANISM: Artificial Sequence
<220> FEATURE:
<223> OTHER INFORMATION: Staple strand_0715 of the 2D DNA nanostructure.

<400> SEQUENCE: 716
gatttagtca ataaagcctc agagaaccct cattcctcta ccacctacat cac      53

<210> SEQ ID NO 717
<211> LENGTH: 53
<212> TYPE: DNA
<213> ORGANISM: Artificial Sequence
<220> FEATURE:
<223> OTHER INFORMATION: Staple strand_0716 of the 2D DNA nanostructure.

<400> SEQUENCE: 717
taaatgaatt ttctgtatgg gattaatttc ttttcctcta ccacctacat cac      53

<210> SEQ ID NO 718
<211> LENGTH: 53
<212> TYPE: DNA
<213> ORGANISM: Artificial Sequence
<220> FEATURE:
<223> OTHER INFORMATION: Staple strand_0717 of the 2D DNA nanostructure.

<400> SEQUENCE: 718
aaacagcttt ttgcgggatc gtcaacacta aattcctcta ccacctacat cac      53

<210> SEQ ID NO 719
<211> LENGTH: 53
<212> TYPE: DNA
<213> ORGANISM: Artificial Sequence
<220> FEATURE:
<223> OTHER INFORMATION: Staple strand_0718 of the 2D DNA nanostructure.

<400> SEQUENCE: 719
aaggccgctg ataccgatag ttgcgacgtt agttcctcta ccacctacat cac      53

<210> SEQ ID NO 720
<211> LENGTH: 53
<212> TYPE: DNA

<213> ORGANISM: Artificial Sequence
<220> FEATURE:
<223> OTHER INFORMATION: Staple strand_0719 of the 2D DNA nanostructure.

<400> SEQUENCE: 720
acactcatcc atgttactta gccgaaagct gcttcctcta ccacctacat cac        53

<210> SEQ ID NO 721
<211> LENGTH: 53
<212> TYPE: DNA
<213> ORGANISM: Artificial Sequence
<220> FEATURE:
<223> OTHER INFORMATION: Staple strand_0720 of the 2D DNA nanostructure.

<400> SEQUENCE: 721
gacctgctct ttgaccccca gcgagggagt tattcctcta ccacctacat cac        53

<210> SEQ ID NO 722
<211> LENGTH: 53
<212> TYPE: DNA
<213> ORGANISM: Artificial Sequence
<220> FEATURE:
<223> OTHER INFORMATION: Staple strand_0721 of the 2D DNA nanostructure.

<400> SEQUENCE: 722
tcattcagat gcgattttaa gaacaggcat agttcctcta ccacctacat cac        53

<210> SEQ ID NO 723
<211> LENGTH: 53
<212> TYPE: DNA
<213> ORGANISM: Artificial Sequence
<220> FEATURE:
<223> OTHER INFORMATION: Staple strand_0722 of the 2D DNA nanostructure.

<400> SEQUENCE: 723
attacctttg aataaggctt gcccaaatcc gcttcctcta ccacctacat cac        53

<210> SEQ ID NO 724
<211> LENGTH: 53
<212> TYPE: DNA
<213> ORGANISM: Artificial Sequence
<220> FEATURE:
<223> OTHER INFORMATION: Staple strand_0723 of the 2D DNA nanostructure.

<400> SEQUENCE: 724
taagagcaaa tgtttagact ggataggaag ccttcctcta ccacctacat cac        53

<210> SEQ ID NO 725
<211> LENGTH: 53
<212> TYPE: DNA
<213> ORGANISM: Artificial Sequence
<220> FEATURE:
<223> OTHER INFORMATION: Staple strand_0724 of the 2D DNA nanostructure.

<400> SEQUENCE: 725
aatagtaaac actatcataa ccctcattgt gattcctcta ccacctacat cac        53

<210> SEQ ID NO 726
<211> LENGTH: 53
<212> TYPE: DNA
<213> ORGANISM: Artificial Sequence
<220> FEATURE:
<223> OTHER INFORMATION: Staple strand_0725 of the 2D DNA nanostructure.

<400> SEQUENCE: 726
cgaaagactt tgataagagg tcatatttcg cattcctcta ccacctacat cac        53

<210> SEQ ID NO 727
<211> LENGTH: 53
<212> TYPE: DNA
<213> ORGANISM: Artificial Sequence
<220> FEATURE:
<223> OTHER INFORMATION: Staple strand_0726 of the 2D DNA nanostructure.

<400> SEQUENCE: 727
ttgctccttt caaatatcgc gtttgagggg gtttcctcta ccacctacat cac    53

<210> SEQ ID NO 728
<211> LENGTH: 53
<212> TYPE: DNA
<213> ORGANISM: Artificial Sequence
<220> FEATURE:
<223> OTHER INFORMATION: Staple strand_0727 of the 2D DNA nanostructure.

<400> SEQUENCE: 728
aatggtcaac aggcaaggca aagagtaatg tgttcctcta ccacctacat cac    53

<210> SEQ ID NO 729
<211> LENGTH: 52
<212> TYPE: DNA
<213> ORGANISM: Artificial Sequence
<220> FEATURE:
<223> OTHER INFORMATION: Staple strand_0728 of the 2D DNA nanostructure.

<400> SEQUENCE: 729
tctaaagttt tgtcgtcttt ccagccgaca attcctctac cacctacatc ac    52

<210> SEQ ID NO 730
<211> LENGTH: 65
<212> TYPE: DNA
<213> ORGANISM: Artificial Sequence
<220> FEATURE:
<223> OTHER INFORMATION: Staple strand_0729 of the 2D DNA nanostructure.

<400> SEQUENCE: 730
tgacaactcg ctgaggcttg cattatacca agcgcgatga taaattcctc taccacctac    60
atcac    65

<210> SEQ ID NO 731
<211> LENGTH: 53
<212> TYPE: DNA
<213> ORGANISM: Artificial Sequence
<220> FEATURE:
<223> OTHER INFORMATION: Staple strand_0730 of the 2D DNA nanostructure.

<400> SEQUENCE: 731
atattcggaa ccatcgccca cgcagagaag gattcctcta ccacctacat cac    53

<210> SEQ ID NO 732
<211> LENGTH: 53
<212> TYPE: DNA
<213> ORGANISM: Artificial Sequence
<220> FEATURE:
<223> OTHER INFORMATION: Staple strand_0731 of the 2D DNA nanostructure.

<400> SEQUENCE: 732
tcatcgccaa caaagtacaa cggacgccag cattcctcta ccacctacat cac    53

<210> SEQ ID NO 733
<211> LENGTH: 53
<212> TYPE: DNA

```
<213> ORGANISM: Artificial Sequence
<220> FEATURE:
<223> OTHER INFORMATION: Staple strand_0732 of the 2D DNA nanostructure.

<400> SEQUENCE: 733
gatggtttga acgagtagta aatttaccat tattcctcta ccacctacat cac         53

<210> SEQ ID NO 734
<211> LENGTH: 59
<212> TYPE: DNA
<213> ORGANISM: Artificial Sequence
<220> FEATURE:
<223> OTHER INFORMATION: Staple strand_0733 of the 2D DNA nanostructure.

<400> SEQUENCE: 734
cgtttaccag acgacaaaga agttttgcca taattcgatt cctctaccac ctacatcac   59

<210> SEQ ID NO 735
<211> LENGTH: 53
<212> TYPE: DNA
<213> ORGANISM: Artificial Sequence
<220> FEATURE:
<223> OTHER INFORMATION: Staple strand_0734 of the 2D DNA nanostructure.

<400> SEQUENCE: 735
cttttgcaga taaaaaccaa aataaagact ccttcctcta ccacctacat cac         53

<210> SEQ ID NO 736
<211> LENGTH: 51
<212> TYPE: DNA
<213> ORGANISM: Artificial Sequence
<220> FEATURE:
<223> OTHER INFORMATION: Staple strand_0735 of the 2D DNA nanostructure.

<400> SEQUENCE: 736
gcttcaatca ggattagaga gttattttca ttcctctacc acctacatca c           51

<210> SEQ ID NO 737
<211> LENGTH: 53
<212> TYPE: DNA
<213> ORGANISM: Artificial Sequence
<220> FEATURE:
<223> OTHER INFORMATION: Staple strand_0736 of the 2D DNA nanostructure.

<400> SEQUENCE: 737
ccaacaggag cgaaccagac cggagccttt acttcctcta ccacctacat cac         53

<210> SEQ ID NO 738
<211> LENGTH: 51
<212> TYPE: DNA
<213> ORGANISM: Artificial Sequence
<220> FEATURE:
<223> OTHER INFORMATION: Staple strand_0737 of the 2D DNA nanostructure.

<400> SEQUENCE: 738
tttggggata gtagtagcat taaaaggccg ttcctctacc acctacatca c           51

<210> SEQ ID NO 739
<211> LENGTH: 53
<212> TYPE: DNA
<213> ORGANISM: Artificial Sequence
<220> FEATURE:
<223> OTHER INFORMATION: Staple strand_0738 of the 2D DNA nanostructure.

<400> SEQUENCE: 739
tccacagaca gccctcatag ttagcgtaac gattcctcta ccacctacat cac         53
```

<210> SEQ ID NO 740
<211> LENGTH: 53
<212> TYPE: DNA
<213> ORGANISM: Artificial Sequence
<220> FEATURE:
<223> OTHER INFORMATION: Staple strand_0739 of the 2D DNA nanostructure.

<400> SEQUENCE: 740
ttaggattgg ctgagactcc tcaataaccg atttcctcta ccacctacat cac        53

<210> SEQ ID NO 741
<211> LENGTH: 51
<212> TYPE: DNA
<213> ORGANISM: Artificial Sequence
<220> FEATURE:
<223> OTHER INFORMATION: Staple strand_0740 of the 2D DNA nanostructure.

<400> SEQUENCE: 741
tattaagaag cggggttttg ctcgtagcat ttcctctacc acctacatca c          51

<210> SEQ ID NO 742
<211> LENGTH: 53
<212> TYPE: DNA
<213> ORGANISM: Artificial Sequence
<220> FEATURE:
<223> OTHER INFORMATION: Staple strand_0741 of the 2D DNA nanostructure.

<400> SEQUENCE: 742
ttgacaggcc accaccagag ccgcgatttg tattcctcta ccacctacat cac        53

<210> SEQ ID NO 743
<211> LENGTH: 51
<212> TYPE: DNA
<213> ORGANISM: Artificial Sequence
<220> FEATURE:
<223> OTHER INFORMATION: Staple strand_0742 of the 2D DNA nanostructure.

<400> SEQUENCE: 743
caccagaaag gttgaggcag gtcatgaaag ttcctctacc acctacatca c          51

<210> SEQ ID NO 744
<211> LENGTH: 53
<212> TYPE: DNA
<213> ORGANISM: Artificial Sequence
<220> FEATURE:
<223> OTHER INFORMATION: Staple strand_0743 of the 2D DNA nanostructure.

<400> SEQUENCE: 744
gcaaggcctc accagtagca ccatgggctt gattcctcta ccacctacat cac        53

<210> SEQ ID NO 745
<211> LENGTH: 51
<212> TYPE: DNA
<213> ORGANISM: Artificial Sequence
<220> FEATURE:
<223> OTHER INFORMATION: Staple strand_0744 of the 2D DNA nanostructure.

<400> SEQUENCE: 745
cagcaaaagg aaacgtcacc aatgagccgc ttcctctacc acctacatca c          51

<210> SEQ ID NO 746
<211> LENGTH: 53
<212> TYPE: DNA
<213> ORGANISM: Artificial Sequence
<220> FEATURE:

<223> OTHER INFORMATION: Staple strand_0745 of the 2D DNA nanostructure.

<400> SEQUENCE: 746
ttattacgaa gaactggcat gattgcgaga ggttcctcta ccacctacat cac    53

<210> SEQ ID NO 747
<211> LENGTH: 51
<212> TYPE: DNA
<213> ORGANISM: Artificial Sequence
<220> FEATURE:
<223> OTHER INFORMATION: Staple strand_0746 of the 2D DNA nanostructure.

<400> SEQUENCE: 747
atacccaaca gtatgttagc aaattagagc ttcctctacc acctacatca c    51

<210> SEQ ID NO 748
<211> LENGTH: 53
<212> TYPE: DNA
<213> ORGANISM: Artificial Sequence
<220> FEATURE:
<223> OTHER INFORMATION: Staple strand_0747 of the 2D DNA nanostructure.

<400> SEQUENCE: 748
agagagaaaa aaatgaaaat agcaagcaaa ctttcctcta ccacctacat cac    53

<210> SEQ ID NO 749
<211> LENGTH: 51
<212> TYPE: DNA
<213> ORGANISM: Artificial Sequence
<220> FEATURE:
<223> OTHER INFORMATION: Staple strand_0748 of the 2D DNA nanostructure.

<400> SEQUENCE: 749
ttaacgtcta acataaaaac aggtaacgga ttcctctacc acctacatca c    51

<210> SEQ ID NO 750
<211> LENGTH: 53
<212> TYPE: DNA
<213> ORGANISM: Artificial Sequence
<220> FEATURE:
<223> OTHER INFORMATION: Staple strand_0749 of the 2D DNA nanostructure.

<400> SEQUENCE: 750
ccaatagctc atcgtaggaa tcatggcatc aattcctcta ccacctacat cac    53

<210> SEQ ID NO 751
<211> LENGTH: 53
<212> TYPE: DNA
<213> ORGANISM: Artificial Sequence
<220> FEATURE:
<223> OTHER INFORMATION: Staple strand_0750 of the 2D DNA nanostructure.

<400> SEQUENCE: 751
tcaccagtac aaactacaac gcctagtacc agttcctcta ccacctacat cac    53

<210> SEQ ID NO 752
<211> LENGTH: 53
<212> TYPE: DNA
<213> ORGANISM: Artificial Sequence
<220> FEATURE:
<223> OTHER INFORMATION: Staple strand_0751 of the 2D DNA nanostructure.

<400> SEQUENCE: 752
gcggataacc tattattctg aaacagacga ttttcctcta ccacctacat cac    53

```
<210> SEQ ID NO 753
<211> LENGTH: 53
<212> TYPE: DNA
<213> ORGANISM: Artificial Sequence
<220> FEATURE:
<223> OTHER INFORMATION: Staple strand_0752 of the 2D DNA nanostructure.

<400> SEQUENCE: 753
tttcggaagt gccgtcgaga gggtgagttt cgttcctcta ccacctacat cac          53

<210> SEQ ID NO 754
<211> LENGTH: 53
<212> TYPE: DNA
<213> ORGANISM: Artificial Sequence
<220> FEATURE:
<223> OTHER INFORMATION: Staple strand_0753 of the 2D DNA nanostructure.

<400> SEQUENCE: 754
ggccttgaag agccaccacc ctcagaaacc atttcctcta ccacctacat cac          53

<210> SEQ ID NO 755
<211> LENGTH: 53
<212> TYPE: DNA
<213> ORGANISM: Artificial Sequence
<220> FEATURE:
<223> OTHER INFORMATION: Staple strand_0754 of the 2D DNA nanostructure.

<400> SEQUENCE: 755
ccaccctcta ttcacaaaca aatacctgcc tattcctcta ccacctacat cac          53

<210> SEQ ID NO 756
<211> LENGTH: 53
<212> TYPE: DNA
<213> ORGANISM: Artificial Sequence
<220> FEATURE:
<223> OTHER INFORMATION: Staple strand_0755 of the 2D DNA nanostructure.

<400> SEQUENCE: 756
cgatagcatt gagccatttg ggaacgtaga aattcctcta ccacctacat cac          53

<210> SEQ ID NO 757
<211> LENGTH: 53
<212> TYPE: DNA
<213> ORGANISM: Artificial Sequence
<220> FEATURE:
<223> OTHER INFORMATION: Staple strand_0756 of the 2D DNA nanostructure.

<400> SEQUENCE: 757
tcaccgacgc accgtaatca gtagcagaac cgttcctcta ccacctacat cac          53

<210> SEQ ID NO 758
<211> LENGTH: 53
<212> TYPE: DNA
<213> ORGANISM: Artificial Sequence
<220> FEATURE:
<223> OTHER INFORMATION: Staple strand_0757 of the 2D DNA nanostructure.

<400> SEQUENCE: 758
atacataccg aggaaacgca ataagaagcg cattcctcta ccacctacat cac          53

<210> SEQ ID NO 759
<211> LENGTH: 53
<212> TYPE: DNA
<213> ORGANISM: Artificial Sequence
<220> FEATURE:
<223> OTHER INFORMATION: Staple strand_0758 of the 2D DNA nanostructure.
```

<400> SEQUENCE: 759
aaggaaacat aaaggtggca acattatcac cgttcctcta ccacctacat cac        53

<210> SEQ ID NO 760
<211> LENGTH: 53
<212> TYPE: DNA
<213> ORGANISM: Artificial Sequence
<220> FEATURE:
<223> OTHER INFORMATION: Staple strand_0759 of the 2D DNA nanostructure.

<400> SEQUENCE: 760
ttagacggcc aaataagaaa cgatagaagg ctttcctcta ccacctacat cac        53

<210> SEQ ID NO 761
<211> LENGTH: 53
<212> TYPE: DNA
<213> ORGANISM: Artificial Sequence
<220> FEATURE:
<223> OTHER INFORMATION: Staple strand_0760 of the 2D DNA nanostructure.

<400> SEQUENCE: 761
atcccaatga gaattaactg aacagttacc agttcctcta ccacctacat cac        53

<210> SEQ ID NO 762
<211> LENGTH: 53
<212> TYPE: DNA
<213> ORGANISM: Artificial Sequence
<220> FEATURE:
<223> OTHER INFORMATION: Staple strand_0761 of the 2D DNA nanostructure.

<400> SEQUENCE: 762
tatccggtct catcgagaac aagcgacaaa agttcctcta ccacctacat cac        53

<210> SEQ ID NO 763
<211> LENGTH: 52
<212> TYPE: DNA
<213> ORGANISM: Artificial Sequence
<220> FEATURE:
<223> OTHER INFORMATION: Staple strand_0762 of the 2D DNA nanostructure.

<400> SEQUENCE: 763
aggaacccat gtaccgtaac acttgatata attcctctac cacctacatc ac         52

<210> SEQ ID NO 764
<211> LENGTH: 51
<212> TYPE: DNA
<213> ORGANISM: Artificial Sequence
<220> FEATURE:
<223> OTHER INFORMATION: Staple strand_0763 of the 2D DNA nanostructure.

<400> SEQUENCE: 764
gtatagcaaa cagttaatgc ccaatcctca ttcctctacc acctacatca c          51

<210> SEQ ID NO 765
<211> LENGTH: 53
<212> TYPE: DNA
<213> ORGANISM: Artificial Sequence
<220> FEATURE:
<223> OTHER INFORMATION: Staple strand_0764 of the 2D DNA nanostructure.

<400> SEQUENCE: 765
gcccgtatcc ggaataggtg tatcagccca atttcctcta ccacctacat cac        53

<210> SEQ ID NO 766
<211> LENGTH: 51

```
<212> TYPE: DNA
<213> ORGANISM: Artificial Sequence
<220> FEATURE:
<223> OTHER INFORMATION: Staple strand_0765 of the 2D DNA nanostructure.

<400> SEQUENCE: 766
ttaaagccag agccgccacc ctcgacagaa ttcctctacc acctacatca c          51

<210> SEQ ID NO 767
<211> LENGTH: 53
<212> TYPE: DNA
<213> ORGANISM: Artificial Sequence
<220> FEATURE:
<223> OTHER INFORMATION: Staple strand_0766 of the 2D DNA nanostructure.

<400> SEQUENCE: 767
gcctccctca gaatggaaag cgcagtaaca gtttcctcta ccacctacat cac         53

<210> SEQ ID NO 768
<211> LENGTH: 51
<212> TYPE: DNA
<213> ORGANISM: Artificial Sequence
<220> FEATURE:
<223> OTHER INFORMATION: Staple strand_0767 of the 2D DNA nanostructure.

<400> SEQUENCE: 768
tcaagtttca ttaaaggtga atataaaga ttcctctacc acctacatca c            51

<210> SEQ ID NO 769
<211> LENGTH: 53
<212> TYPE: DNA
<213> ORGANISM: Artificial Sequence
<220> FEATURE:
<223> OTHER INFORMATION: Staple strand_0768 of the 2D DNA nanostructure.

<400> SEQUENCE: 769
gaaattattg cctttagcgt cagaccggaa ccttcctcta ccacctacat cac         53

<210> SEQ ID NO 770
<211> LENGTH: 51
<212> TYPE: DNA
<213> ORGANISM: Artificial Sequence
<220> FEATURE:
<223> OTHER INFORMATION: Staple strand_0769 of the 2D DNA nanostructure.

<400> SEQUENCE: 770
aacgcaaaga tagccgaaca aaccctgaac ttcctctacc acctacatca c           51

<210> SEQ ID NO 771
<211> LENGTH: 53
<212> TYPE: DNA
<213> ORGANISM: Artificial Sequence
<220> FEATURE:
<223> OTHER INFORMATION: Staple strand_0770 of the 2D DNA nanostructure.

<400> SEQUENCE: 771
aagtaagcag acaccacgga ataatattga cgttcctcta ccacctacat cac         53

<210> SEQ ID NO 772
<211> LENGTH: 51
<212> TYPE: DNA
<213> ORGANISM: Artificial Sequence
<220> FEATURE:
<223> OTHER INFORMATION: Staple strand_0771 of the 2D DNA nanostructure.

<400> SEQUENCE: 772
```
aaagtcacaa aataaacagc cagcgtttta ttcctctacc acctacatca c    51

<210> SEQ ID NO 773
<211> LENGTH: 53
<212> TYPE: DNA
<213> ORGANISM: Artificial Sequence
<220> FEATURE:
<223> OTHER INFORMATION: Staple strand_0772 of the 2D DNA nanostructure.

<400> SEQUENCE: 773
gccagttaga gggtaattga gcgctttaag aattcctcta ccacctacat cac    53

<210> SEQ ID NO 774
<211> LENGTH: 51
<212> TYPE: DNA
<213> ORGANISM: Artificial Sequence
<220> FEATURE:
<223> OTHER INFORMATION: Staple strand_0773 of the 2D DNA nanostructure.

<400> SEQUENCE: 774
gcgaacctcc aagaacgggt atgacaataa ttcctctacc acctacatca c    51

<210> SEQ ID NO 775
<211> LENGTH: 53
<212> TYPE: DNA
<213> ORGANISM: Artificial Sequence
<220> FEATURE:
<223> OTHER INFORMATION: Staple strand_0774 of the 2D DNA nanostructure.

<400> SEQUENCE: 775
ccaccctcat tttcagggat agcaaccgta ctttcctcta ccacctacat cac    53

<210> SEQ ID NO 776
<211> LENGTH: 53
<212> TYPE: DNA
<213> ORGANISM: Artificial Sequence
<220> FEATURE:
<223> OTHER INFORMATION: Staple strand_0775 of the 2D DNA nanostructure.

<400> SEQUENCE: 776
caggaggtgg ggtcagtgcc ttgagtctct gattcctcta ccacctacat cac    53

<210> SEQ ID NO 777
<211> LENGTH: 51
<212> TYPE: DNA
<213> ORGANISM: Artificial Sequence
<220> FEATURE:
<223> OTHER INFORMATION: Staple strand_0776 of the 2D DNA nanostructure.

<400> SEQUENCE: 777
gttttaactt agtaccgcca cccagagcca ttcctctacc acctacatca c    51

<210> SEQ ID NO 778
<211> LENGTH: 53
<212> TYPE: DNA
<213> ORGANISM: Artificial Sequence
<220> FEATURE:
<223> OTHER INFORMATION: Staple strand_0777 of the 2D DNA nanostructure.

<400> SEQUENCE: 778
atttaccggg aaccagagcc accactgtag cgttcctcta ccacctacat cac    53

<210> SEQ ID NO 779
<211> LENGTH: 51
<212> TYPE: DNA
<213> ORGANISM: Artificial Sequence

```
<220> FEATURE:
<223> OTHER INFORMATION: Staple strand_0778 of the 2D DNA nanostructure.

<400> SEQUENCE: 779
aaatcacctt ccagtaagcg tcagtaataa ttcctctacc acctacatca c            51

<210> SEQ ID NO 780
<211> LENGTH: 53
<212> TYPE: DNA
<213> ORGANISM: Artificial Sequence
<220> FEATURE:
<223> OTHER INFORMATION: Staple strand_0779 of the 2D DNA nanostructure.

<400> SEQUENCE: 780
cgttttcaag ggagggaagg taaagtttat ttttcctcta ccacctacat cac          53

<210> SEQ ID NO 781
<211> LENGTH: 51
<212> TYPE: DNA
<213> ORGANISM: Artificial Sequence
<220> FEATURE:
<223> OTHER INFORMATION: Staple strand_0780 of the 2D DNA nanostructure.

<400> SEQUENCE: 781
accgattgtc ggcattttcg gtcataatca ttcctctacc acctacatca c            51

<210> SEQ ID NO 782
<211> LENGTH: 53
<212> TYPE: DNA
<213> ORGANISM: Artificial Sequence
<220> FEATURE:
<223> OTHER INFORMATION: Staple strand_0781 of the 2D DNA nanostructure.

<400> SEQUENCE: 782
tgtcacaatc ttaccgaagc cctttaatat cattcctcta ccacctacat cac          53

<210> SEQ ID NO 783
<211> LENGTH: 51
<212> TYPE: DNA
<213> ORGANISM: Artificial Sequence
<220> FEATURE:
<223> OTHER INFORMATION: Staple strand_0782 of the 2D DNA nanostructure.

<400> SEQUENCE: 783
aatagctatc aatagaaaat tcaacattca ttcctctacc acctacatca c            51

<210> SEQ ID NO 784
<211> LENGTH: 53
<212> TYPE: DNA
<213> ORGANISM: Artificial Sequence
<220> FEATURE:
<223> OTHER INFORMATION: Staple strand_0783 of the 2D DNA nanostructure.

<400> SEQUENCE: 784
gagagataga gcgtctttcc agaggttttg aattcctcta ccacctacat cac          53

<210> SEQ ID NO 785
<211> LENGTH: 51
<212> TYPE: DNA
<213> ORGANISM: Artificial Sequence
<220> FEATURE:
<223> OTHER INFORMATION: Staple strand_0784 of the 2D DNA nanostructure.

<400> SEQUENCE: 785
acgctaacac ccacaagaat tgaaaatagc ttcctctacc acctacatca c            51
```

<210> SEQ ID NO 786
<211> LENGTH: 53
<212> TYPE: DNA
<213> ORGANISM: Artificial Sequence
<220> FEATURE:
<223> OTHER INFORMATION: Staple strand_0785 of the 2D DNA nanostructure.

<400> SEQUENCE: 786
gccttaaacc aatcaataat cggcacgcgc ctttcctcta ccacctacat cac    53

<210> SEQ ID NO 787
<211> LENGTH: 53
<212> TYPE: DNA
<213> ORGANISM: Artificial Sequence
<220> FEATURE:
<223> OTHER INFORMATION: Staple strand_0786 of the 2D DNA nanostructure.

<400> SEQUENCE: 787
taaatcggga ttcccaattc tgcgatataa tgttcctcta ccacctacat cac    53

<210> SEQ ID NO 788
<211> LENGTH: 51
<212> TYPE: DNA
<213> ORGANISM: Artificial Sequence
<220> FEATURE:
<223> OTHER INFORMATION: Staple strand_0787 of the 2D DNA nanostructure.

<400> SEQUENCE: 788
aacgcaaaat cgatgaacgg taccggttga ttcctctacc acctacatca c    51

<210> SEQ ID NO 789
<211> LENGTH: 53
<212> TYPE: DNA
<213> ORGANISM: Artificial Sequence
<220> FEATURE:
<223> OTHER INFORMATION: Staple strand_0788 of the 2D DNA nanostructure.

<400> SEQUENCE: 789
aacaagaggg ataaaaattt ttagcataaa gcttcctcta ccacctacat cac    53

<210> SEQ ID NO 790
<211> LENGTH: 51
<212> TYPE: DNA
<213> ORGANISM: Artificial Sequence
<220> FEATURE:
<223> OTHER INFORMATION: Staple strand_0789 of the 2D DNA nanostructure.

<400> SEQUENCE: 790
taatcagcgg attgaccgta atcgtaaccg ttcctctacc acctacatca c    51

<210> SEQ ID NO 791
<211> LENGTH: 53
<212> TYPE: DNA
<213> ORGANISM: Artificial Sequence
<220> FEATURE:
<223> OTHER INFORMATION: Staple strand_0790 of the 2D DNA nanostructure.

<400> SEQUENCE: 791
acaaacggaa aagcccaaa aacactggag cattcctcta ccacctacat cac    53

<210> SEQ ID NO 792
<211> LENGTH: 51
<212> TYPE: DNA
<213> ORGANISM: Artificial Sequence
<220> FEATURE:
<223> OTHER INFORMATION: Staple strand_0791 of the 2D DNA nanostructure.

```
<400> SEQUENCE: 792
tgcatctttc ccagtcacga cggcctgcag ttcctctacc acctacatca c         51

<210> SEQ ID NO 793
<211> LENGTH: 53
<212> TYPE: DNA
<213> ORGANISM: Artificial Sequence
<220> FEATURE:
<223> OTHER INFORMATION: Staple strand_0792 of the 2D DNA nanostructure.

<400> SEQUENCE: 793
ccagggttgc cagtttgagg ggacccgtgg gattcctcta ccacctacat cac       53

<210> SEQ ID NO 794
<211> LENGTH: 51
<212> TYPE: DNA
<213> ORGANISM: Artificial Sequence
<220> FEATURE:
<223> OTHER INFORMATION: Staple strand_0793 of the 2D DNA nanostructure.

<400> SEQUENCE: 794
gtcgacttcg gccaacgcgc ggggtttttc ttcctctacc acctacatca c         51

<210> SEQ ID NO 795
<211> LENGTH: 53
<212> TYPE: DNA
<213> ORGANISM: Artificial Sequence
<220> FEATURE:
<223> OTHER INFORMATION: Staple strand_0794 of the 2D DNA nanostructure.

<400> SEQUENCE: 795
ttaatgaact agaggatccc cgggggtaa cgttcctcta ccacctacat cac        53

<210> SEQ ID NO 796
<211> LENGTH: 51
<212> TYPE: DNA
<213> ORGANISM: Artificial Sequence
<220> FEATURE:
<223> OTHER INFORMATION: Staple strand_0795 of the 2D DNA nanostructure.

<400> SEQUENCE: 796
ttttcactca aagggcgaaa aaccatcacc ttcctctacc acctacatca c         51

<210> SEQ ID NO 797
<211> LENGTH: 53
<212> TYPE: DNA
<213> ORGANISM: Artificial Sequence
<220> FEATURE:
<223> OTHER INFORMATION: Staple strand_0796 of the 2D DNA nanostructure.

<400> SEQUENCE: 797
ctccaacgca gtgagacggg caaccagctg cattcctcta ccacctacat cac       53

<210> SEQ ID NO 798
<211> LENGTH: 52
<212> TYPE: DNA
<213> ORGANISM: Artificial Sequence
<220> FEATURE:
<223> OTHER INFORMATION: Staple strand_0797 of the 2D DNA nanostructure.

<400> SEQUENCE: 798
caaatcaagt tttttggggt cgaaacgtgg attcctctac cacctacatc ac        52

<210> SEQ ID NO 799
```

```
<211> LENGTH: 51
<212> TYPE: DNA
<213> ORGANISM: Artificial Sequence
<220> FEATURE:
<223> OTHER INFORMATION: Staple strand_0798 of the 2D DNA nanostructure.

<400> SEQUENCE: 799
aaattaagtt gaccattaga tacttttgcg ttcctctacc acctacatca c          51

<210> SEQ ID NO 800
<211> LENGTH: 53
<212> TYPE: DNA
<213> ORGANISM: Artificial Sequence
<220> FEATURE:
<223> OTHER INFORMATION: Staple strand_0799 of the 2D DNA nanostructure.

<400> SEQUENCE: 800
tatattttgt cattgcctga gagtggaaga ttttcctcta ccacctacat cac        53

<210> SEQ ID NO 801
<211> LENGTH: 51
<212> TYPE: DNA
<213> ORGANISM: Artificial Sequence
<220> FEATURE:
<223> OTHER INFORMATION: Staple strand_0800 of the 2D DNA nanostructure.

<400> SEQUENCE: 801
gctatcagaa atgcaatgcc tgaattagca ttcctctacc acctacatca c          51

<210> SEQ ID NO 802
<211> LENGTH: 53
<212> TYPE: DNA
<213> ORGANISM: Artificial Sequence
<220> FEATURE:
<223> OTHER INFORMATION: Staple strand_0801 of the 2D DNA nanostructure.

<400> SEQUENCE: 802
gtataagcca acccgtcgga ttctgacgac agttcctcta ccacctacat cac        53

<210> SEQ ID NO 803
<211> LENGTH: 51
<212> TYPE: DNA
<213> ORGANISM: Artificial Sequence
<220> FEATURE:
<223> OTHER INFORMATION: Staple strand_0802 of the 2D DNA nanostructure.

<400> SEQUENCE: 803
gcgagtaaaa atatttaaat tgttacaaag ttcctctacc acctacatca c          51

<210> SEQ ID NO 804
<211> LENGTH: 53
<212> TYPE: DNA
<213> ORGANISM: Artificial Sequence
<220> FEATURE:
<223> OTHER INFORMATION: Staple strand_0803 of the 2D DNA nanostructure.

<400> SEQUENCE: 804
tatcggccgc aaggcgatta agtttaccga gcttcctcta ccacctacat cac        53

<210> SEQ ID NO 805
<211> LENGTH: 51
<212> TYPE: DNA
<213> ORGANISM: Artificial Sequence
<220> FEATURE:
<223> OTHER INFORMATION: Staple strand_0804 of the 2D DNA nanostructure.

<400> SEQUENCE: 805
```
gatgtgcttc aggaagatcg cacaatgtga ttcctctacc acctacatca c    51

<210> SEQ ID NO 806
<211> LENGTH: 53
<212> TYPE: DNA
<213> ORGANISM: Artificial Sequence
<220> FEATURE:
<223> OTHER INFORMATION: Staple strand_0805 of the 2D DNA nanostructure.

<400> SEQUENCE: 806
tcgaattcgg gaaacctgtc gtgcagctga ttttcctcta ccacctacat cac    53

<210> SEQ ID NO 807
<211> LENGTH: 51
<212> TYPE: DNA
<213> ORGANISM: Artificial Sequence
<220> FEATURE:
<223> OTHER INFORMATION: Staple strand_0806 of the 2D DNA nanostructure.

<400> SEQUENCE: 807
ttccagtcgt aatcatggtc ataaaagggg ttcctctacc acctacatca c    51

<210> SEQ ID NO 808
<211> LENGTH: 53
<212> TYPE: DNA
<213> ORGANISM: Artificial Sequence
<220> FEATURE:
<223> OTHER INFORMATION: Staple strand_0807 of the 2D DNA nanostructure.

<400> SEQUENCE: 808
gcccttcaga gtccactatt aaagggtgcc gtttcctcta ccacctacat cac    53

<210> SEQ ID NO 809
<211> LENGTH: 51
<212> TYPE: DNA
<213> ORGANISM: Artificial Sequence
<220> FEATURE:
<223> OTHER INFORMATION: Staple strand_0808 of the 2D DNA nanostructure.

<400> SEQUENCE: 809
tggaacaacc gcctggccct gaggcccgct ttcctctacc acctacatca c    51

<210> SEQ ID NO 810
<211> LENGTH: 51
<212> TYPE: DNA
<213> ORGANISM: Artificial Sequence
<220> FEATURE:
<223> OTHER INFORMATION: Staple strand_0809 of the 2D DNA nanostructure.

<400> SEQUENCE: 810
aaagcactaa atcggaaccc taatccagtt ttcctctacc acctacatca c    51

<210> SEQ ID NO 811
<211> LENGTH: 53
<212> TYPE: DNA
<213> ORGANISM: Artificial Sequence
<220> FEATURE:
<223> OTHER INFORMATION: Staple strand_0810 of the 2D DNA nanostructure.

<400> SEQUENCE: 811
taaatcatat aacctgttta gctaaccttt aattcctcta ccacctacat cac    53

<210> SEQ ID NO 812
<211> LENGTH: 53
<212> TYPE: DNA

```
<213> ORGANISM: Artificial Sequence
<220> FEATURE:
<223> OTHER INFORMATION: Staple strand_0811 of the 2D DNA nanostructure.

<400> SEQUENCE: 812
taggtaaact attttttgaga gatcaaacgt tattcctcta ccacctacat cac      53

<210> SEQ ID NO 813
<211> LENGTH: 53
<212> TYPE: DNA
<213> ORGANISM: Artificial Sequence
<220> FEATURE:
<223> OTHER INFORMATION: Staple strand_0812 of the 2D DNA nanostructure.

<400> SEQUENCE: 813
gagggtagga ttcaaaaggg tgagacatcc aattcctcta ccacctacat cac      53

<210> SEQ ID NO 814
<211> LENGTH: 53
<212> TYPE: DNA
<213> ORGANISM: Artificial Sequence
<220> FEATURE:
<223> OTHER INFORMATION: Staple strand_0813 of the 2D DNA nanostructure.

<400> SEQUENCE: 814
atattttggc tttcatcaac attatccagc cattcctcta ccacctacat cac      53

<210> SEQ ID NO 815
<211> LENGTH: 53
<212> TYPE: DNA
<213> ORGANISM: Artificial Sequence
<220> FEATURE:
<223> OTHER INFORMATION: Staple strand_0814 of the 2D DNA nanostructure.

<400> SEQUENCE: 815
tgtagccatt aaaattcgca ttaaatgccg gattcctcta ccacctacat cac      53

<210> SEQ ID NO 816
<211> LENGTH: 53
<212> TYPE: DNA
<213> ORGANISM: Artificial Sequence
<220> FEATURE:
<223> OTHER INFORMATION: Staple strand_0815 of the 2D DNA nanostructure.

<400> SEQUENCE: 816
gctttccgat tacgccagct ggcggctgtt tcttcctcta ccacctacat cac      53

<210> SEQ ID NO 817
<211> LENGTH: 53
<212> TYPE: DNA
<213> ORGANISM: Artificial Sequence
<220> FEATURE:
<223> OTHER INFORMATION: Staple strand_0816 of the 2D DNA nanostructure.

<400> SEQUENCE: 817
tcttcgctgc accgcttctg gtgcggcctt ccttcctcta ccacctacat cac      53

<210> SEQ ID NO 818
<211> LENGTH: 53
<212> TYPE: DNA
<213> ORGANISM: Artificial Sequence
<220> FEATURE:
<223> OTHER INFORMATION: Staple strand_0817 of the 2D DNA nanostructure.

<400> SEQUENCE: 818
ctgtgtgatt gcgttgcgct cactagagtt gcttcctcta ccacctacat cac      53
```

<210> SEQ ID NO 819
<211> LENGTH: 53
<212> TYPE: DNA
<213> ORGANISM: Artificial Sequence
<220> FEATURE:
<223> OTHER INFORMATION: Staple strand_0818 of the 2D DNA nanostructure.

<400> SEQUENCE: 819
cacattaaaa ttgttatccg ctcatgcggg ccttcctcta ccacctacat cac    53

<210> SEQ ID NO 820
<211> LENGTH: 53
<212> TYPE: DNA
<213> ORGANISM: Artificial Sequence
<220> FEATURE:
<223> OTHER INFORMATION: Staple strand_0819 of the 2D DNA nanostructure.

<400> SEQUENCE: 820
agcaagcgta gggttgagtg ttgtagggag ccttcctcta ccacctacat cac    53

<210> SEQ ID NO 821
<211> LENGTH: 53
<212> TYPE: DNA
<213> ORGANISM: Artificial Sequence
<220> FEATURE:
<223> OTHER INFORMATION: Staple strand_0820 of the 2D DNA nanostructure.

<400> SEQUENCE: 821
gcccgagagt ccacgctggt ttgcagctaa ctttcctcta ccacctacat cac    53

<210> SEQ ID NO 822
<211> LENGTH: 53
<212> TYPE: DNA
<213> ORGANISM: Artificial Sequence
<220> FEATURE:
<223> OTHER INFORMATION: Staple strand_0821 of the 2D DNA nanostructure.

<400> SEQUENCE: 822
cccgatttag agcttgacgg ggaaaaagaa tattcctcta ccacctacat cac    53

<210> SEQ ID NO 823
<211> LENGTH: 53
<212> TYPE: DNA
<213> ORGANISM: Artificial Sequence
<220> FEATURE:
<223> OTHER INFORMATION: Staple strand_0822 of the 2D DNA nanostructure.

<400> SEQUENCE: 823
ttctactacg cgagctgaaa aggttaccgc gcttcctcta ccacctacat cac    53

<210> SEQ ID NO 824
<211> LENGTH: 51
<212> TYPE: DNA
<213> ORGANISM: Artificial Sequence
<220> FEATURE:
<223> OTHER INFORMATION: Staple strand_0823 of the 2D DNA nanostructure.

<400> SEQUENCE: 824
gagacagcta gctgataaat taatttttgt ttcctctacc acctacatca c    51

<210> SEQ ID NO 825
<211> LENGTH: 53
<212> TYPE: DNA
<213> ORGANISM: Artificial Sequence
<220> FEATURE:

<223> OTHER INFORMATION: Staple strand_0824 of the 2D DNA nanostructure.

<400> SEQUENCE: 825
caaccgtttc aaatcaccat caattcgagc cattcctcta ccacctacat cac        53

<210> SEQ ID NO 826
<211> LENGTH: 65
<212> TYPE: DNA
<213> ORGANISM: Artificial Sequence
<220> FEATURE:
<223> OTHER INFORMATION: Staple strand_0825 of the 2D DNA nanostructure.

<400> SEQUENCE: 826
taaatcaaaa taattcgcgt ctcggaaacc aggcaaaggg aaggttcctc taccacctac    60
atcac    65

<210> SEQ ID NO 827
<211> LENGTH: 53
<212> TYPE: DNA
<213> ORGANISM: Artificial Sequence
<220> FEATURE:
<223> OTHER INFORMATION: Staple strand_0826 of the 2D DNA nanostructure.

<400> SEQUENCE: 827
gccatcaagc tcatttttta accacaaatc cattcctcta ccacctacat cac        53

<210> SEQ ID NO 828
<211> LENGTH: 53
<212> TYPE: DNA
<213> ORGANISM: Artificial Sequence
<220> FEATURE:
<223> OTHER INFORMATION: Staple strand_0827 of the 2D DNA nanostructure.

<400> SEQUENCE: 828
caactgttgc gccattcgcc attcaaacat cattcctcta ccacctacat cac        53

<210> SEQ ID NO 829
<211> LENGTH: 53
<212> TYPE: DNA
<213> ORGANISM: Artificial Sequence
<220> FEATURE:
<223> OTHER INFORMATION: Staple strand_0828 of the 2D DNA nanostructure.

<400> SEQUENCE: 829
aagcctggta cgagccggaa gcatagatga tgttcctcta ccacctacat cac        53

<210> SEQ ID NO 830
<211> LENGTH: 59
<212> TYPE: DNA
<213> ORGANISM: Artificial Sequence
<220> FEATURE:
<223> OTHER INFORMATION: Staple strand_0829 of the 2D DNA nanostructure.

<400> SEQUENCE: 830
cccagcaggc gaaaaatccc ttataaatca agccggcgtt cctctaccac ctacatcac    59

<210> SEQ ID NO 831
<211> LENGTH: 53
<212> TYPE: DNA
<213> ORGANISM: Artificial Sequence
<220> FEATURE:
<223> OTHER INFORMATION: Staple strand_0830 of the 2D DNA nanostructure.

<400> SEQUENCE: 831
tcggcaaatc ctgtttgatg gtggaccctc aattcctcta ccacctacat cac        53

```
<210> SEQ ID NO 832
<211> LENGTH: 52
<212> TYPE: DNA
<213> ORGANISM: Artificial Sequence
<220> FEATURE:
<223> OTHER INFORMATION: Staple strand_0831 of the 2D DNA nanostructure.

<400> SEQUENCE: 832
aacgtggcga gaaaggaagg gaaaccagta attcctctac cacctacatc ac          52

<210> SEQ ID NO 833
<211> LENGTH: 51
<212> TYPE: DNA
<213> ORGANISM: Artificial Sequence
<220> FEATURE:
<223> OTHER INFORMATION: Staple strand_0832 of the 2D DNA nanostructure.

<400> SEQUENCE: 833
ttttatttaa gcaaatcaga tatttttttgt ttcctctacc acctacatca c           51

<210> SEQ ID NO 834
<211> LENGTH: 53
<212> TYPE: DNA
<213> ORGANISM: Artificial Sequence
<220> FEATURE:
<223> OTHER INFORMATION: Staple strand_0833 of the 2D DNA nanostructure.

<400> SEQUENCE: 834
gtaataagtt aggcagaggc atttatgata ttttcctcta ccacctacat cac          53

<210> SEQ ID NO 835
<211> LENGTH: 51
<212> TYPE: DNA
<213> ORGANISM: Artificial Sequence
<220> FEATURE:
<223> OTHER INFORMATION: Staple strand_0834 of the 2D DNA nanostructure.

<400> SEQUENCE: 835
catgtaatag aatataaagt accaagccgt ttcctctacc acctacatca c            51

<210> SEQ ID NO 836
<211> LENGTH: 53
<212> TYPE: DNA
<213> ORGANISM: Artificial Sequence
<220> FEATURE:
<223> OTHER INFORMATION: Staple strand_0835 of the 2D DNA nanostructure.

<400> SEQUENCE: 836
atcgcaagta tgtaaatgct gatgatagga acttcctcta ccacctacat cac          53

<210> SEQ ID NO 837
<211> LENGTH: 51
<212> TYPE: DNA
<213> ORGANISM: Artificial Sequence
<220> FEATURE:
<223> OTHER INFORMATION: Staple strand_0836 of the 2D DNA nanostructure.

<400> SEQUENCE: 837
tataactaac aaagaacgcg agaacgccaa ttcctctacc acctacatca c            51

<210> SEQ ID NO 838
<211> LENGTH: 53
<212> TYPE: DNA
<213> ORGANISM: Artificial Sequence
<220> FEATURE:
```

<223> OTHER INFORMATION: Staple strand_0837 of the 2D DNA nanostructure.

<400> SEQUENCE: 838
agaaaacaaa gaagatgatg aaacaggctg cgttcctcta ccacctacat cac            53

<210> SEQ ID NO 839
<211> LENGTH: 51
<212> TYPE: DNA
<213> ORGANISM: Artificial Sequence
<220> FEATURE:
<223> OTHER INFORMATION: Staple strand_0838 of the 2D DNA nanostructure.

<400> SEQUENCE: 839
ctgagcaaaa attaattaca ttttgggtta ttcctctacc acctacatca c              51

<210> SEQ ID NO 840
<211> LENGTH: 53
<212> TYPE: DNA
<213> ORGANISM: Artificial Sequence
<220> FEATURE:
<223> OTHER INFORMATION: Staple strand_0839 of the 2D DNA nanostructure.

<400> SEQUENCE: 840
gcaattcaca tattcctgat tatcaaagtg tattcctcta ccacctacat cac            53

<210> SEQ ID NO 841
<211> LENGTH: 51
<212> TYPE: DNA
<213> ORGANISM: Artificial Sequence
<220> FEATURE:
<223> OTHER INFORMATION: Staple strand_0840 of the 2D DNA nanostructure.

<400> SEQUENCE: 841
attatcattc aatataatcc tgacaattac ttcctctacc acctacatca c              51

<210> SEQ ID NO 842
<211> LENGTH: 53
<212> TYPE: DNA
<213> ORGANISM: Artificial Sequence
<220> FEATURE:
<223> OTHER INFORMATION: Staple strand_0841 of the 2D DNA nanostructure.

<400> SEQUENCE: 842
tcaatatcga acctcaaata tcaattccga aattcctcta ccacctacat cac            53

<210> SEQ ID NO 843
<211> LENGTH: 51
<212> TYPE: DNA
<213> ORGANISM: Artificial Sequence
<220> FEATURE:
<223> OTHER INFORMATION: Staple strand_0842 of the 2D DNA nanostructure.

<400> SEQUENCE: 843
accttgcttg gtcagttggc aaagagcgga ttcctctacc acctacatca c              51

<210> SEQ ID NO 844
<211> LENGTH: 51
<212> TYPE: DNA
<213> ORGANISM: Artificial Sequence
<220> FEATURE:
<223> OTHER INFORMATION: Staple strand_0843 of the 2D DNA nanostructure.

<400> SEQUENCE: 844
taaaagggac attctggcca acaaagcatc ttcctctacc acctacatca c              51

```
<210> SEQ ID NO 845
<211> LENGTH: 53
<212> TYPE: DNA
<213> ORGANISM: Artificial Sequence
<220> FEATURE:
<223> OTHER INFORMATION: Staple strand_0844 of the 2D DNA nanostructure.

<400> SEQUENCE: 845
gtaccgcaat tctaagaacg cgagtattat ttttcctcta ccacctacat cac      53

<210> SEQ ID NO 846
<211> LENGTH: 53
<212> TYPE: DNA
<213> ORGANISM: Artificial Sequence
<220> FEATURE:
<223> OTHER INFORMATION: Staple strand_0845 of the 2D DNA nanostructure.

<400> SEQUENCE: 846
gtaaagtaat cgccatattt aacaaaactt ttttcctcta ccacctacat cac      53

<210> SEQ ID NO 847
<211> LENGTH: 53
<212> TYPE: DNA
<213> ORGANISM: Artificial Sequence
<220> FEATURE:
<223> OTHER INFORMATION: Staple strand_0846 of the 2D DNA nanostructure.

<400> SEQUENCE: 847
aattgagaat tctgtccaga cgactaaacc aattcctcta ccacctacat cac      53

<210> SEQ ID NO 848
<211> LENGTH: 53
<212> TYPE: DNA
<213> ORGANISM: Artificial Sequence
<220> FEATURE:
<223> OTHER INFORMATION: Staple strand_0847 of the 2D DNA nanostructure.

<400> SEQUENCE: 848
tcaaatataa cctccggctt aggtaacaat ttttcctcta ccacctacat cac      53

<210> SEQ ID NO 849
<211> LENGTH: 53
<212> TYPE: DNA
<213> ORGANISM: Artificial Sequence
<220> FEATURE:
<223> OTHER INFORMATION: Staple strand_0848 of the 2D DNA nanostructure.

<400> SEQUENCE: 849
acctttttat tttagttaat ttcatagggc ttttcctcta ccacctacat cac      53

<210> SEQ ID NO 850
<211> LENGTH: 53
<212> TYPE: DNA
<213> ORGANISM: Artificial Sequence
<220> FEATURE:
<223> OTHER INFORMATION: Staple strand_0849 of the 2D DNA nanostructure.

<400> SEQUENCE: 850
catttgaagg cgaattattc atttttgttt ggttcctcta ccacctacat cac      53

<210> SEQ ID NO 851
<211> LENGTH: 53
<212> TYPE: DNA
<213> ORGANISM: Artificial Sequence
<220> FEATURE:
<223> OTHER INFORMATION: Staple strand_0850 of the 2D DNA nanostructure.
```

-continued

<400> SEQUENCE: 851
cgcgcagatt accttttta atgggagaga ctttcctcta ccacctacat cac    53

<210> SEQ ID NO 852
<211> LENGTH: 53
<212> TYPE: DNA
<213> ORGANISM: Artificial Sequence
<220> FEATURE:
<223> OTHER INFORMATION: Staple strand_0851 of the 2D DNA nanostructure.

<400> SEQUENCE: 852
attatactaa gaaaccacca gaagtcaaca gtttcctcta ccacctacat cac    53

<210> SEQ ID NO 853
<211> LENGTH: 53
<212> TYPE: DNA
<213> ORGANISM: Artificial Sequence
<220> FEATURE:
<223> OTHER INFORMATION: Staple strand_0852 of the 2D DNA nanostructure.

<400> SEQUENCE: 853
gcggaacatc tgaataatgg aaggtacaaa atttcctcta ccacctacat cac    53

<210> SEQ ID NO 854
<211> LENGTH: 53
<212> TYPE: DNA
<213> ORGANISM: Artificial Sequence
<220> FEATURE:
<223> OTHER INFORMATION: Staple strand_0853 of the 2D DNA nanostructure.

<400> SEQUENCE: 854
tgaaaggagc aaatgaaaaa tctagagata gattcctcta ccacctacat cac    53

<210> SEQ ID NO 855
<211> LENGTH: 53
<212> TYPE: DNA
<213> ORGANISM: Artificial Sequence
<220> FEATURE:
<223> OTHER INFORMATION: Staple strand_0854 of the 2D DNA nanostructure.

<400> SEQUENCE: 855
agccagcaat tgaggaaggt tatcatcatt ttttcctcta ccacctacat cac    53

<210> SEQ ID NO 856
<211> LENGTH: 53
<212> TYPE: DNA
<213> ORGANISM: Artificial Sequence
<220> FEATURE:
<223> OTHER INFORMATION: Staple strand_0855 of the 2D DNA nanostructure.

<400> SEQUENCE: 856
acccttctga cctgaaagcg taagacgctg agttcctcta ccacctacat cac    53

<210> SEQ ID NO 857
<211> LENGTH: 53
<212> TYPE: DNA
<213> ORGANISM: Artificial Sequence
<220> FEATURE:
<223> OTHER INFORMATION: Staple strand_0856 of the 2D DNA nanostructure.

<400> SEQUENCE: 857
cttatcattc ccgacttgcg ggagcctaat ttttcctcta ccacctacat cac    53

<210> SEQ ID NO 858
<211> LENGTH: 51

```
<212> TYPE: DNA
<213> ORGANISM: Artificial Sequence
<220> FEATURE:
<223> OTHER INFORMATION: Staple strand_0857 of the 2D DNA nanostructure.

<400> SEQUENCE: 858
acaacatgcc aacgctcaac agtcttctga ttcctctacc acctacatca c         51

<210> SEQ ID NO 859
<211> LENGTH: 53
<212> TYPE: DNA
<213> ORGANISM: Artificial Sequence
<220> FEATURE:
<223> OTHER INFORMATION: Staple strand_0858 of the 2D DNA nanostructure.

<400> SEQUENCE: 859
agtataaagt tcagctaatg cagatgtctt tcttcctcta ccacctacat cac       53

<210> SEQ ID NO 860
<211> LENGTH: 51
<212> TYPE: DNA
<213> ORGANISM: Artificial Sequence
<220> FEATURE:
<223> OTHER INFORMATION: Staple strand_0859 of the 2D DNA nanostructure.

<400> SEQUENCE: 860
cctaaatcaa aatcataggt ctaaacagta ttcctctacc acctacatca c         51

<210> SEQ ID NO 861
<211> LENGTH: 53
<212> TYPE: DNA
<213> ORGANISM: Artificial Sequence
<220> FEATURE:
<223> OTHER INFORMATION: Staple strand_0860 of the 2D DNA nanostructure.

<400> SEQUENCE: 861
gaatttattt aatggtttga aatattctta ccttcctcta ccacctacat cac       53

<210> SEQ ID NO 862
<211> LENGTH: 51
<212> TYPE: DNA
<213> ORGANISM: Artificial Sequence
<220> FEATURE:
<223> OTHER INFORMATION: Staple strand_0861 of the 2D DNA nanostructure.

<400> SEQUENCE: 862
cataaatctt tgaataccaa gtgttagaac ttcctctacc acctacatca c         51

<210> SEQ ID NO 863
<211> LENGTH: 53
<212> TYPE: DNA
<213> ORGANISM: Artificial Sequence
<220> FEATURE:
<223> OTHER INFORMATION: Staple strand_0862 of the 2D DNA nanostructure.

<400> SEQUENCE: 863
cctgattgca atatatgtga gtgatcaata gtttcctcta ccacctacat cac       53

<210> SEQ ID NO 864
<211> LENGTH: 51
<212> TYPE: DNA
<213> ORGANISM: Artificial Sequence
<220> FEATURE:
<223> OTHER INFORMATION: Staple strand_0863 of the 2D DNA nanostructure.

<400> SEQUENCE: 864
```
ctaccatagt tgagtaaca tttaaaatat ttcctctacc acctacatca c    51

<210> SEQ ID NO 865
<211> LENGTH: 53
<212> TYPE: DNA
<213> ORGANISM: Artificial Sequence
<220> FEATURE:
<223> OTHER INFORMATION: Staple strand_0864 of the 2D DNA nanostructure.

<400> SEQUENCE: 865
attttaaaat caaaattatt tgcacggatt cgttcctcta ccacctacat cac    53

<210> SEQ ID NO 866
<211> LENGTH: 51
<212> TYPE: DNA
<213> ORGANISM: Artificial Sequence
<220> FEATURE:
<223> OTHER INFORMATION: Staple strand_0865 of the 2D DNA nanostructure.

<400> SEQUENCE: 866
ctttagggcc tgcaacagtg ccaatacgtg ttcctctacc acctacatca c    51

<210> SEQ ID NO 867
<211> LENGTH: 53
<212> TYPE: DNA
<213> ORGANISM: Artificial Sequence
<220> FEATURE:
<223> OTHER INFORMATION: Staple strand_0866 of the 2D DNA nanostructure.

<400> SEQUENCE: 867
ttaacaccag cactaacaac taatcgttat tattcctcta ccacctacat cac    53

<210> SEQ ID NO 868
<211> LENGTH: 52
<212> TYPE: DNA
<213> ORGANISM: Artificial Sequence
<220> FEATURE:
<223> OTHER INFORMATION: Staple strand_0867 of the 2D DNA nanostructure.

<400> SEQUENCE: 868
gcacagacaa tatttttgaa tggggtcagt attcctctac cacctacatc ac    52

<210> SEQ ID NO 869
<211> LENGTH: 51
<212> TYPE: DNA
<213> ORGANISM: Artificial Sequence
<220> FEATURE:
<223> OTHER INFORMATION: Staple strand_0868 of the 2D DNA nanostructure.

<400> SEQUENCE: 869
tgtagaaatc aagattagtt gctcttacca ttcctctacc acctacatca c    51

<210> SEQ ID NO 870
<211> LENGTH: 53
<212> TYPE: DNA
<213> ORGANISM: Artificial Sequence
<220> FEATURE:
<223> OTHER INFORMATION: Staple strand_0869 of the 2D DNA nanostructure.

<400> SEQUENCE: 870
gtttatcaat atgcgttata caaaccgacc gtttcctcta ccacctacat cac    53

<210> SEQ ID NO 871
<211> LENGTH: 51
<212> TYPE: DNA
<213> ORGANISM: Artificial Sequence

```
<220> FEATURE:
<223> OTHER INFORMATION: Staple strand_0870 of the 2D DNA nanostructure.

<400> SEQUENCE: 871
ttagtatcac aatagataag tccacgagca ttcctctacc acctacatca c              51

<210> SEQ ID NO 872
<211> LENGTH: 53
<212> TYPE: DNA
<213> ORGANISM: Artificial Sequence
<220> FEATURE:
<223> OTHER INFORMATION: Staple strand_0871 of the 2D DNA nanostructure.

<400> SEQUENCE: 872
gtgataaaaa gacgctgaga agagataacc ttttcctcta ccacctacat cac            53

<210> SEQ ID NO 873
<211> LENGTH: 51
<212> TYPE: DNA
<213> ORGANISM: Artificial Sequence
<220> FEATURE:
<223> OTHER INFORMATION: Staple strand_0872 of the 2D DNA nanostructure.

<400> SEQUENCE: 873
cttagattta aggcgttaaa taaagcctgt ttcctctacc acctacatca c              51

<210> SEQ ID NO 874
<211> LENGTH: 53
<212> TYPE: DNA
<213> ORGANISM: Artificial Sequence
<220> FEATURE:
<223> OTHER INFORMATION: Staple strand_0873 of the 2D DNA nanostructure.

<400> SEQUENCE: 874
gcttctgttc gggagaaaca ataacgtaaa acttcctcta ccacctacat cac            53

<210> SEQ ID NO 875
<211> LENGTH: 51
<212> TYPE: DNA
<213> ORGANISM: Artificial Sequence
<220> FEATURE:
<223> OTHER INFORMATION: Staple strand_0874 of the 2D DNA nanostructure.

<400> SEQUENCE: 875
cttttacaaa atcgtcgcta ttagcgatag ttcctctacc acctacatca c              51

<210> SEQ ID NO 876
<211> LENGTH: 53
<212> TYPE: DNA
<213> ORGANISM: Artificial Sequence
<220> FEATURE:
<223> OTHER INFORMATION: Staple strand_0875 of the 2D DNA nanostructure.

<400> SEQUENCE: 876
agaaataaaa atcctttgcc cgaaagatta gattcctcta ccacctacat cac            53

<210> SEQ ID NO 877
<211> LENGTH: 51
<212> TYPE: DNA
<213> ORGANISM: Artificial Sequence
<220> FEATURE:
<223> OTHER INFORMATION: Staple strand_0876 of the 2D DNA nanostructure.

<400> SEQUENCE: 877
ctcgtattag aaattgcgta gatacagtac ttcctctacc acctacatca c              51
```

<210> SEQ ID NO 878
<211> LENGTH: 53
<212> TYPE: DNA
<213> ORGANISM: Artificial Sequence
<220> FEATURE:
<223> OTHER INFORMATION: Staple strand_0877 of the 2D DNA nanostructure.

<400> SEQUENCE: 878
gccgtcaaaa aacagaggtg aggcctatta gtttcctcta ccacctacat cac        53

<210> SEQ ID NO 879
<211> LENGTH: 51
<212> TYPE: DNA
<213> ORGANISM: Artificial Sequence
<220> FEATURE:
<223> OTHER INFORMATION: Staple strand_0878 of the 2D DNA nanostructure.

<400> SEQUENCE: 879
cagaagatta gataatacat ttgtcgacaa ttcctctacc acctacatca c          51

<210> SEQ ID NO 880
<211> LENGTH: 51
<212> TYPE: DNA
<213> ORGANISM: Artificial Sequence
<220> FEATURE:
<223> OTHER INFORMATION: Staple strand_0879 of the 2D DNA nanostructure.

<400> SEQUENCE: 880
ctttaatgcg cgaactgata gccccaccag ttcctctacc acctacatca c          51

<210> SEQ ID NO 881
<211> LENGTH: 52
<212> TYPE: DNA
<213> ORGANISM: Artificial Sequence
<220> FEATURE:
<223> OTHER INFORMATION: Staple strand_0880 of the 2D DNA nanostructure.

<400> SEQUENCE: 881
agaaaggaac aactaaagga attcaaaaaa ataacattcc taacttctca ta         52

<210> SEQ ID NO 882
<211> LENGTH: 51
<212> TYPE: DNA
<213> ORGANISM: Artificial Sequence
<220> FEATURE:
<223> OTHER INFORMATION: Staple strand_0881 of the 2D DNA nanostructure.

<400> SEQUENCE: 882
aggctccaga ggctttgagg acacgggtaa taacattcct aacttctcat a          51

<210> SEQ ID NO 883
<211> LENGTH: 53
<212> TYPE: DNA
<213> ORGANISM: Artificial Sequence
<220> FEATURE:
<223> OTHER INFORMATION: Staple strand_0882 of the 2D DNA nanostructure.

<400> SEQUENCE: 883
acggctacaa aaggagcctt taatgtgaga attaacattc taacttctc ata         53

<210> SEQ ID NO 884
<211> LENGTH: 51
<212> TYPE: DNA
<213> ORGANISM: Artificial Sequence
<220> FEATURE:
<223> OTHER INFORMATION: Staple strand_0883 of the 2D DNA nanostructure.

<400> SEQUENCE: 884
aatacgtttg aaagaggaca gactgacctt taacattcct aacttctcat a        51

<210> SEQ ID NO 885
<211> LENGTH: 53
<212> TYPE: DNA
<213> ORGANISM: Artificial Sequence
<220> FEATURE:
<223> OTHER INFORMATION: Staple strand_0884 of the 2D DNA nanostructure.

<400> SEQUENCE: 885
gaccaactaa tgccactacg aaggggtag cataacattc taacttctc ata         53

<210> SEQ ID NO 886
<211> LENGTH: 51
<212> TYPE: DNA
<213> ORGANISM: Artificial Sequence
<220> FEATURE:
<223> OTHER INFORMATION: Staple strand_0885 of the 2D DNA nanostructure.

<400> SEQUENCE: 886
catcaagtaa aacgaactaa cgagttgaga taacattcct aacttctcat a         51

<210> SEQ ID NO 887
<211> LENGTH: 53
<212> TYPE: DNA
<213> ORGANISM: Artificial Sequence
<220> FEATURE:
<223> OTHER INFORMATION: Staple strand_0886 of the 2D DNA nanostructure.

<400> SEQUENCE: 887
tacgttaaag taatcttgac aagaaccgaa cttaacattc taacttctc ata        53

<210> SEQ ID NO 888
<211> LENGTH: 51
<212> TYPE: DNA
<213> ORGANISM: Artificial Sequence
<220> FEATURE:
<223> OTHER INFORMATION: Staple strand_0887 of the 2D DNA nanostructure.

<400> SEQUENCE: 888
tttaggacaa atgctttaaa caatcaggtc taacattcct aacttctcat a         51

<210> SEQ ID NO 889
<211> LENGTH: 53
<212> TYPE: DNA
<213> ORGANISM: Artificial Sequence
<220> FEATURE:
<223> OTHER INFORMATION: Staple strand_0888 of the 2D DNA nanostructure.

<400> SEQUENCE: 889 atcccctat accacattca actagaaaaa tctaacattc taacttctc ata         53

<210> SEQ ID NO 890
<211> LENGTH: 51
<212> TYPE: DNA
<213> ORGANISM: Artificial Sequence
<220> FEATURE:
<223> OTHER INFORMATION: Staple strand_0889 of the 2D DNA nanostructure.

<400> SEQUENCE: 890
tttaccccaa catgttttaa atttccatat taacattcct aacttctcat a         51

<210> SEQ ID NO 891

<211> LENGTH: 53
<212> TYPE: DNA
<213> ORGANISM: Artificial Sequence
<220> FEATURE:
<223> OTHER INFORMATION: Staple strand_0890 of the 2D DNA nanostructure.

<400> SEQUENCE: 891
ctgtagcttg actattatag tcagttcatt gataacattc ctaacttctc ata          53

<210> SEQ ID NO 892
<211> LENGTH: 51
<212> TYPE: DNA
<213> ORGANISM: Artificial Sequence
<220> FEATURE:
<223> OTHER INFORMATION: Staple strand_0891 of the 2D DNA nanostructure.

<400> SEQUENCE: 892
aacagttttg taccaaaaac attttatttc taacattcct aacttctcat a            51

<210> SEQ ID NO 893
<211> LENGTH: 53
<212> TYPE: DNA
<213> ORGANISM: Artificial Sequence
<220> FEATURE:
<223> OTHER INFORMATION: Staple strand_0892 of the 2D DNA nanostructure.

<400> SEQUENCE: 893
acaactttca acagtttcag cggatgtatc ggtaacattc ctaacttctc ata          53

<210> SEQ ID NO 894
<211> LENGTH: 53
<212> TYPE: DNA
<213> ORGANISM: Artificial Sequence
<220> FEATURE:
<223> OTHER INFORMATION: Staple strand_0893 of the 2D DNA nanostructure.

<400> SEQUENCE: 894
tttatcagga cagcatcgga acgacaccaa cctaacattc ctaacttctc ata          53

<210> SEQ ID NO 895
<211> LENGTH: 51
<212> TYPE: DNA
<213> ORGANISM: Artificial Sequence
<220> FEATURE:
<223> OTHER INFORMATION: Staple strand_0894 of the 2D DNA nanostructure.

<400> SEQUENCE: 895
cagcgaaact tgctttcgag gtgttgctaa taacattcct aacttctcat a            51

<210> SEQ ID NO 896
<211> LENGTH: 53
<212> TYPE: DNA
<213> ORGANISM: Artificial Sequence
<220> FEATURE:
<223> OTHER INFORMATION: Staple strand_0895 of the 2D DNA nanostructure.

<400> SEQUENCE: 896
taaaacgagg tcaatcataa gggaaccgga tataacattc ctaacttctc ata          53

<210> SEQ ID NO 897
<211> LENGTH: 51
<212> TYPE: DNA
<213> ORGANISM: Artificial Sequence
<220> FEATURE:
<223> OTHER INFORMATION: Staple strand_0896 of the 2D DNA nanostructure.

<400> SEQUENCE: 897

```
gcgcagacaa gaggcaaaag aatccctcag taacattcct aacttctcat a            51
```

<210> SEQ ID NO 898
<211> LENGTH: 53
<212> TYPE: DNA
<213> ORGANISM: Artificial Sequence
<220> FEATURE:
<223> OTHER INFORMATION: Staple strand_0897 of the 2D DNA nanostructure.

<400> SEQUENCE: 898

```
ttcattacgt caggacgttg ggaaatgcag attaacattc taacttctc ata           53
```

<210> SEQ ID NO 899
<211> LENGTH: 51
<212> TYPE: DNA
<213> ORGANISM: Artificial Sequence
<220> FEATURE:
<223> OTHER INFORMATION: Staple strand_0898 of the 2D DNA nanostructure.

<400> SEQUENCE: 899

```
ttataccacc aaatcaacgt aacgaacgag taacattcct aacttctcat a            51
```

<210> SEQ ID NO 900
<211> LENGTH: 53
<212> TYPE: DNA
<213> ORGANISM: Artificial Sequence
<220> FEATURE:
<223> OTHER INFORMATION: Staple strand_0899 of the 2D DNA nanostructure.

<400> SEQUENCE: 900

```
acataacggg aatcgtcata aataaagcaa agtaacattc taacttctc ata           53
```

<210> SEQ ID NO 901
<211> LENGTH: 51
<212> TYPE: DNA
<213> ORGANISM: Artificial Sequence
<220> FEATURE:
<223> OTHER INFORMATION: Staple strand_0900 of the 2D DNA nanostructure.

<400> SEQUENCE: 901

```
aatactgccc aaaaggaatt acgtggctca taacattcct aacttctcat a            51
```

<210> SEQ ID NO 902
<211> LENGTH: 53
<212> TYPE: DNA
<213> ORGANISM: Artificial Sequence
<220> FEATURE:
<223> OTHER INFORMATION: Staple strand_0901 of the 2D DNA nanostructure.

<400> SEQUENCE: 902

```
cggattgcag agcttaattg ctgaaacgag tataacattc taacttctc ata           53
```

<210> SEQ ID NO 903
<211> LENGTH: 51
<212> TYPE: DNA
<213> ORGANISM: Artificial Sequence
<220> FEATURE:
<223> OTHER INFORMATION: Staple strand_0902 of the 2D DNA nanostructure.

<400> SEQUENCE: 903

```
gatggcttat caaaaagatt aagagcgtcc taacattcct aacttctcat a            51
```

<210> SEQ ID NO 904
<211> LENGTH: 53
<212> TYPE: DNA

```
<213> ORGANISM: Artificial Sequence
<220> FEATURE:
<223> OTHER INFORMATION: Staple strand_0903 of the 2D DNA nanostructure.

<400> SEQUENCE: 904
gatttagtca ataaagcctc agagaaccct cataacattc ctaacttctc ata        53

<210> SEQ ID NO 905
<211> LENGTH: 53
<212> TYPE: DNA
<213> ORGANISM: Artificial Sequence
<220> FEATURE:
<223> OTHER INFORMATION: Staple strand_0904 of the 2D DNA nanostructure.

<400> SEQUENCE: 905
taaatgaatt ttctgtatgg gattaatttc tttaacattc ctaacttctc ata        53

<210> SEQ ID NO 906
<211> LENGTH: 53
<212> TYPE: DNA
<213> ORGANISM: Artificial Sequence
<220> FEATURE:
<223> OTHER INFORMATION: Staple strand_0905 of the 2D DNA nanostructure.

<400> SEQUENCE: 906
aaacagcttt ttgcgggatc gtcaacacta aataacattc ctaacttctc ata        53

<210> SEQ ID NO 907
<211> LENGTH: 53
<212> TYPE: DNA
<213> ORGANISM: Artificial Sequence
<220> FEATURE:
<223> OTHER INFORMATION: Staple strand_0906 of the 2D DNA nanostructure.

<400> SEQUENCE: 907
aaggccgctg ataccgatag ttgcgacgtt agtaacattc ctaacttctc ata        53

<210> SEQ ID NO 908
<211> LENGTH: 53
<212> TYPE: DNA
<213> ORGANISM: Artificial Sequence
<220> FEATURE:
<223> OTHER INFORMATION: Staple strand_0907 of the 2D DNA nanostructure.

<400> SEQUENCE: 908
acactcatcc atgttactta gccgaaagct gctaacattc ctaacttctc ata        53

<210> SEQ ID NO 909
<211> LENGTH: 53
<212> TYPE: DNA
<213> ORGANISM: Artificial Sequence
<220> FEATURE:
<223> OTHER INFORMATION: Staple strand_0908 of the 2D DNA nanostructure.

<400> SEQUENCE: 909
gacctgctct ttgaccccca gcgagggagt tataacattc ctaacttctc ata        53

<210> SEQ ID NO 910
<211> LENGTH: 53
<212> TYPE: DNA
<213> ORGANISM: Artificial Sequence
<220> FEATURE:
<223> OTHER INFORMATION: Staple strand_0909 of the 2D DNA nanostructure.

<400> SEQUENCE: 910
tcattcagat gcgattttaa gaacaggcat agtaacattc ctaacttctc ata        53
```

<210> SEQ ID NO 911
<211> LENGTH: 53
<212> TYPE: DNA
<213> ORGANISM: Artificial Sequence
<220> FEATURE:
<223> OTHER INFORMATION: Staple strand_0910 of the 2D DNA nanostructure.

<400> SEQUENCE: 911
attacctttg aataaggctt gcccaaatcc gctaacattc ctaacttctc ata         53

<210> SEQ ID NO 912
<211> LENGTH: 53
<212> TYPE: DNA
<213> ORGANISM: Artificial Sequence
<220> FEATURE:
<223> OTHER INFORMATION: Staple strand_0911 of the 2D DNA nanostructure.

<400> SEQUENCE: 912
taagagcaaa tgtttagact ggataggaag cctaacattc ctaacttctc ata         53

<210> SEQ ID NO 913
<211> LENGTH: 53
<212> TYPE: DNA
<213> ORGANISM: Artificial Sequence
<220> FEATURE:
<223> OTHER INFORMATION: Staple strand_0912 of the 2D DNA nanostructure.

<400> SEQUENCE: 913
aatagtaaac actatcataa ccctcattgt gataacattc ctaacttctc ata         53

<210> SEQ ID NO 914
<211> LENGTH: 53
<212> TYPE: DNA
<213> ORGANISM: Artificial Sequence
<220> FEATURE:
<223> OTHER INFORMATION: Staple strand_0913 of the 2D DNA nanostructure.

<400> SEQUENCE: 914
cgaaagactt tgataagagg tcatatttcg cataacattc ctaacttctc ata         53

<210> SEQ ID NO 915
<211> LENGTH: 53
<212> TYPE: DNA
<213> ORGANISM: Artificial Sequence
<220> FEATURE:
<223> OTHER INFORMATION: Staple strand_0914 of the 2D DNA nanostructure.

<400> SEQUENCE: 915 ttgctcctttt caaatatcgc gtttgagggg gttaacattc ctaacttctc ata        53

<210> SEQ ID NO 916
<211> LENGTH: 53
<212> TYPE: DNA
<213> ORGANISM: Artificial Sequence
<220> FEATURE:
<223> OTHER INFORMATION: Staple strand_0915 of the 2D DNA nanostructure.

<400> SEQUENCE: 916
aatggtcaac aggcaaggca aagagtaatg tgtaacattc ctaacttctc ata         53

<210> SEQ ID NO 917
<211> LENGTH: 52
<212> TYPE: DNA
<213> ORGANISM: Artificial Sequence
<220> FEATURE:

<223> OTHER INFORMATION: Staple strand_0916 of the 2D DNA nanostructure.

<400> SEQUENCE: 917
tctaaagttt tgtcgtcttt ccagccgaca ataacattcc taacttctca ta           52

<210> SEQ ID NO 918
<211> LENGTH: 65
<212> TYPE: DNA
<213> ORGANISM: Artificial Sequence
<220> FEATURE:
<223> OTHER INFORMATION: Staple strand_0917 of the 2D DNA nanostructure.

<400> SEQUENCE: 918
tgacaactcg ctgaggcttg cattatacca agcgcgatga taaataacat tcctaacttc    60
tcata                                                                65

<210> SEQ ID NO 919
<211> LENGTH: 53
<212> TYPE: DNA
<213> ORGANISM: Artificial Sequence
<220> FEATURE:
<223> OTHER INFORMATION: Staple strand_0918 of the 2D DNA nanostructure.

<400> SEQUENCE: 919
atattcggaa ccatcgccca cgcagagaag gataacattc ctaacttctc ata           53

<210> SEQ ID NO 920
<211> LENGTH: 53
<212> TYPE: DNA
<213> ORGANISM: Artificial Sequence
<220> FEATURE:
<223> OTHER INFORMATION: Staple strand_0919 of the 2D DNA nanostructure.

<400> SEQUENCE: 920
tcatcgccaa caaagtacaa cggacgccag cataacattc ctaacttctc ata           53

<210> SEQ ID NO 921
<211> LENGTH: 53
<212> TYPE: DNA
<213> ORGANISM: Artificial Sequence
<220> FEATURE:
<223> OTHER INFORMATION: Staple strand_0920 of the 2D DNA nanostructure.

<400> SEQUENCE: 921
gatggtttga acgagtagta aatttaccat tataacattc ctaacttctc ata           53

<210> SEQ ID NO 922
<211> LENGTH: 59
<212> TYPE: DNA
<213> ORGANISM: Artificial Sequence
<220> FEATURE:
<223> OTHER INFORMATION: Staple strand_0921 of the 2D DNA nanostructure.

<400> SEQUENCE: 922
cgtttaccag acgacaaaga agttttgcca taattcgata acattcctaa cttctcata    59

<210> SEQ ID NO 923
<211> LENGTH: 53
<212> TYPE: DNA
<213> ORGANISM: Artificial Sequence
<220> FEATURE:
<223> OTHER INFORMATION: Staple strand_0922 of the 2D DNA nanostructure.

<400> SEQUENCE: 923
cttttgcaga taaaaaccaa aataaagact cctaacattc ctaacttctc ata           53

<210> SEQ ID NO 924
<211> LENGTH: 51
<212> TYPE: DNA
<213> ORGANISM: Artificial Sequence
<220> FEATURE:
<223> OTHER INFORMATION: Staple strand_0923 of the 2D DNA nanostructure.

<400> SEQUENCE: 924
gcttcaatca ggattagaga gttattttca taacattcct aacttctcat a         51

<210> SEQ ID NO 925
<211> LENGTH: 53
<212> TYPE: DNA
<213> ORGANISM: Artificial Sequence
<220> FEATURE:
<223> OTHER INFORMATION: Staple strand_0924 of the 2D DNA nanostructure.

<400> SEQUENCE: 925
ccaacaggag cgaaccagac cggagccttt actaacattc taacttctc ata         53

<210> SEQ ID NO 926
<211> LENGTH: 51
<212> TYPE: DNA
<213> ORGANISM: Artificial Sequence
<220> FEATURE:
<223> OTHER INFORMATION: Staple strand_0925 of the 2D DNA nanostructure.

<400> SEQUENCE: 926
tttggggata gtagtagcat taaaaggccg taacattcct aacttctcat a         51

<210> SEQ ID NO 927
<211> LENGTH: 53
<212> TYPE: DNA
<213> ORGANISM: Artificial Sequence
<220> FEATURE:
<223> OTHER INFORMATION: Staple strand_0926 of the 2D DNA nanostructure.

<400> SEQUENCE: 927
tccacagaca gccctcatag ttagcgtaac gataacattc taacttctc ata         53

<210> SEQ ID NO 928
<211> LENGTH: 53
<212> TYPE: DNA
<213> ORGANISM: Artificial Sequence
<220> FEATURE:
<223> OTHER INFORMATION: Staple strand_0927 of the 2D DNA nanostructure.

<400> SEQUENCE: 928
ttaggattgg ctgagactcc tcaataaccg attaacattc taacttctc ata         53

<210> SEQ ID NO 929
<211> LENGTH: 51
<212> TYPE: DNA
<213> ORGANISM: Artificial Sequence
<220> FEATURE:
<223> OTHER INFORMATION: Staple strand_0928 of the 2D DNA nanostructure.

<400> SEQUENCE: 929
tattaagaag cggggttttg ctcgtagcat taacattcct aacttctcat a         51

<210> SEQ ID NO 930
<211> LENGTH: 53
<212> TYPE: DNA
<213> ORGANISM: Artificial Sequence
<220> FEATURE:

<223> OTHER INFORMATION: Staple strand_0929 of the 2D DNA nanostructure.

<400> SEQUENCE: 930
ttgacaggcc accaccagag ccgcgatttg tataacattc ctaacttctc ata        53

<210> SEQ ID NO 931
<211> LENGTH: 51
<212> TYPE: DNA
<213> ORGANISM: Artificial Sequence
<220> FEATURE:
<223> OTHER INFORMATION: Staple strand_0930 of the 2D DNA nanostructure.

<400> SEQUENCE: 931
caccagaaag gttgaggcag gtcatgaaag taacattcct aacttctcat a          51

<210> SEQ ID NO 932
<211> LENGTH: 53
<212> TYPE: DNA
<213> ORGANISM: Artificial Sequence
<220> FEATURE:
<223> OTHER INFORMATION: Staple strand_0931 of the 2D DNA nanostructure.

<400> SEQUENCE: 932
gcaaggcctc accagtagca ccatgggctt gataacattc ctaacttctc ata        53

<210> SEQ ID NO 933
<211> LENGTH: 51
<212> TYPE: DNA
<213> ORGANISM: Artificial Sequence
<220> FEATURE:
<223> OTHER INFORMATION: Staple strand_0932 of the 2D DNA nanostructure.

<400> SEQUENCE: 933
cagcaaaagg aaacgtcacc aatgagccgc taacattcct aacttctcat a          51

<210> SEQ ID NO 934
<211> LENGTH: 53
<212> TYPE: DNA
<213> ORGANISM: Artificial Sequence
<220> FEATURE:
<223> OTHER INFORMATION: Staple strand_0933 of the 2D DNA nanostructure.

<400> SEQUENCE: 934
ttattacgaa gaactggcat gattgcgaga ggtaacattc ctaacttctc ata        53

<210> SEQ ID NO 935
<211> LENGTH: 51
<212> TYPE: DNA
<213> ORGANISM: Artificial Sequence
<220> FEATURE:
<223> OTHER INFORMATION: Staple strand_0934 of the 2D DNA nanostructure.

<400> SEQUENCE: 935
atacccaaca gtatgttagc aaattagagc taacattcct aacttctcat a          51

<210> SEQ ID NO 936
<211> LENGTH: 53
<212> TYPE: DNA
<213> ORGANISM: Artificial Sequence
<220> FEATURE:
<223> OTHER INFORMATION: Staple strand_0935 of the 2D DNA nanostructure.

<400> SEQUENCE: 936
agagagaaaa aaatgaaaat agcaagcaaa cttaacattc ctaacttctc ata        53

```
<210> SEQ ID NO 937
<211> LENGTH: 51
<212> TYPE: DNA
<213> ORGANISM: Artificial Sequence
<220> FEATURE:
<223> OTHER INFORMATION: Staple strand_0936 of the 2D DNA nanostructure.

<400> SEQUENCE: 937
ttaacgtcta acataaaaac aggtaacgga taacattcct aacttctcat a            51

<210> SEQ ID NO 938
<211> LENGTH: 53
<212> TYPE: DNA
<213> ORGANISM: Artificial Sequence
<220> FEATURE:
<223> OTHER INFORMATION: Staple strand_0937 of the 2D DNA nanostructure.

<400> SEQUENCE: 938
ccaatagctc atcgtaggaa tcatggcatc aataacattc taacttctc ata           53

<210> SEQ ID NO 939
<211> LENGTH: 53
<212> TYPE: DNA
<213> ORGANISM: Artificial Sequence
<220> FEATURE:
<223> OTHER INFORMATION: Staple strand_0938 of the 2D DNA nanostructure.

<400> SEQUENCE: 939
tcaccagtac aaactacaac gcctagtacc agtaacattc taacttctc ata           53

<210> SEQ ID NO 940
<211> LENGTH: 53
<212> TYPE: DNA
<213> ORGANISM: Artificial Sequence
<220> FEATURE:
<223> OTHER INFORMATION: Staple strand_0939 of the 2D DNA nanostructure.

<400> SEQUENCE: 940
gcggataacc tattattctg aaacagacga tttaacattc taacttctc ata           53

<210> SEQ ID NO 941
<211> LENGTH: 53
<212> TYPE: DNA
<213> ORGANISM: Artificial Sequence
<220> FEATURE:
<223> OTHER INFORMATION: Staple strand_0940 of the 2D DNA nanostructure.

<400> SEQUENCE: 941
tttcggaagt gccgtcgaga gggtgagttt cgtaacattc taacttctc ata           53

<210> SEQ ID NO 942
<211> LENGTH: 53
<212> TYPE: DNA
<213> ORGANISM: Artificial Sequence
<220> FEATURE:
<223> OTHER INFORMATION: Staple strand_0941 of the 2D DNA nanostructure.

<400> SEQUENCE: 942
ggccttgaag agccaccacc ctcagaaacc attaacattc taacttctc ata           53

<210> SEQ ID NO 943
<211> LENGTH: 53
<212> TYPE: DNA
<213> ORGANISM: Artificial Sequence
<220> FEATURE:
<223> OTHER INFORMATION: Staple strand_0942 of the 2D DNA nanostructure.
```

<400> SEQUENCE: 943
ccaccctcta ttcacaaaca aatacctgcc tataacattc ctaacttctc ata            53

<210> SEQ ID NO 944
<211> LENGTH: 53
<212> TYPE: DNA
<213> ORGANISM: Artificial Sequence
<220> FEATURE:
<223> OTHER INFORMATION: Staple strand_0943 of the 2D DNA nanostructure.

<400> SEQUENCE: 944
cgatagcatt gagccatttg ggaacgtaga aataacattc ctaacttctc ata            53

<210> SEQ ID NO 945
<211> LENGTH: 53
<212> TYPE: DNA
<213> ORGANISM: Artificial Sequence
<220> FEATURE:
<223> OTHER INFORMATION: Staple strand_0944 of the 2D DNA nanostructure.

<400> SEQUENCE: 945
tcaccgacgc accgtaatca gtagcagaac cgtaacattc ctaacttctc ata            53

<210> SEQ ID NO 946
<211> LENGTH: 53
<212> TYPE: DNA
<213> ORGANISM: Artificial Sequence
<220> FEATURE:
<223> OTHER INFORMATION: Staple strand_0945 of the 2D DNA nanostructure.

<400> SEQUENCE: 946
atacataccg aggaaacgca ataagaagcg cataacattc ctaacttctc ata            53

<210> SEQ ID NO 947
<211> LENGTH: 53
<212> TYPE: DNA
<213> ORGANISM: Artificial Sequence
<220> FEATURE:
<223> OTHER INFORMATION: Staple strand_0946 of the 2D DNA nanostructure.

<400> SEQUENCE: 947
aaggaaacat aaaggtggca acattatcac cgtaacattc ctaacttctc ata            53

<210> SEQ ID NO 948
<211> LENGTH: 53
<212> TYPE: DNA
<213> ORGANISM: Artificial Sequence
<220> FEATURE:
<223> OTHER INFORMATION: Staple strand_0947 of the 2D DNA nanostructure.

<400> SEQUENCE: 948
ttagacggcc aaataagaaa cgatagaagg cttaacattc ctaacttctc ata            53

<210> SEQ ID NO 949
<211> LENGTH: 53
<212> TYPE: DNA
<213> ORGANISM: Artificial Sequence
<220> FEATURE:
<223> OTHER INFORMATION: Staple strand_0948 of the 2D DNA nanostructure.

<400> SEQUENCE: 949
atcccaatga gaattaactg aacagttacc agtaacattc ctaacttctc ata            53

<210> SEQ ID NO 950
<211> LENGTH: 53

```
<212> TYPE: DNA
<213> ORGANISM: Artificial Sequence
<220> FEATURE:
<223> OTHER INFORMATION: Staple strand_0949 of the 2D DNA nanostructure.

<400> SEQUENCE: 950
tatccggtct catcgagaac aagcgacaaa agtaacattc ctaacttctc ata          53

<210> SEQ ID NO 951
<211> LENGTH: 52
<212> TYPE: DNA
<213> ORGANISM: Artificial Sequence
<220> FEATURE:
<223> OTHER INFORMATION: Staple strand_0950 of the 2D DNA nanostructure.

<400> SEQUENCE: 951
aggaacccat gtaccgtaac acttgatata ataacattcc taacttctca ta           52

<210> SEQ ID NO 952
<211> LENGTH: 51
<212> TYPE: DNA
<213> ORGANISM: Artificial Sequence
<220> FEATURE:
<223> OTHER INFORMATION: Staple strand_0951 of the 2D DNA nanostructure.

<400> SEQUENCE: 952
gtatagcaaa cagttaatgc ccaatcctca taacattcct aacttctcat a            51

<210> SEQ ID NO 953
<211> LENGTH: 53
<212> TYPE: DNA
<213> ORGANISM: Artificial Sequence
<220> FEATURE:
<223> OTHER INFORMATION: Staple strand_0952 of the 2D DNA nanostructure.

<400> SEQUENCE: 953
gcccgtatcc ggaataggtg tatcagccca attaacattc ctaacttctc ata          53

<210> SEQ ID NO 954
<211> LENGTH: 51
<212> TYPE: DNA
<213> ORGANISM: Artificial Sequence
<220> FEATURE:
<223> OTHER INFORMATION: Staple strand_0953 of the 2D DNA nanostructure.

<400> SEQUENCE: 954
ttaaagccag agccgccacc ctcgacagaa taacattcct aacttctcat a            51

<210> SEQ ID NO 955
<211> LENGTH: 53
<212> TYPE: DNA
<213> ORGANISM: Artificial Sequence
<220> FEATURE:
<223> OTHER INFORMATION: Staple strand_0954 of the 2D DNA nanostructure.

<400> SEQUENCE: 955
gcctccctca gaatggaaag cgcagtaaca gttaacattc ctaacttctc ata          53

<210> SEQ ID NO 956
<211> LENGTH: 51
<212> TYPE: DNA
<213> ORGANISM: Artificial Sequence
<220> FEATURE:
<223> OTHER INFORMATION: Staple strand_0955 of the 2D DNA nanostructure.

<400> SEQUENCE: 956
```
tcaagtttca ttaaaggtga atataaaaga taacattcct aacttctcat a    51

<210> SEQ ID NO 957
<211> LENGTH: 53
<212> TYPE: DNA
<213> ORGANISM: Artificial Sequence
<220> FEATURE:
<223> OTHER INFORMATION: Staple strand_0956 of the 2D DNA nanostructure.

<400> SEQUENCE: 957
gaaattattg cctttagcgt cagaccggaa cctaacattc taacttctc ata    53

<210> SEQ ID NO 958
<211> LENGTH: 51
<212> TYPE: DNA
<213> ORGANISM: Artificial Sequence
<220> FEATURE:
<223> OTHER INFORMATION: Staple strand_0957 of the 2D DNA nanostructure.

<400> SEQUENCE: 958
aacgcaaaga tagccgaaca aaccctgaac taacattcct aacttctcat a    51

<210> SEQ ID NO 959
<211> LENGTH: 53
<212> TYPE: DNA
<213> ORGANISM: Artificial Sequence
<220> FEATURE:
<223> OTHER INFORMATION: Staple strand_0958 of the 2D DNA nanostructure.

<400> SEQUENCE: 959
aagtaagcag acaccacgga ataatattga cgtaacattc taacttctc ata    53

<210> SEQ ID NO 960
<211> LENGTH: 51
<212> TYPE: DNA
<213> ORGANISM: Artificial Sequence
<220> FEATURE:
<223> OTHER INFORMATION: Staple strand_0959 of the 2D DNA nanostructure.

<400> SEQUENCE: 960
aaagtcacaa ataaacagc cagcgtttta taacattcct aacttctcat a    51

<210> SEQ ID NO 961
<211> LENGTH: 53
<212> TYPE: DNA
<213> ORGANISM: Artificial Sequence
<220> FEATURE:
<223> OTHER INFORMATION: Staple strand_0960 of the 2D DNA nanostructure.

<400> SEQUENCE: 961
gccagttaga gggtaattga gcgctttaag aataacattc taacttctc ata    53

<210> SEQ ID NO 962
<211> LENGTH: 51
<212> TYPE: DNA
<213> ORGANISM: Artificial Sequence
<220> FEATURE:
<223> OTHER INFORMATION: Staple strand_0961 of the 2D DNA nanostructure.

<400> SEQUENCE: 962
gcgaacctcc aagaacgggt atgacaataa taacattcct aacttctcat a    51

<210> SEQ ID NO 963
<211> LENGTH: 53
<212> TYPE: DNA
<213> ORGANISM: Artificial Sequence

```
<220> FEATURE:
<223> OTHER INFORMATION: Staple strand_0962 of the 2D DNA nanostructure.

<400> SEQUENCE: 963
ccaccctcat tttcagggat agcaaccgta cttaacattc ctaacttctc ata        53

<210> SEQ ID NO 964
<211> LENGTH: 53
<212> TYPE: DNA
<213> ORGANISM: Artificial Sequence
<220> FEATURE:
<223> OTHER INFORMATION: Staple strand_0963 of the 2D DNA nanostructure.

<400> SEQUENCE: 964
caggaggtgg ggtcagtgcc ttgagtctct gataacattc ctaacttctc ata        53

<210> SEQ ID NO 965
<211> LENGTH: 51
<212> TYPE: DNA
<213> ORGANISM: Artificial Sequence
<220> FEATURE:
<223> OTHER INFORMATION: Staple strand_0964 of the 2D DNA nanostructure.

<400> SEQUENCE: 965
gttttaactt agtaccgcca cccagagcca taacattcct aacttctcat a          51

<210> SEQ ID NO 966
<211> LENGTH: 53
<212> TYPE: DNA
<213> ORGANISM: Artificial Sequence
<220> FEATURE:
<223> OTHER INFORMATION: Staple strand_0965 of the 2D DNA nanostructure.

<400> SEQUENCE: 966
atttaccggg aaccagagcc accactgtag cgtaacattc ctaacttctc ata        53

<210> SEQ ID NO 967
<211> LENGTH: 51
<212> TYPE: DNA
<213> ORGANISM: Artificial Sequence
<220> FEATURE:
<223> OTHER INFORMATION: Staple strand_0966 of the 2D DNA nanostructure.

<400> SEQUENCE: 967
aaatcacctt ccagtaagcg tcagtaataa taacattcct aacttctcat a          51

<210> SEQ ID NO 968
<211> LENGTH: 53
<212> TYPE: DNA
<213> ORGANISM: Artificial Sequence
<220> FEATURE:
<223> OTHER INFORMATION: Staple strand_0967 of the 2D DNA nanostructure.

<400> SEQUENCE: 968
cgttttcaag ggagggaagg taaagtttat tttaacattc ctaacttctc ata        53

<210> SEQ ID NO 969
<211> LENGTH: 51
<212> TYPE: DNA
<213> ORGANISM: Artificial Sequence
<220> FEATURE:
<223> OTHER INFORMATION: Staple strand_0968 of the 2D DNA nanostructure.

<400> SEQUENCE: 969
accgattgtc ggcattttcg gtcataatca taacattcct aacttctcat a          51
```

```
<210> SEQ ID NO 970
<211> LENGTH: 53
<212> TYPE: DNA
<213> ORGANISM: Artificial Sequence
<220> FEATURE:
<223> OTHER INFORMATION: Staple strand_0969 of the 2D DNA nanostructure.

<400> SEQUENCE: 970
tgtcacaatc ttaccgaagc cctttaatat cataacattc ctaacttctc ata           53

<210> SEQ ID NO 971
<211> LENGTH: 51
<212> TYPE: DNA
<213> ORGANISM: Artificial Sequence
<220> FEATURE:
<223> OTHER INFORMATION: Staple strand_0970 of the 2D DNA nanostructure.

<400> SEQUENCE: 971
aatagctatc aatagaaaat tcaacattca taacattcct aacttctcat a             51

<210> SEQ ID NO 972
<211> LENGTH: 53
<212> TYPE: DNA
<213> ORGANISM: Artificial Sequence
<220> FEATURE:
<223> OTHER INFORMATION: Staple strand_0971 of the 2D DNA nanostructure.

<400> SEQUENCE: 972
gagagataga gcgtctttcc agaggttttg aataacattc ctaacttctc ata           53

<210> SEQ ID NO 973
<211> LENGTH: 51
<212> TYPE: DNA
<213> ORGANISM: Artificial Sequence
<220> FEATURE:
<223> OTHER INFORMATION: Staple strand_0972 of the 2D DNA nanostructure.

<400> SEQUENCE: 973
acgctaacac ccacaagaat tgaaaatagc taacattcct aacttctcat a             51

<210> SEQ ID NO 974
<211> LENGTH: 53
<212> TYPE: DNA
<213> ORGANISM: Artificial Sequence
<220> FEATURE:
<223> OTHER INFORMATION: Staple strand_0973 of the 2D DNA nanostructure.

<400> SEQUENCE: 974
gccttaaacc aatcaataat cggcacgcgc cttaacattc ctaacttctc ata           53

<210> SEQ ID NO 975
<211> LENGTH: 53
<212> TYPE: DNA
<213> ORGANISM: Artificial Sequence
<220> FEATURE:
<223> OTHER INFORMATION: Staple strand_0974 of the 2D DNA nanostructure.

<400> SEQUENCE: 975
taaatcggga ttcccaattc tgcgatataa tgtaacattc ctaacttctc ata           53

<210> SEQ ID NO 976
<211> LENGTH: 51
<212> TYPE: DNA
<213> ORGANISM: Artificial Sequence
<220> FEATURE:
<223> OTHER INFORMATION: Staple strand_0975 of the 2D DNA nanostructure.
```

<400> SEQUENCE: 976
aacgcaaaat cgatgaacgg taccggttga taacattcct aacttctcat a        51

<210> SEQ ID NO 977
<211> LENGTH: 53
<212> TYPE: DNA
<213> ORGANISM: Artificial Sequence
<220> FEATURE:
<223> OTHER INFORMATION: Staple strand_0976 of the 2D DNA nanostructure.

<400> SEQUENCE: 977
aacaagaggg ataaaaattt ttagcataaa gctaacattc taacttctc ata        53

<210> SEQ ID NO 978
<211> LENGTH: 51
<212> TYPE: DNA
<213> ORGANISM: Artificial Sequence
<220> FEATURE:
<223> OTHER INFORMATION: Staple strand_0977 of the 2D DNA nanostructure.

<400> SEQUENCE: 978
taatcagcgg attgaccgta atcgtaaccg taacattcct aacttctcat a        51

<210> SEQ ID NO 979
<211> LENGTH: 53
<212> TYPE: DNA
<213> ORGANISM: Artificial Sequence
<220> FEATURE:
<223> OTHER INFORMATION: Staple strand_0978 of the 2D DNA nanostructure.

<400> SEQUENCE: 979
acaaacggaa aagccccaaa aacactggag cataacattc taacttctc ata        53

<210> SEQ ID NO 980
<211> LENGTH: 51
<212> TYPE: DNA
<213> ORGANISM: Artificial Sequence
<220> FEATURE:
<223> OTHER INFORMATION: Staple strand_0979 of the 2D DNA nanostructure.

<400> SEQUENCE: 980
tgcatctttc ccagtcacga cggcctgcag taacattcct aacttctcat a        51

<210> SEQ ID NO 981
<211> LENGTH: 53
<212> TYPE: DNA
<213> ORGANISM: Artificial Sequence
<220> FEATURE:
<223> OTHER INFORMATION: Staple strand_0980 of the 2D DNA nanostructure.

<400> SEQUENCE: 981
ccagggttgc cagtttgagg ggacccgtgg gataacattc taacttctc ata        53

<210> SEQ ID NO 982
<211> LENGTH: 51
<212> TYPE: DNA
<213> ORGANISM: Artificial Sequence
<220> FEATURE:
<223> OTHER INFORMATION: Staple strand_0981 of the 2D DNA nanostructure.

<400> SEQUENCE: 982
gtcgacttcg gccaacgcgc ggggtttttc taacattcct aacttctcat a        51

<210> SEQ ID NO 983

```
<211> LENGTH: 53
<212> TYPE: DNA
<213> ORGANISM: Artificial Sequence
<220> FEATURE:
<223> OTHER INFORMATION: Staple strand_0982 of the 2D DNA nanostructure.

<400> SEQUENCE: 983
ttaatgaact agaggatccc cgggggtaa cgtaacattc taacttctc ata            53

<210> SEQ ID NO 984
<211> LENGTH: 51
<212> TYPE: DNA
<213> ORGANISM: Artificial Sequence
<220> FEATURE:
<223> OTHER INFORMATION: Staple strand_0983 of the 2D DNA nanostructure.

<400> SEQUENCE: 984
ttttcactca aagggcgaaa aaccatcacc taacattcct aacttctcat a            51

<210> SEQ ID NO 985
<211> LENGTH: 53
<212> TYPE: DNA
<213> ORGANISM: Artificial Sequence
<220> FEATURE:
<223> OTHER INFORMATION: Staple strand_0984 of the 2D DNA nanostructure.

<400> SEQUENCE: 985
ctccaacgca gtgagacggg caaccagctg cataacattc taacttctc ata           53

<210> SEQ ID NO 986
<211> LENGTH: 52
<212> TYPE: DNA
<213> ORGANISM: Artificial Sequence
<220> FEATURE:
<223> OTHER INFORMATION: Staple strand_0985 of the 2D DNA nanostructure.

<400> SEQUENCE: 986
caaatcaagt tttttggggt cgaaacgtgg ataacattcc taacttctca ta           52

<210> SEQ ID NO 987
<211> LENGTH: 51
<212> TYPE: DNA
<213> ORGANISM: Artificial Sequence
<220> FEATURE:
<223> OTHER INFORMATION: Staple strand_0986 of the 2D DNA nanostructure.

<400> SEQUENCE: 987
aaattaagtt gaccattaga tacttttgcg taacattcct aacttctcat a            51

<210> SEQ ID NO 988
<211> LENGTH: 53
<212> TYPE: DNA
<213> ORGANISM: Artificial Sequence
<220> FEATURE:
<223> OTHER INFORMATION: Staple strand_0987 of the 2D DNA nanostructure.

<400> SEQUENCE: 988
tatattttgt cattgcctga gagtggaaga tttaacattc taacttctc ata           53

<210> SEQ ID NO 989
<211> LENGTH: 51
<212> TYPE: DNA
<213> ORGANISM: Artificial Sequence
<220> FEATURE:
<223> OTHER INFORMATION: Staple strand_0988 of the 2D DNA nanostructure.

<400> SEQUENCE: 989
```
gctatcagaa atgcaatgcc tgaattagca taacattcct aacttctcat a        51

<210> SEQ ID NO 990
<211> LENGTH: 53
<212> TYPE: DNA
<213> ORGANISM: Artificial Sequence
<220> FEATURE:
<223> OTHER INFORMATION: Staple strand_0989 of the 2D DNA nanostructure.

<400> SEQUENCE: 990
gtataagcca acccgtcgga ttctgacgac agtaacattc taacttctc ata        53

<210> SEQ ID NO 991
<211> LENGTH: 51
<212> TYPE: DNA
<213> ORGANISM: Artificial Sequence
<220> FEATURE:
<223> OTHER INFORMATION: Staple strand_0990 of the 2D DNA nanostructure.

<400> SEQUENCE: 991
gcgagtaaaa atatttaaat tgttacaaag taacattcct aacttctcat a        51

<210> SEQ ID NO 992
<211> LENGTH: 53
<212> TYPE: DNA
<213> ORGANISM: Artificial Sequence
<220> FEATURE:
<223> OTHER INFORMATION: Staple strand_0991 of the 2D DNA nanostructure.

<400> SEQUENCE: 992
tatcggccgc aaggcgatta agtttaccga gctaacattc taacttctc ata        53

<210> SEQ ID NO 993
<211> LENGTH: 51
<212> TYPE: DNA
<213> ORGANISM: Artificial Sequence
<220> FEATURE:
<223> OTHER INFORMATION: Staple strand_0992 of the 2D DNA nanostructure.

<400> SEQUENCE: 993
gatgtgcttc aggaagatcg cacaatgtga taacattcct aacttctcat a        51

<210> SEQ ID NO 994
<211> LENGTH: 53
<212> TYPE: DNA
<213> ORGANISM: Artificial Sequence
<220> FEATURE:
<223> OTHER INFORMATION: Staple strand_0993 of the 2D DNA nanostructure.

<400> SEQUENCE: 994
tcgaattcgg gaaacctgtc gtgcagctga tttaacattc taacttctc ata        53

<210> SEQ ID NO 995
<211> LENGTH: 51
<212> TYPE: DNA
<213> ORGANISM: Artificial Sequence
<220> FEATURE:
<223> OTHER INFORMATION: Staple strand_0994 of the 2D DNA nanostructure.

<400> SEQUENCE: 995
ttccagtcgt aatcatggtc ataaaagggg taacattcct aacttctcat a        51

<210> SEQ ID NO 996
<211> LENGTH: 53
<212> TYPE: DNA

```
<213> ORGANISM: Artificial Sequence
<220> FEATURE:
<223> OTHER INFORMATION: Staple strand_0995 of the 2D DNA nanostructure.

<400> SEQUENCE: 996
gcccttcaga gtccactatt aaagggtgcc gttaacattc ctaacttctc ata        53

<210> SEQ ID NO 997
<211> LENGTH: 51
<212> TYPE: DNA
<213> ORGANISM: Artificial Sequence
<220> FEATURE:
<223> OTHER INFORMATION: Staple strand_0996 of the 2D DNA nanostructure.

<400> SEQUENCE: 997
tggaacaacc gcctggccct gaggcccgct taacattcct aacttctcat a          51

<210> SEQ ID NO 998
<211> LENGTH: 51
<212> TYPE: DNA
<213> ORGANISM: Artificial Sequence
<220> FEATURE:
<223> OTHER INFORMATION: Staple strand_0997 of the 2D DNA nanostructure.

<400> SEQUENCE: 998
aaagcactaa atcggaaccc taatccagtt taacattcct aacttctcat a          51

<210> SEQ ID NO 999
<211> LENGTH: 53
<212> TYPE: DNA
<213> ORGANISM: Artificial Sequence
<220> FEATURE:
<223> OTHER INFORMATION: Staple strand_0998 of the 2D DNA nanostructure.

<400> SEQUENCE: 999
taaatcatat aacctgttta gctaaccttt aataacattc ctaacttctc ata        53

<210> SEQ ID NO 1000
<211> LENGTH: 53
<212> TYPE: DNA
<213> ORGANISM: Artificial Sequence
<220> FEATURE:
<223> OTHER INFORMATION: Staple strand_0999 of the 2D DNA nanostructure.

<400> SEQUENCE: 1000
taggtaaact atttttgaga gatcaaacgt tataacattc ctaacttctc ata        53

<210> SEQ ID NO 1001
<211> LENGTH: 53
<212> TYPE: DNA
<213> ORGANISM: Artificial Sequence
<220> FEATURE:
<223> OTHER INFORMATION: Staple strand_1000 of the 2D DNA nanostructure.

<400> SEQUENCE: 1001
gagggtagga ttcaaaaggg tgagacatcc aataacattc ctaacttctc ata        53

<210> SEQ ID NO 1002
<211> LENGTH: 53
<212> TYPE: DNA
<213> ORGANISM: Artificial Sequence
<220> FEATURE:
<223> OTHER INFORMATION: Staple strand_1001 of the 2D DNA nanostructure.

<400> SEQUENCE: 1002
atattttggc tttcatcaac attatccagc cataacattc ctaacttctc ata        53
```

<210> SEQ ID NO 1003
<211> LENGTH: 53
<212> TYPE: DNA
<213> ORGANISM: Artificial Sequence
<220> FEATURE:
<223> OTHER INFORMATION: Staple strand_1002 of the 2D DNA nanostructure.

<400> SEQUENCE: 1003
tgtagccatt aaaattcgca ttaaatgccg gataacattc ctaacttctc ata        53

<210> SEQ ID NO 1004
<211> LENGTH: 53
<212> TYPE: DNA
<213> ORGANISM: Artificial Sequence
<220> FEATURE:
<223> OTHER INFORMATION: Staple strand_1003 of the 2D DNA nanostructure.

<400> SEQUENCE: 1004
gctttccgat tacgccagct ggcggctgtt tctaacattc ctaacttctc ata        53

<210> SEQ ID NO 1005
<211> LENGTH: 53
<212> TYPE: DNA
<213> ORGANISM: Artificial Sequence
<220> FEATURE:
<223> OTHER INFORMATION: Staple strand_1004 of the 2D DNA nanostructure.

<400> SEQUENCE: 1005
tcttcgctgc accgcttctg gtgcggcctt cctaacattc ctaacttctc ata        53

<210> SEQ ID NO 1006
<211> LENGTH: 53
<212> TYPE: DNA
<213> ORGANISM: Artificial Sequence
<220> FEATURE:
<223> OTHER INFORMATION: Staple strand_1005 of the 2D DNA nanostructure.

<400> SEQUENCE: 1006
ctgtgtgatt gcgttgcgct cactagagtt gctaacattc ctaacttctc ata        53

<210> SEQ ID NO 1007
<211> LENGTH: 53
<212> TYPE: DNA
<213> ORGANISM: Artificial Sequence
<220> FEATURE:
<223> OTHER INFORMATION: Staple strand_1006 of the 2D DNA nanostructure.

<400> SEQUENCE: 1007
cacattaaaa ttgttatccg ctcatgcggg cctaacattc ctaacttctc ata        53

<210> SEQ ID NO 1008
<211> LENGTH: 53
<212> TYPE: DNA
<213> ORGANISM: Artificial Sequence
<220> FEATURE:
<223> OTHER INFORMATION: Staple strand_1007 of the 2D DNA nanostructure.

<400> SEQUENCE: 1008
agcaagcgta gggttgagtg ttgtagggag cctaacattc ctaacttctc ata        53

<210> SEQ ID NO 1009
<211> LENGTH: 53
<212> TYPE: DNA
<213> ORGANISM: Artificial Sequence
<220> FEATURE:

<223> OTHER INFORMATION: Staple strand_1008 of the 2D DNA nanostructure.

<400> SEQUENCE: 1009
gcccgagagt ccacgctggt ttgcagctaa cttaacattc ctaacttctc ata         53

<210> SEQ ID NO 1010
<211> LENGTH: 53
<212> TYPE: DNA
<213> ORGANISM: Artificial Sequence
<220> FEATURE:
<223> OTHER INFORMATION: Staple strand_1009 of the 2D DNA nanostructure.

<400> SEQUENCE: 1010
cccgatttag agcttgacgg ggaaaaagaa tataacattc ctaacttctc ata         53

<210> SEQ ID NO 1011
<211> LENGTH: 53
<212> TYPE: DNA
<213> ORGANISM: Artificial Sequence
<220> FEATURE:
<223> OTHER INFORMATION: Staple strand_1010 of the 2D DNA nanostructure.

<400> SEQUENCE: 1011
ttctactacg cgagctgaaa aggttaccgc gctaacattc ctaacttctc ata         53

<210> SEQ ID NO 1012
<211> LENGTH: 51
<212> TYPE: DNA
<213> ORGANISM: Artificial Sequence
<220> FEATURE:
<223> OTHER INFORMATION: Staple strand_1011 of the 2D DNA nanostructure.

<400> SEQUENCE: 1012
gagacagcta gctgataaat taatttttgt taacattcct aacttctcat a           51

<210> SEQ ID NO 1013
<211> LENGTH: 53
<212> TYPE: DNA
<213> ORGANISM: Artificial Sequence
<220> FEATURE:
<223> OTHER INFORMATION: Staple strand_1012 of the 2D DNA nanostructure.

<400> SEQUENCE: 1013
caaccgtttc aaatcaccat caattcgagc cataacattc ctaacttctc ata         53

<210> SEQ ID NO 1014
<211> LENGTH: 65
<212> TYPE: DNA
<213> ORGANISM: Artificial Sequence
<220> FEATURE:
<223> OTHER INFORMATION: Staple strand_1013 of the 2D DNA nanostructure.

<400> SEQUENCE: 1014
taaatcaaaa taattcgcgt ctcggaaacc aggcaaaggg aaggtaacat tcctaacttc   60
tcata                                                              65

<210> SEQ ID NO 1015
<211> LENGTH: 53
<212> TYPE: DNA
<213> ORGANISM: Artificial Sequence
<220> FEATURE:
<223> OTHER INFORMATION: Staple strand_1014 of the 2D DNA nanostructure.

<400> SEQUENCE: 1015
gccatcaagc tcattttttta accacaaatc cataacattc ctaacttctc ata        53

<210> SEQ ID NO 1016
<211> LENGTH: 53
<212> TYPE: DNA
<213> ORGANISM: Artificial Sequence
<220> FEATURE:
<223> OTHER INFORMATION: Staple strand_1015 of the 2D DNA nanostructure.

<400> SEQUENCE: 1016
caactgttgc gccattcgcc attcaaacat cataacattc ctaacttctc ata           53

<210> SEQ ID NO 1017
<211> LENGTH: 53
<212> TYPE: DNA
<213> ORGANISM: Artificial Sequence
<220> FEATURE:
<223> OTHER INFORMATION: Staple strand_1016 of the 2D DNA nanostructure.

<400> SEQUENCE: 1017
aagcctggta cgagccggaa gcatagatga tgtaacattc ctaacttctc ata           53

<210> SEQ ID NO 1018
<211> LENGTH: 59
<212> TYPE: DNA
<213> ORGANISM: Artificial Sequence
<220> FEATURE:
<223> OTHER INFORMATION: Staple strand_1017 of the 2D DNA nanostructure.

<400> SEQUENCE: 1018
cccagcaggc gaaaaatccc ttataaatca agccggcgta acattcctaa cttctcata    59

<210> SEQ ID NO 1019
<211> LENGTH: 53
<212> TYPE: DNA
<213> ORGANISM: Artificial Sequence
<220> FEATURE:
<223> OTHER INFORMATION: Staple strand_1018 of the 2D DNA nanostructure.

<400> SEQUENCE: 1019
tcggcaaatc ctgtttgatg gtggaccctc aataacattc ctaacttctc ata           53

<210> SEQ ID NO 1020
<211> LENGTH: 52
<212> TYPE: DNA
<213> ORGANISM: Artificial Sequence
<220> FEATURE:
<223> OTHER INFORMATION: Staple strand_1019 of the 2D DNA nanostructure.

<400> SEQUENCE: 1020
aacgtggcga gaaaggaagg gaaaccagta ataacattcc taacttctca ta            52

<210> SEQ ID NO 1021
<211> LENGTH: 51
<212> TYPE: DNA
<213> ORGANISM: Artificial Sequence
<220> FEATURE:
<223> OTHER INFORMATION: Staple strand_1020 of the 2D DNA nanostructure.

<400> SEQUENCE: 1021
ttttatttaa gcaaatcaga tattttttgt taacattcct aacttctcat a             51

<210> SEQ ID NO 1022
<211> LENGTH: 53
<212> TYPE: DNA
<213> ORGANISM: Artificial Sequence
<220> FEATURE:

```
<223> OTHER INFORMATION: Staple strand_1021 of the 2D DNA nanostructure.

<400> SEQUENCE: 1022
gtaataagtt aggcagaggc atttatgata tttaacattc ctaacttctc ata          53

<210> SEQ ID NO 1023
<211> LENGTH: 51
<212> TYPE: DNA
<213> ORGANISM: Artificial Sequence
<220> FEATURE:
<223> OTHER INFORMATION: Staple strand_1022 of the 2D DNA nanostructure.

<400> SEQUENCE: 1023
catgtaatag aatataaagt accaagccgt taacattcct aacttctcat a            51

<210> SEQ ID NO 1024
<211> LENGTH: 53
<212> TYPE: DNA
<213> ORGANISM: Artificial Sequence
<220> FEATURE:
<223> OTHER INFORMATION: Staple strand_1023 of the 2D DNA nanostructure.

<400> SEQUENCE: 1024
atcgcaagta tgtaaatgct gatgatagga actaacattc ctaacttctc ata          53

<210> SEQ ID NO 1025
<211> LENGTH: 51
<212> TYPE: DNA
<213> ORGANISM: Artificial Sequence
<220> FEATURE:
<223> OTHER INFORMATION: Staple strand_1024 of the 2D DNA nanostructure.

<400> SEQUENCE: 1025
tataactaac aaagaacgcg agaacgccaa taacattcct aacttctcat a            51

<210> SEQ ID NO 1026
<211> LENGTH: 53
<212> TYPE: DNA
<213> ORGANISM: Artificial Sequence
<220> FEATURE:
<223> OTHER INFORMATION: Staple strand_1025 of the 2D DNA nanostructure.

<400> SEQUENCE: 1026
agaaaacaaa gaagatgatg aaacaggctg cgtaacattc ctaacttctc ata          53

<210> SEQ ID NO 1027
<211> LENGTH: 51
<212> TYPE: DNA
<213> ORGANISM: Artificial Sequence
<220> FEATURE:
<223> OTHER INFORMATION: Staple strand_1026 of the 2D DNA nanostructure.

<400> SEQUENCE: 1027
ctgagcaaaa attaattaca ttttgggtta taacattcct aacttctcat a            51

<210> SEQ ID NO 1028
<211> LENGTH: 53
<212> TYPE: DNA
<213> ORGANISM: Artificial Sequence
<220> FEATURE:
<223> OTHER INFORMATION: Staple strand_1027 of the 2D DNA nanostructure.

<400> SEQUENCE: 1028
gcaattcaca tattcctgat tatcaaagtg tataacattc ctaacttctc ata          53
```

```
<210> SEQ ID NO 1029
<211> LENGTH: 51
<212> TYPE: DNA
<213> ORGANISM: Artificial Sequence
<220> FEATURE:
<223> OTHER INFORMATION: Staple strand_1028 of the 2D DNA nanostructure.

<400> SEQUENCE: 1029
attatcattc aatataatcc tgacaattac taacattcct aacttctcat a          51

<210> SEQ ID NO 1030
<211> LENGTH: 53
<212> TYPE: DNA
<213> ORGANISM: Artificial Sequence
<220> FEATURE:
<223> OTHER INFORMATION: Staple strand_1029 of the 2D DNA nanostructure.

<400> SEQUENCE: 1030
tcaatatcga acctcaaata tcaattccga aataacattc taacttctc ata         53

<210> SEQ ID NO 1031
<211> LENGTH: 51
<212> TYPE: DNA
<213> ORGANISM: Artificial Sequence
<220> FEATURE:
<223> OTHER INFORMATION: Staple strand_1030 of the 2D DNA nanostructure.

<400> SEQUENCE: 1031
accttgcttg gtcagttggc aaagagcgga taacattcct aacttctcat a          51

<210> SEQ ID NO 1032
<211> LENGTH: 51
<212> TYPE: DNA
<213> ORGANISM: Artificial Sequence
<220> FEATURE:
<223> OTHER INFORMATION: Staple strand_1031 of the 2D DNA nanostructure.

<400> SEQUENCE: 1032 taaagggac attctggcca acaaagcatc taacattcct aacttctcat a           51

<210> SEQ ID NO 1033
<211> LENGTH: 53
<212> TYPE: DNA
<213> ORGANISM: Artificial Sequence
<220> FEATURE:
<223> OTHER INFORMATION: Staple strand_1032 of the 2D DNA nanostructure.

<400> SEQUENCE: 1033
gtaccgcaat tctaagaacg cgagtattat tttaacattc taacttctc ata         53

<210> SEQ ID NO 1034
<211> LENGTH: 53
<212> TYPE: DNA
<213> ORGANISM: Artificial Sequence
<220> FEATURE:
<223> OTHER INFORMATION: Staple strand_1033 of the 2D DNA nanostructure.

<400> SEQUENCE: 1034
gtaaagtaat cgccatattt aacaaaactt tttaacattc taacttctc ata         53

<210> SEQ ID NO 1035
<211> LENGTH: 53
<212> TYPE: DNA
<213> ORGANISM: Artificial Sequence
<220> FEATURE:
<223> OTHER INFORMATION: Staple strand_1034 of the 2D DNA nanostructure.
```

<400> SEQUENCE: 1035
aattgagaat tctgtccaga cgactaaacc aataacattc ctaacttctc ata    53

<210> SEQ ID NO 1036
<211> LENGTH: 53
<212> TYPE: DNA
<213> ORGANISM: Artificial Sequence
<220> FEATURE:
<223> OTHER INFORMATION: Staple strand_1035 of the 2D DNA nanostructure.

<400> SEQUENCE: 1036
tcaaatataa cctccggctt aggtaacaat tttaacattc ctaacttctc ata    53

<210> SEQ ID NO 1037
<211> LENGTH: 53
<212> TYPE: DNA
<213> ORGANISM: Artificial Sequence
<220> FEATURE:
<223> OTHER INFORMATION: Staple strand_1036 of the 2D DNA nanostructure.

<400> SEQUENCE: 1037 accttttat tttagttaat ttcatagggc tttaacattc ctaacttctc ata    53

<210> SEQ ID NO 1038
<211> LENGTH: 53
<212> TYPE: DNA
<213> ORGANISM: Artificial Sequence
<220> FEATURE:
<223> OTHER INFORMATION: Staple strand_1037 of the 2D DNA nanostructure.

<400> SEQUENCE: 1038
catttgaagg cgaattattc attttttgttt ggtaacattc ctaacttctc ata    53

<210> SEQ ID NO 1039
<211> LENGTH: 53
<212> TYPE: DNA
<213> ORGANISM: Artificial Sequence
<220> FEATURE:
<223> OTHER INFORMATION: Staple strand_1038 of the 2D DNA nanostructure.

<400> SEQUENCE: 1039
cgcgcagatt accttttta atgggagaga cttaacattc ctaacttctc ata    53

<210> SEQ ID NO 1040
<211> LENGTH: 53
<212> TYPE: DNA
<213> ORGANISM: Artificial Sequence
<220> FEATURE:
<223> OTHER INFORMATION: Staple strand_1039 of the 2D DNA nanostructure.

<400> SEQUENCE: 1040
attatactaa gaaaccacca gaagtcaaca gttaacattc ctaacttctc ata    53

<210> SEQ ID NO 1041
<211> LENGTH: 53
<212> TYPE: DNA
<213> ORGANISM: Artificial Sequence
<220> FEATURE:
<223> OTHER INFORMATION: Staple strand_1040 of the 2D DNA nanostructure.

<400> SEQUENCE: 1041
gcggaacatc tgaataatgg aaggtacaaa attaacattc ctaacttctc ata    53

<210> SEQ ID NO 1042
<211> LENGTH: 53

```
<212> TYPE: DNA
<213> ORGANISM: Artificial Sequence
<220> FEATURE:
<223> OTHER INFORMATION: Staple strand_1041 of the 2D DNA nanostructure.

<400> SEQUENCE: 1042
tgaaaggagc aaatgaaaaa tctagagata gataacattc ctaacttctc ata          53

<210> SEQ ID NO 1043
<211> LENGTH: 53
<212> TYPE: DNA
<213> ORGANISM: Artificial Sequence
<220> FEATURE:
<223> OTHER INFORMATION: Staple strand_1042 of the 2D DNA nanostructure.

<400> SEQUENCE: 1043
agccagcaat tgaggaaggt tatcatcatt tttaacattc ctaacttctc ata          53

<210> SEQ ID NO 1044
<211> LENGTH: 53
<212> TYPE: DNA
<213> ORGANISM: Artificial Sequence
<220> FEATURE:
<223> OTHER INFORMATION: Staple strand_1043 of the 2D DNA nanostructure.

<400> SEQUENCE: 1044
acccttctga cctgaaagcg taagacgctg agtaacattc ctaacttctc ata          53

<210> SEQ ID NO 1045
<211> LENGTH: 53
<212> TYPE: DNA
<213> ORGANISM: Artificial Sequence
<220> FEATURE:
<223> OTHER INFORMATION: Staple strand_1044 of the 2D DNA nanostructure.

<400> SEQUENCE: 1045
cttatcattc ccgacttgcg ggagcctaat tttaacattc ctaacttctc ata          53

<210> SEQ ID NO 1046
<211> LENGTH: 51
<212> TYPE: DNA
<213> ORGANISM: Artificial Sequence
<220> FEATURE:
<223> OTHER INFORMATION: Staple strand_1045 of the 2D DNA nanostructure.

<400> SEQUENCE: 1046
acaacatgcc aacgctcaac agtcttctga taacattcct aacttctcat a            51

<210> SEQ ID NO 1047
<211> LENGTH: 53
<212> TYPE: DNA
<213> ORGANISM: Artificial Sequence
<220> FEATURE:
<223> OTHER INFORMATION: Staple strand_1046 of the 2D DNA nanostructure.

<400> SEQUENCE: 1047
agtataaagt tcagctaatg cagatgtctt tctaacattc ctaacttctc ata          53

<210> SEQ ID NO 1048
<211> LENGTH: 51
<212> TYPE: DNA
<213> ORGANISM: Artificial Sequence
<220> FEATURE:
<223> OTHER INFORMATION: Staple strand_1047 of the 2D DNA nanostructure.

<400> SEQUENCE: 1048
```

```
cctaaatcaa atcataggt ctaaacagta taacattcct aacttctcat a         51
```

<210> SEQ ID NO 1049
<211> LENGTH: 53
<212> TYPE: DNA
<213> ORGANISM: Artificial Sequence
<220> FEATURE:
<223> OTHER INFORMATION: Staple strand_1048 of the 2D DNA nanostructure.

<400> SEQUENCE: 1049

```
gaatttattt aatggtttga aatattctta cctaacattc taacttctc ata        53
```

<210> SEQ ID NO 1050
<211> LENGTH: 51
<212> TYPE: DNA
<213> ORGANISM: Artificial Sequence
<220> FEATURE:
<223> OTHER INFORMATION: Staple strand_1049 of the 2D DNA nanostructure.

<400> SEQUENCE: 1050

```
cataaatctt tgaataccaa gtgttagaac taacattcct aacttctcat a         51
```

<210> SEQ ID NO 1051
<211> LENGTH: 53
<212> TYPE: DNA
<213> ORGANISM: Artificial Sequence
<220> FEATURE:
<223> OTHER INFORMATION: Staple strand_1050 of the 2D DNA nanostructure.

<400> SEQUENCE: 1051

```
cctgattgca atatatgtga gtgatcaata gttaacattc taacttctc ata        53
```

<210> SEQ ID NO 1052
<211> LENGTH: 51
<212> TYPE: DNA
<213> ORGANISM: Artificial Sequence
<220> FEATURE:
<223> OTHER INFORMATION: Staple strand_1051 of the 2D DNA nanostructure.

<400> SEQUENCE: 1052

```
ctaccatagt ttgagtaaca tttaaaatat taacattcct aacttctcat a         51
```

<210> SEQ ID NO 1053
<211> LENGTH: 53
<212> TYPE: DNA
<213> ORGANISM: Artificial Sequence
<220> FEATURE:
<223> OTHER INFORMATION: Staple strand_1052 of the 2D DNA nanostructure.

<400> SEQUENCE: 1053

```
attttaaaat caaaattatt tgcacggatt cgtaacattc taacttctc ata        53
```

<210> SEQ ID NO 1054
<211> LENGTH: 51
<212> TYPE: DNA
<213> ORGANISM: Artificial Sequence
<220> FEATURE:
<223> OTHER INFORMATION: Staple strand_1053 of the 2D DNA nanostructure.

<400> SEQUENCE: 1054

```
ctttagggcc tgcaacagtg ccaatacgtg taacattcct aacttctcat a         51
```

<210> SEQ ID NO 1055
<211> LENGTH: 53
<212> TYPE: DNA
<213> ORGANISM: Artificial Sequence

```
<220> FEATURE:
<223> OTHER INFORMATION: Staple strand_1054 of the 2D DNA nanostructure.

<400> SEQUENCE: 1055
ttaacaccag cactaacaac taatcgttat tataacattc ctaacttctc ata          53

<210> SEQ ID NO 1056
<211> LENGTH: 52
<212> TYPE: DNA
<213> ORGANISM: Artificial Sequence
<220> FEATURE:
<223> OTHER INFORMATION: Staple strand_1055 of the 2D DNA nanostructure.

<400> SEQUENCE: 1056
gcacagacaa tattttttgaa tggggtcagt ataacattcc taacttctca ta           52

<210> SEQ ID NO 1057
<211> LENGTH: 51
<212> TYPE: DNA
<213> ORGANISM: Artificial Sequence
<220> FEATURE:
<223> OTHER INFORMATION: Staple strand_1056 of the 2D DNA nanostructure.

<400> SEQUENCE: 1057
tgtagaaatc aagattagtt gctcttacca taacattcct aacttctcat a            51

<210> SEQ ID NO 1058
<211> LENGTH: 53
<212> TYPE: DNA
<213> ORGANISM: Artificial Sequence
<220> FEATURE:
<223> OTHER INFORMATION: Staple strand_1057 of the 2D DNA nanostructure.

<400> SEQUENCE: 1058
gtttatcaat atgcgttata caaccgacc gttaacattc ctaacttctc ata            53

<210> SEQ ID NO 1059
<211> LENGTH: 51
<212> TYPE: DNA
<213> ORGANISM: Artificial Sequence
<220> FEATURE:
<223> OTHER INFORMATION: Staple strand_1058 of the 2D DNA nanostructure.

<400> SEQUENCE: 1059
ttagtatcac aatagataag tccacgagca taacattcct aacttctcat a            51

<210> SEQ ID NO 1060
<211> LENGTH: 53
<212> TYPE: DNA
<213> ORGANISM: Artificial Sequence
<220> FEATURE:
<223> OTHER INFORMATION: Staple strand_1059 of the 2D DNA nanostructure.

<400> SEQUENCE: 1060
gtgataaaaa gacgctgaga agagataacc tttaacattc ctaacttctc ata           53

<210> SEQ ID NO 1061
<211> LENGTH: 51
<212> TYPE: DNA
<213> ORGANISM: Artificial Sequence
<220> FEATURE:
<223> OTHER INFORMATION: Staple strand_1060 of the 2D DNA nanostructure.

<400> SEQUENCE: 1061
cttagattta aggcgttaaa taaagcctgt taacattcct aacttctcat a             51
```

<210> SEQ ID NO 1062
<211> LENGTH: 53
<212> TYPE: DNA
<213> ORGANISM: Artificial Sequence
<220> FEATURE:
<223> OTHER INFORMATION: Staple strand_1061 of the 2D DNA nanostructure.

<400> SEQUENCE: 1062
gcttctgttc gggagaaaca ataacgtaaa actaacattc ctaacttctc ata        53

<210> SEQ ID NO 1063
<211> LENGTH: 51
<212> TYPE: DNA
<213> ORGANISM: Artificial Sequence
<220> FEATURE:
<223> OTHER INFORMATION: Staple strand_1062 of the 2D DNA nanostructure.

<400> SEQUENCE: 1063
cttttacaaa atcgtcgcta ttagcgatag taacattcct aacttctcat a          51

<210> SEQ ID NO 1064
<211> LENGTH: 53
<212> TYPE: DNA
<213> ORGANISM: Artificial Sequence
<220> FEATURE:
<223> OTHER INFORMATION: Staple strand_1063 of the 2D DNA nanostructure.

<400> SEQUENCE: 1064
agaaataaaa atcctttgcc cgaaagatta gataacattc ctaacttctc ata        53

<210> SEQ ID NO 1065
<211> LENGTH: 51
<212> TYPE: DNA
<213> ORGANISM: Artificial Sequence
<220> FEATURE:
<223> OTHER INFORMATION: Staple strand_1064 of the 2D DNA nanostructure.

<400> SEQUENCE: 1065
ctcgtattag aaattgcgta gatacagtac taacattcct aacttctcat a          51

<210> SEQ ID NO 1066
<211> LENGTH: 53
<212> TYPE: DNA
<213> ORGANISM: Artificial Sequence
<220> FEATURE:
<223> OTHER INFORMATION: Staple strand_1065 of the 2D DNA nanostructure.

<400> SEQUENCE: 1066
gccgtcaaaa aacagaggtg aggcctatta gttaacattc ctaacttctc ata        53

<210> SEQ ID NO 1067
<211> LENGTH: 51
<212> TYPE: DNA
<213> ORGANISM: Artificial Sequence
<220> FEATURE:
<223> OTHER INFORMATION: Staple strand_1066 of the 2D DNA nanostructure.

<400> SEQUENCE: 1067
cagaagatta gataatacat ttgtcgacaa taacattcct aacttctcat a          51

<210> SEQ ID NO 1068
<211> LENGTH: 51
<212> TYPE: DNA
<213> ORGANISM: Artificial Sequence
<220> FEATURE:
<223> OTHER INFORMATION: Staple strand_1067 of the 2D DNA nanostructure.

<400> SEQUENCE: 1068
ctttaatgcg cgaactgata gccccaccag taacattcct aacttctcat a           51

<210> SEQ ID NO 1069
<211> LENGTH: 52
<212> TYPE: DNA
<213> ORGANISM: Artificial Sequence
<220> FEATURE:
<223> OTHER INFORMATION: Staple strand_1068 of the 2D DNA nanostructure.

<400> SEQUENCE: 1069
agaaaggaac aactaaagga attcaaaaaa attaccatct ctcctaaact cg          52

<210> SEQ ID NO 1070
<211> LENGTH: 51
<212> TYPE: DNA
<213> ORGANISM: Artificial Sequence
<220> FEATURE:
<223> OTHER INFORMATION: Staple strand_1069 of the 2D DNA nanostructure.

<400> SEQUENCE: 1070
aggctccaga ggctttgagg acacgggtaa ttaccatctc tcctaaactc g           51

<210> SEQ ID NO 1071
<211> LENGTH: 53
<212> TYPE: DNA
<213> ORGANISM: Artificial Sequence
<220> FEATURE:
<223> OTHER INFORMATION: Staple strand_1070 of the 2D DNA nanostructure.

<400> SEQUENCE: 1071
acggctacaa aaggagcctt taatgtgaga atttaccatc tctcctaaac tcg         53

<210> SEQ ID NO 1072
<211> LENGTH: 51
<212> TYPE: DNA
<213> ORGANISM: Artificial Sequence
<220> FEATURE:
<223> OTHER INFORMATION: Staple strand_1071 of the 2D DNA nanostructure.

<400> SEQUENCE: 1072
aatacgtttg aaagaggaca gactgacctt ttaccatctc tcctaaactc g           51

<210> SEQ ID NO 1073
<211> LENGTH: 53
<212> TYPE: DNA
<213> ORGANISM: Artificial Sequence
<220> FEATURE:
<223> OTHER INFORMATION: Staple strand_1072 of the 2D DNA nanostructure.

<400> SEQUENCE: 1073
gaccaactaa tgccactacg aaggggtag cattaccatc tctcctaaac tcg          53

<210> SEQ ID NO 1074
<211> LENGTH: 51
<212> TYPE: DNA
<213> ORGANISM: Artificial Sequence
<220> FEATURE:
<223> OTHER INFORMATION: Staple strand_1073 of the 2D DNA nanostructure.

<400> SEQUENCE: 1074
catcaagtaa aacgaactaa cgagttgaga ttaccatctc tcctaaactc g           51

<210> SEQ ID NO 1075

```
<211> LENGTH: 53
<212> TYPE: DNA
<213> ORGANISM: Artificial Sequence
<220> FEATURE:
<223> OTHER INFORMATION: Staple strand_1074 of the 2D DNA nanostructure.

<400> SEQUENCE: 1075
tacgttaaag taatcttgac aagaaccgaa ctttaccatc tctcctaaac tcg          53

<210> SEQ ID NO 1076
<211> LENGTH: 51
<212> TYPE: DNA
<213> ORGANISM: Artificial Sequence
<220> FEATURE:
<223> OTHER INFORMATION: Staple strand_1075 of the 2D DNA nanostructure.

<400> SEQUENCE: 1076
tttaggacaa atgctttaaa caatcaggtc ttaccatctc tcctaaactc g            51

<210> SEQ ID NO 1077
<211> LENGTH: 53
<212> TYPE: DNA
<213> ORGANISM: Artificial Sequence
<220> FEATURE:
<223> OTHER INFORMATION: Staple strand_1076 of the 2D DNA nanostructure.

<400> SEQUENCE: 1077 atcccctat accacattca actagaaaaa tcttaccatc tctcctaaac tcg           53

<210> SEQ ID NO 1078
<211> LENGTH: 51
<212> TYPE: DNA
<213> ORGANISM: Artificial Sequence
<220> FEATURE:
<223> OTHER INFORMATION: Staple strand_1077 of the 2D DNA nanostructure.

<400> SEQUENCE: 1078
tttaccccaa catgttttaa atttccatat ttaccatctc tcctaaactc g            51

<210> SEQ ID NO 1079
<211> LENGTH: 53
<212> TYPE: DNA
<213> ORGANISM: Artificial Sequence
<220> FEATURE:
<223> OTHER INFORMATION: Staple strand_1078 of the 2D DNA nanostructure.

<400> SEQUENCE: 1079
ctgtagcttg actattatag tcagttcatt gattaccatc tctcctaaac tcg          53

<210> SEQ ID NO 1080
<211> LENGTH: 51
<212> TYPE: DNA
<213> ORGANISM: Artificial Sequence
<220> FEATURE:
<223> OTHER INFORMATION: Staple strand_1079 of the 2D DNA nanostructure.

<400> SEQUENCE: 1080
aacagttttg taccaaaaac attttatttc ttaccatctc tcctaaactc g            51

<210> SEQ ID NO 1081
<211> LENGTH: 53
<212> TYPE: DNA
<213> ORGANISM: Artificial Sequence
<220> FEATURE:
<223> OTHER INFORMATION: Staple strand_1080 of the 2D DNA nanostructure.

<400> SEQUENCE: 1081
```

```
acaactttca acagtttcag cggatgtatc ggttaccatc tctcctaaac tcg        53

<210> SEQ ID NO 1082
<211> LENGTH: 53
<212> TYPE: DNA
<213> ORGANISM: Artificial Sequence
<220> FEATURE:
<223> OTHER INFORMATION: Staple strand_1081 of the 2D DNA nanostructure.

<400> SEQUENCE: 1082
tttatcagga cagcatcgga acgacaccaa ccttaccatc tctcctaaac tcg        53

<210> SEQ ID NO 1083
<211> LENGTH: 51
<212> TYPE: DNA
<213> ORGANISM: Artificial Sequence
<220> FEATURE:
<223> OTHER INFORMATION: Staple strand_1082 of the 2D DNA nanostructure.

<400> SEQUENCE: 1083
cagcgaaact tgctttcgag gtgttgctaa ttaccatctc tcctaaactc g          51

<210> SEQ ID NO 1084
<211> LENGTH: 53
<212> TYPE: DNA
<213> ORGANISM: Artificial Sequence
<220> FEATURE:
<223> OTHER INFORMATION: Staple strand_1083 of the 2D DNA nanostructure.

<400> SEQUENCE: 1084
taaaacgagg tcaatcataa gggaaccgga tattaccatc tctcctaaac tcg        53

<210> SEQ ID NO 1085
<211> LENGTH: 51
<212> TYPE: DNA
<213> ORGANISM: Artificial Sequence
<220> FEATURE:
<223> OTHER INFORMATION: Staple strand_1084 of the 2D DNA nanostructure.

<400> SEQUENCE: 1085
gcgcagacaa gaggcaaaag aatccctcag ttaccatctc tcctaaactc g          51

<210> SEQ ID NO 1086
<211> LENGTH: 53
<212> TYPE: DNA
<213> ORGANISM: Artificial Sequence
<220> FEATURE:
<223> OTHER INFORMATION: Staple strand_1085 of the 2D DNA nanostructure.

<400> SEQUENCE: 1086
ttcattacgt caggacgttg ggaaatgcag atttaccatc tctcctaaac tcg        53

<210> SEQ ID NO 1087
<211> LENGTH: 51
<212> TYPE: DNA
<213> ORGANISM: Artificial Sequence
<220> FEATURE:
<223> OTHER INFORMATION: Staple strand_1086 of the 2D DNA nanostructure.

<400> SEQUENCE: 1087
ttataccacc aaatcaacgt aacgaacgag ttaccatctc tcctaaactc g          51

<210> SEQ ID NO 1088
<211> LENGTH: 53
<212> TYPE: DNA
```

```
<213> ORGANISM: Artificial Sequence
<220> FEATURE:
<223> OTHER INFORMATION: Staple strand_1087 of the 2D DNA nanostructure.

<400> SEQUENCE: 1088
acataacggg aatcgtcata aataaagcaa agttaccatc tctcctaaac tcg          53

<210> SEQ ID NO 1089
<211> LENGTH: 51
<212> TYPE: DNA
<213> ORGANISM: Artificial Sequence
<220> FEATURE:
<223> OTHER INFORMATION: Staple strand_1088 of the 2D DNA nanostructure.

<400> SEQUENCE: 1089
aatactgccc aaaaggaatt acgtggctca ttaccatctc tcctaaactc g            51

<210> SEQ ID NO 1090
<211> LENGTH: 53
<212> TYPE: DNA
<213> ORGANISM: Artificial Sequence
<220> FEATURE:
<223> OTHER INFORMATION: Staple strand_1089 of the 2D DNA nanostructure.

<400> SEQUENCE: 1090
cggattgcag agcttaattg ctgaaacgag tattaccatc tctcctaaac tcg          53

<210> SEQ ID NO 1091
<211> LENGTH: 51
<212> TYPE: DNA
<213> ORGANISM: Artificial Sequence
<220> FEATURE:
<223> OTHER INFORMATION: Staple strand_1090 of the 2D DNA nanostructure.

<400> SEQUENCE: 1091
gatggcttat caaaagatt aagagcgtcc ttaccatctc tcctaaactc g             51

<210> SEQ ID NO 1092
<211> LENGTH: 53
<212> TYPE: DNA
<213> ORGANISM: Artificial Sequence
<220> FEATURE:
<223> OTHER INFORMATION: Staple strand_1091 of the 2D DNA nanostructure.

<400> SEQUENCE: 1092
gatttagtca ataaagcctc agagaaccct cattaccatc tctcctaaac tcg          53

<210> SEQ ID NO 1093
<211> LENGTH: 53
<212> TYPE: DNA
<213> ORGANISM: Artificial Sequence
<220> FEATURE:
<223> OTHER INFORMATION: Staple strand_1092 of the 2D DNA nanostructure.

<400> SEQUENCE: 1093
taaatgaatt ttctgtatgg gattaatttc ttttaccatc tctcctaaac tcg          53

<210> SEQ ID NO 1094
<211> LENGTH: 53
<212> TYPE: DNA
<213> ORGANISM: Artificial Sequence
<220> FEATURE:
<223> OTHER INFORMATION: Staple strand_1093 of the 2D DNA nanostructure.

<400> SEQUENCE: 1094
aaacagcttt ttgcgggatc gtcaacacta aattaccatc tctcctaaac tcg          53
```

<210> SEQ ID NO 1095
<211> LENGTH: 53
<212> TYPE: DNA
<213> ORGANISM: Artificial Sequence
<220> FEATURE:
<223> OTHER INFORMATION: Staple strand_1094 of the 2D DNA nanostructure.

<400> SEQUENCE: 1095
aaggccgctg ataccgatag ttgcgacgtt agttaccatc tctcctaaac tcg    53

<210> SEQ ID NO 1096
<211> LENGTH: 53
<212> TYPE: DNA
<213> ORGANISM: Artificial Sequence
<220> FEATURE:
<223> OTHER INFORMATION: Staple strand_1095 of the 2D DNA nanostructure.

<400> SEQUENCE: 1096
acactcatcc atgttactta gccgaaagct gcttaccatc tctcctaaac tcg    53

<210> SEQ ID NO 1097
<211> LENGTH: 53
<212> TYPE: DNA
<213> ORGANISM: Artificial Sequence
<220> FEATURE:
<223> OTHER INFORMATION: Staple strand_1096 of the 2D DNA nanostructure.

<400> SEQUENCE: 1097
gacctgctct ttgaccccca gcgagggagt tattaccatc tctcctaaac tcg    53

<210> SEQ ID NO 1098
<211> LENGTH: 53
<212> TYPE: DNA
<213> ORGANISM: Artificial Sequence
<220> FEATURE:
<223> OTHER INFORMATION: Staple strand_1097 of the 2D DNA nanostructure.

<400> SEQUENCE: 1098
tcattcagat gcgattttaa gaacaggcat agttaccatc tctcctaaac tcg    53

<210> SEQ ID NO 1099
<211> LENGTH: 53
<212> TYPE: DNA
<213> ORGANISM: Artificial Sequence
<220> FEATURE:
<223> OTHER INFORMATION: Staple strand_1098 of the 2D DNA nanostructure.

<400> SEQUENCE: 1099
attacctttg aataaggctt gcccaaatcc gcttaccatc tctcctaaac tcg    53

<210> SEQ ID NO 1100
<211> LENGTH: 53
<212> TYPE: DNA
<213> ORGANISM: Artificial Sequence
<220> FEATURE:
<223> OTHER INFORMATION: Staple strand_1099 of the 2D DNA nanostructure.

<400> SEQUENCE: 1100
taagagcaaa tgtttagact ggataggaag ccttaccatc tctcctaaac tcg    53

<210> SEQ ID NO 1101
<211> LENGTH: 53
<212> TYPE: DNA
<213> ORGANISM: Artificial Sequence
<220> FEATURE:

<223> OTHER INFORMATION: Staple strand_1100 of the 2D DNA nanostructure.

<400> SEQUENCE: 1101
aatagtaaac actatcataa ccctcattgt gattaccatc tctcctaaac tcg            53

<210> SEQ ID NO 1102
<211> LENGTH: 53
<212> TYPE: DNA
<213> ORGANISM: Artificial Sequence
<220> FEATURE:
<223> OTHER INFORMATION: Staple strand_1101 of the 2D DNA nanostructure.

<400> SEQUENCE: 1102
cgaaagactt tgataagagg tcatatttcg cattaccatc tctcctaaac tcg            53

<210> SEQ ID NO 1103
<211> LENGTH: 53
<212> TYPE: DNA
<213> ORGANISM: Artificial Sequence
<220> FEATURE:
<223> OTHER INFORMATION: Staple strand_1102 of the 2D DNA nanostructure.

<400> SEQUENCE: 1103
ttgctccttt caaatatcgc gtttgagggg gtttaccatc tctcctaaac tcg            53

<210> SEQ ID NO 1104
<211> LENGTH: 53
<212> TYPE: DNA
<213> ORGANISM: Artificial Sequence
<220> FEATURE:
<223> OTHER INFORMATION: Staple strand_1103 of the 2D DNA nanostructure.

<400> SEQUENCE: 1104
aatggtcaac aggcaaggca aagagtaatg tgttaccatc tctcctaaac tcg            53

<210> SEQ ID NO 1105
<211> LENGTH: 52
<212> TYPE: DNA
<213> ORGANISM: Artificial Sequence
<220> FEATURE:
<223> OTHER INFORMATION: Staple strand_1104 of the 2D DNA nanostructure.

<400> SEQUENCE: 1105
tctaaagttt tgtcgtcttt ccagccgaca attaccatct ctcctaaact cg             52

<210> SEQ ID NO 1106
<211> LENGTH: 65
<212> TYPE: DNA
<213> ORGANISM: Artificial Sequence
<220> FEATURE:
<223> OTHER INFORMATION: Staple strand_1105 of the 2D DNA nanostructure.

<400> SEQUENCE: 1106
tgacaactcg ctgaggcttg cattatacca agcgcgatga taaattacca tctctcctaa     60
actcg                                                                 65

<210> SEQ ID NO 1107
<211> LENGTH: 53
<212> TYPE: DNA
<213> ORGANISM: Artificial Sequence
<220> FEATURE:
<223> OTHER INFORMATION: Staple strand_1106 of the 2D DNA nanostructure.

<400> SEQUENCE: 1107
atattcggaa ccatcgccca cgcagagaag gattaccatc tctcctaaac tcg            53

<210> SEQ ID NO 1108
<211> LENGTH: 53
<212> TYPE: DNA
<213> ORGANISM: Artificial Sequence
<220> FEATURE:
<223> OTHER INFORMATION: Staple strand_1107 of the 2D DNA nanostructure.

<400> SEQUENCE: 1108
tcatcgccaa caaagtacaa cggacgccag cattaccatc tctcctaaac tcg         53

<210> SEQ ID NO 1109
<211> LENGTH: 53
<212> TYPE: DNA
<213> ORGANISM: Artificial Sequence
<220> FEATURE:
<223> OTHER INFORMATION: Staple strand_1108 of the 2D DNA nanostructure.

<400> SEQUENCE: 1109
gatggtttga acgagtagta aatttaccat tattaccatc tctcctaaac tcg         53

<210> SEQ ID NO 1110
<211> LENGTH: 59
<212> TYPE: DNA
<213> ORGANISM: Artificial Sequence
<220> FEATURE:
<223> OTHER INFORMATION: Staple strand_1109 of the 2D DNA nanostructure.

<400> SEQUENCE: 1110
cgtttaccag acgacaaaga agttttgcca taattcgatt accatctctc ctaaactcg   59

<210> SEQ ID NO 1111
<211> LENGTH: 53
<212> TYPE: DNA
<213> ORGANISM: Artificial Sequence
<220> FEATURE:
<223> OTHER INFORMATION: Staple strand_1110 of the 2D DNA nanostructure.

<400> SEQUENCE: 1111
cttttgcaga taaaaaccaa aataaagact ccttaccatc tctcctaaac tcg         53

<210> SEQ ID NO 1112
<211> LENGTH: 51
<212> TYPE: DNA
<213> ORGANISM: Artificial Sequence
<220> FEATURE:
<223> OTHER INFORMATION: Staple strand_1111 of the 2D DNA nanostructure.

<400> SEQUENCE: 1112
gcttcaatca ggattagaga gttattttca ttaccatctc tcctaaactc g           51

<210> SEQ ID NO 1113
<211> LENGTH: 53
<212> TYPE: DNA
<213> ORGANISM: Artificial Sequence
<220> FEATURE:
<223> OTHER INFORMATION: Staple strand_1112 of the 2D DNA nanostructure.

<400> SEQUENCE: 1113
ccaacaggag cgaaccagac cggagccttt acttaccatc tctcctaaac tcg         53

<210> SEQ ID NO 1114
<211> LENGTH: 51
<212> TYPE: DNA
<213> ORGANISM: Artificial Sequence
<220> FEATURE:

<223> OTHER INFORMATION: Staple strand_1113 of the 2D DNA nanostructure.

<400> SEQUENCE: 1114
tttggggata gtagtagcat taaaaggccg ttaccatctc tcctaaactc g         51

<210> SEQ ID NO 1115
<211> LENGTH: 53
<212> TYPE: DNA
<213> ORGANISM: Artificial Sequence
<220> FEATURE:
<223> OTHER INFORMATION: Staple strand_1114 of the 2D DNA nanostructure.

<400> SEQUENCE: 1115
tccacagaca gccctcatag ttagcgtaac gattaccatc tctcctaaac tcg       53

<210> SEQ ID NO 1116
<211> LENGTH: 53
<212> TYPE: DNA
<213> ORGANISM: Artificial Sequence
<220> FEATURE:
<223> OTHER INFORMATION: Staple strand_1115 of the 2D DNA nanostructure.

<400> SEQUENCE: 1116
ttaggattgg ctgagactcc tcaataaccg atttaccatc tctcctaaac tcg       53

<210> SEQ ID NO 1117
<211> LENGTH: 51
<212> TYPE: DNA
<213> ORGANISM: Artificial Sequence
<220> FEATURE:
<223> OTHER INFORMATION: Staple strand_1116 of the 2D DNA nanostructure.

<400> SEQUENCE: 1117
tattaagaag cggggttttg ctcgtagcat ttaccatctc tcctaaactc g         51

<210> SEQ ID NO 1118
<211> LENGTH: 53
<212> TYPE: DNA
<213> ORGANISM: Artificial Sequence
<220> FEATURE:
<223> OTHER INFORMATION: Staple strand_1117 of the 2D DNA nanostructure.

<400> SEQUENCE: 1118
ttgacaggcc accaccagag ccgcgatttg tattaccatc tctcctaaac tcg       53

<210> SEQ ID NO 1119
<211> LENGTH: 51
<212> TYPE: DNA
<213> ORGANISM: Artificial Sequence
<220> FEATURE:
<223> OTHER INFORMATION: Staple strand_1118 of the 2D DNA nanostructure.

<400> SEQUENCE: 1119
caccagaaag gttgaggcag gtcatgaaag ttaccatctc tcctaaactc g         51

<210> SEQ ID NO 1120
<211> LENGTH: 53
<212> TYPE: DNA
<213> ORGANISM: Artificial Sequence
<220> FEATURE:
<223> OTHER INFORMATION: Staple strand_1119 of the 2D DNA nanostructure.

<400> SEQUENCE: 1120
gcaaggcctc accagtagca ccatgggctt gattaccatc tctcctaaac tcg       53

```
<210> SEQ ID NO 1121
<211> LENGTH: 51
<212> TYPE: DNA
<213> ORGANISM: Artificial Sequence
<220> FEATURE:
<223> OTHER INFORMATION: Staple strand_1120 of the 2D DNA nanostructure.

<400> SEQUENCE: 1121
cagcaaaagg aaacgtcacc aatgagccgc ttaccatctc tcctaaactc g           51

<210> SEQ ID NO 1122
<211> LENGTH: 53
<212> TYPE: DNA
<213> ORGANISM: Artificial Sequence
<220> FEATURE:
<223> OTHER INFORMATION: Staple strand_1121 of the 2D DNA nanostructure.

<400> SEQUENCE: 1122
ttattacgaa gaactggcat gattgcgaga ggttaccatc tctcctaaac tcg         53

<210> SEQ ID NO 1123
<211> LENGTH: 51
<212> TYPE: DNA
<213> ORGANISM: Artificial Sequence
<220> FEATURE:
<223> OTHER INFORMATION: Staple strand_1122 of the 2D DNA nanostructure.

<400> SEQUENCE: 1123
atacccaaca gtatgttagc aaattagagc ttaccatctc tcctaaactc g           51

<210> SEQ ID NO 1124
<211> LENGTH: 53
<212> TYPE: DNA
<213> ORGANISM: Artificial Sequence
<220> FEATURE:
<223> OTHER INFORMATION: Staple strand_1123 of the 2D DNA nanostructure.

<400> SEQUENCE: 1124
agagagaaaa aaatgaaaat agcaagcaaa ctttaccatc tctcctaaac tcg         53

<210> SEQ ID NO 1125
<211> LENGTH: 51
<212> TYPE: DNA
<213> ORGANISM: Artificial Sequence
<220> FEATURE:
<223> OTHER INFORMATION: Staple strand_1124 of the 2D DNA nanostructure.

<400> SEQUENCE: 1125
ttaacgtcta acataaaaac aggtaacgga ttaccatctc tcctaaactc g           51

<210> SEQ ID NO 1126
<211> LENGTH: 53
<212> TYPE: DNA
<213> ORGANISM: Artificial Sequence
<220> FEATURE:
<223> OTHER INFORMATION: Staple strand_1125 of the 2D DNA nanostructure.

<400> SEQUENCE: 1126
ccaatagctc atcgtaggaa tcatggcatc aattaccatc tctcctaaac tcg         53

<210> SEQ ID NO 1127
<211> LENGTH: 53
<212> TYPE: DNA
<213> ORGANISM: Artificial Sequence
<220> FEATURE:
<223> OTHER INFORMATION: Staple strand_1126 of the 2D DNA nanostructure.
```

<400> SEQUENCE: 1127
tcaccagtac aaactacaac gcctagtacc agttaccatc tctcctaaac tcg        53

<210> SEQ ID NO 1128
<211> LENGTH: 53
<212> TYPE: DNA
<213> ORGANISM: Artificial Sequence
<220> FEATURE:
<223> OTHER INFORMATION: Staple strand_1127 of the 2D DNA nanostructure.

<400> SEQUENCE: 1128
gcggataacc tattattctg aaacagacga ttttaccatc tctcctaaac tcg        53

<210> SEQ ID NO 1129
<211> LENGTH: 53
<212> TYPE: DNA
<213> ORGANISM: Artificial Sequence
<220> FEATURE:
<223> OTHER INFORMATION: Staple strand_1128 of the 2D DNA nanostructure.

<400> SEQUENCE: 1129
tttcggaagt gccgtcgaga gggtgagttt cgttaccatc tctcctaaac tcg        53

<210> SEQ ID NO 1130
<211> LENGTH: 53
<212> TYPE: DNA
<213> ORGANISM: Artificial Sequence
<220> FEATURE:
<223> OTHER INFORMATION: Staple strand_1129 of the 2D DNA nanostructure.

<400> SEQUENCE: 1130
ggccttgaag agccaccacc ctcagaaacc atttaccatc tctcctaaac tcg        53

<210> SEQ ID NO 1131
<211> LENGTH: 53
<212> TYPE: DNA
<213> ORGANISM: Artificial Sequence
<220> FEATURE:
<223> OTHER INFORMATION: Staple strand_1130 of the 2D DNA nanostructure.

<400> SEQUENCE: 1131
ccaccctcta ttcacaaaca aatacctgcc tattaccatc tctcctaaac tcg        53

<210> SEQ ID NO 1132
<211> LENGTH: 53
<212> TYPE: DNA
<213> ORGANISM: Artificial Sequence
<220> FEATURE:
<223> OTHER INFORMATION: Staple strand_1131 of the 2D DNA nanostructure.

<400> SEQUENCE: 1132
cgatagcatt gagccatttg ggaacgtaga aattaccatc tctcctaaac tcg        53

<210> SEQ ID NO 1133
<211> LENGTH: 53
<212> TYPE: DNA
<213> ORGANISM: Artificial Sequence
<220> FEATURE:
<223> OTHER INFORMATION: Staple strand_1132 of the 2D DNA nanostructure.

<400> SEQUENCE: 1133
tcaccgacgc accgtaatca gtagcagaac cgttaccatc tctcctaaac tcg        53

<210> SEQ ID NO 1134
<211> LENGTH: 53

```
<212> TYPE: DNA
<213> ORGANISM: Artificial Sequence
<220> FEATURE:
<223> OTHER INFORMATION: Staple strand_1133 of the 2D DNA nanostructure.

<400> SEQUENCE: 1134
atacataccg aggaaacgca ataagaagcg cattaccatc tctcctaaac tcg          53

<210> SEQ ID NO 1135
<211> LENGTH: 53
<212> TYPE: DNA
<213> ORGANISM: Artificial Sequence
<220> FEATURE:
<223> OTHER INFORMATION: Staple strand_1134 of the 2D DNA nanostructure.

<400> SEQUENCE: 1135
aaggaaacat aaaggtggca acattatcac cgttaccatc tctcctaaac tcg          53

<210> SEQ ID NO 1136
<211> LENGTH: 53
<212> TYPE: DNA
<213> ORGANISM: Artificial Sequence
<220> FEATURE:
<223> OTHER INFORMATION: Staple strand_1135 of the 2D DNA nanostructure.

<400> SEQUENCE: 1136
ttagacggcc aaataagaaa cgatagaagg ctttaccatc tctcctaaac tcg          53

<210> SEQ ID NO 1137
<211> LENGTH: 53
<212> TYPE: DNA
<213> ORGANISM: Artificial Sequence
<220> FEATURE:
<223> OTHER INFORMATION: Staple strand_1136 of the 2D DNA nanostructure.

<400> SEQUENCE: 1137
atcccaatga gaattaactg aacagttacc agttaccatc tctcctaaac tcg          53

<210> SEQ ID NO 1138
<211> LENGTH: 53
<212> TYPE: DNA
<213> ORGANISM: Artificial Sequence
<220> FEATURE:
<223> OTHER INFORMATION: Staple strand_1137 of the 2D DNA nanostructure.

<400> SEQUENCE: 1138
tatccggtct catcgagaac aagcgacaaa agttaccatc tctcctaaac tcg          53

<210> SEQ ID NO 1139
<211> LENGTH: 52
<212> TYPE: DNA
<213> ORGANISM: Artificial Sequence
<220> FEATURE:
<223> OTHER INFORMATION: Staple strand_1138 of the 2D DNA nanostructure.

<400> SEQUENCE: 1139
aggaacccat gtaccgtaac acttgatata attaccatct ctcctaaact cg           52

<210> SEQ ID NO 1140
<211> LENGTH: 51
<212> TYPE: DNA
<213> ORGANISM: Artificial Sequence
<220> FEATURE:
<223> OTHER INFORMATION: Staple strand_1139 of the 2D DNA nanostructure.

<400> SEQUENCE: 1140
```
gtatagcaaa cagttaatgc ccaatcctca ttaccatctc tcctaaactc g    51

<210> SEQ ID NO 1141
<211> LENGTH: 53
<212> TYPE: DNA
<213> ORGANISM: Artificial Sequence
<220> FEATURE:
<223> OTHER INFORMATION: Staple strand_1140 of the 2D DNA nanostructure.

<400> SEQUENCE: 1141
gcccgtatcc ggaataggtg tatcagccca atttaccatc tctcctaaac tcg    53

<210> SEQ ID NO 1142
<211> LENGTH: 51
<212> TYPE: DNA
<213> ORGANISM: Artificial Sequence
<220> FEATURE:
<223> OTHER INFORMATION: Staple strand_1141 of the 2D DNA nanostructure.

<400> SEQUENCE: 1142
ttaaagccag agccgccacc ctcgacagaa ttaccatctc tcctaaactc g    51

<210> SEQ ID NO 1143
<211> LENGTH: 53
<212> TYPE: DNA
<213> ORGANISM: Artificial Sequence
<220> FEATURE:
<223> OTHER INFORMATION: Staple strand_1142 of the 2D DNA nanostructure.

<400> SEQUENCE: 1143
gcctccctca gaatggaaag cgcagtaaca gtttaccatc tctcctaaac tcg    53

<210> SEQ ID NO 1144
<211> LENGTH: 51
<212> TYPE: DNA
<213> ORGANISM: Artificial Sequence
<220> FEATURE:
<223> OTHER INFORMATION: Staple strand_1143 of the 2D DNA nanostructure.

<400> SEQUENCE: 1144
tcaagtttca ttaaaggtga atataaaga ttaccatctc tcctaaactc g    51

<210> SEQ ID NO 1145
<211> LENGTH: 53
<212> TYPE: DNA
<213> ORGANISM: Artificial Sequence
<220> FEATURE:
<223> OTHER INFORMATION: Staple strand_1144 of the 2D DNA nanostructure.

<400> SEQUENCE: 1145
gaaattattg cctttagcgt cagaccggaa ccttaccatc tctcctaaac tcg    53

<210> SEQ ID NO 1146
<211> LENGTH: 51
<212> TYPE: DNA
<213> ORGANISM: Artificial Sequence
<220> FEATURE:
<223> OTHER INFORMATION: Staple strand_1145 of the 2D DNA nanostructure.

<400> SEQUENCE: 1146
aacgcaaaga tagccgaaca aaccctgaac ttaccatctc tcctaaactc g    51

<210> SEQ ID NO 1147
<211> LENGTH: 53
<212> TYPE: DNA
<213> ORGANISM: Artificial Sequence
<220> FEATURE:
<223> OTHER INFORMATION: Staple strand_1146 of the 2D DNA nanostructure.

<400> SEQUENCE: 1147
aagtaagcag acaccacgga ataatattga cgttaccatc tctcctaaac tcg    53

<210> SEQ ID NO 1148
<211> LENGTH: 51
<212> TYPE: DNA
<213> ORGANISM: Artificial Sequence
<220> FEATURE:
<223> OTHER INFORMATION: Staple strand_1147 of the 2D DNA nanostructure.

<400> SEQUENCE: 1148
aaagtcacaa aataaacagc cagcgtttta ttaccatctc tcctaaactc g    51

<210> SEQ ID NO 1149
<211> LENGTH: 53
<212> TYPE: DNA
<213> ORGANISM: Artificial Sequence
<220> FEATURE:
<223> OTHER INFORMATION: Staple strand_1148 of the 2D DNA nanostructure.

<400> SEQUENCE: 1149
gccagttaga gggtaattga gcgctttaag aattaccatc tctcctaaac tcg    53

<210> SEQ ID NO 1150
<211> LENGTH: 51
<212> TYPE: DNA
<213> ORGANISM: Artificial Sequence
<220> FEATURE:
<223> OTHER INFORMATION: Staple strand_1149 of the 2D DNA nanostructure.

<400> SEQUENCE: 1150
gcgaacctcc aagaacgggt atgacaataa ttaccatctc tcctaaactc g    51

<210> SEQ ID NO 1151
<211> LENGTH: 53
<212> TYPE: DNA
<213> ORGANISM: Artificial Sequence
<220> FEATURE:
<223> OTHER INFORMATION: Staple strand_1150 of the 2D DNA nanostructure.

<400> SEQUENCE: 1151
ccaccctcat tttcagggat agcaaccgta ctttaccatc tctcctaaac tcg    53

<210> SEQ ID NO 1152
<211> LENGTH: 53
<212> TYPE: DNA
<213> ORGANISM: Artificial Sequence
<220> FEATURE:
<223> OTHER INFORMATION: Staple strand_1151 of the 2D DNA nanostructure.

<400> SEQUENCE: 1152
caggaggtgg ggtcagtgcc ttgagtctct gattaccatc tctcctaaac tcg    53

<210> SEQ ID NO 1153
<211> LENGTH: 51
<212> TYPE: DNA
<213> ORGANISM: Artificial Sequence
<220> FEATURE:
<223> OTHER INFORMATION: Staple strand_1152 of the 2D DNA nanostructure.

<400> SEQUENCE: 1153
gttttaactt agtaccgcca cccagagcca ttaccatctc tcctaaactc g    51

<210> SEQ ID NO 1154
<211> LENGTH: 53
<212> TYPE: DNA
<213> ORGANISM: Artificial Sequence
<220> FEATURE:
<223> OTHER INFORMATION: Staple strand_1153 of the 2D DNA nanostructure.

<400> SEQUENCE: 1154
atttaccggg aaccagagcc accactgtag cgttaccatc tctcctaaac tcg    53

<210> SEQ ID NO 1155
<211> LENGTH: 51
<212> TYPE: DNA
<213> ORGANISM: Artificial Sequence
<220> FEATURE:
<223> OTHER INFORMATION: Staple strand_1154 of the 2D DNA nanostructure.

<400> SEQUENCE: 1155
aaatcacctt ccagtaagcg tcagtaataa ttaccatctc tcctaaactc g    51

<210> SEQ ID NO 1156
<211> LENGTH: 53
<212> TYPE: DNA
<213> ORGANISM: Artificial Sequence
<220> FEATURE:
<223> OTHER INFORMATION: Staple strand_1155 of the 2D DNA nanostructure.

<400> SEQUENCE: 1156
cgttttcaag ggagggaagg taaagtttat ttttaccatc tctcctaaac tcg    53

<210> SEQ ID NO 1157
<211> LENGTH: 51
<212> TYPE: DNA
<213> ORGANISM: Artificial Sequence
<220> FEATURE:
<223> OTHER INFORMATION: Staple strand_1156 of the 2D DNA nanostructure.

<400> SEQUENCE: 1157
accgattgtc ggcattttcg gtcataatca ttaccatctc tcctaaactc g    51

<210> SEQ ID NO 1158
<211> LENGTH: 53
<212> TYPE: DNA
<213> ORGANISM: Artificial Sequence
<220> FEATURE:
<223> OTHER INFORMATION: Staple strand_1157 of the 2D DNA nanostructure.

<400> SEQUENCE: 1158
tgtcacaatc ttaccgaagc cctttaatat cattaccatc tctcctaaac tcg    53

<210> SEQ ID NO 1159
<211> LENGTH: 51
<212> TYPE: DNA
<213> ORGANISM: Artificial Sequence
<220> FEATURE:
<223> OTHER INFORMATION: Staple strand_1158 of the 2D DNA nanostructure.

<400> SEQUENCE: 1159
aatagctatc aatagaaaat tcaacattca ttaccatctc tcctaaactc g    51

<210> SEQ ID NO 1160
<211> LENGTH: 53
<212> TYPE: DNA
<213> ORGANISM: Artificial Sequence
<220> FEATURE:
<223> OTHER INFORMATION: Staple strand_1159 of the 2D DNA nanostructure.

<400> SEQUENCE: 1160
gagagataga gcgtctttcc agaggttttg aattaccatc tctcctaaac tcg         53

<210> SEQ ID NO 1161
<211> LENGTH: 51
<212> TYPE: DNA
<213> ORGANISM: Artificial Sequence
<220> FEATURE:
<223> OTHER INFORMATION: Staple strand_1160 of the 2D DNA nanostructure.

<400> SEQUENCE: 1161
acgctaacac ccacaagaat tgaaaatagc ttaccatctc tcctaaactc g           51

<210> SEQ ID NO 1162
<211> LENGTH: 53
<212> TYPE: DNA
<213> ORGANISM: Artificial Sequence
<220> FEATURE:
<223> OTHER INFORMATION: Staple strand_1161 of the 2D DNA nanostructure.

<400> SEQUENCE: 1162
gccttaaacc aatcaataat cggcacgcgc ctttaccatc tctcctaaac tcg         53

<210> SEQ ID NO 1163
<211> LENGTH: 53
<212> TYPE: DNA
<213> ORGANISM: Artificial Sequence
<220> FEATURE:
<223> OTHER INFORMATION: Staple strand_1162 of the 2D DNA nanostructure.

<400> SEQUENCE: 1163
taaatcggga ttcccaattc tgcgatataa tgttaccatc tctcctaaac tcg         53

<210> SEQ ID NO 1164
<211> LENGTH: 51
<212> TYPE: DNA
<213> ORGANISM: Artificial Sequence
<220> FEATURE:
<223> OTHER INFORMATION: Staple strand_1163 of the 2D DNA nanostructure.

<400> SEQUENCE: 1164
aacgcaaaat cgatgaacgg taccggttga ttaccatctc tcctaaactc g           51

<210> SEQ ID NO 1165
<211> LENGTH: 53
<212> TYPE: DNA
<213> ORGANISM: Artificial Sequence
<220> FEATURE:
<223> OTHER INFORMATION: Staple strand_1164 of the 2D DNA nanostructure.

<400> SEQUENCE: 1165
aacaagaggg ataaaaattt ttagcataaa gcttaccatc tctcctaaac tcg         53

<210> SEQ ID NO 1166
<211> LENGTH: 51
<212> TYPE: DNA
<213> ORGANISM: Artificial Sequence
<220> FEATURE:
<223> OTHER INFORMATION: Staple strand_1165 of the 2D DNA nanostructure.

<400> SEQUENCE: 1166
taatcagcgg attgaccgta atcgtaaccg ttaccatctc tcctaaactc g           51

<210> SEQ ID NO 1167

```
<211> LENGTH: 53
<212> TYPE: DNA
<213> ORGANISM: Artificial Sequence
<220> FEATURE:
<223> OTHER INFORMATION: Staple strand_1166 of the 2D DNA nanostructure.

<400> SEQUENCE: 1167
acaaacggaa aagccccaaa aacactggag cattaccatc tctcctaaac tcg          53

<210> SEQ ID NO 1168
<211> LENGTH: 51
<212> TYPE: DNA
<213> ORGANISM: Artificial Sequence
<220> FEATURE:
<223> OTHER INFORMATION: Staple strand_1167 of the 2D DNA nanostructure.

<400> SEQUENCE: 1168
tgcatctttc ccagtcacga cggcctgcag ttaccatctc tcctaaactc g            51

<210> SEQ ID NO 1169
<211> LENGTH: 53
<212> TYPE: DNA
<213> ORGANISM: Artificial Sequence
<220> FEATURE:
<223> OTHER INFORMATION: Staple strand_1168 of the 2D DNA nanostructure.

<400> SEQUENCE: 1169
ccagggttgc cagtttgagg ggacccgtgg gattaccatc tctcctaaac tcg          53

<210> SEQ ID NO 1170
<211> LENGTH: 51
<212> TYPE: DNA
<213> ORGANISM: Artificial Sequence
<220> FEATURE:
<223> OTHER INFORMATION: Staple strand_1169 of the 2D DNA nanostructure.

<400> SEQUENCE: 1170
gtcgacttcg gccaacgcgc ggggttttttc ttaccatctc tcctaaactc g           51

<210> SEQ ID NO 1171
<211> LENGTH: 53
<212> TYPE: DNA
<213> ORGANISM: Artificial Sequence
<220> FEATURE:
<223> OTHER INFORMATION: Staple strand_1170 of the 2D DNA nanostructure.

<400> SEQUENCE: 1171
ttaatgaact agaggatccc cgggggggtaa cgttaccatc tctcctaaac tcg         53

<210> SEQ ID NO 1172
<211> LENGTH: 51
<212> TYPE: DNA
<213> ORGANISM: Artificial Sequence
<220> FEATURE:
<223> OTHER INFORMATION: Staple strand_1171 of the 2D DNA nanostructure.

<400> SEQUENCE: 1172
ttttcactca aagggcgaaa aaccatcacc ttaccatctc tcctaaactc g            51

<210> SEQ ID NO 1173
<211> LENGTH: 53
<212> TYPE: DNA
<213> ORGANISM: Artificial Sequence
<220> FEATURE:
<223> OTHER INFORMATION: Staple strand_1172 of the 2D DNA nanostructure.

<400> SEQUENCE: 1173
```
ctccaacgca gtgagacggg caaccagctg cattaccatc tctcctaaac tcg        53

<210> SEQ ID NO 1174
<211> LENGTH: 52
<212> TYPE: DNA
<213> ORGANISM: Artificial Sequence
<220> FEATURE:
<223> OTHER INFORMATION: Staple strand_1173 of the 2D DNA nanostructure.

<400> SEQUENCE: 1174
caaatcaagt tttttggggt cgaaacgtgg attaccatct ctcctaaact cg          52

<210> SEQ ID NO 1175
<211> LENGTH: 51
<212> TYPE: DNA
<213> ORGANISM: Artificial Sequence
<220> FEATURE:
<223> OTHER INFORMATION: Staple strand_1174 of the 2D DNA nanostructure.

<400> SEQUENCE: 1175
aaattaagtt gaccattaga tacttttgcg ttaccatctc tcctaaactc g           51

<210> SEQ ID NO 1176
<211> LENGTH: 53
<212> TYPE: DNA
<213> ORGANISM: Artificial Sequence
<220> FEATURE:
<223> OTHER INFORMATION: Staple strand_1175 of the 2D DNA nanostructure.

<400> SEQUENCE: 1176
tatattttgt cattgcctga gagtggaaga ttttaccatc tctcctaaac tcg         53

<210> SEQ ID NO 1177
<211> LENGTH: 51
<212> TYPE: DNA
<213> ORGANISM: Artificial Sequence
<220> FEATURE:
<223> OTHER INFORMATION: Staple strand_1176 of the 2D DNA nanostructure.

<400> SEQUENCE: 1177
gctatcagaa atgcaatgcc tgaattagca ttaccatctc tcctaaactc g           51

<210> SEQ ID NO 1178
<211> LENGTH: 53
<212> TYPE: DNA
<213> ORGANISM: Artificial Sequence
<220> FEATURE:
<223> OTHER INFORMATION: Staple strand_1177 of the 2D DNA nanostructure.

<400> SEQUENCE: 1178
gtataagcca acccgtcgga ttctgacgac agttaccatc tctcctaaac tcg         53

<210> SEQ ID NO 1179
<211> LENGTH: 51
<212> TYPE: DNA
<213> ORGANISM: Artificial Sequence
<220> FEATURE:
<223> OTHER INFORMATION: Staple strand_1178 of the 2D DNA nanostructure.

<400> SEQUENCE: 1179
gcgagtaaaa atatttaaat tgttacaaag ttaccatctc tcctaaactc g           51

<210> SEQ ID NO 1180
<211> LENGTH: 53
<212> TYPE: DNA

```
<213> ORGANISM: Artificial Sequence
<220> FEATURE:
<223> OTHER INFORMATION: Staple strand_1179 of the 2D DNA nanostructure.

<400> SEQUENCE: 1180
tatcggccgc aaggcgatta agtttaccga gcttaccatc tctcctaaac tcg         53

<210> SEQ ID NO 1181
<211> LENGTH: 51
<212> TYPE: DNA
<213> ORGANISM: Artificial Sequence
<220> FEATURE:
<223> OTHER INFORMATION: Staple strand_1180 of the 2D DNA nanostructure.

<400> SEQUENCE: 1181
gatgtgcttc aggaagatcg cacaatgtga ttaccatctc tcctaaactc g           51

<210> SEQ ID NO 1182
<211> LENGTH: 53
<212> TYPE: DNA
<213> ORGANISM: Artificial Sequence
<220> FEATURE:
<223> OTHER INFORMATION: Staple strand_1181 of the 2D DNA nanostructure.

<400> SEQUENCE: 1182
tcgaattcgg gaaacctgtc gtgcagctga ttttaccatc tctcctaaac tcg         53

<210> SEQ ID NO 1183
<211> LENGTH: 51
<212> TYPE: DNA
<213> ORGANISM: Artificial Sequence
<220> FEATURE:
<223> OTHER INFORMATION: Staple strand_1182 of the 2D DNA nanostructure.

<400> SEQUENCE: 1183
ttccagtcgt aatcatggtc ataaaagggg ttaccatctc tcctaaactc g           51

<210> SEQ ID NO 1184
<211> LENGTH: 53
<212> TYPE: DNA
<213> ORGANISM: Artificial Sequence
<220> FEATURE:
<223> OTHER INFORMATION: Staple strand_1183 of the 2D DNA nanostructure.

<400> SEQUENCE: 1184
gcccttcaga gtccactatt aaagggtgcc gtttaccatc tctcctaaac tcg         53

<210> SEQ ID NO 1185
<211> LENGTH: 51
<212> TYPE: DNA
<213> ORGANISM: Artificial Sequence
<220> FEATURE:
<223> OTHER INFORMATION: Staple strand_1184 of the 2D DNA nanostructure.

<400> SEQUENCE: 1185
tggaacaacc gcctggccct gaggcccgct ttaccatctc tcctaaactc g           51

<210> SEQ ID NO 1186
<211> LENGTH: 51
<212> TYPE: DNA
<213> ORGANISM: Artificial Sequence
<220> FEATURE:
<223> OTHER INFORMATION: Staple strand_1185 of the 2D DNA nanostructure.

<400> SEQUENCE: 1186
aaagcactaa atcggaaccc taatccagtt ttaccatctc tcctaaactc g           51
```

<210> SEQ ID NO 1187
<211> LENGTH: 53
<212> TYPE: DNA
<213> ORGANISM: Artificial Sequence
<220> FEATURE:
<223> OTHER INFORMATION: Staple strand_1186 of the 2D DNA nanostructure.

<400> SEQUENCE: 1187
taaatcatat aacctgttta gctaaccttt aattaccatc tctcctaaac tcg    53

<210> SEQ ID NO 1188
<211> LENGTH: 53
<212> TYPE: DNA
<213> ORGANISM: Artificial Sequence
<220> FEATURE:
<223> OTHER INFORMATION: Staple strand_1187 of the 2D DNA nanostructure.

<400> SEQUENCE: 1188
taggtaaact atttttgaga gatcaaacgt tattaccatc tctcctaaac tcg    53

<210> SEQ ID NO 1189
<211> LENGTH: 53
<212> TYPE: DNA
<213> ORGANISM: Artificial Sequence
<220> FEATURE:
<223> OTHER INFORMATION: Staple strand_1188 of the 2D DNA nanostructure.

<400> SEQUENCE: 1189
gagggtagga ttcaaaaggg tgagacatcc aattaccatc tctcctaaac tcg    53

<210> SEQ ID NO 1190
<211> LENGTH: 53
<212> TYPE: DNA
<213> ORGANISM: Artificial Sequence
<220> FEATURE:
<223> OTHER INFORMATION: Staple strand_1189 of the 2D DNA nanostructure.

<400> SEQUENCE: 1190
atattttggc tttcatcaac attatccagc cattaccatc tctcctaaac tcg    53

<210> SEQ ID NO 1191
<211> LENGTH: 53
<212> TYPE: DNA
<213> ORGANISM: Artificial Sequence
<220> FEATURE:
<223> OTHER INFORMATION: Staple strand_1190 of the 2D DNA nanostructure.

<400> SEQUENCE: 1191
tgtagccatt aaaattcgca ttaaatgccg gattaccatc tctcctaaac tcg    53

<210> SEQ ID NO 1192
<211> LENGTH: 53
<212> TYPE: DNA
<213> ORGANISM: Artificial Sequence
<220> FEATURE:
<223> OTHER INFORMATION: Staple strand_1191 of the 2D DNA nanostructure.

<400> SEQUENCE: 1192
gctttccgat tacgccagct ggcggctgtt tcttaccatc tctcctaaac tcg    53

<210> SEQ ID NO 1193
<211> LENGTH: 53
<212> TYPE: DNA
<213> ORGANISM: Artificial Sequence
<220> FEATURE:

<223> OTHER INFORMATION: Staple strand_1192 of the 2D DNA nanostructure.

<400> SEQUENCE: 1193
tcttcgctgc accgcttctg gtgcggcctt ccttaccatc tctcctaaac tcg        53

<210> SEQ ID NO 1194
<211> LENGTH: 53
<212> TYPE: DNA
<213> ORGANISM: Artificial Sequence
<220> FEATURE:
<223> OTHER INFORMATION: Staple strand_1193 of the 2D DNA nanostructure.

<400> SEQUENCE: 1194
ctgtgtgatt gcgttgcgct cactagagtt gcttaccatc tctcctaaac tcg        53

<210> SEQ ID NO 1195
<211> LENGTH: 53
<212> TYPE: DNA
<213> ORGANISM: Artificial Sequence
<220> FEATURE:
<223> OTHER INFORMATION: Staple strand_1194 of the 2D DNA nanostructure.

<400> SEQUENCE: 1195
cacattaaaa ttgttatccg ctcatgcggg ccttaccatc tctcctaaac tcg        53

<210> SEQ ID NO 1196
<211> LENGTH: 53
<212> TYPE: DNA
<213> ORGANISM: Artificial Sequence
<220> FEATURE:
<223> OTHER INFORMATION: Staple strand_1195 of the 2D DNA nanostructure.

<400> SEQUENCE: 1196
agcaagcgta gggttgagtg ttgtagggag ccttaccatc tctcctaaac tcg        53

<210> SEQ ID NO 1197
<211> LENGTH: 53
<212> TYPE: DNA
<213> ORGANISM: Artificial Sequence
<220> FEATURE:
<223> OTHER INFORMATION: Staple strand_1196 of the 2D DNA nanostructure.

<400> SEQUENCE: 1197
gcccgagagt ccacgctggt ttgcagctaa ctttaccatc tctcctaaac tcg        53

<210> SEQ ID NO 1198
<211> LENGTH: 53
<212> TYPE: DNA
<213> ORGANISM: Artificial Sequence
<220> FEATURE:
<223> OTHER INFORMATION: Staple strand_1197 of the 2D DNA nanostructure.

<400> SEQUENCE: 1198
cccgatttag agcttgacgg ggaaaaagaa tattaccatc tctcctaaac tcg        53

<210> SEQ ID NO 1199
<211> LENGTH: 53
<212> TYPE: DNA
<213> ORGANISM: Artificial Sequence
<220> FEATURE:
<223> OTHER INFORMATION: Staple strand_1198 of the 2D DNA nanostructure.

<400> SEQUENCE: 1199
ttctactacg cgagctgaaa aggttaccgc gcttaccatc tctcctaaac tcg        53

```
<210> SEQ ID NO 1200
<211> LENGTH: 51
<212> TYPE: DNA
<213> ORGANISM: Artificial Sequence
<220> FEATURE:
<223> OTHER INFORMATION: Staple strand_1199 of the 2D DNA nanostructure.

<400> SEQUENCE: 1200
gagacagcta gctgataaat taattttttgt ttaccatctc tcctaaactc g        51

<210> SEQ ID NO 1201
<211> LENGTH: 53
<212> TYPE: DNA
<213> ORGANISM: Artificial Sequence
<220> FEATURE:
<223> OTHER INFORMATION: Staple strand_1200 of the 2D DNA nanostructure.

<400> SEQUENCE: 1201
caaccgtttc aaatcaccat caattcgagc cattaccatc tctcctaaac tcg      53

<210> SEQ ID NO 1202
<211> LENGTH: 65
<212> TYPE: DNA
<213> ORGANISM: Artificial Sequence
<220> FEATURE:
<223> OTHER INFORMATION: Staple strand_1201 of the 2D DNA nanostructure.

<400> SEQUENCE: 1202
taaatcaaaa taattcgcgt ctcggaaacc aggcaaaggg aaggttacca tctctcctaa    60
actcg                                                               65

<210> SEQ ID NO 1203
<211> LENGTH: 53
<212> TYPE: DNA
<213> ORGANISM: Artificial Sequence
<220> FEATURE:
<223> OTHER INFORMATION: Staple strand_1202 of the 2D DNA nanostructure.

<400> SEQUENCE: 1203
gccatcaagc tcattttta accacaaatc cattaccatc tctcctaaac tcg        53

<210> SEQ ID NO 1204
<211> LENGTH: 53
<212> TYPE: DNA
<213> ORGANISM: Artificial Sequence
<220> FEATURE:
<223> OTHER INFORMATION: Staple strand_1203 of the 2D DNA nanostructure.

<400> SEQUENCE: 1204
caactgttgc gccattcgcc attcaaacat cattaccatc tctcctaaac tcg       53

<210> SEQ ID NO 1205
<211> LENGTH: 53
<212> TYPE: DNA
<213> ORGANISM: Artificial Sequence
<220> FEATURE:
<223> OTHER INFORMATION: Staple strand_1204 of the 2D DNA nanostructure.

<400> SEQUENCE: 1205
aagcctggta cgagccggaa gcatagatga tgttaccatc tctcctaaac tcg       53

<210> SEQ ID NO 1206
<211> LENGTH: 59
<212> TYPE: DNA
<213> ORGANISM: Artificial Sequence
<220> FEATURE:
```

<223> OTHER INFORMATION: Staple strand_1205 of the 2D DNA nanostructure.

<400> SEQUENCE: 1206
cccagcaggc gaaaaatccc ttataaatca agccggcgtt accatctctc ctaaactcg    59

<210> SEQ ID NO 1207
<211> LENGTH: 53
<212> TYPE: DNA
<213> ORGANISM: Artificial Sequence
<220> FEATURE:
<223> OTHER INFORMATION: Staple strand_1206 of the 2D DNA nanostructure.

<400> SEQUENCE: 1207
tcggcaaatc ctgtttgatg gtggaccctc aattaccatc tctcctaaac tcg    53

<210> SEQ ID NO 1208
<211> LENGTH: 52
<212> TYPE: DNA
<213> ORGANISM: Artificial Sequence
<220> FEATURE:
<223> OTHER INFORMATION: Staple strand_1207 of the 2D DNA nanostructure.

<400> SEQUENCE: 1208
aacgtggcga gaaggaagg gaaaccagta attaccatct ctcctaaact cg    52

<210> SEQ ID NO 1209
<211> LENGTH: 51
<212> TYPE: DNA
<213> ORGANISM: Artificial Sequence
<220> FEATURE:
<223> OTHER INFORMATION: Staple strand_1208 of the 2D DNA nanostructure.

<400> SEQUENCE: 1209
ttttatttaa gcaaatcaga tattttttgt ttaccatctc tcctaaactc g    51

<210> SEQ ID NO 1210
<211> LENGTH: 53
<212> TYPE: DNA
<213> ORGANISM: Artificial Sequence
<220> FEATURE:
<223> OTHER INFORMATION: Staple strand_1209 of the 2D DNA nanostructure.

<400> SEQUENCE: 1210
gtaataagtt aggcagaggc atttatgata ttttaccatc tctcctaaac tcg    53

<210> SEQ ID NO 1211
<211> LENGTH: 51
<212> TYPE: DNA
<213> ORGANISM: Artificial Sequence
<220> FEATURE:
<223> OTHER INFORMATION: Staple strand_1210 of the 2D DNA nanostructure.

<400> SEQUENCE: 1211
catgtaatag aatataaagt accaagccgt ttaccatctc tcctaaactc g    51

<210> SEQ ID NO 1212
<211> LENGTH: 53
<212> TYPE: DNA
<213> ORGANISM: Artificial Sequence
<220> FEATURE:
<223> OTHER INFORMATION: Staple strand_1211 of the 2D DNA nanostructure.

<400> SEQUENCE: 1212
atcgcaagta tgtaaatgct gatgatagga acttaccatc tctcctaaac tcg    53

```
<210> SEQ ID NO 1213
<211> LENGTH: 51
<212> TYPE: DNA
<213> ORGANISM: Artificial Sequence
<220> FEATURE:
<223> OTHER INFORMATION: Staple strand_1212 of the 2D DNA nanostructure.

<400> SEQUENCE: 1213
tataactaac aaagaacgcg agaacgccaa ttaccatctc tcctaaactc g          51

<210> SEQ ID NO 1214
<211> LENGTH: 53
<212> TYPE: DNA
<213> ORGANISM: Artificial Sequence
<220> FEATURE:
<223> OTHER INFORMATION: Staple strand_1213 of the 2D DNA nanostructure.

<400> SEQUENCE: 1214
agaaaacaaa gaagatgatg aaacaggctg cgttaccatc tctcctaaac tcg        53

<210> SEQ ID NO 1215
<211> LENGTH: 51
<212> TYPE: DNA
<213> ORGANISM: Artificial Sequence
<220> FEATURE:
<223> OTHER INFORMATION: Staple strand_1214 of the 2D DNA nanostructure.

<400> SEQUENCE: 1215
ctgagcaaaa attaattaca ttttgggtta ttaccatctc tcctaaactc g          51

<210> SEQ ID NO 1216
<211> LENGTH: 53
<212> TYPE: DNA
<213> ORGANISM: Artificial Sequence
<220> FEATURE:
<223> OTHER INFORMATION: Staple strand_1215 of the 2D DNA nanostructure.

<400> SEQUENCE: 1216
gcaattcaca tattcctgat tatcaaagtg tattaccatc tctcctaaac tcg        53

<210> SEQ ID NO 1217
<211> LENGTH: 51
<212> TYPE: DNA
<213> ORGANISM: Artificial Sequence
<220> FEATURE:
<223> OTHER INFORMATION: Staple strand_1216 of the 2D DNA nanostructure.

<400> SEQUENCE: 1217
attatcattc aatataatcc tgacaattac ttaccatctc tcctaaactc g          51

<210> SEQ ID NO 1218
<211> LENGTH: 53
<212> TYPE: DNA
<213> ORGANISM: Artificial Sequence
<220> FEATURE:
<223> OTHER INFORMATION: Staple strand_1217 of the 2D DNA nanostructure.

<400> SEQUENCE: 1218
tcaatatcga acctcaaata tcaattccga aattaccatc tctcctaaac tcg        53

<210> SEQ ID NO 1219
<211> LENGTH: 51
<212> TYPE: DNA
<213> ORGANISM: Artificial Sequence
<220> FEATURE:
<223> OTHER INFORMATION: Staple strand_1218 of the 2D DNA nanostructure.
```

<400> SEQUENCE: 1219
accttgcttg gtcagttggc aaagagcgga ttaccatctc tcctaaactc g        51

<210> SEQ ID NO 1220
<211> LENGTH: 51
<212> TYPE: DNA
<213> ORGANISM: Artificial Sequence
<220> FEATURE:
<223> OTHER INFORMATION: Staple strand_1219 of the 2D DNA nanostructure.

<400> SEQUENCE: 1220
taaaagggac attctggcca acaaagcatc ttaccatctc tcctaaactc g        51

<210> SEQ ID NO 1221
<211> LENGTH: 53
<212> TYPE: DNA
<213> ORGANISM: Artificial Sequence
<220> FEATURE:
<223> OTHER INFORMATION: Staple strand_1220 of the 2D DNA nanostructure.

<400> SEQUENCE: 1221
gtaccgcaat tctaagaacg cgagtattat ttttaccatc tctcctaaac tcg      53

<210> SEQ ID NO 1222
<211> LENGTH: 53
<212> TYPE: DNA
<213> ORGANISM: Artificial Sequence
<220> FEATURE:
<223> OTHER INFORMATION: Staple strand_1221 of the 2D DNA nanostructure.

<400> SEQUENCE: 1222
gtaaagtaat cgccatattt aacaaaactt ttttaccatc tctcctaaac tcg      53

<210> SEQ ID NO 1223
<211> LENGTH: 53
<212> TYPE: DNA
<213> ORGANISM: Artificial Sequence
<220> FEATURE:
<223> OTHER INFORMATION: Staple strand_1222 of the 2D DNA nanostructure.

<400> SEQUENCE: 1223
aattgagaat tctgtccaga cgactaaacc aattaccatc tctcctaaac tcg      53

<210> SEQ ID NO 1224
<211> LENGTH: 53
<212> TYPE: DNA
<213> ORGANISM: Artificial Sequence
<220> FEATURE:
<223> OTHER INFORMATION: Staple strand_1223 of the 2D DNA nanostructure.

<400> SEQUENCE: 1224
tcaaatataa cctccggctt aggtaacaat ttttaccatc tctcctaaac tcg      53

<210> SEQ ID NO 1225
<211> LENGTH: 53
<212> TYPE: DNA
<213> ORGANISM: Artificial Sequence
<220> FEATURE:
<223> OTHER INFORMATION: Staple strand_1224 of the 2D DNA nanostructure.

<400> SEQUENCE: 1225 accttttat tttagttaat ttcatagggc ttttaccatc tctcctaaac tcg       53

<210> SEQ ID NO 1226
<211> LENGTH: 53

```
<212> TYPE: DNA
<213> ORGANISM: Artificial Sequence
<220> FEATURE:
<223> OTHER INFORMATION: Staple strand_1225 of the 2D DNA nanostructure.

<400> SEQUENCE: 1226
catttgaagg cgaattattc atttttgttt ggttaccatc tctcctaaac tcg            53

<210> SEQ ID NO 1227
<211> LENGTH: 53
<212> TYPE: DNA
<213> ORGANISM: Artificial Sequence
<220> FEATURE:
<223> OTHER INFORMATION: Staple strand_1226 of the 2D DNA nanostructure.

<400> SEQUENCE: 1227
cgcgcagatt acctttttta atgggagaga ctttaccatc tctcctaaac tcg            53

<210> SEQ ID NO 1228
<211> LENGTH: 53
<212> TYPE: DNA
<213> ORGANISM: Artificial Sequence
<220> FEATURE:
<223> OTHER INFORMATION: Staple strand_1227 of the 2D DNA nanostructure.

<400> SEQUENCE: 1228
attatactaa gaaaccacca gaagtcaaca gtttaccatc tctcctaaac tcg            53

<210> SEQ ID NO 1229
<211> LENGTH: 53
<212> TYPE: DNA
<213> ORGANISM: Artificial Sequence
<220> FEATURE:
<223> OTHER INFORMATION: Staple strand_1228 of the 2D DNA nanostructure.

<400> SEQUENCE: 1229
gcggaacatc tgaataatgg aaggtacaaa atttaccatc tctcctaaac tcg            53

<210> SEQ ID NO 1230
<211> LENGTH: 53
<212> TYPE: DNA
<213> ORGANISM: Artificial Sequence
<220> FEATURE:
<223> OTHER INFORMATION: Staple strand_1229 of the 2D DNA nanostructure.

<400> SEQUENCE: 1230
tgaaaggagc aaatgaaaaa tctagagata gattaccatc tctcctaaac tcg            53

<210> SEQ ID NO 1231
<211> LENGTH: 53
<212> TYPE: DNA
<213> ORGANISM: Artificial Sequence
<220> FEATURE:
<223> OTHER INFORMATION: Staple strand_1230 of the 2D DNA nanostructure.

<400> SEQUENCE: 1231
agccagcaat tgaggaaggt tatcatcatt ttttaccatc tctcctaaac tcg            53

<210> SEQ ID NO 1232
<211> LENGTH: 53
<212> TYPE: DNA
<213> ORGANISM: Artificial Sequence
<220> FEATURE:
<223> OTHER INFORMATION: Staple strand_1231 of the 2D DNA nanostructure.

<400> SEQUENCE: 1232
``` accccttctga cctgaaagcg taagacgctg agttaccatc tctcctaaac tcg        53

<210> SEQ ID NO 1233
<211> LENGTH: 53
<212> TYPE: DNA
<213> ORGANISM: Artificial Sequence
<220> FEATURE:
<223> OTHER INFORMATION: Staple strand_1232 of the 2D DNA nanostructure.

<400> SEQUENCE: 1233
cttatcattc ccgacttgcg ggagcctaat ttttaccatc tctcctaaac tcg        53

<210> SEQ ID NO 1234
<211> LENGTH: 51
<212> TYPE: DNA
<213> ORGANISM: Artificial Sequence
<220> FEATURE:
<223> OTHER INFORMATION: Staple strand_1233 of the 2D DNA nanostructure.

<400> SEQUENCE: 1234
acaacatgcc aacgctcaac agtcttctga ttaccatctc tcctaaactc g          51

<210> SEQ ID NO 1235
<211> LENGTH: 53
<212> TYPE: DNA
<213> ORGANISM: Artificial Sequence
<220> FEATURE:
<223> OTHER INFORMATION: Staple strand_1234 of the 2D DNA nanostructure.

<400> SEQUENCE: 1235
agtataaagt tcagctaatg cagatgtctt tcttaccatc tctcctaaac tcg        53

<210> SEQ ID NO 1236
<211> LENGTH: 51
<212> TYPE: DNA
<213> ORGANISM: Artificial Sequence
<220> FEATURE:
<223> OTHER INFORMATION: Staple strand_1235 of the 2D DNA nanostructure.

<400> SEQUENCE: 1236
cctaaatcaa aatcataggt ctaaacagta ttaccatctc tcctaaactc g          51

<210> SEQ ID NO 1237
<211> LENGTH: 53
<212> TYPE: DNA
<213> ORGANISM: Artificial Sequence
<220> FEATURE:
<223> OTHER INFORMATION: Staple strand_1236 of the 2D DNA nanostructure.

<400> SEQUENCE: 1237
gaatttattt aatggtttga aatattctta ccttaccatc tctcctaaac tcg        53

<210> SEQ ID NO 1238
<211> LENGTH: 51
<212> TYPE: DNA
<213> ORGANISM: Artificial Sequence
<220> FEATURE:
<223> OTHER INFORMATION: Staple strand_1237 of the 2D DNA nanostructure.

<400> SEQUENCE: 1238
cataaatctt tgaataccaa gtgttagaac ttaccatctc tcctaaactc g          51

<210> SEQ ID NO 1239
<211> LENGTH: 53
<212> TYPE: DNA
<213> ORGANISM: Artificial Sequence

```
<220> FEATURE:
<223> OTHER INFORMATION: Staple strand_1238 of the 2D DNA nanostructure.

<400> SEQUENCE: 1239
cctgattgca atatatgtga gtgatcaata gtttaccatc tctcctaaac tcg              53

<210> SEQ ID NO 1240
<211> LENGTH: 51
<212> TYPE: DNA
<213> ORGANISM: Artificial Sequence
<220> FEATURE:
<223> OTHER INFORMATION: Staple strand_1239 of the 2D DNA nanostructure.

<400> SEQUENCE: 1240
ctaccatagt ttgagtaaca tttaaaatat ttaccatctc tcctaaactc g                51

<210> SEQ ID NO 1241
<211> LENGTH: 53
<212> TYPE: DNA
<213> ORGANISM: Artificial Sequence
<220> FEATURE:
<223> OTHER INFORMATION: Staple strand_1240 of the 2D DNA nanostructure.

<400> SEQUENCE: 1241
attttaaaat caaattatt tgcacggatt cgttaccatc tctcctaaac tcg               53

<210> SEQ ID NO 1242
<211> LENGTH: 51
<212> TYPE: DNA
<213> ORGANISM: Artificial Sequence
<220> FEATURE:
<223> OTHER INFORMATION: Staple strand_1241 of the 2D DNA nanostructure.

<400> SEQUENCE: 1242
ctttagggcc tgcaacagtg ccaatacgtg ttaccatctc tcctaaactc g                51

<210> SEQ ID NO 1243
<211> LENGTH: 53
<212> TYPE: DNA
<213> ORGANISM: Artificial Sequence
<220> FEATURE:
<223> OTHER INFORMATION: Staple strand_1242 of the 2D DNA nanostructure.

<400> SEQUENCE: 1243
ttaacaccag cactaacaac taatcgttat tattaccatc tctcctaaac tcg              53

<210> SEQ ID NO 1244
<211> LENGTH: 52
<212> TYPE: DNA
<213> ORGANISM: Artificial Sequence
<220> FEATURE:
<223> OTHER INFORMATION: Staple strand_1243 of the 2D DNA nanostructure.

<400> SEQUENCE: 1244
gcacagacaa tatttttgaa tggggtcagt attaccatct ctcctaaact cg               52

<210> SEQ ID NO 1245
<211> LENGTH: 51
<212> TYPE: DNA
<213> ORGANISM: Artificial Sequence
<220> FEATURE:
<223> OTHER INFORMATION: Staple strand_1244 of the 2D DNA nanostructure.

<400> SEQUENCE: 1245
tgtagaaatc aagattagtt gctcttacca ttaccatctc tcctaaactc g                51
```

```
<210> SEQ ID NO 1246
<211> LENGTH: 53
<212> TYPE: DNA
<213> ORGANISM: Artificial Sequence
<220> FEATURE:
<223> OTHER INFORMATION: Staple strand_1245 of the 2D DNA nanostructure.

<400> SEQUENCE: 1246
gtttatcaat atgcgttata caaaccgacc gtttaccatc tctcctaaac tcg         53

<210> SEQ ID NO 1247
<211> LENGTH: 51
<212> TYPE: DNA
<213> ORGANISM: Artificial Sequence
<220> FEATURE:
<223> OTHER INFORMATION: Staple strand_1246 of the 2D DNA nanostructure.

<400> SEQUENCE: 1247
ttagtatcac aatagataag tccacgagca ttaccatctc tcctaaactc g           51

<210> SEQ ID NO 1248
<211> LENGTH: 53
<212> TYPE: DNA
<213> ORGANISM: Artificial Sequence
<220> FEATURE:
<223> OTHER INFORMATION: Staple strand_1247 of the 2D DNA nanostructure.

<400> SEQUENCE: 1248
gtgataaaaa gacgctgaga agagataacc ttttaccatc tctcctaaac tcg         53

<210> SEQ ID NO 1249
<211> LENGTH: 51
<212> TYPE: DNA
<213> ORGANISM: Artificial Sequence
<220> FEATURE:
<223> OTHER INFORMATION: Staple strand_1248 of the 2D DNA nanostructure.

<400> SEQUENCE: 1249
cttagattta aggcgttaaa taaagcctgt ttaccatctc tcctaaactc g           51

<210> SEQ ID NO 1250
<211> LENGTH: 53
<212> TYPE: DNA
<213> ORGANISM: Artificial Sequence
<220> FEATURE:
<223> OTHER INFORMATION: Staple strand_1249 of the 2D DNA nanostructure.

<400> SEQUENCE: 1250
gcttctgttc gggagaaaca ataacgtaaa acttaccatc tctcctaaac tcg         53

<210> SEQ ID NO 1251
<211> LENGTH: 51
<212> TYPE: DNA
<213> ORGANISM: Artificial Sequence
<220> FEATURE:
<223> OTHER INFORMATION: Staple strand_1250 of the 2D DNA nanostructure.

<400> SEQUENCE: 1251
cttttacaaa atcgtcgcta ttagcgatag ttaccatctc tcctaaactc g           51

<210> SEQ ID NO 1252
<211> LENGTH: 53
<212> TYPE: DNA
<213> ORGANISM: Artificial Sequence
<220> FEATURE:
<223> OTHER INFORMATION: Staple strand_1251 of the 2D DNA nanostructure.
```

<400> SEQUENCE: 1252
agaaataaaa atcctttgcc cgaaagatta gattaccatc tctcctaaac tcg          53

<210> SEQ ID NO 1253
<211> LENGTH: 51
<212> TYPE: DNA
<213> ORGANISM: Artificial Sequence
<220> FEATURE:
<223> OTHER INFORMATION: Staple strand_1252 of the 2D DNA nanostructure.

<400> SEQUENCE: 1253
ctcgtattag aaattgcgta gatacagtac ttaccatctc tcctaaactc g            51

<210> SEQ ID NO 1254
<211> LENGTH: 53
<212> TYPE: DNA
<213> ORGANISM: Artificial Sequence
<220> FEATURE:
<223> OTHER INFORMATION: Staple strand_1253 of the 2D DNA nanostructure.

<400> SEQUENCE: 1254
gccgtcaaaa aacagaggtg aggcctatta gtttaccatc tctcctaaac tcg          53

<210> SEQ ID NO 1255
<211> LENGTH: 51
<212> TYPE: DNA
<213> ORGANISM: Artificial Sequence
<220> FEATURE:
<223> OTHER INFORMATION: Staple strand_1254 of the 2D DNA nanostructure.

<400> SEQUENCE: 1255
cagaagatta gataatacat tgtcgacaa ttaccatctc tcctaaactc g             51

<210> SEQ ID NO 1256
<211> LENGTH: 51
<212> TYPE: DNA
<213> ORGANISM: Artificial Sequence
<220> FEATURE:
<223> OTHER INFORMATION: Staple strand_1255 of the 2D DNA nanostructure.

<400> SEQUENCE: 1256
ctttaatgcg cgaactgata gccccaccag ttaccatctc tcctaaactc g            51

<210> SEQ ID NO 1257
<211> LENGTH: 7249
<212> TYPE: DNA
<213> ORGANISM: Phage M13mp18
<220> FEATURE:
<223> OTHER INFORMATION: scaffold DNA p7249_tillibit.txt

<400> SEQUENCE: 1257
aatgctacta ctattagtag aattgatgcc accttttcag ctcgcgcccc aaatgaaaat     60
atagctaaac aggttattga ccatttgcga aatgtatcta atggtcaaac taatctcact    120
cgttcgcaga attgggaatc aactgttata tggaatgaaa cttccagaca ccgtacttta    180
gttgcatatt taaaacatgt tgagctacag cattatattc agcaattaag ctctaagcca    240
tccgcaaaaa tgacctctta tcaaaaggag caattaaagg tactctctaa tcctgacctg    300
ttggagtttg cttccggtct ggttcgcttt gaagctcgaa ttaaaacgcg atatttgaag    360
tctttcgggc ttcctcttaa tctttttgat gcaatccgct ttgcttctga ctataatagt    420
cagggtaaag acctgatttt tgatttatgg tcattctcgt tttctgaact gtttaaagca    480

```
tttgaggggg attcaatgaa tatttatgac gattccgcag tattggacgc tatccagtct    540
aaacatttta ctattacccc ctctggcaaa acttcttttg caaaagcctc tcgctatttt    600 ggttttatc gtcgtctggt aaacgagggt tatgatagtg ttgctcttac tatgcctcgt     660
aattcctttt ggcgttatgt atctgcatta gttgaatgtg gtattcctaa atctcaactg    720
atgaatcttt ctacctgtaa taatgttgtt ccgttagttc gttttattaa cgtagatttt    780
tcttcccaac gtcctgactg gtataatgag ccagttctta aaatcgcata aggtaattca    840
caatgattaa agttgaaatt aaaccatctc aagcccaatt tactactcgt tctggtgttt    900
ctcgtcaggg caagccttat tcactgaatg agcagctttg ttacgttgat ttgggtaatg    960
aatatccggt tcttgtcaag attactcttg atgaaggtca gccagcctat gcgcctggtc   1020
tgtacaccgt tcatctgtcc tctttcaaag ttggtcagtt cggttccctt atgattgacc   1080
gtctgcgcct cgttccggct aagtaacatg gagcaggtcg cggatttcga cacaatttat   1140
caggcgatga tacaaatctc cgttgtactt tgtttcgcgc ttggtataat cgctgggggt   1200
caaagatgag tgttttagtg tattcttttg cctctttcgt tttaggttgg tgccttcgta   1260
gtggcattac gtattttacc cgtttaatgg aaacttcctc atgaaaaagt ctttagtcct   1320
caaagcctct gtagccgttg ctaccctcgt tccgatgctg tctttcgctg ctgagggtga   1380
cgatcccgca aaagcggcct ttaactccct gcaagcctca gcgaccgaat atatcggtta   1440
tgcgtgggcg atggttgttg tcattgtcgg cgcaactatc ggtatcaagc tgtttaagaa   1500
attcacctcg aaagcaagct gataaaccga caattaaa ggctccttttt ggagcctttt   1560 ttttggagat tttcaacgtg aaaaaattat tattcgcaat tcctttagtt gttcctttct   1620
attctcactc cgctgaaact gttgaaagtt gtttagcaaa atcccataca gaaaattcat   1680
ttactaacgt ctggaaagac gacaaaactt tagatcgtta cgctaactat gagggctgtc   1740
tgtggaatgc tacaggcgtt gtagtttgta ctggtgacga aactcagtgt tacggtacat   1800
gggttcctat tgggcttgct atccctgaaa atgagggtgg tggctctgag ggtggcggtt   1860
ctgagggtgg cggttctgag ggtggcggta ctaaacctcc tgagtacggt gatacaccta   1920
ttccgggcta cttatatc aaccctctcg acggcactta tccgcctggt actgagcaaa    1980
accccgctaa tcctaatcct tctcttgagg agtctcagcc tcttaatact ttcatgtttc   2040
agaataatag gttccgaaat aggcagggg cattaactgt ttatacgggc actgttactc    2100
aaggcactga ccccgttaaa acttattacc agtacactcc tgtatcatca aaagccatgt   2160
atgacgctta ctggaacggt aaattcagag actgcgcttt ccattctggc tttaatgagg   2220
atttatttgt ttgtgaatat caaggccaat cgtctgacct gcctcaacct cctgtcaatg   2280
ctggcggcgg ctctggtggt ggttctggtg gcggctctga gggtggtggc tctgagggtg   2340
gcggttctga gggtggcggc tctgagggag gcggttccgg tggtggctct ggttccggtg   2400
attttgatta tgaaaagatg gcaaacgcta ataaggggc tatgaccgaa atgccgatg     2460 aaaacgcgct acagtctgac gctaaaggca aacttgattc tgtcgctact gattacggtg   2520
ctgctatcga tggtttcatt ggtgacgttt ccggccttgc taatggtaat ggtgctactg   2580
gtgattttgc tggctctaat tcccaaatgg ctcaagtcgg tgacggtgat aattcacctt   2640
taatgaataa tttccgtcaa tatttacctt ccctccctca atcggttgaa tgtcgccctt   2700
ttgtctttgg cgctggtaaa ccatatgaat tttctattga ttgtgacaaa ataaacttat   2760
tccgtggtgt ctttgcgttt cttttatatg ttgccacctt tatgtatgta ttttctacgt   2820
ttgctaacat actgcgtaat aaggagtctt aatcatgcca gttcttttgg gtattccgtt   2880
```

```
attattgcgt tcctcggtt tccttctggt aactttgttc ggctatctgc ttacttttct    2940
taaaaagggc ttcggtaaga tagctattgc tatttcattg tttcttgctc ttattattgg    3000
gcttaactca attcttgtgg gttatctctc tgatattagc gctcaattac cctctgactt    3060
tgttcagggt gttcagttaa ttctcccgtc taatgcgctt ccctgttttt atgttattct    3120
ctctgtaaag gctgctattt tcattttga cgttaaacaa aaaatcgttt cttatttgga    3180
ttgggataaa taatatggct gtttattttg taactggcaa attaggctct ggaaagacgc    3240
tcgttagcgt tggtaagatt caggataaaa ttgtagctgg gtgcaaaata gcaactaatc    3300
ttgatttaag gcttcaaaac ctcccgcaag tcgggaggtt cgctaaaacg cctcgcgttc    3360
ttagaatacc ggataagcct tctatatctg atttgcttgc tattgggcgc ggtaatgatt    3420
cctacgatga aaataaaaac ggcttgcttg ttctcgatga gtgcggtact tggtttaata    3480
cccgttcttg gaatgataag gaaagacagc cgattattga ttggtttcta catgctcgta    3540
aattaggatg ggatattatt tttcttgttc aggacttatc tattgttgat aaacaggcgc    3600
gttctgcatt agctgaacat gttgtttatt gtcgtcgtct ggacagaatt actttacctt    3660
ttgtcggtac tttatattct cttattactg gctcgaaaat gcctctgcct aaattacatg    3720
ttggcgttgt taaatatggc gattctcaat taagccctac tgttgagcgt tggctttata    3780
ctggtaagaa tttgtataac gcatatgata ctaaacaggc ttttttctagt aattatgatt    3840
ccggtgttta ttcttatttta acgccttatt tatcacacgg tcggtatttc aaaccattaa    3900
atttaggtca gaagatgaaa ttaactaaaa tatatttgaa aaagttttct cgcgttcttt    3960
gtcttgcgat tggatttgca tcagcattta catatagtta tataacccaa cctaagccgg    4020
aggttaaaaa ggtagtctct cagacctatg attttgataa attcactatt gactcttctc    4080
agcgtcttaa tctaagctat cgctatgttt tcaaggattc taagggaaaa ttaattaata    4140
gcgacgattt acagaagcaa ggttattcac tcacatatat tgatttatgt actgtttcca    4200
ttaaaaaagg taattcaaat gaaattgtta aatgtaatta attttgtttt cttgatgttt    4260
gtttcatcat cttcttttgc tcaggtaatt gaaatgaata attcgcctct gcgcgatttt    4320
gtaacttggt attcaaagca atcaggcgaa tccgttattg tttctcccga tgtaaaaggt    4380
actgttactg tatattcatc tgacgttaaa cctgaaaatc tacgcaattt ctttatttct    4440
gttttacgtg caaataattt tgatatggta ggttctaacc cttccattat tcagaagtat    4500
aatccaaaca atcaggatta tattgatgaa ttgccatcat ctgataatca ggaatatgat    4560
gataattccg ctccttctgg tggtttcttt gttccgcaaa atgataatgt tactcaaact    4620
tttaaaatta ataacgttcg ggcaaaggat ttaatacgag ttgtcgaatt gtttgtaaag    4680
tctaatactt ctaaatcctc aaatgtatta tctattgacg gctctaatct attagttgtt    4740
agtgctccta agatattttt agataacctt cctcaattcc tttcaactgt tgatttgcca    4800
actgaccaga tattgattga gggtttgata tttgaggttc agcaaggtga tgctttagat    4860
ttttcatttg ctgctggctc tcagcgtggc actgttgcag gcggtgttaa tactgaccgc    4920
ctcacctctg ttttatcttc tgctggtggt tcgttcggta ttttaatgg cgatgtttta    4980
gggctatcag ttcgcgcatt aaagactaat agccattcaa aaatattgtc tgtgccacgt    5040
attcttacgc tttcaggtca gaagggttct atctctgttg gccagaatgt cccttttatt    5100
actggtcgtg tgactggtga atctgccaat gtaaataatc catttcagac gattgagcgt    5160
caaaatgtag gtatttccat gagcgttttt cctgttgcaa tggctggcgg taatattgtt    5220
```

-continued

```
ctggatatta ccagcaaggc cgatagtttg agttcttcta ctcaggcaag tgatgttatt      5280
actaatcaaa gaagtattgc tacaacggtt aatttgcgtg atggacagac tcttttactc      5340
ggtggcctca ctgattataa aaacacttct caggattctg gcgtaccgtt cctgtctaaa      5400
atccctttaa tcggcctcct gtttagctcc cgctctgatt ctaacgagga agcacgtta       5460 tacgtgctcg tcaaagcaac catagtacgc gccctgtagc ggcgcattaa gcgcggcggg      5520
tgtggtggtt acgcgcagcg tgaccgctac acttgccagc gccctagcgc ccgctccttt      5580
cgctttcttc ccttcctttc tcgccacgtt cgccggcttt ccccgtcaag ctctaaatcg      5640
ggggctccct ttagggttcc gatttagtgc tttacggcac ctcgacccca aaaaacttga      5700
tttgggtgat ggttcacgta gtgggccatc gccctgatag acggtttttc gccctttgac      5760
gttggagtcc acgttcttta atagtggact cttgttccaa actggaacaa cactcaaccc      5820
tatctcgggc tattcttttg atttataagg gattttgccg atttcggaac caccatcaaa      5880
caggattttc gcctgctggg gcaaaccagc gtggaccgct tgctgcaact ctctcagggc      5940
caggcggtga agggcaatca gctgttgccc gtctcactgg tgaaaagaaa aaccaccctg      6000
gcgcccaata cgcaaaccgc ctctccccgc gcgttggccg attcattaat gcagctggca      6060
cgacaggttt cccgactgga aagcgggcag tgagcgcaac gcaattaatg tgagttagct      6120
cactcattag gcaccccagg ctttacactt tatgcttccg gctcgtatgt tgtgtggaat      6180
tgtgagcgga taacaatttc acacaggaaa cagctatgac catgattacg aattcgagct      6240
cggtacccgg ggatcctcta gagtcgacct gcaggcatgc aagcttggca ctggccgtcg      6300
ttttacaacg tcgtgactgg gaaaaccctg gcgttaccca acttaatcgc cttgcagcac      6360 atccccttt cgccagctgg cgtaatagcg aagaggcccg caccgatcgc ccttcccaac       6420
agttgcgcag cctgaatggc gaatggcgct ttgcctggtt tccggcacca gaagcggtgc      6480
cggaaagctg gctggagtgc gatcttcctg aggccgatac tgtcgtcgtc ccctcaaact      6540
ggcagatgca cggttacgat gcgcccatct acaccaacgt gacctatccc attacggtca      6600
atccgccgtt tgttcccacg gagaatccga cgggttgtta ctcgctcaca tttaatgttg      6660
atgaaagctg gctacaggaa ggccagacgc gaattatttt tgatggcgtt cctattggtt      6720
aaaaaatgag ctgatttaac aaaaatttaa tgcgaatttt aacaaaatat taacgtttac      6780
aatttaaata tttgcttata caatcttcct gttttggggg cttttctgat tatcaaccgg      6840
ggtacatatg attgacatgc tagttttacg attaccgttc atcgattctc ttgtttgctc      6900
cagactctca ggcaatgacc tgatagcctt tgtagatctc tcaaaaatag ctaccctctc      6960
cggcattaat ttatcagcta gaacggttga atatcatatt gatggtgatt tgactgtctc      7020
cggcctttct cacccttttg aatctttacc tacacattac tcaggcattg catttaaaat      7080
atatgagggt tctaaaaatt tttatccttg cgttgaaata aaggcttctc ccgcaaaagt      7140
attacagggt cataatgttt ttggtacaac cgatttagct ttatgctctg aggctttatt      7200
gcttaatttt gctaattctt tgccttgcct gtatgattta ttggatgtt                  7249
```

<210> SEQ ID NO 1258
<211> LENGTH: 7308
<212> TYPE: DNA
<213> ORGANISM: Phage M13mp18
<220> FEATURE:
<223> OTHER INFORMATION: scaffold DNA p7308_NatChem2012.txt

<400> SEQUENCE: 1258

```
aatgctacta ctattagtag aattgatgcc acctttcag ctcgcgcccc aaatgaaaat       60
```

```
atagctaaac aggttattga ccatttgcga aatgtatcta atggtcaaac taaatctact      120
cgttcgcaga attgggaatc aactgttata tggaatgaaa cttccagaca ccgtacttta      180
gttgcatatt taaaacatgt tgagctacag cattatattc agcaattaag ctctaagcca      240
tccgcaaaaa tgacctctta tcaaaaggag caattaaagg tactctctaa tcctgacctg      300
ttggagtttg cttccggtct ggttcgcttt gaagctcgaa ttaaaacgcg atatttgaag      360
tctttcgggc ttcctcttaa tcttttcgat gcaatccgct ttgcttctga ctataatagt      420
cagggtaaag acctgatttt tgatttatgg tcattctcgt tttctgaact gtttaaagca      480
tttgaggggg attcaatgaa tatttatgac gattccgcag tattggacgc tatccagtct      540
aaacatttta ctattacccc ctctggcaaa acttcttttg caaaagcctc tcgctatttt      600
ggtttttatc gtcgtctggt aaacgagggt tatgatagtg ttgctcttac tatgcctcgt      660
aattcctttt ggcgttatgt atctgcatta gttgaatgtg gtattcctaa atctcaactg      720
atgaatcttt ctacctgtaa taatgttgtt ccgttagttc gttttattaa cgtagatttt      780
tcttcccaac gtcctgactg gtataatgag ccagttctta aaatcgcata aggtaattca      840
caatgattaa agttgaaatt aaaccatctc aagcccaatt tactactcgt tctggtgttt      900
ctcgtcaggg caagccttat tcactgaatg agcagctttg ttacgttgat ttgggtaatg      960
aatatccggt tcttgtcaag attactcttg atgaaggtca gccagcctat gcgcctggtc     1020
tgtacaccgt tcatctgtcc tctttcaaag ttggtcagtt cggttccctt atgattgacc     1080
gtctgcgcct cgttccggct aagtaacatg gagcaggtcg cggatttcga cacaatttat     1140
caggcgatga tacaaatctc cgttgtactt tgtttcgcgc ttggtataat cgctgggggt     1200
caaagatgag tgttttagtg tattcttttg cctctttcgt tttaggttgg tgccttcgta     1260
gtggcattac gtatttttacc cgtttaatgg aaacttcctc atgaaaaagt ctttagtcct     1320
caaagcctct gtagccgttg ctaccctcgt tccgatgctg tctttcgctg ctgagggtga     1380
cgatcccgca aaagcggcct ttaactccct gcaagcctca gcgaccgaat atatcggtta     1440
tgcgtgggcg atggttgttg tcattgtcgg cgcaactatc ggtatcaagc tgtttaagaa     1500
attcacctcg aaagcaagct gataaaccga tacaattaaa ggctcctttt ggagcctttt     1560
ttttggagat tttcaacgtg aaaaaattat tattcgcaat tcctttagtt gttcctttct     1620
attctcactc cgctgaaact gttgaaagtt gtttagcaaa atcccataca gaaaattcat     1680
ttactaacgt ctggaaagac gacaaaactt tagatcgtta cgctaactat gagggctgtc     1740
tgtggaatgc tacaggcgtt gtagtttgta ctggtgacga aactcagtgt tacggtacat     1800
gggttcctat tgggcttgct atccctgaaa atgagggtgg tggctctgag ggtggcggtt     1860
ctgagggtgg cggttctgag gtggcggta ctaaacctcc tgagtacggt gatacaccta     1920
ttccgggcta cttatatatc aaccctctcg acggcactta tccgcctggt actgagcaaa     1980
accccgctaa tcctaatcct tctcttgagg agtctcagcc tcttaatact ttcatgtttc     2040
agaataatag gttccgaaat aggcaggggg cattaactgt ttatacgggc actgttactc     2100
aaggcactga ccccgttaaa acttattacc agtacactcc tgtatcatca aaagccatgt     2160
atgacgctta ctggaacggt aaattcagag actgcgcttt ccattctggc tttaatgagg     2220
atttatttgt ttgtgaatat caaggccaat cgtctgacct gcctcaacct cctgtcaatg     2280
ctggcggcgg ctctggtggt ggttctggtg cggctctga gggtggtggc tctgagggtg     2340
gcggttctga gggtggcggc tctgagggag gcggttccgg tggtggctct ggttccggtg     2400
```

```
attttgatta tgaaaagatg gcaaacgcta ataaggggc tatgaccgaa aatgccgatg     2460
aaaacgcgct acagtctgac gctaaaggca aacttgattc tgtcgctact gattacggtg     2520
ctgctatcga tggtttcatt ggtgacgttt ccggccttgc taatggtaat ggtgctactg     2580
gtgattttgc tggctctaat tcccaaatgg ctcaagtcgg tgacggtgat aattcacctt     2640
taatgaataa tttccgtcaa tatttacctt ccctccctca atcggttgaa tgtcgccctt     2700
ttgtctttgg cgctggtaaa ccatatgaat tttctattga ttgtgacaaa ataaacttat     2760
tccgtggtgt ctttgcgttt cttttatatg ttgccacctt tatgtatgta ttttctacgt     2820
ttgctaacat actgcgtaat aaggagtctt aatcatgcca gttcttttgg gtattccgtt     2880
attattgcgt ttcctcggtt tccttctggt aactttgttc ggctatctgc ttacttttct     2940 taaaagggc ttcggtaaga tagctattgc tatttcattg tttcttgctc ttattattgg     3000
gcttaactca attcttgtgg gttatctctc tgatattagc gctcaattac cctctgactt     3060
tgttcagggt gttcagttaa ttctcccgtc taatgcgctt ccctgttttt atgttattct     3120
ctctgtaaag gctgctattt tcatttttga cgttaaacaa aaaatcgttt cttatttgga     3180
ttgggataaa taatatggct gtttattttg taactggcaa attaggctct ggaaagacgc     3240
tcgttagcgt tggtaagatt caggataaaa ttgtagctgg gtgcaaaata gcaactaatc     3300
ttgatttaag gcttcaaaac ctcccgcaag tcgggaggtt cgctaaaacg cctcgcgttc     3360
ttagaatacc ggataagcct tctatatctg atttgcttgc tattgggcgc ggtaatgatt     3420
cctacgatga aaataaaaac ggcttgcttg ttctcgatga gtgcggtact tggtttaata     3480
cccgttcttg gaatgataag gaaagacagc cgattattga ttggtttcta catgctcgta     3540
aattaggatg ggatattatt tttcttgttc aggacttatc tattgttgat aaacaggcgc     3600
gttctgcatt agctgaacat gttgtttatt gtcgtcgtct ggacagaatt actttacctt     3660
ttgtcggtac tttatattct cttattactg gctcgaaaat gcctctgcct aaattacatg     3720
ttggcgttgt taaatatggc gattctcaat taagccctac tgttgagcgt tggctttata     3780
ctggtaagaa tttgtataac gcatatgata ctaaacaggc ttttttctagt aattatgatt     3840 ccggtgttta ttcttattta acgccttatt tatcacacgg tcggtatttc aaaccattaa     3900
atttaggtca agatgaaa ttaactaaaa tatatttgaa aaagttttct cgcgttcttt     3960
gtcttgcgat tggatttgca tcagcattta catatagtta tataacccaa cctaagccgg     4020
aggttaaaaa ggtagtctct cagacctatg attttgataa attcactatt gactcttctc     4080
agcgtcttaa tctaagctat cgctatgttt tcaaggattc taagggaaaa ttaattaata     4140
gcgacgattt acagaagcaa ggttattcac tcacatatat tgatttatgt actgtttcca     4200
ttaaaaaagg taattcaaat gaaattgtta aatgtaatta attttgtttt cttgatgttt     4260
gtttcatcat cttcttttgc tcaggtaatt gaaatgaata attcgcctct gcgcgatttt     4320
gtaacttggt attcaaagca atcaggcgaa tccgttattg tttctcccga tgtaaaaggt     4380
actgttactg tatattcatc tgacgttaaa cctgaaaatc tacgcaattt ctttatttct     4440
gttttacgtg caaataattt tgatatggta ggttctaacc cttccattat tcagaagtat     4500
aatccaaaca atcaggatta tattgatgaa ttgccatcat ctgataatca ggaatatgat     4560
gataattccg ctccttctgg tggtttcttt gttccgcaaa atgataatgt tactcaaact     4620
tttaaaatta ataacgttcg ggcaaaggat ttaatacgag ttgtcgaatt gtttgtaaag     4680
tctaatactt ctaaatcctc aaatgtatta tctattgacg gctctaatct attagttgtt     4740
agtgctccta aagatatttt agataacctt cctcaattcc tttcaactgt tgatttgcca     4800
```

```
actgaccaga tattgattga gggtttgata tttgaggttc agcaaggtga tgctttagat   4860
tttttcatttg ctgctggctc tcagcgtggc actgttgcag cggtgttaa tactgaccgc   4920
ctcacctctg ttttatcttc tgctggtggt tcgttcggta ttttttaatgg cgatgtttta  4980
gggctatcag ttcgcgcatt aaagactaat agccattcaa aaatattgtc tgtgccacgt   5040
attcttacgc tttcaggtca gaagggttct atctctgttg ccagaatgt ccctttttatt  5100
actggtcgtg tgactggtga atctgccaat gtaaataatc catttcagac gattgagcgt  5160
caaaatgtag gtatttccat gagcgttttt cctgttgcaa tggctggcgg taatattgtt  5220
ctggatatta ccagcaaggc cgatagtttg agttcttcta ctcaggcaag tgatgttatt  5280
actaatcaaa gaagtattgc tacaacggtt aatttgcgtg atggacagac tcttttactc  5340
ggtggcctca ctgattataa aaacacttct caggattctg gcgtaccgtt cctgtctaaa  5400
atccctttaa tcggcctcct gtttagctcc cgctctgatt ctaacgagga aagcacgtta  5460
tacgtgctcg tcaaagcaac catagtacgc gccctgtagc ggcgcattaa gcgcggcggg  5520
tgtggtggtt acgcgcagcg tgaccgctac acttgccagc gccctagcgc ccgctccttt  5580
cgctttcttc ccttcctttc tcgccacgtt cgccggcttt ccccgtcaag ctctaaatcg  5640
ggggctccct ttagggttcc gatttagtgc tttacggcac ctcgacccca aaaaacttga  5700
tttgggtgat ggttcacgta gtgggccatc gccctgatag acggtttttc gccctttgac  5760
gttggagtcc acgttcttta atagtggact cttgttccaa actggaacaa cactcaaccc  5820
tatctcgggc tattcttttg atttataagg gattttgccg atttcggaac caccatcaaa  5880
caggattttc gcctgctggg gcaaaccagc gtggaccgct tgctgcaact ctctcagggc  5940
caggcggtga agggcaatca gctgttgccc gtctcactgg tgaaaagaaa aaccaccctg  6000
gcgcccaata cgcaaaccgc ctctccccgc gcgttggccg attcattaat gcagctggca  6060
cgacaggttt cccgactgga aagcgggcag tgagcgcaac gcaattaatg tgagttagct  6120
cactcattag gcaccccagg ctttacactt tatgcttccg gctcgtatgt tgtgtggaat  6180
tgtgagcgga taacaatttc acacaggaaa cagctatgac catgattacg aattcgagct  6240
cggtacccgg ggatccttat acgggtacta gccatgcgta tacggtcgct agcggacttg  6300
cctcgctatc aaaggtctag agtcgacctg caggcatgca agcttggcac tggccgtcgt  6360
tttacaacgt cgtgactggg aaaaccctgg cgttacccaa cttaatcgcc ttgcagcaca  6420
tccccctttc gccagctggc gtaatagcga agaggcccgc accgatcgcc cttcccaaca  6480
gttgcgcagc ctgaatggcg aatggcgctt tgcctggttt ccggcaccag aagcggtgcc  6540
ggaaagctgg ctggagtgcg atcttcctga ggccgatact gtcgtcgtcc cctcaaactg  6600
gcagatgcac ggttacgatg cgcccatcta caccaacgtg acctatccca ttacggtcaa  6660
tccgccgttt gttcccacgg agaatccgac gggttgttac tcgctcacat ttaatgttga  6720
tgaaagctgg ctacaggaag gccagacgcg aattatttt tgatggcgttc ctattggtta  6780
aaaaatgagc tgatttaaca aaaatttaat gcgaatttta acaaaatatt aacgtttaca  6840
atttaaatat ttgcttatac aatcttcctg ttttggggc ttttctgatt atcaaccggg   6900
gtacatatga ttgacatgct agttttacga ttaccgttca tcgattctct tgtttgctcc  6960
agactctcag gcaatgacct gatagccttt gtagatctct caaaaatagc taccctctcc  7020
ggcattaatt tatcagctag aacggttgaa tatcatattg atggtgattt gactgtctcc  7080
ggcctttctc acccttttga atctttacct acacattact caggcattgc atttaaaata  7140
```

-continued tatgagggtt ctaaaaattt ttatccttgc gttgaaataa aggcttctcc cgcaaaagta      7200
ttacagggtc ataatgtttt tggtacaacc gatttagctt tatgctctga ggctttattg      7260
cttaattttg ctaattcttt gccttgcctg tatgatttat tggatgtt                  7308

<210> SEQ ID NO 1259
<211> LENGTH: 21
<212> TYPE: DNA
<213> ORGANISM: Artificial Sequence
<220> FEATURE:
<223> OTHER INFORMATION: DNA dye adapter red, 3' modification: Atto 647N

<400> SEQUENCE: 1259
gtgatgtagg tggtagagga a                                                21

<210> SEQ ID NO 1260
<211> LENGTH: 21
<212> TYPE: DNA
<213> ORGANISM: Artificial Sequence
<220> FEATURE:
<223> OTHER INFORMATION: DNA dye adapter green, 3' modification: Atto
      565

<400> SEQUENCE: 1260
tatgagaagt taggaatgtt a                                                21

<210> SEQ ID NO 1261
<211> LENGTH: 21
<212> TYPE: DNA
<213> ORGANISM: Artificial Sequence
<220> FEATURE:
<223> OTHER INFORMATION: DNA dye adapter blue, 3' modification: Atto 488

<400> SEQUENCE: 1261
cgagtttagg agagatggta a                                                21

<210> SEQ ID NO 1262
<211> LENGTH: 21
<212> TYPE: DNA
<213> ORGANISM: Artificial Sequence
<220> FEATURE:
<223> OTHER INFORMATION: DNA carrier adapter, 5' modification: biotin

<400> SEQUENCE: 1262
gaatcggtca cagtacaacc g                                                21

<210> SEQ ID NO 1263
<211> LENGTH: 68
<212> TYPE: DNA
<213> ORGANISM: Artificial Sequence
<220> FEATURE:
<223> OTHER INFORMATION: DNA T1 target adapter 3D

<400> SEQUENCE: 1263 taatttaaa agtctcgtat gtcagtatta acaccaccag cagccttgag acgatgttga       60
ccttaacc                                                               68

<210> SEQ ID NO 1264
<211> LENGTH: 68
<212> TYPE: DNA
<213> ORGANISM: Artificial Sequence
<220> FEATURE:
<223> OTHER INFORMATION: DNA T2 target adapter 3D

<400> SEQUENCE: 1264

| | |
|---|---|
| taattttaaa agtctcgtat gtcagtatta acaccaccag cagccttcat gtcaggagat | 60 |
| tttcagcc | 68 |

<210> SEQ ID NO 1265
<211> LENGTH: 68
<212> TYPE: DNA
<213> ORGANISM: Artificial Sequence
<220> FEATURE:
<223> OTHER INFORMATION: DNA T3 target adapter 3D

<400> SEQUENCE: 1265

| | |
|---|---|
| taattttaaa agtctcgtat gtcagtatta acaccaccag cagcctttac cctatctgag | 60 |
| tgagtagc | 68 |

<210> SEQ ID NO 1266
<211> LENGTH: 61
<212> TYPE: DNA
<213> ORGANISM: Artificial Sequence
<220> FEATURE:
<223> OTHER INFORMATION: DNA T1 target adapter 2D

<400> SEQUENCE: 1266

| | |
|---|---|
| ttgtgtcgtg acgagaaaca ccaaatttca actttaattt gagacgatgt tgaccttaac | 60 |
| c | 61 |

<210> SEQ ID NO 1267
<211> LENGTH: 61
<212> TYPE: DNA
<213> ORGANISM: Artificial Sequence
<220> FEATURE:
<223> OTHER INFORMATION: DNA T2 target adapter 2D

<400> SEQUENCE: 1267

| | |
|---|---|
| ttgtgtcgtg acgagaaaca ccaaatttca actttaattt catgtcagga gattttcagc | 60 |
| c | 61 |

<210> SEQ ID NO 1268
<211> LENGTH: 61
<212> TYPE: DNA
<213> ORGANISM: Artificial Sequence
<220> FEATURE:
<223> OTHER INFORMATION: DNA T3 target adapter 2D

<400> SEQUENCE: 1268

| | |
|---|---|
| ttgtgtcgtg acgagaaaca ccaaatttca actttaattt taccctatct gagtgagtag | 60 |
| c | 61 |

<210> SEQ ID NO 1269
<211> LENGTH: 87
<212> TYPE: DNA
<213> ORGANISM: Artificial Sequence
<220> FEATURE:
<223> OTHER INFORMATION: DNA target structure

<400> SEQUENCE: 1269

| | |
|---|---|
| gctactcact cagatagggt atggctgaaa atctcctgac atgtggttaa ggtcaacatc | 60 |
| gtctctcggt tgtactgtga ccgattc | 87 |

SINGLE MOLECULE DETECTION OR QUANTIFICATION USING DNA NANOTECHNOLOGY

CROSS-REFERENCE TO RELATED APPLICATIONS

This present application is a U.S. national stage application of PCT Application No. PCT/EP2017/064634, filed Jun. 14, 2017, which claims priority to German Patent Application 10 2016 007 270.9 filed Jun. 15, 2016, both of which are hereby incorporated by reference their entirety.

The present invention relates to a method and a DNA nanostructure for detecting a target structure. In particular, the present invention relates to a DNA nanostructure, which ensures a preferably linear dependence on the number of marker molecules and the measurement signal regardless of the physical arrangement of a plurality of such DNA nanostructures by virtue of the skilled selection of the shape of the DNA nanostructure and the placement of the marker molecules attached to it. The invention additionally relates to the use of said DNA nanostructures and other nanoreporters, preferably in combination with adapters which bind specifically to target molecules, in a method for quantifying a plurality of target molecules using a multiplex method, preferably in a simultaneous manner A frequently occurring question in research as well as in applied medicine and biotechnology is the analysis, i.e. the detection, of particular target structures. For example, in the case of sepsis of a patient, the detection of the relevant toxins may be necessary or, in the case of a disease entailing altered cellular constitution, e.g. with cancer, a quantitative analysis of the conversion of genetic information may be necessary.

The quantitative analysis of the conversion of genetic information, the so-called gene expression profiling (GEP) requires the detection and identification of a number of different target mRNA molecules (Stadler, Z. K. et al. *Critical Reviews in Oncology Hematology* 69, 1-11 (2009)). mRNA is the established abbreviation for the English term messenger RNA (in German "Boten-RNA"), which is also used in German Since the mRNA sequences are specifically produced in the expression process of the corresponding genes, the gene expression of the analyzed material can be quantified in that manner GEP is able to provide information on the state or type of individual cells or also a tissue sample (plurality of cells) and thereby enable, e.g., the molecular diagnosis of tumor tissue. The GEP comprises the analysis of the expression of at least one gene, preferably the analysis of the expression of a plurality of genes. In order to achieve this ultimate objective, a technology is required, which at the same time allows for quantitative analysis having the highest possible specificity and sensitivity, preferably for a number of genes that is as high as possible. For comprehensive applicability in clinical practice, this technology must additionally be characterized by expeditious analysis times, low costs and simple use.

There is a plurality of GEP techniques, which have different advantages and disadvantages, depending on the question at issue.

Microarrays.

GEP analysis using microarrays is based on the surface hybridization of fluorescent DNA molecules to specific, physical separate target sequences on a chip (Trevino, V. et al. *Mol Med* 13, 527-541 (2007)). These molecules are generated in a preceding step by reverse transcription and polymerase chain reaction (PCR) amplification of RNA molecules. Thereby, microarrays allow for the parallel detection of up to several thousand sequences. However, an exact quantification is impossible, since enzymatic reactions such as reverse transcription and PCR amplification entail systematic errors. Moreover, microarray-based methods require a relatively long time of process of about one day and are therefore not suited for the majority of clinical applications.

qPCR/dPCR. Using PCR, specific DNA molecules may be exponentially duplicated in an enzymatic process (Van-Guilder, H. D. et al. *Biotechniques* 44, 619-626 (2008)). For PCR reactions, mRNA targets must be generally converted enzymatically using reverse transcription of RNA into DNA. The amplification can be measured by adding fluorescent, DNA-binding molecules and the original concentration can be roughly determined (qPCR). Since the amplification rate significantly depends on various parameters (inter alfa target sequence, target length, primer, instruments, reagents, reaction volume), said quantification must be calibrated precisely. For compensation of these disadvantages, digital PCR (dPCR) was developed. It allows for a more precise quantification by compartmentalization of individual target molecules (Baker, M. *Nature Methods* 9, 541-544 (2012)). However, said high preciseness of dPCR is offset by limitation to typically two targets. dPCR is therefore not suited for GEP analyses.

RNA-Seq/NGS. With the so-called next generation sequencing (NGS), on which also RNA sequencing (RNA seq) is based, sequences are read out and identified in several steps by base (Wang, Z. et al. *Nat Rev Genet* 10, 57-63 (2009)). With RNA seq, too, RNA must initially be enzymatically converted into DNA. The advantage and the unique feature of NGS in transcription analysis is the possibility to recognize novel or altered sequences. Due to the great number of complex process steps, the analysis devices are complex and expensive and the process duration is lengthy. This excludes its use in the field of point-of-care. Just as in the above-described methods, enzymatic processes prevent exact quantifiability.

nCounter. The nCounter system of NanoString Technologies is based on the detection of RNA molecules by hybridization using a fluorescent reporter (barcode), on the one hand, as well as a second DNA molecule (capture strand) for attachment to a microscopy chip, on the other hand (Geiss, G. K. et al. *Nat Biotechnol* 26, 317-325 (2008)). The fluorescent reporters are linear geometric barcodes that are micrometers in length and that consist of the arrangement of different areas labeled with fluorescent dyes. One of the advantages of the nCounter system is the enzyme-free and quantitative detection of up to 800 different RNA target molecules. One disadvantage of the method is the necessity to stretch the geometric barcode molecule after target hybridization and surface immobilization, in order to be able to read the respective barcode. This has two important implications: (1) The electrophoretic stretching of the reporters is a complex process step, (2) Conditioned by the low efficiency of this step, approximately 80% of the target molecules are excluded due to non-identifiable barcodes. Furthermore, complex and time-consuming purification steps are necessary, e.g., using magnetic particles. In sum, these process steps lead to expensive analysis devices (>200, 000 euros) and long measuring times (24-48 hours). #

Thus, these traditional methods do not meet all of the above-mentioned preferred requirements for GEP and sacrifice e.g. partial quantifiability for necessary sensitivity.

A further promising analysis approach for GEPs is based on direct labeling of individual target mRNA sequences by so-called hybridization using fluorescent reporters. Fluorescent methods allow for the sensitive detection of single molecules (Joo, C. et al. *Annu Rev Biochem* 77, 51-76 (2008)). However, established methods are not able to determine a great number of different reporters.

Quantitative GEP on single-cell basis employing the available methods is possible only in a limited manner, but would be highly advantageous for both scientific research and industrial research and development as well as for clinical applications.

Essential desirable features of a GEP would be the exact quantification and the efficient implementation of the analysis. This results in the following preferred criteria for an improved GEP:
  direct detection of the mRNA, in particular no translation into DNA, e.g. by reverse transcription
  no amplification of the target molecules, since an amplification that is not precise impairs quantification
  thereby: detection of individual target molecules
  fast-as-possible analysis (order of minutes)
  simple-as-possible analysis, in particular: few working steps.

Apart from nucleic acids and proteins, there is a myriad of further problems with which units in the order of a few nanometers to several tens of nanometers must be detected and preferably counted and/or the concentration be determined; such as inorganic complexes and nanoparticles.

All these problems have in common that molecules or other structures should be detected in a fast, simple and exact manner and be preferably counted. Exact counting in particular entails that the probability of the false positive and/or false negative counting events must be kept as low as possible. The invention aims at an improvement of one or more of said properties, in particular at a reduction of the probability of the false positive and/or false negative counting events.

This problem is solved by the present invention according to the independent claims.

Thus, the present invention is directed to a method for the detection (preferably quantification) of a target structure, comprising:
  a) formation of an identification structure, comprising:
    (i) the target structure, and
    (ii) at least two 3D DNA nanostructures, wherein each of the 3D DNA nanostructures comprises one or more inwardly disposed fluorescence dye molecules, wherein each of the 3D DNA nanostructures is specifically bound to the target structure;
  b) detection (preferably quantification) of the target structure by measuring at least one fluorescence signal,
  wherein the 3D DNA nanostructures and the parameters of fluorescence measurement are selected such that the at least one measured fluorescence signal of the identification structure formed in a) is distinguishable from the fluorescence signal of each of the at least two isolated 3D DNA nanostructures, when these are not bound in the identification structure.

Furthermore, the invention is inter alfa directed to a 3D DNA nanostructure, on which at least one fluorescence dye molecule is attached, wherein the shape of the 3D DNA nanostructure prevents that when approaching a second 3D DNA nanostructure, on which at least one fluorescence dye molecule is attached, the fluorescence dye molecules of the two 3D DNA nanostructures interact significantly.

Preferably, the 3D DNA nanostructure of the invention is a 3D DNA nanostructure having a cavity and at least one inwardly disposed fluorescence dye molecule, wherein the distance of the at least one inwardly disposed fluorescence dye molecule to the rim of the 3D DNA nanostructure is at least 2 nm, preferably at least 3 nm and particularly preferably at least 5 nm.

The skilled choice of the shape of the 3D nanostructures and the arrangement of the fluorescence dye molecules in the inside of/in the cavity of the 3D nanostructure ensures that the dye molecules do not sterically interact with their surroundings. As shown in the experimental Examples as attached, the 3D nanostructures of the invention thereby interact, e.g., to a significantly lesser extent with surfaces, such as a glass surface, than 2D nanostructures comprising the same dyes. This is highly advantageous for the use of such a 3D DNA nanostructure in the method according to the invention. For example, the rate of false positive detection of a target structure can be reduced in that manner, in particular if a carrier structure is used. Moreover, an advantage of shielding the fluorescence dye molecules is that the fluorescence dye molecules of the two 3D DNA nanostructures do not significantly interact (optically and/or sterically). This permits the fluorescence signal of a 3D DNA nanostructure of the invention not being significantly affected by a very close adjacent 3D DNA nanostructure. Moreover, the unspecific interaction of 3D DNA nanostructures which is mediated by fluorescence dye molecules is prevented. Taken as a whole, this is highly advantageous in the use of said 3D nanostructures for the detection of target structures. In particular, like in the method of the invention, this allows for the binding of at least two 3D DNA nanostructures to a target structure, without the fluorescence signal of the individual 3D DNA nanostructures being influenced due to their proximity (e.g. by quenching, fluorescence quenching or FRET).

Depending on the measurement method, the use of at least two DNA nanostructures may even be necessary in order to distinguish the identification structure of target structure and bound DNA nanostructures from the free DNA nanostructures. This is in particular the case with measurement methods which are implemented in solution. When the identification structure is bound to a carrier and/or a carrier surface in the method for detection (as in a preferred embodiment of the method of the invention), this allows for the removal of free DNA nanostructures using one or more washing steps. The use of at least two DNA nanostructures, which bind to a target structure, in a method that uses a carrier has the advantage that the rate of false positive detections may be lowered. First, an identification structure having at least two DNA nanostructures can be clearly distinguished from DNA nanostructures which interact with the surface in an unspecific manner. This is not possible in an analogous method, in which only one DNA nanostructure recognizes the target structure. Second, the use of at least two DNA nanostructures, both of which recognize different regions of the target structure, may significantly reduce and in many cases exclude the probability that other similar target structures are erroneously detected as an alleged target structure.

Moreover, with independent coupling of at least two 3D DNA nanostructures (e.g. different orthogonal measurable nanoreporters) to target molecules, the sensitivity of measuring may be significantly increased. It increases with the potency of the number of independent coupling reactions. This is highly advantageous in particular for high dynamics, i.e., for example, for simultaneously measuring of genes with a very low expression and a very high expression.

In a preferred embodiment, the present invention is also directed to a method for the detection and/or the quantification of at least two different target structures (e.g. two mRNAs, which are derived from different genes, i.e. which comprise a different nucleic acid sequence), preferably of a plurality of different target structures. The different target structures are pairwise distinguishable.

Preferably, said method comprises the following steps:
a) formation of an identification structure for each of the at least two different target structures, comprising:
   (i) the respective target structure, and
   (ii) at least two 3D DNA nanostructures, wherein each of the at least two 3D DNA nanostructures comprises one or more inwardly disposed fluorescence dye molecule and wherein each of the at least two 3D DNA nanostructures is specifically bound to the respective target structure, and wherein the at least two 3D DNA nanostructures are bound to regions of the respective target regions which are pairwise different;
b) detection of the at least two target structures by measuring at least one fluorescence signal, wherein all 3D DNA nanostructures and the parameters of fluorescence measurement are selected such that the at least one measured fluorescence signal of the identification structures formed in a) is distinguishable from the fluorescence signal of all isolated 3D DNA nanostructures, when these are not bound in one of the respective identification structure, and that the measured fluorescence signals of the identification structures that are formed for the individual different target structures are pairwise distinguishable from each other.

Preferably, each of the different target structures is detected several times, i.e. each of the identification structures that is assigned to a specific target structure is formed several times.

All of the above-mentioned advantages of the method according to the invention apply mulatis mutandis in this case. Having the relevant form, DNA nanostructures offer the possibility to attach a plurality of identical and/or different fluorescence dye molecules. As is known from WO 2016/14072 A2 and WO 2016/140726 A2, a plurality of DNA nanostructures having a distinguishable fluorescence signal can thus be generated. However, the amount of the distinguishable combinations critically depends on the size of the DNA nanostructure, which limits the number of fluorescence dye molecules which may be attached thereon, without interacting with each other. However, large DNA nanostructures require more effort and are expensive as regards their production and furthermore poorer than smaller structures as regards kinetics in a method for the detection of a target structure. Due to the use of at least two DNA nanostructures, which become part of the identification structure, the method of the invention has the advantage that also with significantly smaller DNA nanostructures, a similar plurality of fluorescence molecule combinations, which are bound to a target structure, may be generated. Furthermore, the use of at least two DNA nanostructures in an identification structure to further increase the number of the different distinguishable combinations of fluorescence dye molecules on a target structure and/or in an identification structure having the same maximum size as described in WO 2016/140727 A2 and WO 2016/140726 A2. Thereby, the number of different target structures that can be detected in a method can be considerably increased. Apart from the use of at least two DNA nanostructures, in particular the form of the 3D nanostructure and the orientation of the fluorescence dye molecules into the inside of the structure are decisive. As mentioned above, it is only then that an interaction of the dyes of two DNA nanostructures is prevented and the signal of a combination of two or more 3D DNA nanostructures is reliably predictable and measurable.

According to the invention, nucleic acid nanostructures, also referred to as DNA nanostructures or DNA origami, are used. Nucleic acid nanostructures, also referred to as DNA nanostructures or DNA origami, are two- or three-dimensional structures, which inter alfa consist of nucleic acids. The term "origami" describes that one or more strands or components of nucleic acids, preferably DNA, may be folded into almost any pre-defined structure or shape. Such a DNA strand is also referred to as scaffold strand. The one or the more scaffold strands is/are kept in shape by shorter nucleic acid strands (relative to the at least one scaffold strand), which are also referred to as staple strands. Here, it is of major importance that the shorter strands (staple strands) are placed very precisely on well-defined positions on the DNA origami. DNA origami are described in more detail for example in Rothemund, "Folding DNA to create nano-scale shapes and patterns", Nature, March 2006, pp. 297-302, vol. 440; Douglas et al., Nature, 459, pp. 414-418 (2009); and Seeman, "Nanomaterials based on DNA", An. Rev. Biochem. 79, pp. 65-87 (2010). Reference to all of these documents is made herein in their entirety as part of the application.

Said DNA origami nanostructures can be functionalized with photoactive molecules, in particular with one or more fluorescent dye molecules. Thereby, the DNA origami as a whole becomes a fluorescent particle. Such DNA nanostructures, which are based on DNA origami, are described in WO 2016/140727 A2 and WO 2016/140726 A2. Reference to all of these documents is made herein in their entirety as part of the application.

Preferably, a DNA nanostructure of the invention is a 3D DNA nanostructure on which at least one fluorescence dye molecule is attached, wherein the shape of the 3D DNA nanostructure prevents that with approaching a second similar or identical 3D DNA nanostructure, on which the at least one fluorescence dye molecule is attached, the fluorescence dye molecules of the two 3D DNA nanostructures significantly interact. Thus, by means of steric effects, the geometry of the DNA nanostructures prevents fluorescence dye molecules of different DNA nanostructures from coming too close to each other.

As can be inferred from its name, a DNA nanostructure preferably consists of DNA. In principle, a DNA nanostructure of the invention may, however, also contain other nucleic acids such as e.g. RNA, RNA analogues such as LNA, or DNA analogues or consist of these. Therefore, the present invention also comprises all embodiments described herein, in which the DNA nanostructure(s) and/or the 3D DNA nanostructure(s) are nucleic acid nanostructures and/or 3D nucleic acid nanostructures. A nanostructure formed of DNA is preferred, e.g. due to significantly lower production costs for such nanostructures.

A fluorescence dye molecule may be, for example, RFP, GFP, YFP or any of their derivatives (see for example P J Cranfill et al., "Quantitative assessment of fluorescent proteins", Nature Methods, 13, 557 562 (2016)), an Atto dye (e.g. Atto647N, Atto565 or Atto488), an Alexa dye, DAPI, rhodamine, rhodamine derivative, cyanine, cyanine derivative, coumarin, coumarin derivative (for different organic fluorescence dyes see for example Q. Zheng and L Lavis, "Development of photostable fluorophores for molecular imaging", Curr. Op. Chem. Biol. 39 p32-38 (2017)) or quantum dot (quantum dot, see E. Petryayeva et al, "Quantum dots in Bioanalysis: a review of applications across various platforms for fluorescence spectroscopy and imaging", Appl. spectroscopy 67 (2013).

A 3D DNA nanostructure preferably refers to a structure, which substantially extends into three dimensions and is therefore different from an essentially two-dimensional structure such as, e.g., a slightly bent, rough or rippled surface. In other words, the minimal dimensions in three spatial directions that are perpendicular to each other are at least 2 nm, preferably at least 5 nm, more preferably at least 10 nm and particularly preferably at least 20 nm.

The interaction of two fluorescence dye molecules may in particular comprise fluorescence quenching and/or FRET.

In particular, at least two fluorescence dye molecules may be attached on the 3D DNA nanostructure, wherein the distance between the at least two fluorescence dye molecules is pairwise greater than that at which the fluorescence dye molecules significantly interact pairwise. For the exemplary case of a 3D DNA nanostructure having two fluorescence dye molecules, this means that the two fluorescence dye molecules have a distance, which is greater than the distance of interaction. For the exemplary case of a 3D DNA nanostructure having three fluorescence dye molecules, this means that each fluorescence dye molecule has a distance to the other two fluorescence dye molecules, which is greater than the respective interaction distance. For more fluorescence dye molecules, the same applies accordingly. That means, irrespective of which fluorescence dye molecule pair of the 3D DNA nanostructure is observed, the distance of the fluorescence dye molecules of the observed pair is always greater than the interaction radius of the observed pair. "Interaction radius" refers to the distance, which fluorescence dye molecules must have at the minimum in order to show negligible interactions (such as, e.g., fluorescence quenching or FRET). Which kind of dye pair has which kind of interaction radius is known to the skilled person. For example, corresponding interaction radii are described in Novotny, Lukas: Principles of nano-optics 2.ed, Cambridge Univ. Press, 2013, Kapitel "Optical Interactions", pp 224 et seqq.; Peter Atkins: Physikalische Chemie, $5^{th}$ edition, 2013, Wiley-VCH, Weinheim, Chapter 17 "Wechselwirkungen zwischen Molekülen", pp 657 et seqq.; Förster T: Zwischenmolekulare Energiewanderung and Fluoreszenz. In: Ann. Physik. 437, 1948, S. 55. doi:10.1002/and p. 19484370105. With regard to FRET, an interaction radius may be e.g. the distance at which a FRET rate of 50% is given.

The DNA nanostructures preferably serve the purpose of precise arrangement of a well-defined number of marker molecules (preferably fluorescence dye molecules) of one or more kinds. The geometric arrangement is of crucial importance, in order to prevent interactions between marker molecules (preferably fluorescence dye molecules). The defined number of marker molecules (preferably fluorescence dye molecules) allows for programming the intensity values and therefore the subsequent definite identification. The number of different combinations is $N=k^m$, wherein k is the number of intensity levels and m is the number of different (in this case orthogonally measurable) marker molecules (preferably fluorescence dye molecules). By this multiplexing, a great number of different DNA nanostructures can be distinguished, without multiplexing, the number would only be m. In an Example, there are 5 intensity levels and three types of marker molecules and therefore 124 instead of 3 simultaneously distinguishable species. Thus, the DNA nanostructures are nanoreporters.

Thus, the term "nanoreporter" is used herein in order to define structures with attached marker molecules, which have measurable and identifying signatures, with measurements in the nanometer range. In particular, the DNA nanostructures of the invention may be nanoreporters. Other DNA origami, e.g. according to Rothemund, can also be nanoreporters, as well as cascades of fluorescent proteins.

The term "orthogonally measurable" describes the property that it can be clearly extrapolated from a linear combination of measurement values of marker molecules (e.g. fluorescence dye molecules) to a linear combination of the underlying marker molecules and/or a combination of nanostructures. With the example of fluorescence detection, this may be realized by spectrally far-apart dyes and hence far-separated excitement and detection wave length (e.g. blue and red) or by closer-adjacent dyes in combination with multispectral detection, so that the orthogonal components may be calculated by "linear unmixing".

A DNA nanostructure of the invention is preferably characterized in that one or multiple marker molecules (e.g. fluorescence dye molecules) of one or more kinds of marker molecules are attached such that the distance between two marker molecules is greater than that at which they significantly interact, and their form prevents that with approaching a similar DNA nanostructure, their marker molecules significantly interact with those of the other DNA nanostructure. A preferred DNA nanostructure of the invention is a DNA nanostructure, on which one or more marker molecules of one or more kinds of marker molecules is/are attached such that the distance between identical marker molecules is greater than that at which fluorescence quenching occurs and the distance between different marker molecules is greater than the Fröster resonant energy transfer (FRET) radius, and their shape prevents that with approaching a similar DNA nanostructure, its marker molecule(s) interact with one or more marker molecules of the other DNA nanostructure by fluorescence quenching or FRET.

"Marker molecules" refer to particles which emit measurable signals. In particular, fluorescence dye molecules are marker molecules. The signal of fluorescence dye molecules may be the intensity, but also lifetime, polarization, blink kinetics or similar quantities. Gold particles are also marker molecules within this meaning.

Two marker molecules, in particular two fluorescence dye molecules, significantly interact, when the signal emitted by at least one of them significantly depends on the presence or absence of the other. For our purposes, for example a decline in intensity of the signal by 1% due to the presence of another molecule can be neglected, whereas a decline by 20% cannot be neglected. In the first case, the marker molecules (in particular fluorescence dye molecules) do not interact significantly, whereas they do so in the second case. In the case of similar fluorescence dye molecules, the interaction mechanism prevalent for us is fluorescence quenching, which is different depending on the fluorescence dye molecule, but which becomes negligible starting from a distance between the fluorescence dye molecules of about 2-3 nanometers. For fluorescence dye molecules of different types, the prevalent interaction mechanism is the Förster resonant energy transfer (FRET) and the distance from which the fluorescence dye molecule pairs no longer interact significantly (also referred to as FRET distance) varies in the range of 2-20 nanometers, depending on the individual pair. FRET distances are known for a plurality of fluorescence dye pairs, for example many dye producers publish lists for FRET distances of their dyes (e.g. www.atto-tec.com/fileadmin/user_upload/Katalog_Flyer_Support/R_0_-Tabelle_2016_web.pdf). Moreover, FRET distances may be calculated using the spectral properties of the fluorescence dye molecules (see Atkins, Physikalische Chemie).

Preferably, a significant interaction between two fluorescence dye molecules is an interaction, in which the measured fluorescence signal (with common excitation) of the one molecule is reduced by the presence of the other molecule in comparison to a measured fluorescence signal of the one molecule in the absence of the other molecule to 80% or less, preferably 90% or less, particularly preferably 95% or less, highly particularly preferably 99% or less.

A 3D DNA nanostructure of the invention preferably comprises a cavity, wherein the cavity has a volume of at least 0.1 zeptoliters (1e-22 liters), preferably at least 10 zeptoliters and particularly preferably at least 100 zeptoliters.

A 3D DNA nanostructure of the invention may essentially be formed as a hollow cylindrical DNA nanostructure, i.e. as hollow cylinder, wherein at least one fluorescence dye molecule is attached on the inside of the hollow-cylindrical DNA nanostructure. The cavity of the hollow cylinder preferably has a volume as indicated above.

The part of the 3D DNA nanostructure, which corresponds to the shell of the hollow cylinder, may comprise gaps. Those parts of the 3D DNA nanostructure, which correspond to the top and bottom surface of the hollow cylinder, are preferably open but may also each be at least partially closed and/or entirely closed. The barrel and optionally the top and bottom surface of the hollow cylinder are formed by the 3D DNA nanostructure, which means that it is not a mathematically precise cylinder, since e.g. the individual helices of the nanostructure form uneven surfaces with projections and recesses. However, the envelope of the 3D nanostructure is essentially the form of a cylinder.

Preferably, in a 3D DNA nanostructure of the invention, at least 2, more preferably at least 3, more preferably at least 4, more preferably at least 5, more preferably at least 6, more preferably at least 15, particularly preferably at least 30, particularly preferably at least 60 fluorescence dye molecules are attached. Preferably, the fluorescence dye molecules on a 3D DNA nanostructure are uniform, i.e. of the same type.

Preferably, a 3D DNA nanostructure of the invention comprises a cavity and at least one inwardly disposed fluorescence dye molecule, wherein the distance of the at least one inwardly disposed fluorescence dye molecule to the rim and/or the outer surface of the envelope of the 3D DNA nanostructure is at least 2 nm, preferably at least 3 nm and particularly preferably at least 5 nm. This has the advantage that due to the arrangement in the inside of the 3D DNA nanostructure and the minimum distance to the rim of the 3D DNA nanostructure, the dyes of the 3D DNA nanostructure also comprise said minimum distance to other structures with which the 3D DNA nanostructures may interact in the course of a method. For example, to a surface of a carrier, for example a substrate, the dyes have a distance that is greater than or equal to the minimum distance, when the 3D DNA nanostructure contacts said surface.

Preferably, a 3D DNA nanostructure of the invention comprises at least two inwardly disposed fluorescence dye molecules, wherein the pairwise distance of the at least two inwardly disposed fluorescence dye molecule is at least 2 nm, preferably at least 5 nm and particularly preferably at least 9 nm. For the exemplary case of a 3D DNA nanostructure with two dye molecules, this means that the two dye molecules comprise a distance of at least 2 nm, preferably at least 5 nm and particularly preferably at least 9 nm. For the exemplary case of a 3D DNA nanostructure with three dye molecules, this means that each dye comprises a distance to the two other dyes of at least 2 nm, preferably at least 5 nm and particularly preferably at least 9 nm. For more dyes the same applies mutatis mutandis. That means, irrespective of which dye pair of the 3D DNA nanostructure is observed, the distance of the dyes of the observed pair is always at least 2 nm, preferably at least 5 nm and particularly preferably at least 9 nm.

The distance of the dye molecules may, for example, be determined by identifying the structure of the 3D DNA nanostructure, from which can be inferred at which positions the dye molecules are positioned. To this end, sequence analysis may, for example, be required. For this purpose, a solution with DNA nanostructures is transferred to a solution with individual nucleic acid stands for example by reduction of the salt concentration. With a reduction of the salt concentration, the negative charges of the DNA backbone become more prevalent due to reduced shielding as compared to the permanently constant binding energies of the base pair-forming hydrogen bonds. Thus, with the reduction of the salt concentration, the DNA nanostructures are initially destabilized and with further reduction, the individual DNA double helices break and are sequenced, for example, with MySeq or another method provided by Illumina, Inc. and with the protocol as indicated by the manufacturer. Thus, the sequences of all nucleic acid strands present in the sample get known. The form of the DNA nanostructure may be reconstructed with this sequence information. To this end, any sequence editor (e.g. ApE 2.0 biologylabs.utah.edu/jorgensen/wayned/ape/) can be used. The longest DNA strand of the analysis is the scaffold strand. It is loaded into the editor and the sequence regions complementary to the scaffold strand are calculated and noted for each single staple sequence. There are two different regions on the scaffold strand for each staple strand. As described at a different point in this specification, with this information, the topology can in turn be defined in CaDNAno and thus the DNA nanostructure design can be reconstructed. In the next step, it must be determined which of the staple strands are provided with dyes. This is simple with the use of dye adapters, since a particular number of staple strands have further identical sequences, which remain single-stranded after the above reconstruction of the DNA nanostructure. If the staple strands are directly modified, the individual staple strands must be isolated and be analyzed for their fluorescence properties. Each individual staple strand may be loaded by hybridization to a complementary strand with additional molecular weight and be isolated in an agarose gel electrophoresis from the above solution with individual nucleic acid strands. Finally, a respective fluorescence measurement shows which of the staple strands is labeled with a fluorophore. These can be identified in caDNAno and the distances between fluorescence molecules can be calculated.

As an alternative to this method, using mass spectrometry (Sauer S, Lechner D, Berlin K et al. (2000) Full flexibility genotyping of single nucleotide polymorphisms by the GOOD assay. Nucleic Acids Res 28:E100; Haff LA, Smirnov IP (1997) Single-nucleotide polymorphism identification assays using a thermostable DNA polymerase and delayed extraction MALDI-TOF mass spectrometry. Genome Res 7:378-388; Wenzel T, Elssner T, Fahr K et al. (2003) Genosnip: SNP genotyping by MALDI-TOF MS using photocleavable oligonucleotides. Nucleosides Nucleotides Nucleic Acids 22:1579-1581; Braun A, Little DP, Koster H (1997) Detecting CFTR gene mutations by using primer oligo base extension and mass spectrometry. Clin Chem 43:1151-1158; Sun X, Ding H, Hung K et al. (2000) A new MALDI-TOF based mini-sequencing assay for genotyping of SNPS. Nucleic Acids Res 28:E68), the solution with DNA nanostructures can be directly sequenced and it can be simultaneously established which staple strands have fluorescent molecules attached. In analogy to the above, the topology of the DNA structure can subsequently be reconstructed in CaDNAno using complementary sequence analysis of staple strands and scaffold strand (which is again the longest strand). The co-measured information, on which strands the fluorescence molecules are attached, can be directly used to calculate the distances of the fluorescence molecules using CaDNAno.

In a preferred embodiment, the 3D DNA nanostructure is essentially formed as elliptic cylinder, preferably essentially as circular cylinder.

As already set forth above, the structures according to the invention are not a mathematically precise cylinder, since the surface of the structure at the single-atom level is extremely uneven and, e.g. at the level of the individual helices of the nanostructure, may comprise unevenness of the order of a helix radius or helix diameter. However, these structures are cylindrical to a skilled person nonetheless, since, e.g., the envelope of the 3D nanostructure may essentially have the form of a cylinder.

In a preferred embodiment, the hollow cylinder of the 3D DNA nanostructure is a circular cylinder and comprises an outer radius of at least 5 nm, at least 10 nm, preferably of at least 20 nm, preferably of at least 20 nm, preferably an outer radius of 30 nm to 80 nm, preferably of 50 nm to 70 nm and particularly preferably an outer radius of 60 nm. The outer radius refers to the structure of the outer radius of the envelope.

In a preferred embodiment, the hollow cylinder of the 3D DNA nanostructure, which is preferably a circular cylinder, has a height of at most 200 nm, preferably a height of 60 nm-30 nm, particularly preferably a height of 30 nm. The height of the structure refers to the height of the envelope.

The preferred embodiments ensure a sufficient size of the 3D DNA nanostructure in order to attach a sufficient number of dye molecules at sufficient distance of the dye molecules from each other and preferably in the inside of the 3D DNA nanostructure.

In a preferred embodiment, the hollow cylinder of the 3D DNA nanostructure comprises a wall thickness of at least 2 nm, preferably 2 nm to 7 nm, particularly preferably 5 nm. The wall thickness of the structure refers to the difference between outer radius and inner radius. In other words, the wall thickness corresponds to the distance between the outer envelope of the cylinder and the inner envelop of the cylinder cavity.

Preferably, a 3D DNA nanostructure of the invention comprises a wall thickness that at least corresponds to the diameter of a DNA double helix. Preferably, the wall thickness has space for 2-4, particularly preferably 3 DNA double strands, wherein the DNA strands are preferably arranged perpendicularly to the wall thickness in their length and are additionally arranged on adjacent lattice sites of a honeycomb lattice.

The inner diameter of the hollow cylinder is defined as the difference of outer diameter of the hollow cylinder and the wall thickness. Thus, preferred inner diameters result from the details on the outer diameter and on wall thickness as indicated herein.

The described minimum wall thicknesses in combination with the shape of the 3D DNA nanostructure, which shields the dyes from their surroundings, also contribute to the fact that an interaction of the dyes of the 3D DNA nanostructure with a surface of a carrier and/or another dye, which may be attached in another 3D DNA nanostructure, is prevented by steric hindrance. Thus, in particular, quenching and/or FRET with another dye and/or unspecific binding to a carrier, in particular a substrate surface, is prevented.

As is common for DNA origami, the 3D nanostructures of the invention preferably comprise a DNA single strand as "scaffold strand". The scaffold strand preferably comprises at least 3000 bases, preferably 5000-50000 bases, particularly preferably 10000-11000 bases. However, a different number of bases is possible. Preferably, the scaffold strand is circular. Here, circular means that the DNA strand comprises no open 5'-end and no open 3'-end. A non-limiting example for a scaffold strand is mentioned in the attached Examples and is shown in SEQ ID NO:1258.

Moreover, as is common for DNA origami, the 3D nanostructures preferably comprise a plurality of further shorter single-stranded DNA molecules. These are preferably referred to as "staple strands". According to the invention, the number of the staple strands of the 3D DNA nanostructure is preferably selected that it is adjusted to the length of the at least one scaffold strand of the 3D DNA nanostructure. Preferably, the 3D DNA nanostructure comprises 100-500 staple strands. A staple strand preferably comprises 30-100 bases. Non-limiting examples for staple strands are mentioned in the attached Examples and/or shown in SEQ ID NOs.:1 to 504.

The 3D DNA nanostructures may be of cylindrical shape, in which the marker molecules are inwardly disposed with a distance to the rim of at least half of the interaction radius. This ensures that the marker molecules of different DNA structures are not closer to each other than the interaction radius, irrespective of the position of the DNA structures relative to each other. To this end, a cylinder with side view that is approximately square provides a good ratio of steric hindrance (and thus shielding), small hydrodynamic radius (and thus diffusion rate) and inwardly disposed marker molecule positions with sufficient distance between marker molecules. In particular, a DNA nanostructure hollow cylinder with a diameter of about 30-90 nanometers and a height of about 30-90 nanometers is envisaged.

Alternatively, the DNA structures may be basket-shaped, with dyes positioned on the "bottom" of the basket and a basket rim that is at least as large as the largest interaction radius of all combinations of marker molecule types. The basket rim may have any angle to the basket bottom, preferably the angle is in a range of −45° to +45°, however. Preferably, the basket rim has a height of at most 200 nm, preferably a height of 60 nm to 30 nm, particularly preferably a height of 30 nm. The height of the structure again refers to the height of the envelope.

The open side of the basket preferably comprises an outer diameter of at least 5 nm, preferably an inner radius of 30 nm to 60 nm, particularly preferably an inner radius of 60 nm. A hollow cylinder with an open and a closed top surface is an specific case of a basket.

The 3D DNA nanostructure of the invention may comprise a substantially square projection, i.e. a ratio of height to width or diameter is in the range of 0.8 to 1.2. In particular, a 3D DNA nanostructure designed as a hollow cylinder and/or basket may comprise a substantially square projection.

A 3D DNA nanostructure of the invention may comprise the form of a hollow ball and preferably be provided with inwardly disposed marker molecules.

3D DNA nanostructures of the invention are also wireframe geometries such as tetrahedron, octahedron, cube, hexahedron, pyramids etc.

The general principle of the production of DNA origami and thus DNA nanostructures in different shapes is well-established, e.g. from Rothemund, "Folding DNA to create nano-scale shapes and patterns", Nature, March 2006, pp. 297-302, vol. 440; Douglas et al., Nature, 459, pp. 414-418 (2009); and Seeman, "Nanomaterials based on DNA", An. Rev. Biochem. 79, pp. 65-87 (2010). As already mentioned, the production principle for DNA origami is based on the joint incubation of at least one scaffold strand, which is preferably a single strand, and a plurality of staple strands. The staple strands comprise at least two binding segments that have the purpose of binding each to complementary segments of the scaffold strand. During incubation, which is preferably initiated at a temperature of 50-70° C. that is subsequently reduced, the staple strands and the scaffold strand bind via their respective complementary binding segments. Thereby, the generated DNA nanostructure folds into a conformation. By directed design of the scaffold strand and the staple strands as well as their complementary binding segments, a DNA origami may be designed and produced in accordance with the need of the user. For designing the DNA origami, freely-accessible software is available. For example, the program CaDNAno 2.5 (source code available at: github.com/cadnano; user manuals available at: cadnano.org/docs.html or cando-dna-origami.org/tutorial/ (see also S.M. Douglas et al, "Rapid prototyping of 3D DNA-origami shapes with caDNAno, Nucleic Acids Res., 37(15), 2009) may be used.

In this program, any scaffold strand sequence, which is preferably available for production of the DNA nanostructures, is predefined; particularly preferred are scaffold strands p7308 (SEQ ID NO: 1258) or p7249 (SEQ ID NO: 1257). In addition, the desired topology of the DNA nanostructure is specified. Specifically, CaDNAno calculates the number and sequences of the required scaffold strands and staple strands with the specification of (1) length and (2) sequence of the scaffold strand, (3) spatial shape of the scaffold strand and (4) starting position of the scaffold strand. The spatial shape of the scaffold strand defines the shape of the envisaged structure and contains the number and arrangement of the helices and the course of the scaffold strand through these helices. On the push of a button, the program is able to connect the determined scaffold strand with the staple strands in an autonomous manner. Subsequently, the staple strands can be output in tabular form. The table contains in particular starting and end position of the staple strand (defined by helix and number of bases from the rim of the helix, e.g. 7[128] refers to a position on the 7th helix, 128 bases from the arbitrarily but uniformly defined left rim) for unambiguous identification, the number of bases (i.e. the length of the staple strand) and the sequence of the staple strand. It is worth noting that with identical structure design (point (1)-(3)) but different starting position of the circular scaffold strand, other staple strand sequences are generated. These are equally usable without limitation as those having a different starting position, yet not compatible with these.

For bends of a DNA helix that are occasionally useful in 3D structures, positions along the scaffold strand may be defined at which the corresponding staple strand comprises one base more or less. Additional staple strand-staple strand pairings may also be defined, which add further DNA-helix contour length to the structure beyond the prescribed length of the scaffold strand. It is of note that CaDNAno merely shows representations on one plane, and 3D representation must be made by the spatial imagination of the user or a plugin of CaDNAno for the design program Autodesk Maya (D Selnihin and E S Andersen, "Computer-aided design of DNA origami structures", Comp. Meth. Synth. Biol. 1244, pp 23-44 (2014)). CaDNAno eventually provides a list of staple strands, by means of which the desired structure can be produced.

Each of these staple strands may in principle be provided with a fluorophor/fluorescence dye molecule. However, the program does not envisage a function for the definition of fluorescence dye molecule positions for direct labeling in the exported staple strand list. However, the program assists in the visualization of this process, because it shows the starting and end position of the strands as well as the shape of the scaffold strand and the arrangement of the helices. Using this tool, the user can readily calculate relative distances of possible positions on the staple strands within the designed 3D DNA nanostructure. Concretely and preferably, the user selects positions on staple strands that are to be modified. These are, for example, the 5'-ends or the 3'-ends. Subsequently, the user selects the staple strands which meet the positioning requirements for the fluorescence dye molecules, for example, that they are positioned inside the cavity structure and have the desired, sufficient distance to the rim of the structure. As described above, this can be inferred from CaDNAno. Finally, the user calculates the minimum distance of the positions to be modified on the staple strands that can still be selected, which is limited to 2-3 calculations and can be readily accomplished due to the lattice structure of the design and the visualization in CaDNAno. Finally, depending on the number of fluorescence dye molecules to be realized, the user selects an arbitrary subset of the selectable staple strands, notes the staple strand IDs and orders the corresponding sequences in the exported staple strand list with fluorescence dye molecule modification at the selected position. For an attachment of fluorescence dye molecules on the DNA nanostructures based on fluorescence dye molecule adapters, the strategy is analogous, with the only difference that the exported staple strand sequences are not used with fluorescence dye molecule modification but with a sequence that is extended by the adapter sequence complementary to the fluorescence dye molecule adapter(s). Moreover, the selected position along the staple strands is preferably an end of the staple strands which particularly preferably protrudes from the structure into the inside (and/or into the cavity). With this adapter-based fluorescence dye molecule attachment on the DNA structures, many adapter strands of similar kind provided with fluorescence dye molecule (and SEQ ID NO, for example 1259-1261 for the different fluorescence dye molecule colors) to many different staple strands, which are each extended with the same complementary sequence for the adapters, on the DNA nanostructure. When using fluorescence dye molecule adapters, the fluorescence dye molecule is preferably bound on the side of the structure of the fluorescence dye molecule adapter that is directed to the rim or the wall. This allows a reduced mobility. For example, this is the 3' end of the fluorescence dye molecule adapter, when the 5' end of the staple strands as defined by CaDNAno is extended by the complementary adapter sequence. However, the opposite case is also conceivable.

According to the same model as for the staple strands for fluorophore adapters, one staple strand is designed for target adapters for each 3D DNA nanostructure, wherein the selection criteria for the staple strand position may be different, for example exposedness for good binding efficiency with target structures.

The production of 3D nanostructures in different 3D shapes, e.g., in a structure of a hollow cylinder, is also known from Knudsen J. et al. (Nature Nanotechnology 10, 892-898 (2015) doi:10.1038/nnano 2015.190). In order to produce 3D DNA nanostructures of the invention that are based on the design therein, preferably all or a subset of the oligomers, which exclusively bind helices that point to the inside of the hollow cylinder and that are not located at one of the edges (rims) of the hollow cylinder, are provided with a dye at one end or extended by adapter sequences (to which a fluorescence adapter, which comprises a fluorescence dye molecule, can be bound). For the target adapter or carrier adapter, an oligomer can be selected which is incorporated in a helix that is located at the rim of the hollow cylinder.

Moreover, in the attached Examples (in particular in Example 1), an exemplary example is explained for a production method of a 3D DNA nanostructure of the invention. Based on the sequences used for this method and based on the method provided for the production, a skilled person may also produce similar 3D DNA nanostructures (e.g. with entirely different sequences (which, however, e.g., have complementary DNA sequences at similar or at the same positions)).

In another aspect, the present invention relates to a set of multiple 3D DNA nanostructures (wherein these are preferably 3D DNA nanostructures as described in this application), wherein the set comprises N pairwise different 3D DNA nanostructures and wherein the N pairwise different 3D DNA nanostructures of the set are pairwise different from each other in the fluorescence dye molecules. Preferably, the N pairwise different 3D DNA nanostructures contain a different number of fluorescence dye molecules and/or different fluorescence dye molecules, so that with the N pairwise different 3D DNA nanostructures of the set, k intensity levels that are distinguishable from each other and/or m color levels that are distinguishable from each other can be generated. Preferably, at least a part of the N pairwise different 3D DNA nanostructures are contained in the set multiple times, so that each of the k intensity levels is formed by intensity distribution, and wherein the k intensity distributions are distinguishable from each other, preferably statistically. Preferably, at least a part of the N pairwise different 3D DNA nanostructures are contained in the set multiple times, so that each of the m color levels is formed by color distribution, and wherein the m color distributions are distinguishable from each other, preferably statistically. The overlap of adjacent distributions is lower than 30%, preferably lower than 20%, preferably lower than 10%, more preferably lower than 5%, even more preferably lower than 2% and particularly preferably lower than 1%.

In this context it applies preferably that: $k>2$, preferably $k>3$, more preferably $k>4$, even more preferably $k>5$, particularly preferably $k>6$; and/or $m>2$, preferably $m>3$, more preferably $m>4$, even more preferably $m>5$, particularly preferably $m>6$.

In another aspect, the present invention is also directed to a method for the detection of a target structure. This method comprises:
  a) formation of a identification structure, comprising:
    (i) the target structure, and
    (ii) at least two 3D DNA nanostructures, wherein each of the 3D DNA nanostructures comprises one or more inwardly disposed fluorescence dye molecules and wherein each of the 3D DNA nanostructures is (specifically) bound to the target structure,
  b) detection of the target structure by measuring at least one fluorescence signal, wherein the 3D DNA nanostructures and the parameters of fluorescence measurement are selected such that the at least one measured fluorescence signal of the identification structure formed in a) is distinguishable from the fluorescence signal of each of the at least two isolated 3D DNA nanostructures, when these are not bound in the identification structure.

Preferably, the at least two 3D DNA nanostructures bind to regions/segments of the target molecule that are pairwise different. Thus, a higher specificity for the detection of a target structure is achieved.

A target structure that is detected with a method of the invention may be a molecule, a complex of several molecules or a particle. In particular, a target structure may be a DNA (preferably an at least partially single-stranded DNA), an RNA (preferably an at least partially single-stranded RNA, e.g. mRNA), an LNA (preferably an at least partially single-stranded LNA) or a protein. However, a target structure that is a complex, which contains or consists of one or more DNAs (preferably at least an at least partially single-stranded DNA), one or more RNAs (preferably at least an at least partially single-stranded RNA), one or more LNAs (preferably at least an at least partially single-stranded LNA) and/or one or more proteins, is also applicable. In principle, the target structure may also be an inorganic particle. Preferably, the target structure comprises or is a polynucleotide (i.e., e.g., a DNA, an RNA or LNA), particularly preferably an at least partially single-stranded polynucleotide and particularly preferably a single-stranded polynucleotide. Particularly preferably, the target structure comprises or is a single-stranded DNA, a single-stranded RNA or a single-stranded LNA. In a preferred aspect, the method of the invention is used for gene expression analysis. In this case, the target structure preferably is an mRNA or a protein, particularly preferably mRNA. Consequently, the target structure may be a protein or an mRNA. "Partially" single-stranded means that the poly nucleic acid (i.e., e.g., a DNA, an RNA or LNA) comprises a single-stranded area of at least 10 bases, preferably at least 15 bases and particularly preferably at least 21 bases.

Consequently, in a preferred embodiment, the method of the invention may be a method for gene expression analysis, wherein an mRNA is detected and the method comprises:
  a) Formation of an identification structure, comprising:
    (i) an mRNA, and
    (ii) at least two 3D DNA nanostructures, wherein each of the 3D DNA nanostructures comprises one or more inwardly disposed fluorescence dye molecules and wherein each of the 3D DNA nanostructures is (specifically) bound to sequence segments of the mRNA that are pairwise different,
  d) detection of the target structure by measuring at least one fluorescence signal, wherein the 3D DNA nanostructures and the parameters of fluorescence measurement are selected such that the at least one measured fluorescence signal of the identification structure formed in a) is distinguishable from the fluorescence signal of each of the at least two isolated 3D DNA nanostructures, when these are not bound in the identification structure.

With respect to the method of the invention, a "3D DNA nanostructure" refers to the same as defined above in connection with the 3D DNA nanostructures of the invention. In other words, a 3D DNA nanostructure may be referred to as DNA origami.

Preferably, at least one, preferably all, of the at least two 3D DNA nanostructures, which comprise the identification structure, are 3D DNA nanostructures as described herein.

The skilled person knows how to select the 3D DNA nanostructures and the measurement parameters and what fluorescence signals can be differentiated with what kinds of measurement methods and what kinds of measurement parameters. The 3D DNA nanostructures that are different from each other may be different from each other in their fluorescence response, for example by color and/or intensity. It is clear to the skilled person that when using different colors, accordingly suitable excitation wave lengths and filters adjusted to the colors must be used. The maximum number of obtainable color levels m depends inter alfa on how precisely two adjacent color distributions can be technically resolved. The same applies to the maximum number of achievable intensity levels, since the method is based on the fact that two adjacent intensity distributions (the intensity levels k1 and k1+1) can still be separated (at least statistically). For example, individual intensity distributions can be modeled and the mixture distribution of multiple partially overlapping intensity distributions can be calculated by deconvolution or statistical interference, preferably Bayesian inference relative population sizes of the individual distributions.

Instead of color and/or intensity also other variables can be employed, which are suited to distinguish the fluorescence signals of different identification structures such as e.g. the bleaching rate of the color molecule or fluorescence lifetime.

The detection of a target structure may comprise the detection that a target structure is present. However, in principle, the detection may also comprise the exclusion that a target structure is not present. In particular, the method of the invention is also suited for the quantification of the target structure. In other words, the detection of the target structure preferably comprises the quantification of a target structure (e.g. in a sample solution). The quantification may be relative, i.e. in relation to another component (e.g. a second structure/target structure in a sample solution) or absolute (i.e. in form of a concentration or absolute number). For example, it may be quantified in absolute terms when the detection of the identification structure(s) is in solution, such as in flow cytometry, FCS or light sheet microscopy-based measurement geometries. Then, all identification structures can be measured in a given sample volume and an absolute number and/or concentration can be indicated. For more precise statements, the sample can be measured multiple times in different dilution steps and/or the number of the target structures not considered can be estimated by statistical methods, preferably sorted out measurement events (for example due to the presence of less than the expected number of DNA nanostructures in a measurement event) may be estimated by Bayesian inference. For the measurement of identification structures that are bound to a carrier or a carrier surface, an analogous approach is conceivable. To this end, the parameters must be selected such that the probability that identification structures do not bind to the carrier and/or the (first) carrier surface is low. This may be achieved, for example, by a high ratio of carrier surface and/or the first carrier surface to the sample volume (for example 0.01/µm, preferably 0.1/µm, more preferably 0.5/µm, highly preferably 1/µm) and/or by a long incubation period (for example 30 min, preferably 2 h, more preferably 10 h, highly preferably 24 h). Then, all identification structures can again be measured and their number can optionally be divided by the sample volume. As in the above case, further steps in the analysis can refine the estimation. Preferably, the measurement can be performed in a sample chamber where only one of the surface comprises carrier adapters (preferably the surface easiest to measure) and all other surfaces are passivated (e.g. as described elsewhere herein) so that the measurement of all identification structures is more simple.

The quantification can also be carried out on the basis of an internal standard or on empirical data. Preferably, the internal standard preferably defines a comparative value with a known concentration.

The method of the invention for the detection of a target structure may further comprise that the identification structure formed in a) is bound or is being bound to a carrier. Consequently, the formed identification structure can be bound to a carrier, preferably to a first surface of the carrier. Thus, the method may comprise the step of binding of the formed identification structures to a carrier, preferably to a first surface of the carrier.

If the identification structure is bound to carrier, it preferably means that the identification structure is formed on the carrier. The binding of the identification structure to the carrier may be mediated in that the target structure and/or one of the at least two 3D DNA nanostructures (preferably the target structure) is/are pre-bound or is/are bound to the carrier already prior to formation. In other words, the target structure and/or one of the at least two 3D DNA nanostructures (preferably the target structure) may be bound to the carrier (prior to formation of the identification structure). Thus, the method may further comprise the step of binding of the target structure and/or at least one of the at least two 3D DNA nanostructures (preferably the target structure) to the carrier. For example, this step may comprise the incubation of the carrier and/or the first carrier surface with a sample solution that contains the target structure (and optionally also further components such as e.g. further polynucleotides, preferably mRNAs). Furthermore, this step can comprise one or more washing steps (with a buffer solution). The pre-binding of the target structure to the carrier and/or the first carrier surface in combination with the at least one washing step has the advantage that the target structure can already be removed from the context of the sample solution prior to formation of the identification structure. This is particularly advantageous with complex samples having many and optionally similar components.

The buffer solution can contain 1× to 8×SSC, preferably 3× to 5×SSC, and particularly preferably 4×SSC. Therein, SSC refers to the so-called saline sodium citrate buffer, which consists of an aqueous solution of 150 mM sodium chloride and 15 mM trisodiumcitrate, which is adjusted to pH 7.0 with HCl. As a buffer basis, also Tris or PBS can be used as an alternative to a citrate buffer. The buffer can also comprise NaCl and/or Mg $Cl_2$ (preferably as an alternative to SSC). The concentration of NaCl is preferably 50 mM to 1200 mM, particularly preferably 200 mM to 800 mM. For example, the NaCl concentration can be 600 mM, preferably 500 mM and particularly preferably 300 mM. The concentration of $MgCl_2$ can be 2 mM to 20 mM, preferably 5 mM to 15 mM, preferably 8 mM to 12 mM and particularly preferably 10 mM. Moreover, the buffer solution can comprise 4% to 6%, 2% to 10%, 15% or 20% dextran sulfates. Preferably, the buffer comprises, for example, 5% dextran sulfates. The buffer solution can also comprise polyethylene glycol (PEG), e.g. PEG8000, PEG2000, PEG4000, PEG1000. The buffer can also comprise 0.01 to 5% Tween-20. Optionally, the buffer can comprise EDTA, preferably at a concentration of 0.1 mM to 5 mM, particularly preferably 1 mM. A further optional component of the buffer is "sheared salmon sperm" (commercially available), preferably at a concentration of 0.1 mg/ml. "Sheared salmon sperm" can potentially increase specificity. The buffer can also comprise Denhardts medium (consisting of an aqueous solution of 0.02% (w/v) BSA (Fraction V), 0.02% Ficoll 400 (commercially available) as well as 0.02% polyvinylpyrrolidone (PVP), see also Cold Spring Harb Protoc 2008, doi: 10.1101/pdb.rec11538), preferably in 1-fold, 2-fold, 3-fold, 4-fold or 5-fold concentration. A particularly preferred buffer comprises or has the composition 4×SSC, 5% dextran sulfate and 0.1% Tween 20. This buffer is used particularly preferably, when at least one of, preferably all of, the target structures to be detected are a polynucleic acid, e.g. an mRNA.

If the identification structure is being bound to a carrier, this preferably means that the identification structure is not only formed but also gets bound on the carrier, preferably on the first surface of the carrier. In other words, none of the components of the identification structure is pre-bound. Therefore, the method can comprise the step of binding of the identification structure to the carrier, preferably the first surface of the carrier. The binding can occur in one step with the formation of the identification structure in a) (i.e. the carrier and all components required for the formation of the identification structure (and optionally components that are necessary for binding to the carrier, e.g. the carrier adapter described below) are mixed in one step and incubated). Alternatively, the binding to the carrier can occur subsequently (preferably prior to measurement in b)). In both cases, after the binding of the identification structure to the carrier and/or the first carrier surface, the method can further comprise at least one washing step (e.g. with one of the above-mentioned buffer solutions) to remove non-bound components (e.g. 3D DNA nanostructures and/or other components contained in a sample solution) from the carrier. When the identification structure is being bound, the binding can be mediated by the target structure and/or one of the at least two 3D DNA nanostructures (preferably the target structure) in analogy to "is bound".

The bond (if the identification structure is bound to carriers) or the binding (if the identification structure is being bound to carriers) of the identification structure can be mediated by the target structure and/or one of the at least two 3D DNA nanostructures (preferably target structure). It is particularly preferred that the bond or the binding is mediated by the target structure.

The bond or the binding of the identification structure to the carrier and/or the first surface of the carrier can be mediated directly or by a carrier adapter. Consequently, the bond or the binding of the target structure and/or at least one of the 3D DNA nanostructures (preferably the target structure) bound in the identification structure can be directly to the carrier or the first carrier surface (e.g. by a covalent or non-covalent bond) or be mediated by a carrier adapter (i.e. be indirect). To this end, the carrier adapter itself binds the target structure (specifically) and is bound or is being bound to the carrier and/or the first carrier surface. The binding of the carrier adapter to the carrier and/or the first carrier surface can again be direct (e.g. by a covalent or non-covalent bond) or mediated by an intermediate carrier adapter which specifically binds the carrier adapter and which specifically binds or is bound to the carrier adapter and/or the first surface thereof itself. In principle, further intermediate carrier adapters according to the same concept are conceivable. It is preferred that the carrier adapter itself is bound/is being bound to the carrier and/or the first carrier surface. The carrier and/or the first carrier surface can, for example, be coated with the carrier adapter.

"Carrier adapter" preferably refers to a particle that can bind specifically to subregions of target structures (e.g. target molecules) or a nanoreporter (i.e. one of the at least two 3D DNA nanostructures) and that can be coupled to a carrier (directly or indirectly). The specific binding to the target structure can be achieved, for example, by Watson-Crick base pairing, by Van Der Waals interactions or hydrogen bridges and be realized, inter alia, with nucleic acids, antibodies, aptamers, adhirons or nanobodies (depending on the target structure).

A carrier on which the identification structure is /is being bound can have different shapes and be formed of different materials. Preferably, the carrier has a first carrier surface and the identification structure is bound on the first carrier surface. Consequently, in the method for the detection of a target structure, the identification structure preferably is bound or is to be bound to a carrier surface. The first carrier surface of a carrier can comprise a complete lateral surface of a carrier structure. Alternatively, only a part of a lateral surface of a carrier structure can be the first surface. The first carrier surface can be a surface of at least $0.01$ mm$^2$, preferably at least 1 mm$^2$ or particularly preferably at least 10 mm$^2$. The first carrier surface can comprise an area of at most 1000 mm$^2$, preferably at most 400 mm$^2$ or particularly preferably at most 100 mm$^2$. A carrier surface and/or the first surface of the carrier preferably comprises a glass surface (e.g. a borosilicate glass surface or a quartz glass surface) or a polymer surface (such as e.g.

Slide VI$^{0.1}$ of ibidi GmbH, or surfaces that are based on other polymers suited for fluorescence microscopy). Further, a carrier surface and/or the first surface of the carrier can be a glass surface (e.g. a borosilicate glass surface or a quartz glass surface) or a polymer surface (such as e.g. µ-Slide VI$^{0.1}$ of ibidi GmbH, or surfaces that are based on other polymers suited for fluorescence microscopy). In other words, the first surface of the carrier preferably is a glass surface (e.g. a borosilicate glass surface or a quartz glass surface) or a polymer surface (such as e.g. µ-Slide VI$^{0.1}$ of ibidi GmbH, or surfaces that are based on other polymers suited for fluorescence microscopy). Consequently, a carrier can comprise a first surface which comprises or consists of a glass surface (e.g. a borosilicate glass surface or a quartz glass surface) or a polymer surface (such as e.g. µ-Slide VI$^{0.1}$ of ibidi GmbH, or surfaces that are based on other polymers suited for fluorescence microscopy). The carrier can also comprise a polymer network which preferably comprises one of or a combination of the following materials: biopolymer, agarose, collagen. A preferred carrier in the context of the invention is a microscopy chip, a well or a plate (preferably suited for high-resolution fluorescence microscopy; e.g. a µ a plate of Ibidi) or a cover slip.

The carrier or the first carrier surface is preferably passivated. "Passivated" means that the carrier or the carrier surface are coated or treated such that unspecific binding of a target structure and/or a 3D DNA nanostructure and/or optionally further components, which get in contact with the carrier and/or the first carrier surface (e.g. further components of the sample which contains the target structure), is minimized Preferably, passivate can mean that the surface is contacted with and/or washed with a BSA solution having a concentration of 0.1 mg/ml to 10 mg/ml, preferably 0.5 mg/ml to 1 mg/ml. Passivating can also be carried out by PEGylation (for example described in the following publications: S Chandradoss et al, Jove 2014, "Surface Passivation for Single-molecule Protein Studies", J Pichler et al, Biosensors & Bioelectronics 2000, "A high-density poly (ethylene glycol) polymer brush for immobilization on glass-type surfaces", R Schlapak et al, Langmuir 2006, "Glass Surfaces Grafted with High-Density Poly(ethylene glycol) as Substrates for DNA Oligonucleotide Microarrays") or silanization (for example described in the following publications: B Hua et al. and Tj Ha, Nature Methods 2014, "An improved surface passivation method for single-molecule studies", A. Kumar et al, Nuc Ac Research 2000, "Silanized nucleic acids: a general platform for DNA immobilization", H Labit et al, BioTechniques 2008, "A simple and optimized method of producing silanized surfaces for FISH and replication mapping on combed DNA fibers"). Moreover, passivating can also comprise washing the carrier or the carrier surface with a solution that comprises structures that are of the same type as the target structure (i.e. single-stranded polynucleotides), but not identical to the target structure. The carrier and/or the first surface of the carrier is particularly preferably passivated, when the first carrier surface is or comprises a glass surface. With glass surfaces, it is preferably passivated with a BSA solution, PEGylation or silanization.

A carrier can also be a matrix, such as, e.g., a polymer matrix. This is particularly advantageous for analyses at a single-cell level. In this case, it is preferred that the identification structure is/or is being embedded in the polymer matrix. Alternatively or additionally, the identification structure can be bound/being bound to a surface of the polymer matrix. As starting substance for the matrix and/or polymer matrix, in particular agarose, collagen, DNA or a combination of the same are suited. Agarose is particularly preferred. Methods for the production and embedding of an identification structure or a component of an identification structure (in the case of pre-binding of the target structure and/or one of the at least two 3D DNA nanostructures) are well-known to the skilled person. To this end, the agarose matrix can be produced of a mixture of agarose and biotinylated agarose (commercially available) or streptavidin agarose (commercially available), and target adapters or carrier adapters can be bound to these functionalizations (in the case of biotinylated agarose with previous streptavidin rinsing). Alternatively and for the other optional matrix materials, the adapter can be coupled (directly or via biotin-streptavidin) to an antibody that specifically binds to the matrix material (i.e. anti-agarose, anti-collagen, etc.). It is further possible that the adapter is bought in maleimid or NHS ester modified form and is directly covalently bound to the corresponding chemical groups of the matrix material. In the case of a DNA polymer matrix as a carrier, it can per se contain single-stranded segments having carrier sequences.

The above-mentioned polymer matrix can limit the diffusion of target structures that were released from a cell by lysis such that even if several cells are contained in the polymer matrix, it can still be determined in which region of the polymer the target structure(s) released from a cell is/are located. Preferably, the individual cells are embedded in the polymer matrix such that they essentially have a minimum distance of 50 µm, preferably 200 µm and more preferably 500 µm. In this context, essentially means that at least 80%, preferably at least 90% and particularly preferably at least 99% of the cells at least have the above-mentioned distance of adjacent cells. The polymer network preferably comprises an average mesh size of 1 µm to 50 µm, preferably 2 µm to 10 µm. This serves to limit the diffusion as well as to provide a sufficient number of binding sites for carrier adapters or carrier adapter binding sites. The pairwise minimum distance of the carrier adapters or carrier adapter binding sites can essentially be 200 nm to 10 µm, preferably 500 nm to 5 µm, particularly preferably 2 µm to 3 µm. In this context, essentially means that at least 80%, preferably at least 90% and particularly preferably at least 99% of the carrier adapters or carrier adapter binding sites at least have the above-mentioned distance of adjacent carrier adapters or carrier adapter binding sites. #

The bond or the binding of the identification structure to the carrier or the carrier surface (e.g. via target structure or at least one of the at least two DNA nanostructures of an identification structure) can be carried out via different covalent and non-covalent bonds known to the skilled person irrespective of whether it is direct or via a carrier adapter or an intermediate carrier adapter bound to the carrier adapter. For example, the binding can be achieved via biotin-streptavidin coupling. Consequently, the component that directly interacts with the carrier (e.g. carrier adapter, target structure, one of the DNA nanostructures or an intermediate carrier adapter) can either comprise biotin or streptavidin. Accordingly, the carrier and/or the carrier surface can comprise streptatvidin or biotin as a counterpart so that a streptavidin-biotin interaction is possible. Apart from streptavidin-biotin interactions, also other interactions such as, e.g., antibody bindings can be used. It is also conceivable that the component which directly interacts with the carrier (e.g. carrier adapter, target structure, one of the DNA nanostructures or an intermediate carrier adapter) is (being) attached via a carrier adapter by NHS reaction on an amine-modified carrier and/or an amine-modified carrier surface. The application of click-chemistry methods (for example described in H. C. Kolb; M. G. Finn; K. B. Sharpless (2001). "Click Chemistry: Diverse Chemical Function from a Few Good Reactions". Angewandte Chemie International Edition. 40 (11): 2004-2021) is also conceivable.

By means of the method of the invention, several copies of the target structure can be detected. If several copies of the target structure are detected (i.e. if the identification structure forms multiple times), preferably the majority of, preferably all, identification structures formed for said target structure is/are bound to the carrier, preferably to the first surface of the carrier. Preferably the majority or essentially all of the identification structures is/are attached to the carrier such that these are still resolvable by the measurement method used for the measurement of the at least one fluorescence signal in b). This may mean that all or essentially all identification structures or their measurement events do not overlap spatially (e.g. the diffraction-limited images of the identification structures when using fluorescence microscopy). Preferably all or essentially all identification structures have a distance of at least 250 nm, preferably at least 500 nm and particularly preferably at least 1 µm. This may mean that several carrier adapters or intermediate carrier adapters are attached with the mentioned minimum distance on the carrier and/or the first carrier surface. Essentially all means that at least 80%, preferably at least 90% and particularly preferably at least 95% of the formed identification structures fulfill these requirements.

Preferably, several identification structures are/are being bound to the carrier and/or the carrier surface such that the fluorescence signal of the individual identification structures can be measured separately. Via the density and/or the distance of the binding sites on the surface, i.e., for example, via the density of the streptavidin or biotin or the carrier adapter or intermediated carrier adapter, which is attached to/in the carrier and/or its surface, it can be regulated in which spatial distance identification structures bind to the carrier and/or carrier surface.

Preferably, the binding sites, for example, the streptavidin, the biotin, the carrier adapter or the intermediate carrier adapter are arranged on the carrier and/or the carrier surface in the following distance/pattern/density.

Preferably, all or essentially all binding sites have a distance of at least 250 nm, preferably of at least 500 nm and particularly preferably of at least 1 µm. Preferably, the binding sites are arranged in a hexagonal lattice having the above-mentioned edge length. The binding sites can preferably also be arranged on the carrier or its surface in an arbitrary manner, with a surface density of 1e-5/µm²-1e3/µm², preferably 1e-3/µm²-4/µm² and particularly preferably 0,1/µm²-1/µm². Said surface density ensures sufficient distance of the binding sites.

Additionally or alternatively, the regulation of the spatial distance of the identification structures on the carrier or its surface can be regulated via the concentration of the identification structures. If the concentration is selected such that no saturation of the binding sites on the carrier occurs, every further reduction of the concentration (i.e. dilution) causes a reduction in the attachment density on the carrier. Optionally, in order to determine the necessary dilution, the method is carried out once or several times in a dilution series until the suitable dilution/concentration has been established. Accordingly, after the formation of the identification structure(s), the method of the invention can also comprise the step of diluting the solution in which the identification structure formed prior to binding of the identification structure to the carrier.

As mentioned above, the target structure in the present method can be or comprise a partially single-stranded polynucleotide or single-stranded polynucleotide. In this case, it is particularly preferred that the carrier adapter comprises or is an oligonucleotide, the nucleic acid sequence of which is designed such that it specifically binds to a first single-stranded segment of the nucleic acid sequence of the target structure of claim 2. It is particularly preferred that the target structure is an mRNA having a poly-(A) tail, wherein the carrier adapter comprises or is an oligonucleotide, the nucleic acid sequence of which is designed such that it specifically binds to the poly-(A) tail of the mRNA target structure. Being designed in order to bind to a poly-(A) tail can include comprising a poly-(T) sequence segment.

As mentioned above, the target structure in the present method can also be a protein or comprise a protein. In this case, it is particularly preferred that the carrier adapter comprises or is an antibody or an antigen-binding domain of an antibody, which (specifically) binds to the target structure.

The method for the detection of a target structure after a) and prior to b) can further comprise washing of the carrier or the first carrier surface with a buffer solution. Such a washing step can have the purpose of removing components that are not bound to the surface. In particular, such a washing step can ensure that free 3D DNA nanostructure that are not bound on the identification structure are washed off the carrier and/or the first carrier surface. This has, inter alia, the advantage that a possibly disruptive background of fluorescence signal by free 3D nanostructures is reduced or prevented.

The washing step is preferably carried out with a buffer solution. The composition of the buffer is preferred as defined already above in connection with other washing steps.

In an identification structure, a 3D DNA nanostructure can be bound either directly or via a target adapter to the target structure.

Therefore, at least one, preferably all of the at least two 3D DNA nanostructures may be designed for direct binding to the target structure and be directly bound to the target molecule. Preferably, at least one, particularly preferably all of the at least two 3D DNA nanostructures are designed such that it/they is/are directly designed to the respective region (s) of the target structure and directly bound to the target molecule. Direct binding can for example occur by via base pairing (e.g., with a partially single-stranded or single-stranded polynucleotide as target structure). Consequently, at least one, preferably all of the at least two 3D DNA nanostructures can contain a single-stranded sequence segment, which can specifically bind to the target structure (e.g. a partially single-stranded or single-stranded polynucleic acid). Preferably, said sequence segment is disposed outwardly or arranged at an outer surface of the 3D DNA nanostructure. It is thereby ensured that the sequence segment is accessible in the best possible way.

Alternatively, the specific binding of at least one, preferably all 3D DNA nanostructures can be mediated by a respectively designed target adapter. The target adapter or each of the target adapters is designed to bind to the respective DNA nanostructure and to the respective region (s) of the target structure. Thus, a target adapter can comprise a first segment that is designed to (specifically) bind to the respective 3D DNA nanostructure. Moreover, a target adapter can comprise a second segment (also referred to as target binding segment) which is designed to (specifically) bind to the target structure. Preferably, a 3D DNA nanostructure, the binding of which to the target structure is mediated by a target adapter, comprises at least one single-stranded DNA segment that is designed such that it specifically binds the target adapter. This single-stranded DNA segment is preferably disposed outwardly, i.e. is accessible from the outside. The above-mentioned first segment of the target adapter preferably is a polynucleic acid sequence (e.g. a DNA, LNA or RNA sequence) which is designed such that it specifically binds to the single-stranded DNA segment of the 3D DNA nanostructure by hybridization (i.e. is complementary to at least a part of the single-stranded DNA segment of the 3D DNA nanostructure). The binding occurs via base pairing. Preferably, at least 15, preferably at least 18 and particularly preferably 21 bases of the two single-stranded segments hybridize.

A target binding adapter preferably comprises one (or at least one) target binding segment. The target binding segment is preferably designed such that it mediates the specific binding to the target structure or the respective region of the target structure, to which the respective identification structure binds.

If the target structure is or comprises a partially single-stranded polynucleotide or preferably a single-stranded polynucleotide (e.g. mRNA), the target binding segment preferably comprises a nucleic acid sequence that is designed such that it specifically binds to a single-stranded segment of the target structure. Preferably, the target binding segment is complementary to the single-stranded segment of the target structure. The binding to the target structure preferably occurs via base pairing. Preferably, at least 14, preferably at least 18 and particularly preferably 21 bases of the two single-stranded segments hybridize.

If the target structure is or comprises a protein, the target binding segment of the target adapter can comprise or be a peptide/protein or an antibody (or an antigen-binding fragment of an antibody) which specifically binds to the protein.

The method for the detection of a target structure can further comprise the provision of a preferably aqueous sample solution, which contains the target structure, and of the at least two 3D DNA nanostructures. The sample solution can, for example, comprise cell lysate, nucleic acids extracted from cell suspension or tissue and/or mRNA. Optionally, the method can further comprise the provision of the carrier, the carrier adapter(s) and/or the target adapter(s). One or both of said provision steps can be comprised by the step of the formation of the identification structure.

The method can further comprise mixing of a preferably aqueous sample solution, which contains the target structure, with the at least two 3D DNA nanostructures and optionally the carrier adapter and/or the target adapters. The sample solution can for example comprise cell lysate, nucleic acids extracted from cell suspension or tissue and/or mRNA. Furthermore, the method can comprise contacting said mixture with the carrier and/or the first carrier surface. The mixing of the components can also be stepwise.

A sample solution that contains the target structure can be a cell lysate, preferably the cell lysate of an individual cell. The sample solution can also be a mixture of nucleic acids, e.g. purified nucleic acids. In particular, the sample solution can also be a purified whole-RNA of cells. Said whole-RNA can be obtained by commercially available kits from cells (e.g. TRIzol® Reagent, TRIzol® LS, PureLink™ Total RNA Blood Kit, RecoverAll™ Total Nucleic Acid Isolation Kit for FFPE by Thermo Scientific, or RNeasy Kits, PAXgene Blood RNA Kit, or RNAlater reagent by Qiagen GmbH).

Preferably, the method of the invention for the detection of a target structure is also configured for the detection of further target structures that are different from the first target structure (wherein the different target structures are pairwise different). Consequently, the method can also be referred to as a method for the detection of at least two different target structures, wherein the at least two different target structures are pairwise distinguishable from each other.

The method of the invention for the detection of a target structure, which is further a method for the detection of several different target structures that are pairwise distinguishable from each other, further preferably comprises:
  c) Formation of a respectively assigned identification structure for each further different target structure, wherein each identification structure comprises:
    (i) the respective target structure, and
    (ii) at least two 3D DNA nanostructures, wherein each of the 3D DNA nanostructures comprises one or more inwardly disposed fluorescence dye molecules and wherein each of the 3D DNA nanostructures is (specifically) bound to the target structure, and wherein step b) further comprises:
  d) detection of the one or more further target structures by measuring the at least one fluorescence signal,
  wherein all 3D DNA nanostructures and the parameters of fluorescence measurement are selected such that the at least one measured fluorescence signal of the identification structures formed in a) and c) is distinguishable from the fluorescence signal of all isolated 3D DNA nanostructures, when these are not bound in one of the identification structures, and that the measured fluorescence signals of the identification structures formed for the respective different target structures are pairwise distinguishable from each other.

Preferably, each of the different target structures is detected multiple times, i.e. each of the identification structures is preferably formed multiple times. In other words, for example N different target structures can be detected, which are each pairwise distinguishable from each other, wherein each of the one or more of the N different target structures is, detected multiple times. This implies that those identification structures that are assigned to the target structures that are detected multiple times are formed multiple times accordingly. As a matter of course, the fluorescence signals of the same identification structures that were formed for the respective same target structures do not have to be different from each other. Rather, the repeated measurement of the same fluorescence signal serves for quantification of the corresponding target structure.

For example, the method of the invention can have the purpose of detecting the target structures A, B and C that are different from each other in an aqueous solution. To this end, the 3D DNA nanostructures a1, a2, b1, b2, c1 and c2 assigned to these are provided, which together with the target structures A, B and C form the identification structures Aa1a2, Bb1b2 and Cc1c2. Here, the fluorescence signals of identification structures Aa1a2, Bb1b2 and Cc1c2 are pairwise different from each other and different from the isolated 3D DNA nanostructures a1, a2, b1, b2, c1 and c2. If the target structures A, B and C are each provided multiple times, the fluorescence signals of, for example, the same identification structures Aa1a2 do not have to be different from each other. Each measurement of a fluorescence signal of the identification structure Aa1a2 then corresponds to the detection of a target structure A so that the concentration can be derived from the number of measurement points.

What was mentioned above for the detection of a target structure applies mutatis mutandis to the detection of the further and/or each further target structure of the different target structures. In particular, everything above with regard to the target structure, identification structure, the bond or the binding of the identification structure to a carrier, the carrier adapter, the 3D DNA nanostructure(s), the target adapter and the further optional method steps is applicable mutatis mutandis to at least one, preferably all the further identification structures.

With respect to the preferred detection of multiple different target structures, the present invention is in one aspect also directed to a method for the detection of at least two different target structures, wherein the at least two different target structures are all pairwise distinguishable from each other and the method comprises:
  a) Formation of an identification structure for each of the at least two target structures, comprising:
    (i) the respective target structure, and
    (ii) at least two 3D DNA nanostructures, wherein each of the 3D DNA nanostructures comprises one or more inwardly disposed fluorescence dye molecules and wherein each of the 3D DNA nanostructures is (specifically) bound to the target structure,
  b) detection of the at least two target structures by measuring at least one fluorescence signal, wherein all 3D DNA nanostructures and the parameters of fluorescence measurement are selected such that the at least one measured fluorescence signal of the identification structures formed in a) is distinguishable from the fluorescence signal of all isolated 3D DNA nanostructures, when these are not bound in one of the respective identification structures, and that the measured fluorescence signals of the identification structures formed for the respective different target structures are pairwise distinguishable from each other.

Also in this case, the preferred features specified above for the method for the detection of a target structure can be applied mutatis mutandis. In particular, everything mentioned above with regard to the target structure, identification structure, the bond or the binding of the identification structure to a carrier, the carrier adapter, the 3D DNA nanostructure(s), the target adapter and the further optional method steps is applicable mutatis mutandis to at least one, preferably each of the at least two identification structures.

If the method for the detection of a target structure is designed for the detection of further target structures which differ from the first target structure, or if the method is for the detection of at least two different target structures, the target structures can be target structures of the same type (e.g. several mRNAs) with pairwise different structure/sequence, or the target structures comprise several different target structures of the same type. Alternatively, also target structures of different types (e.g., at least one partially single-stranded DNA or single-stranded DNA and at least a partially single-stranded or single-stranded RNA; or at least a partially single-stranded or single-stranded RNA) are conceivable. Preferably, however, the target structures are of the same type and are pairwise distinguishable from each other in structure or in sequence. In particular, it is intended that the method of the invention is a method for gene expression analysis. For gene expression analysis, preferably all the target structures are RNAs, particularly preferably mRNAs, or proteins. In the case of gene expression analysis, particularly preferably all the target structures are RNAs, particularly preferably mRNAs.

If the method is for the detection of more than one target structure, particularly preferably at least one further identification structure comprising one of the further target structures, preferably all the further identification structures, are/are being bound to the carrier. Particularly preferably, all the identification structures are bound to the same carrier. The above "is being bound" and "is bound" mentioned in connection with an identification structure applies mutatis mutandis for the "are bound" and "are being bound" in the case of more/further identification structures.

In the embodiments where one, more or all the identification structures are bound/being bound to a carrier and/or a first carrier surface, preferably all or essentially all the identification structures are being bound/bound to the carrier in such a way that they can still be resolved by means of the measurement method used in b) for measuring the at least one fluorescence signal. This may mean that all or essentially all the identification structures and/or their measurement events (e.g. (diffraction-limited) images in the case of fluorescence microscopy) do not overlap spatially. Preferably, all the identification structures (of the same target structure or several target structures) comprise a distance of at least 250 nm, preferably at least 500 nm and particularly preferably at least 1 μm. Essentially all, in this context, means that at least 80%, preferably at least 90% and particularly preferably 95% of the identification structures formed meet this requirement.

The methods explained above, based on the example of the method for the detection of a target structure, as to how such density of the identification structures can be achieved, apply accordingly. In particular, a carrier and/or the first carrier surface may comprise (pre-)bound carrier adapters binding one or more target structures. These one or more target structures may be bound to the carrier and/or the first carrier surface with the distances mentioned above.

How "specifically bind" or "specifically bound" is to be understood in a method of the invention for the detection of one or more target structures is known to the person skilled in the art. In particular, in the context of hybridisation of polynucleotide single-strands, "specifically bind" can mean that at least 14, preferably at least 18 and particularly preferably at least 21 complementary bases pair. In particular, "specifically bind" can also mean that at least 90%, preferably 95%, particularly preferably 99% of the bases of the two complementary polynucleotide single-strands pair (preferably with the minimal number of base pairs mentioned in the previous sentence). In the context of protein-protein interactions (e.g. antibody antigen binding), "specifically bind" may preferably mean a binding affinity ($-\Delta \Delta G$) of at least 5 kcal/mol, preferably at least 8 kcal/mol and particularly preferably at least 11 kcal/mol. Binding affinities can be determined, e.g., by means of thermophoretic measurements (M. Jerabek-Willemsen et al., "Molecular Interaction Studies Using Microscale Thermophoresis", Assay Drug Dev Technol, 9(4): 342-353 (2011). Another possibility are electrodynamic measurements as offered by e.g. Dynamic Biosensors GmbH (A. Langer et al, "Protein analysis by time-resolved measurements with an electro-switchable DNA chip", Nat. Comm. 4:2099 (2013)).

In the method of the invention, the one or more different target structures can be present in a crude lysate (typical designation for result of a lysis without subsequent purification steps) or a cell lysate (where some cell components can be filtered already but the RNA is not present in pure form), a tissue embedded in formalin-fixed paraffin ("FFPE" tissue). Preferably, several or all the target structures are present in the same cell lysate or the same formalin-fixed paraffin-embedded ("FFPE") tissue. Particularly preferably, the target structure or the target structures is/are in solution, preferably all the target structures are in the same solution. Preferably, each target structure is present in a concentration of at least 1 fM, preferably at least 100 fM and particularly preferably 1 pM. Preferably, the target structure is present in a concentration of at most 10 pM and particularly preferably at most 1 nM. Thus, a preferred concentration range of each target structure may be, e.g., 1 fM to 1 nM or 100 fM to 1 nM. If a higher concentration of one or more target structure(s) in a solution is to be expected, the method may further comprise diluting the sample solution prior to the formation of the identification structure(s).

In the method of the invention, 3D nanostructures are preferably used in concentrations of 10 pM to 10 μM each.

In the method of the invention, the formation of one or more identification structures preferably takes place in a buffer solution which is preferably designated hybridization buffer. The buffer solution can contain 1× to 8×, SSC, preferably 3× to 5×SSC and particularly preferably 4×SSC. "SSC" refers to the so-called saline sodium citrate buffer consisting of an aqueous solution of 150 mM sodium chloride and 15 mM trisodium citrate, which is adjusted to pH 7.0 with HCl. As an alternative to a citrate buffer such as SCC, Tris or PBS can be also used as buffer bases. The buffer can (preferably as an alternative to SSC) also comprise NaCl and/or MgCl$_2$. The concentration of NaCl preferably is 50 mM to 1200 mM, particularly preferably 200 mM to 800 mM. For example, the NaCl concentration can be 600 mM, preferably 500 mM and particularly preferably 300 mM. The concentration of MgCl$_2$ can be 2 mM to 20 mM, preferably 5 mM to 15 mM, preferably 8 mM to 12 mM and particularly preferably 10 mM. Furthermore, the buffer solution can comprise 4% to 6%, 2% to 10%, 15% or 20% dextran sulphate. Preferably, the buffer comprises, for example, 5% dextran sulphate. The buffer solution can also comprise polyethylenglycol (PEG), e.g. PEG8000, PEG2000, PEG4000, PEG1000. The buffer can also comprise 0.01 to 5% Tween-20. Optionally, the buffer can also comprise EDTA, preferably in a concentration of 0.1 to 5 mM, particularly preferred 1 mM. A further optional component of the buffer is "sheared salmon sperm" (commercially available), preferably in a concentration of 0.1 mg/ml. Sheared salmon sperm can increase specificity. The buffer can also comprise Denhardt's medium (consisting of an aqueous solution of 0.02% (w/v) BSA (Fraction V), 0.02% Ficoll 400 (commercially available) and 0.02% polyvinylpyrrolidone (PVP), see also Cold Spring Harb Protoc 2008, doi:10.1101/pdb.rec11538), preferably in one-fold, two-fold, three-fold, four-fold or five-fold concentration. A particularly preferred buffer comprises or has the composition 4×SSC, 5% dextran sulphate and 0.1% Tween 20. This buffer is used particularly preferably if at least one, preferably all, the target structures to be detected is/are (a) polynucleic acid(s), e.g. an mRNA.

In the method of the invention, the formation of the identification structure(s) in the method of the invention preferably takes place at a temperature of 4° C. to 50° C., preferably 18° C. to 40° C. For example, the temperature can be 40° C. 30° C. is used particularly preferably. The temperatures stated are particularly preferred if one or more partially single-stranded or single-stranded polynucleotides are to be detected.

The formation of the identification structure can comprise an incubation period of a mixture of the components bound therein. Preferably, the incubation period can be 5 min to 20 h, preferably 1 h to 20 h (e.g. 1 h, 2 h, 4 h, 8 h) and particularly preferably 10 h to 20 h.

In the methods of the invention, the one or several identification structure(s) can be formed in solution (preferably in the buffer solution mentioned above) and subsequently be bound to a carrier.

For the formation of the identification structure in solution, preferably a sample comprising the target structures to be detected is mixed with the DNA nanostructures (at least 2 per target structure; preferably in the concentration mentioned above). Optionally, also one or more carrier adapters can be added to the solution. Carrier adapters can, however, already be pre-bound to the carrier. The incubation of the reaction partners in solution instead of, for example, on the substrate in combination with small dimensions of the nanoreporter and high concentrations (achievable range 10 pM-10 µM) increases the reaction kinetics drastically. Thus, the time period from begin of the preparation until the result of the analysis can be reduced drastically. This can be important, in particular, with gene expression analysis of time-sensitive clinical samples such as, for example, for the determination of sepsis pathogens. Also in general, however, it is advantageous economically.

For example, the carrier adapter can be added at a concentration of 1 nM per target structure bound to the carrier adapter. Preferably, carrier adapters are added in the total concentration of the 3D DNA nanostructures per target structures (e.g. 3 nM, with 3D DNA nanostructures for a target with 1 nM each. A total volume for the formation of the identification structure(s) can, for example, be 1 µl to 500 µl. For the formation of the formed identification structure, preferably, the mixture described above is added to the carrier and/or the first carrier surface. The carrier adapter can either be pre-bound (if it is not part of the solution for the formation of the identification structure) or be bound to the carrier surface during the incubation. The binding the bond is either covalently or non-covalently (e.g. biotin streptavidin interaction). The binding to the carrier can comprise an incubation period of 1 min to 2 h, 5 min to 1 h, 8 min to 25 min and particularly preferably 10 min. Further examples for incubation periods are 2 min, 5 min, 20 min. Incubation can take place at 4° C. to 30° C., preferably room temperature (e.g. 20° C. to 25° C.). Prior to application to the carrier surface, the solution can be diluted again (e.g. with PBS or the above-mentioned buffer used for the formation of the identification structure) to, e.g., reduce the amount of dextran, cover a larger area or adjust the concentration. Prior to measurement, the surface can be washed with a buffer. Preferably, a buffer as defined above can be used for the washing steps.

Preferably, measurement of at least one fluorescence signal in the method of the invention comprises:
  e) Creating a data set containing data concerning fluorescence signals emitted from a sample portion/section, by means of fluorescence microscopy, preferably in epifluorescence, TIRF, lightsheet and/or confocal microscopy. In other words, the measurement of at least one fluorescence signal can comprise the measurement of several fluorescence signals or a plurality of fluorescence signals in that, for example, the intensity emitted by a two- or three-dimensional sample portion is measured and stored in pixels or in voxels. In this context, measurement can also comprise a simultaneous or sequential measurement with several excitation wavelengths and/or several detection wavelengths (regions).

Preferably, the detection of the target structure and/or the one or more further target structures comprises:
  f) Identification of the one or more datum contained in the data set, representing the fluorescence signal of one of the identification structures.

This identification can comprise, for example, the comparison of the measured intensity of a pixel or a voxel with a specific excitation wavelength and/or several detection wavelength with a set of such predetermined combinations so that the comparison is indicative of the identification structure assigned to the combination.

Accordingly, step e) can comprise: recording of at least one image file containing fluorescence data of the sample portion/section. Furthermore, the identification in step f) can comprise the following steps:
  f1) readout of a color and/or an intensity information (and preferably) of a datum and/or image element; and
  f2) comparing the color and/or intensity information (and preferably) of the datum and/or image element with a color and/or intensity information, being representative for the identification structure.

Preferably, the samples are visualized by means of fluorescence microscopy technique. For further processing of the information, the provided image can be analyzed directly. Preferably, however, it is saved. Images are preferably saved digitally; however, images can also be recorded analogously. Image information can comprise the illustration of one or more image elements. An image element is part of an image. An image element can be, for example, an extended point or another structure of a first intensity on a background of a second intensity.

Depending on the selection of the fluorescence dyes on the DNA nanostructures, the target structures are distinguishable by their color and/or by their intensity. Preferably, the sample portion is recorded in every color individually and saved in a separate image. However, the sample portion can also be recorded in several colors simultaneously, wherein the recordings of different colors are saved in a common image or in separate images.

These steps can take place manually, aided manually supported by software or automatically by analysis software.

In a manual analysis, a user knowing the color and/or intensity information of the target structure to be detected can search and identify the corresponding color and/or intensity information in the image. Optionally, the user can analyze the number of such identified target structures and/or the corresponding location information. If the color and/or intensity information in multicolored identification structures are present in different images, the image elements can be analyzed for each color, i.e. each image, separately, including the location information. Subsequently the colored elements can be recognized by identification of image elements of different colors with sufficiently similar location information. Alternatively, first, a colored image can be created by superimposing the individual single-colored images. A colored identification structure can then be identified as image element with the corresponding mixed color. Care has to be taken in that the images do not have to be stored in the real color. Color can of course be added to the images, be it the real color or a false color, at a later point in time.

The manual analysis can take place by means of image analysis software, for example Fiji or the like, or by software support. There is a smooth transition towards fully automated analysis. In general, it is possible to carry out any individual step manually or with software.

One aspect of the invention relates to the analysis with software, wherein the analysis is based on the density based spatial clustering of applications with noise method (in short DBSCAN). The description is based on the application for the case that the image to be analyzed has several fluorescence elements. The analysis, of course, works in the same way if only one or no fluorescence element is present in the image.

Preferably, the analysis software programmed for this purpose is python-based. The python-based analysis software loads image data. Preferably, it determines local maxima in image boxes. Preferably, the size of the image boxes is adjusted dependent on the magnification or the numeric aperture of the object used and is for example 9 to 15 pixels. Preferably, the software calculates the cumulative absolute value of the gradient as background-independent measurement value of the signal. In order to differentiate between image boxes with and without DNA nanostructures, preferably DBSCAN (density based spatial clustering of applications with noise) (published in: Ester, Martin; Kriegel, Hans-Peter; Sander, Jörg; Xu, Xiaowei "A density-based algorithm for discovering clusters in large spatial databases with noise", Proceedings of the Second International Conference on Knowledge Discovery and Data Mining (KDD-96). AAAI Press. pp. 226-231 (1996)) is used. Alternatively, also other clustering algorithms such as HDBSCAN (Ricardo J. G. B. Campello, Davoud Moulavi, Jörg Sander; "Density-Based Clustering Based on Hierarchical Density Estimates", Advances in Knowledge Discovery and Data Mining 2013, pp. 160-172), k-means or hierarchical clustering (Rokach, Lior, and Oded Maimon "Clustering methods." Data mining and knowledge discovery handbook. Springer U S, 2005. 321-352) can be used. Optionally, the image boxes are divided into groups of different values of the cumulative absolute value of the gradient, which corresponds to a division according to different numbers of fluorophores. This can take place in particular if different target structures are identified by means of identification structures of different intensities. Due to their transversal (x, y) positions, the image boxes with DNA nanostructures of a color channel can be compared with all the image boxes with DNA nanostructures of other color channels in order to recognize multicolored fluorescence elements, for example spots, in the image. This, of course, does not have to take place at all if only identification structures of a single color are present. The software can store the determined values for the number of single-color spots as well as optionally their locations in the image and the values for the number of the multicolored spots as well as optionally their locations in the image for further use. The software can also store the intensity values of the spots. For example, the software can be used to determine the number of the single-color fluorescence elements in comparison with the multicolored fluorescence elements. For example, the software can be used to compare the number of the fluorescence elements detected in experiments with samples with or without target structure. This is explained in detail in the appended Examples 1 to 3.

Due to the variation in the number of color dye molecules per 3 D nanostructure that can occasionally occur during their production as well as due to measurement errors, one is typically confronted with, for example, intensity distributions. If two adjacent intensity distributions have a significant overlap, one might not be able to conclude, simply due to an identity measurement, without doubt that there is exactly one identification structure. In order to address this problem, statistical methods are preferred by means of which a statistical assignment can be achieved. These distributions can be described one- or multi-dimensionally along intensity or color gradients and by means of one or more measured values, such as the mentioned cumulative gradient, the average value over the box, the maximum pixel value within the box or other measured values. The measured, optionally, multi-dimensional distribution is a mixture distribution of the individual distributions of the identification structures with the same target structures. The aim of the analysis is to calculate the contribution of these individual distributions to the mixture distribution and, thus, to learn something about the relative number of the different target structures. These individual distributions can be determined either by separate measurements or approximated by means of models (for example Gaussian distributions and/or Poisson distributions or mixtures thereof, possibly different in different dimensions). Thus, the different contributions can be calculated by deconvolution or by statistical methods, preferably based on Bayesian inference (cf. D. S. Sivia "Data Analysis, a bayesian tutorial", Oxford science publications, second edition, ISBN: 0198568320 and/ore A. B. Downey, "Think Bayes", O'Reilly, Sebastopol C A, fourth edition 2013 ISBN: 9781449370787). In this context, there is the possibility to initially assume a uniform distribution of the number of target structures and starting from there, to calculate—for each measurement event—the probability to originate from each of the distributions, thereby updating the assumption as to the distribution of the number of target structures. With a sufficiently high number of identification structure measurement events (over 50, preferably more than 100, particularly preferably more than 1000), this method is independent from the initial assumption of the distribution of the number of target structures.

We allow for the case that the intensity distributions of different nanoreporters overlap and are only clearly distinguishable from each other by statistical means by taking the distribution histograms into account as described in method step (h/ii). This adds complexity to the analysis because for each measurement event the probability to be derived from the various nanoreporters is calculated, and with greater overlap and the same amount of measurement events, the result becomes more uncertain. However, the number of different nanoreporter combinations and thus the number of target molecules can be increased since the intensity levels are reduced. Thus, there is a weighing between the size of overlap of the intensity distributions and the number of target molecules quantifiable simultaneously. Thus, the optimum configuration can be selected for each application.

Preferably, the fluorescence signals of the identification structures formed for the individual different target structures are different from the fluorescence signal of all the isolated 3D DNA nanostructures when those are not bound in one of the identification structures, and the fluorescence signals of the identification structures formed for the individual different target structures are pairwise different in that the corresponding fluorescence signals comprise a different distinguishable combination of color and/or intensity information. As explained above, a "different distinguishable combination" can be a combination that can be distinguished statistically, i.e. the distinguishability is guaranteed by means of statistical methods.

Preferably, in the 3D DNA nanostructures, k pairwise (statistically) distinguishable intensity levels and/or m pairwise (statistically) distinguishable color levels are used, wherein preferably, each of the k intensity levels is formed by an intensity distribution and wherein the k intensity distributions are distinguishable from each other, preferably statistically, and/or wherein preferably, each of the m color level is formed by a color distribution and wherein the m color distributions, are distinguishable from each other, preferably statistically. For this purpose, preferably, the overlap of adjacent distributions is less than 30%, preferably less than 10%, particularly preferably less than 5%, particularly preferably less than 2% and highly particularly preferably less than 1%.

In this context, the following preferably applies: $k>2$, preferably $k>3$, more preferably $k>4$, even more preferably $k>5$, particularly preferably $k>6$. Furthermore, the following preferably applies: $m>2$, preferably $m>3$, more preferably $m>4$, even more preferably $m>5$, particularly preferably $m>6$.

It is further preferred that step f1) comprises one or a combination of the following steps and/or techniques: Determining the average value of the image element, determining a maximum of the image element, calculating a cumulative gradient, calculating one or more statistical moments such as, e.g., variance of the pixel in the image element, variation coefficient, fano factor. It is further preferred that step f2) is based on a clustering method, preferably a DBSCAN (density based spatial clustering of application with noise) method. It is further preferred that step f1) and/or f2) are based on probabilistic consideration, preferably taking in to account the Bayesian theorem.

In particular, the intensity gradations of the nanoreporters and/or the 3D DNA nanostructures of each orthogonal measurable type can be selected differently, for example, by variation of number, distance or orientation. The gradations can be so great that the intensity distributions which are extended due to factors such as Poisson statistics of the photons or incomplete marker molecule attachment do not overlap. Thus, the analysis is simple and the measurement values can be identified directly by means of nanoreporters. On the other hand, the gradients can also be smaller so that the intensity distributions of adjacent intensity gradations overlap up to 0.1 to 10% and even 5 to 80%. Then, after measurement, the vectors from distributions of the orthogonal measurement results can be compared with those to be expected, and the relative frequency of the target molecules can be determined by means of Least Squares- or Maximum Likelihood-based methods. The same can be achieved with Cluster-based methods of machine learning with or without including the expected distributions.

It is also preferred that one of the orthogonal measurable nanoreporters is designed in a fixed amplitude value, the measurement value of which is clearly distinguishable from the one of the double amplitude value, and is designed onto each target molecule. Thus, the number of target molecules in a measurement event can be measured directly, which facilitates the measurement and analysis within a liquid (as is the case with FCS-like, flow and microfluidics detection).

For the method discussed above, preferably, a set of several 3D DNA nanostructures is used (wherein the 3D DNA nanostructures preferably are the ones as described in this application), wherein the set comprises N 3D DNA nanostructures which are different from each other and wherein the N 3D DNA nanostructures of the set which are different from each other are pairwise different due to the fluorescence dye molecules. Preferably, the N 3D DNA nanostructures which are different from each other comprise a different number of fluorescence dye molecules and/or different fluorescence dye molecules so that k distinguishable intensity level and/or m distinguishable color level can be generated by means of the N pairwise distinguishable 3D DNA nanostructures of the set. Preferably, at least a part of N pairwise distinguishable 3D DNA nanostructures is contained several times in the set so that each of the k intensity levels is formed by an intensity distribution and wherein the k intensity distributions are distinguishable from each other, preferably statistically. Preferably, at least a part of the N pairwise different 3D DNA nanostructures is contained several times in the set so that each of the m color levels is formed by a color distribution and wherein the color distributions are distinguishable from each other, preferably statistically. The overlap of the adjacent distributions is less than 30%, preferably less than 10%, more preferably less than 5%, even more preferably less than 2% and particularly preferably less than 1%.

Also in this context, the following applies preferably: $k>2$, preferably $k>3$, more preferably $k>4$, even more preferably $k>5$, particularly preferably $k>6$; and/or $m>2$, preferably $m>3$, more preferably $m>4$, even more preferably $m>5$, particularly preferably $m>6$.

Preferably, the method of the invention can be used in a microfluidics system, wherein the method preferably comprises:

Introducing a solution containing the target structure into a microfluidics system; and measuring at least one fluorescence signal at the solution in the microfluidics system.

Alternatively, the method may comprise:

Forming of the target structure in a microfluidics system; and measuring at least one fluorescence signal of the target structure p resent in the microfluidics system.

In the method of the invention, the measuring of the at least one fluorescence signal can be carried out by fluorescence microscopy, preferably by one or a combination of the following techniques: point scanning, wide field microscopy, (spinning disc) confocal microscopy; wherein each time preferably an alternating laser excitation (ALEX) or an excitation by means of pulsed-interleaved light sources takes place.

In the method of the invention, the measuring of the at least one fluorescence signal can be carried out by flow cytometry (e.g. if no carrier is used) and/or fluorescence correlation spectrometry (FCS), preferably by means of one or a combination of the following techniques: confocal microscopy, two photons spectroscopy, epifluorescence, light sheet microscopy; TIRF; wherein each time preferably an alternating laser excitation (ALEX) or an excitation by means of pulsed-interleaved light sources takes place.

In a preferred embodiment, a volume, kept constant in situ, which is illuminated and observed by point detectors is used as measuring device, as with FCS (fluorescence correlation spectroscopy). The sample fluid may be a small 0.5-5 µl droplet on a microscope objective and/or on the end of an optical fibre or be located in a sample chamber with a volume of up to 50 ml. The excitation and/or detection may be caused by an optical single- or multi-mode fibre, however also by classical optical elements such as for example a microscope objective. Complexes diffusing in the illuminated sample volume are detected and analyzed as measuring results. One advantage of this configuration is that only an extremely low amount of sample volume has to be used. Thus, it is advantageously used in clinical applications where only a small amount of starting material is available.

In a further preferred embodiment, a flow capillary is used as measuring device similar to "flow cytometry". However, in this case, attention has to be paid that all detected complexes of target molecules, adapters and nanoreporters should have similar velocity, since, otherwise, they would create measuring signals depending on their velocity. Due to the velocity gradient prevailing in a capillary, the fluid filament containing the sample should flow in the middle of the capillary and should be surrounded by a thick fluid enveloping the cylinder and moving with the flow, which ideally has low viscosity and does not easily mix with the sample fluid. Moreover, the excitation intensity should be high in the case of fluorescence detection in order to allow the detection of a number of markers, as small as possible, with a nanostructure of the lowest intensity level. Thus, a capillary of approximately one millimetre internal diameter can be used, limiting the sample fluid to a filament of 5-100 micrometre diameter. This limitation can be done by first generating a thicker filament of sample fluid in a region where the capillary has a larger internal diameter that is tapered in a second step. Instead or in addition, acoustical waves may be used in order to move the nanoreporter-adapter-target-molecule complexes to the middle of the capillary. In order to maximize the detection efficacy, a hollow ellipsoid can be used as mirror in the focus of which the capillary and the illumination region are located and in the other focus of which a detector is located so that light is collected by the detector independently of the direction in which it is radiated. In order to extend multi-color detection with the same excitation wavelength, it is possible to integrate a dichroic mirror into such a hollow ellipsoid and to increase the cavity for the reflected portion in such a way that an ellipsoid is topologically present for both the radiation transmitted through the dichroic mirror and the reflected radiation. Thus, the capillary can be located in the common focus and individual detectors for the different spectral components of the emitted light can be located in the relevant focus differing from the common focus. This can be extended to more spectral distributions. Such detection apparatuses may be present at different sites along the capillary for the different light wavelengths wherein the possibility to correlate the measuring events of the different detection apparatuses due to the temporal delay resulting from flow rate and distance exists. This variant embodiment provides particularly high measuring rates and for this reason it is to be preferred for time sensitive applications.

In a further preferred embodiment, the measuring device can be based on microfluidics. Here, the microfluidic channel may have side lengths and heights of 1-100 µm. For the different light wavelengths, the same or different regions along the channel can be used. At least one side of the channel should be transparent in the illuminated regions. The other sides may, for example, consist of silicon and thus provide a higher proportion of the emitted light for detection. The illumination may be by laser or LED via lens-based optics or via LED or diode laser directly installed in the channel wall or behind a window, or via an optical single- or multi-mode fibre that may be pressed or permanently fixed to the channel. The detection may also be carried out using a camera or a point detector via lens-based optics or via a detector that is installed directly in the wall of the channel or behind a window, or via an optical single- or multi-mode fibre that may be pressed or permanently fixed to the channel. The optical path of illumination and detection can partially use the same components.

An exemplary method to achieve the desired objective with said DNA nanostructures or other nanoreporters has the following steps or consists in that a. each type of target molecule is assigned to an unambiguous combination of one or more orthogonally measurable nanoreporters (e.g. 3D DNA nanostructures of the invention) in such a way that every type of target molecule is distinguishable and identifiable in an unambiguous manner, b. for each type of target molecules, at least as many binding regions, as nanoreporters, are identified and adapters are selected which are able to bind specifically and unambiguously to the binding regions, c. nanoreporters and adapters which are assigned to one type of target molecule are unambiguously paired and coupled, d. optionally, the adapters which are not assigned to nanoreporters are coupled to substrate or matrix, e. the complexes consisting of nanoreporters and adapters are incubated with the targets in solution, f. the resulting complexes consisting of target molecules, adapters and nanoreporters are measured with measuring apparatuses for the markers present in such a way that, only with an acceptable low probability, more than one complex is responsible for a measuring event, g. measuring events which do not have the minimum number of orthogonal signals are filtered out, h. the other measuring events are either
  i. directly assigned a combination of nanoreporters by the individual signals, or
  ii. statistically assigned a probability of being derived from a combination of nanoreporters by comparison of the measured distribution of measuring signals and the distribution expected for each nanoreporter, or
  iii. assigned a probability of being derived from a combination of nanoreporters by cluster-based algorithms;

i. the relative number of target molecules is determined by the total number of calculated combinations of nanoreporters or the probabilities thereof; and j. optionally, with known absolute concentration of at least one of the target molecules or with known measuring volumes, the absolute number of target molecules is determined; and k. optionally, a nanoreporter which can be measured orthogonally with respect to all other nanoreporters, can be designed for all target molecules so that its measuring signals provides information on the number of target molecules on which one measuring event is based.

In particular, it is envisaged that the methods of the invention and/or the 3D DNA nanostructures are used for the gene expression analysis, preferably the gene expression analysis at a single cell level.

For the analysis of gene expression at single cell level, a polymer matrix is preferably used as carrier which preferably envelops the cell partially or completely. In this case, the formation of the identification structure preferably comprises:

1) Providing a cell which is partially or completely enveloped by a polymer matrix (i.e. the carrier);
2) Lysing the cell (e.g. mechanically by ultrasonication, pressure (for example with a French Press or nitrogen decompression), or freezing; or chemically, for example by modification of the pH value, introduction of EDTA, enzymes such as for example lysozyme, toluol, Triton-X or Trizol, which all destabilize the cell walls or membranes or induces autolysis), so that the mRNAs are released from the cell.

With corresponding selection of cell concentration and density of the polymer matrix, the polymer matrix limits the diffusion of target structures released from the cell in such a way that, even if several cells are contained in the polymer matrix, it is still possible to determine in which region of the polymer the mRNAs are released from the cell. Preferably, the individual cells are embedded in the polymer matrix in such a way that they essentially have a minimum distance of 50 µm, preferably of 200 µm, and more preferably of 500 µm. In this context, "essentially" means that at least 80%, preferably at least 90% and most preferably at least 99% of the cells have at least the above-indicated distance from adjacent cells. The polymer network has preferably an average mesh size of 1 µm to 50 µm, preferably 2 µm to 10 µm. This is to limit diffusion as well as to provide a sufficient number of binding sites for carrier adapters and carrier adapter binding sites, respectively. The minimum distance of pairs of carrier adapters and/or carrier adapter binding sites can be substantially 200 nm to 10 µm, preferably 500 nm to 5 µm, most preferably 2 µm to 3 µm. In this context, "essentially" means that at least 80%, preferably at least 90% and most preferably at least 99% of the adapter carrier and/or carrier adapter binding sites have the above-indicated distance from adjacent adapter carrier and/or carrier adapter binding sites.

For the analysis of gene expression or of other cell components at single cell level, it can be preferred (a) to envelop a cell partially or completely with a polymer matrix; if this is done only partially, it may be advantageous that the sides that are not covered by the polymer matrix are not or only to a certain extent permeable to fluid;
(b) to decorate the polymer matrix with elements which are able to bind to the target molecules, such as complementary oligonucleotides;
(c) to lyse the cell so that the target molecules diffuse and bind to the decoration elements;
(d) to add nanostructures or other elements and to wash these out after an appropriate incubation period;
(e) to image the sample for example on an epifluorescence, lightsheet or confocal microscope and to analyze it as described above.

In this context, it is important to bear in mind that the decoration density of the elements binding target molecules on the polymer matrix should be sufficiently low so that the majority of complexes do not overlap in the image. In order to achieve this aim, optionally "Expansion Microscopy" (F. Chen, P. Tillberg, E. Boyden, "Expansion Microscopy", Science Express 2015) may be used in a last preparation step in order to increase the distance of the complexes. A suitable starting material for the polymer matrix is in particular agarose, however also collagen, DNA or other materials.

In a further application for the analysis of single cell gene expression or other molecular cell components at single-cell level, it is possible (a) to fix and perforate a cell;
(b) to add nanostructures or other orthogonally measurable elements, which were optimized for binding to the target molecules, and to wash these out after an appropriate incubation period;
(c) to swell the sample using "Expansion Microscopy" to an appropriate degree;
(d) to image the sample, for example, using an epifluorescence, lightsheet or confocal microscope and to analyze it as described above. The frequency of overlapping images of target molecule nanostructure complexes again shows the suitability of the degree of swelling.

Herein, the term 'cells' includes all biologic organisms, in particular human cells, cells from tissue samples, animal cells, bacteria, fungi, algae.

The term 'matrix' includes a gel from agarose or other substances the purpose of which is:
to limit the diffusion of target molecules to such a degree that they may be locally assigned to a cell and/or to limit the diffusion to 2.5D near the surface in order to minimize target loss due to diffusion;
and/or to provide anchor points for the target molecules near the surface.

A gene expression analysis having single-cell accuracy may comprise:

1. Deposit of the cells to be analyzed on a surface, in some cases a microscope glass slide, which, in some cases, is coated in such a way that the cells adhere, and/or with a matrix and/or anchor points to bind the target molecules.
2. In some cases, the cells are covered by a matrix.
3. The cells are lysed so that the target molecules are released from the cell.
4. The released targets are bound on the surface and/or in some cases to the matrix.
5. Nanoreporters bind the targets.
6. The nanoreporters are detected with corresponding instruments.
7. The data are analyzed and the detected nanoreporters and the corresponding targets are assigned to their original cell using cluster analysis.

A gene expression analysis of single cells can, for example, be carried out using microfluidics. The term microfluidics encompasses channels and tubes, valves and surfaces of glass, PDMS, polymer, silicon and the like.

Microfluidics is microfluidics on a glass surface of a microscope consisting of at least one chamber which is larger than the cell to be analyzed and has a surface area suitable to receive a suitable number of nanoreportes so that they are physically separate (in some cases 100 µm×100 µm), inlets and outlets at the chamber through which cells, solutions and nanoreporters and the like can be channelled, as well as valves at the inlets and outlets to open and to close these. In some cases, the chamber outlet is smaller than the cell or obstructed in such a way that the cell remains in the chamber prior to lysis even in a washing step. In some cases, there is a device in front of the chamber, which allows placing exactly one cell in each chamber.

In the following, we assume that a plurality of chambers are dealt with simultaneously, however, the procedure can be applied to a single chamber without limitation.

A method using microfluidics can, for example, include:
1. Attaching anchors (e.g. carrier adapter(s)) to the surfaces of the chambers by introducing the corresponding materials and washing them out after a suitable reaction time;
2. Introducing the cells through the inlets, in some cases by targeted sorting and/or random sorting wherein, in the majority of chambers, there is to be exactly one cell or no cell;
3. Inflow of lysation buffer and closing of the chamber. In some cases, the cells are lysated by light.

Closing the chambers prevents that the nucleic acid targets that are now set free diffuse out of the chamber.

4. The nucleic acid targets bind to the anchors (e.g. carrier adapter(s)) on the surface.
5. After an appropriate reaction time, the inlets and outlets are opened and components that are not bound at the surface are washed out of the chamber.
6. Introducing the nanoreporters (e.g. 3D DNA nanostructures) and reacting the nanoreporters with targets attached at the surface. In some cases, the nanoreporters may be already introduced in the lysation step.
7. Washing out the non-bound nanoreporters.
8. Detection and identification of the nanoreporters bound by targets on the surface in each chamber The present invention is inter alfa directed to the following aspects:

(1) A DNA nanostructure, characterized in that one or more marker molecules of one or more type of marker molecules are attached on it in such a way that the distance between two marker molecules is greater than the distance at which they interact significantly and the form of which prevents that when approaching a similar DNA nanostructure, its marker molecules interact significantly with those of the other DNA nanostructure.

(2) A plurality of DNA nanostructures of aspect (1), characterized in that the intensity distributions resulting from a measurement of groups of different DNA nanostructures have an overlap of 0.1-80% between one group and another.

(3) A plurality of DNA nanostructures, characterized in that, on each of these, one or more marker molecules of one or more type of marker molecules are attached in such a way that the distance between two marker molcules is greater than that at which they interact significantly and the intensity distributions resulting from a measurement of groups of different DNA nanostructures have an overlap of 0.1-80% between one group and another.

(4) A method to quantify a plurality of target molecules, characterized in that
  a. each type of target molecule is assigned an unambiguous combination of one or more orthogonally measurable nanoreporters (of aspect 1, or others) in such a way that each type of target molecule can be distinguished and identified unambiguously
  b. for each type of target molecules, at least as many of binding regions, as nanoreporters previously, are identified and adapters are selected which are able to bind specifically and unambiguously to the binding regions,
  c. nanoreporters and adapters assigned to one type of target molecule are unambiguously paired and coupled,
  d. optionally, the adapters which are not assigned to nanoreporters are coupled to substrate or matrix,
  e. the complexes of nanoreporters and adapters are incubated with the targets in solution,
  f. the resulting complexes of target molecules, adapters and nanoreporters are measured with measuring apparatuses for the markers present in such a way that, with only an acceptable low probability, more than one complex is responsible for one measuring event,
  g. measuring events which have not the minimum number of orthogonal signals are filtered out,
  h. to the other measuring events, either
    i. are directly assigned a combination of nanoreporters based on the individual signals, or
    ii. are statistically assigned a probability of originating from a combination of nanoreporters based on the comparison of the measured distribution of measuring signals and the distribution expected for each nanoreporter, or
    iii. are assigned a probability of originating from a combination of nanoreporters by cluster-based algorithms;
  i. The relative number of target molecules are determined based on the total number of calculated combinations of nanoreporters or their probabilities; and
  j. Optionally, with known absolute concentration of at least one of the target molecules or with known measurement volumes, the absolute number of target molecules is determined; and
  k. Optionally, a nanoreporter which is orthogonally measurable with respect to all the others can be designed for all target molecules so that its measuring signal provides information on the number of target molecules which underlie a measuring event.

(5) A method according to aspect (4), characterized in that the target molecules are immobilized on a substrate by means of substrate-binding adapters and the majority of resulting images of different complexes do not spatially overlap.

(6) A method according to aspects (4-5), characterized in that the target molecules, the adapters and the nanoreporters diffuse in aqueous solution and the latter are detected in a locally limited volume, wherein the simultaneous detection of several nanoparticles is an indicator of the binding of the nanoparticles by a target molecule and the combination of measurement results allows the identification of the target molecule.

(7) A method according to aspects (4-5), characterized in that the target molecules, the adapters and the nanoreporters are pumped in aqueous solution through a capillary passing one or more detection volumes, wherein the simultaneous detection of several nanoparticles is an indicator of the binding of the nanoparticles by a target molecule and the combination of measurement results allows the identification of the target molecule.

(8) A method according to aspects (4-5), characterized in that the target molecules, the adapters and the nanoreporters are pumped in aqueous solution through a microfluidics channel passsing one or more detection volumes, wherein the simultaneous detection of several nanoparticles is an indicator of the binding of the nanoparticles by a target molecule and the combination of measurement results allows the identification of the target molecule.

(9) A method for gene expression analysis with single-cell assignment, characterized in that a. the cells to be analyzed are deposited on a substrate which is selectively or collectively cell-adhesively coated with a matrix and/or with anchor points for target molecule binding;
b. the cells are optionally covered with a matrix;
c. the cells are lysed so that the target molecules may be released from the cell;
d. the released target molecules are bound at the surface of the substrate and/or the matrix;
e. the nanoreporters of claims 1-3) or of other origin are introduced with adapters and bind the targets;
f. the nanoreporters are detected with corresponding instruments;
g. the data are analyzed and the target molecules identified are assigned to their cell of origin using cluster-analyses.

(10) A method of gene expression analysis of single cells in a microfluidics system, characterized in that
a. adapters are attached on the surface of the substrate by introducing corresponding materials and by washing after an appropriate reaction time;
b. the cells to be analyzed are introduced into closable chambers, in some cases by targeted sorting and/or random sorting, wherein the parameters are adjusted such that, in the majority of chambers, exactly one cell or no cell is located;
c. the chambers are closed;
d. the cells are lysed using buffer or light, in some cases, after adapters and nanoreporters of claims 1-3) or of other origin have been introduced;
e. the nucleic acid target molecules are given time to bind to the adapters on the surface of the substrate;
f after appropriate reaction time, the inlets and outlets are opened and components that are not bound on the surface are washed out of the chamber;
g. the nanoreporters of claims 1-3) or of other origin are introduced with suitable adapters coupled, if not previously introduced;
h. after an appropriate reaction time, the non-bound nanoreporters are washed out;
i. the nanoreporters bound by target molecules to the surface of the substrate of the chambers are detected and identified.

Figure 2:
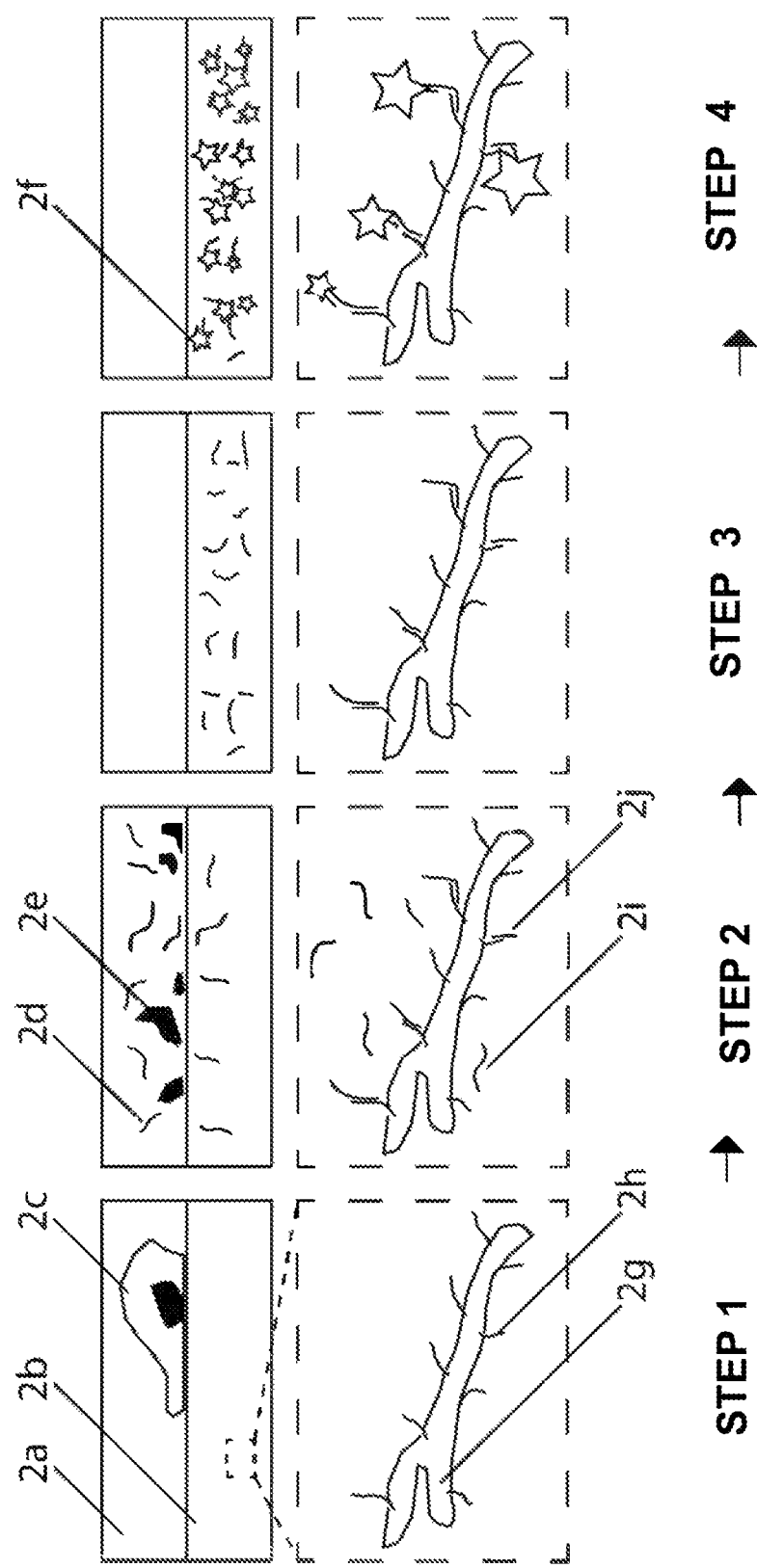
Figure 3:
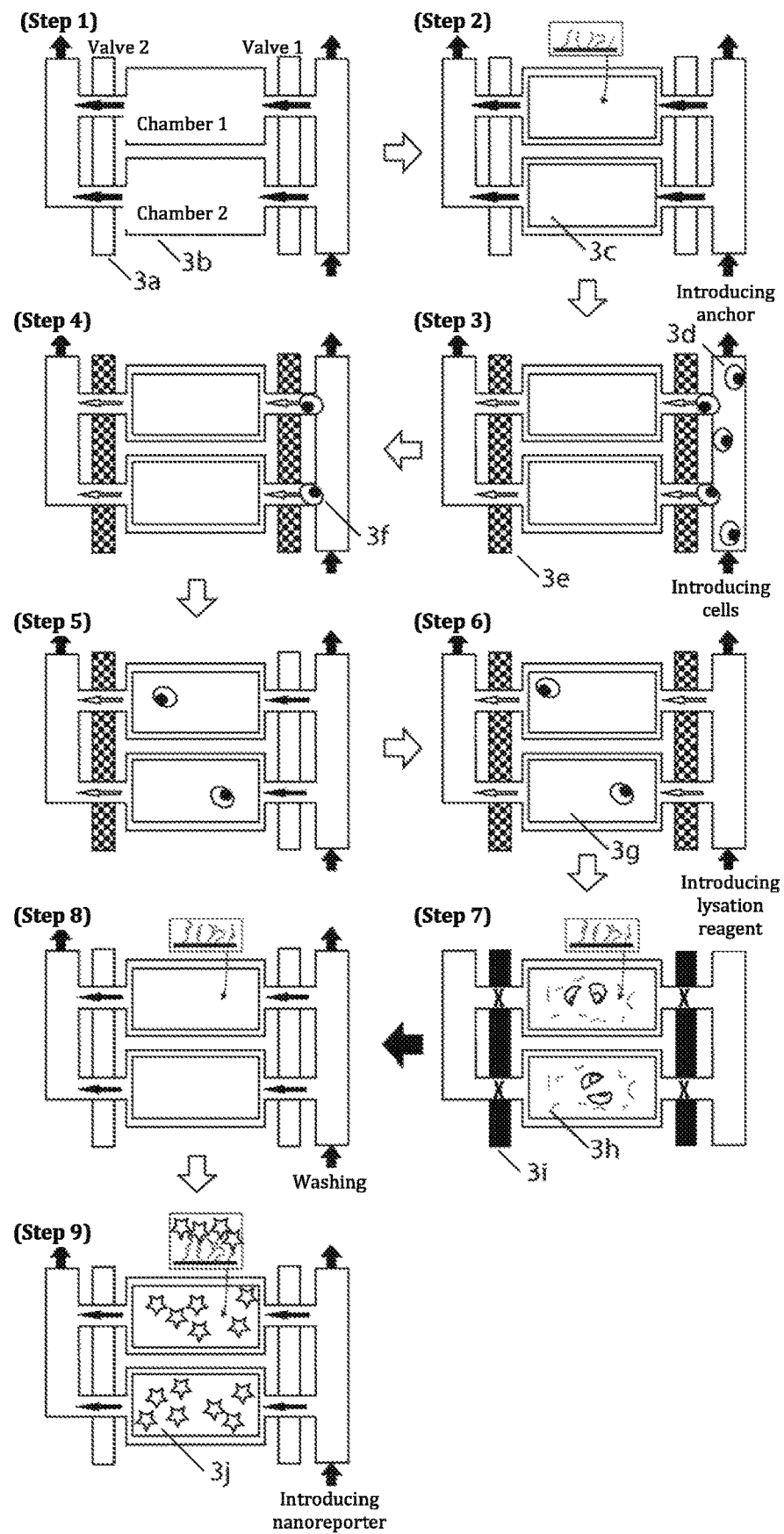

In the following, preferred embodiments of the invention are explained in more detail with reference to the figures. The figures show:

FIG. 1 schematically, the basic principle underlying the invention for the exemplary case of gene expression analysis;

FIG. 2 schematically, the course of a single-cell gene expression analysis according to a preferred embodiment of the method of the invention;

FIG. 3 schematically, the course of the method of the invention using a microfluidics system according to a preferred embodiment;

FIG. 4 the results of an experiment; and

FIG. 5 a 3D DNA nanostructure according to a preferred embodiment.

FIG. 1 shows, schematically, the basic principle underlying the invention for the exemplary case of gene expression analysis. The cylindrical 3D DNA nanostructure 1d of the case shown (see top of FIG. 1) with inwardly disposed fluorescence dye molecules 1b (with a distance 1c) is formed, as schematically indicated, by bending or rolling an 2D DNA nanostructure 1a forming the cylinder wall and the cylinder is stabilized by means of corresponding staple strands in its form. The cylinder comprises an adapter if coupled to it by means of which the 3D DNA nanostructure 1d can bind to a target structure 1g (see bottom of FIG. 1), in this case mRNA by hybridisation. The reference number 1h is to indicate, by way of example, a Watson Crick base pairing for the specific binding of the 3D DNA nanostructure and the target structure. The sequence indicated is to illustrate the mechanism only in an exemplary manner and does not reflect the actual sequence. The optional situation that the target structure is coupled via an adapter to a substrate 1j is represented in square brackets 1i.

At the bottom of FIG. 1 three 3D DNA nanostructures 1e are bound to the target structure 1g in an exemplary manner, wherein the intensities of the three 3D DNA nanostructures 1e measured under fluorescence conditions are different from each other, which is indicated by "BRIGHT", "WEAK" and "MEDIUM", and are caused by a different number of fluorescence molecules present in the 3D DNA nanostructures.

FIG. 2 shows, schematically, the course of a single-cell gene expression analysis according to a preferred embodiment of the method of the invention. Single cells 2c are on or in a polymer matrix 2b. A zoom into the polymer matrix (see Figure at the bottom) shows a polymer filament 2g of this matrix on which carrier adapters 2h are located. Between step 1 and step 2 the cells are lysed so that target structures, e.g. mRNAs (2d) as well as other cell components (2e) may move freely. Target structures bind to the carrier adapters in step 3. Step 4 shows the added 3D DNA nanostructures with target adapters which bind to the target structures. Due to the high local density of the carrier adapters, the target structures of individual cells can be particularly well captured so that target structures can be assigned to the individual cells and do not mix with adjacent cells. However, due to the three-dimensionality of the polymer matrix, it is possible to image densely arranged identification structures, for example, by using confocal microscopy, separately from each other in a satisfying manner FIG. 3 shows, schematically, the course of the method of the invention using a microfluidics system according to a preferred embodiment. The microfluidics system consists of inlet and outlet channels, valves and chambers. These are rinsed in step 1. In step 2, anchor or carrier adapters are introduced and fixed at the bottom of the chambers 3c, for example, by means of biotin streptavidin binding. In step 3, the chamber inlet valves are tapered so that single cells 3d which are introduced through the inlet channels are stuck in the openings. In step 4, the cells are removed from the inlet channel and in step 5, the stuck cells 3f are allowed to flow through the openings. The outlet valves are closed so far that the cells do not flow out of the chamber. Thus, it is ensured that each chamber contains exactly one cell. Step 6 shows the introduction of lysation reagents for the lysis of the cells. In step 7, the valves are closed in order to prevent the target structures (for example mRNA) from escaping and incubation is carried out until the target structures 3h have bound to the carrier adapters on the bottom of the chambers. Step 8 shows the washing-out of the unbound cell components from the chambers and the target structures bound to the carrier adapters. In step 9, the 3D DNA nanostructures (also "nanoreporters") 3j are introduced into the chambers and are bound to target structures so that identification structures are formed. This illustrates a method for single-cell gene expression analysis which is not based on stochastics and thus has a low error rate.

FIG. 5A shows, schematically, a 3D DNA nanostructure according to a preferred embodiment in form of a hollow cylinder with a diameter d of 60 nm and a height h of 30 nm.

In the example shown, the cylinder is formed by 22 DNA double-helices with a diameter of approximately 2 nm, with each circle representing the cross-section of a helix. As can easily be seen, the external face of the wall of the hollow cylinder is not smooth (or even mathematically perfect). Rather, the external face of the wall comprises projections and recesses in circumferential direction. The same applies to the inner wall. The helices are arranged on a grid-like or honeycomb-form structure in such a way that the wall thickness b corresponds to about 2.5 helix diameters (or approximately 5 nm).

The following non-limiting examples are to illustrate the present invention.

EXAMPLE 1

Preparation of 3D Nanostructures of the Invention

1. Description of the 3D DNA Nanostructures Prepared

3D DNA nanostructures having the form of a hollow cylinder with 60 inwardly disposed dye molecules each, which show pairwise distances of at least 9 nm to the adjacent dye molecules within the same 3D DNA nanostructure, were prepared in three different dye variants, i.e. variants 3D_1, 3D_2 and 3D_3:

3D DNA nanostructure variant 3D_1: red fluorescent:
The 3D_1 DNA nanostructure comprises 60 inwardly disposed DNA staple strands with additional single-stranded sequences complementary to fluorophore adapters for red dyes (designated as sequence S1), and 60 related fluorophore adapters which are each provided with an Atto647N dye molecule (oligomers SEQ_ID_NO 1259). The staples strands to be extended for fluorophore adapters binding were selected in the design program CaDNAno based on the criteria that they are located within the hollow cylinder, that they are located at a distance of more than 2 nm from the rim of the hollow cylinder, have a free end on the internal surface of the hollow cylinder and have a distance of more than 5 nm from each other (due to the design and the sequence lengths, the latter condition applies to all staple strands which meet the above criteria). The dye adapters are dye-modified at the 3' end. This end was selected to ensure that the dyes are located as close as possible to the internal surface of the hollow cylinder and have little leeway and thus, to approach each other as little as possible. Several modifications per dye adapter would be conceivable, however, they would imply higher costs and a certain loss of control of their positioning. Moreover, the 3D_1 nanostructure was provided with a T1 target adapter (oligomer SEQ_ID_NO 1263). The SEQ ID NOs of all staple strands used for the 3D_1 nanostructure are summarized in definition oligopool3D_S1 below. Strand p7308 (SEQ ID NO 1258) was used as scaffold strand.

3D DNA nanostructure variant 3D_2: green fluorescent:
The 3D_2 DNA nanostructure comprises 60 inwardly disposed DNA staple strands with additional single-stranded sequences complementary to fluorophore adapters for green dyes (designated as sequence S2), and 60 related fluorophore adapters which are each provided with an Atto565 dye molecule (oligomers SEQ_ID_NO 1260). The staples strands to be extended for fluorophore adapters binding were selected in the design program CaDNAno based on the criteria that they are located within the hollow cylinder, that they are located at a distance of not more than 2 nm from the rim of the hollow cylinder, have a free end on the internal surface of the hollow cylinder and have a distance of more than 5 nm from each other (due to the design and the sequence lengths, the latter condition applies to all staple strands which meet the above criteria). The dye adapters are dye-modified at the 3' end. This end was selected to ensure that the dyes are located as close as possible to the internal surface of the hollow cylinder and have little leeway and thus, to approach each other as little as possible. Several modifications per dye adapter would be conceivable, however, they would imply higher costs and a certain loss of control of their positioning. The 3D_2 nanostructure was provided with a T2 target adapter (oligomer SEQ_ID_NO 1264). The SEQ ID NOs of all staple strands used for the 3D_2 nanostructure are summarized in definition oligopool3D_S2 below. Strand p7308 (SEQ ID NO 1258) was used as scaffold strand.

3D DNA nanostructure variant 3D_3: blue fluorescent:
A 3D_3 DNA nanostructure comprises 60 inwardly disposed DNA staple strands with additional single-stranded sequences complementary to fluorophore adapters for blue dyes (designated as sequence S3), and 60 related fluorophore adapters which are each provided with an Atto488 dye (oligomers SEQ_ID_NO 1261). The staples strands to be extended for fluorophore adapter binding were selected in the design program CaDNAno based on the criteria that they are located within the hollow cylinder, that they are located at a distance of not more than 2 nm from the rim of the hollow cylinder, have a free end on the internal surface of the hollow cylinder and have a distance of more than 5 nm from each other (due to the design and the sequence lengths, the latter condition applies to all staple strands which meet the above criteria). The dye adapter are dye-modified at the 3' end. This end was selected to ensure that the dyes are located as close as possible to the internal surface of the hollow cylinder and have little leeway and thus, to approach each other as little as possible. Several modifications per dye adapter would be conceivable, however, they would imply higher costs and a certain loss of control of their positioning. The 3D_3 nanostructure was provided with a T3 target adapter (oligomer SEQ_ID_NO 1265). The SEQ ID NOs of all staple strands used for the 3D_3 nanostructure are summarized in definition oliaopool3D_S3 below. Strand p7308 (SEQ ID NO 1258) was used as scaffold strand.

All DNA oligomers (also the DNA oligomers provided with fluorescence dye) were acquired from Eurofins Genomics GmbH.

An illustration of a 3D DNA nanostructure of Example 1 is shown in FIG. 5 already discussed above. FIG. 5A shows a schematic representation of 3D DNA nanostructures 3D_1, 3D_2 and 3D_3 which differ only with respect to the type of the attached fluorescence dye molecules. FIG. 5B shows the hollow cylinder of FIG. 5A cut and unrolled (for illustration purposes), with the internal surface of the hollow cylinder of FIG. 5A being shown in plan view. Each x represents a fluorescence dye molecule. Between the nearest neighbors the pairwise dye molecules distances a are 9 nm. Between the other dye molecules, the pairwise distances, for example the distance g, are greater. The dye molecules are each located at the innermost helix in FIG. 5A so that the distance of the dye molecules from the outer rim of the hollow cylinder corresponds approximately to the wall thickness of the cylinder wall, i.e. approximately 2.5 helix diameters (corresponding approximately to 5 nm).

2. Preparation Protocol:

In the present example, the 3D DNA nanostructures 3D_1-3 were prepared according to the preparation protocol described in the following.

For the preparation of the 3D DNA nanostructures 3D_1, 3D_2 and 3D_3, first the following components were mixed to obtain a final volume of 200 µl:

10 nM p7308 scaffold strand (SEQ ID NO 1258)

100 nM of each of the staple strands (SEQ ID NOs from oligopool3D_S1 for DNA nanostructure 3D_1, SEQ ID NOs from oligopool3D_S2 for DNA nanostructure 3D_2 and SEQ ID NOs from oligopool3D_S3 for DNA nanostructure 3D_3)

120 nM fluorescence dye modified DNA oligos (SEQ ID NO 1259 for DNA nanostructure 3D_1, SEQ ID NO 1260 for DNA nanostructure 3D_2 and SEQ ID NO 1261 for DNA nanostructure 3D_3)

400 nM target-binding DNA oligos (SEQ ID NO 1263 for DNA nanostructure 3D_1, SEQ ID NO 1264 for DNA nanostructure 3D_2 and SEQ ID NO 1265 for DNA nanostructure 3D_3) 1× buffer FB02 (buffer composition see below)

In order to have the DNA nanostructures fold into their shape, the above-mentioned mixtures were first heated to melt secondary structures possibly present, then slowly cooled so that the base pairings were able to find the thermal equilibrium and accordingly the planed conformation. To this end, the following thermocycler program was used (using Mastercycler Nexus X2 by Eppendorf GmbH, Hamburg, Germany):

Maintain 15 minutes at 65° C. and cool within one minute to 50° C.

Decrease from 50° C. to 40° C. in 66 hours with constant rate

At the end of 66 h (optionally, it is possible to incubate for a few additional hours at 40° C.) cool within one minute to 4° C. and store at 2-8° C.

Subsequently, the correctly folded 3D DNA nanostructures were separated from single DNA oligomers or smaller DNA oligomer complexes. To this end, the following PEG purification (purification with polyethylene glycol) was used:

Mix the liquid derived from the thermocycler with the same volume of PEGX01 (for buffer composition see below)

Centrifugation for 35 min at 13000-16000 rfc at room temperature (20-25° C.)

Remove the supernatant with a pipette

Resuspend in 200 µl FB02 (for buffer composition see below) and 200 µl PEGX01 (for buffer composition see below)

Centrifugation for 35 min at 13000-16000 rfc at room temperature (20-25° C.)

Resuspend in 100 µl FB01(for buffer composition see below)

Incubation on the shaker for 8 to 16, preferably 10 hours (in this case over night) in the dark at room temperature and with 600 rpm in order to dissolve the pellet completely Store at 4° C. for further use (up to 12 months possible, however, in the present case, the storage was only a few days)

While in the present case, PEG purification of the DNA nanostructures was used, in the alternative, it would in principle be possible to carry out purification with agarose gel electrophoresis with subsequent extraction of the DNA nanostructures from the gel. An agarose gel electrophoresis-based purification could for example be carried out as follows:

Prepare 1.5% w/v agarose gel

Add 5× Orange G loading buffer to the sample

Electrophoresis at 4.5 V/cm voltage for 1.5 h with ice cooling

Excise pieces of gel with DNA origami band. The latter has a breadth of approximately 2 mm, and it is optionally possible to identify it more easily by loading an adjacent lane with scaffold strand, place it in Freeze 'N Squeeze™ DNA Gel Extraction Spin Columns (Bio-Rad Laboratories GmbH) and centrifuge for 4.5 min at room temperature and at 1050 rcf.

Buffer Solutions Used

PEGX01:

15% PEG 8000

1×TAE (Tris acetate EDTA buffer: 40 mM Tris, 20 mM acetic acid, 1 mM EDTA)

12.5 mM MgCl2

500 mM NaCl

FB01:

10 mM Tris pH8.0

1 mM EDTA 288, 481, 490, 491, 492, 482, 483, 484, 485, 486, 487, 488, 489, 490, 491, 492, 337, 346, 347, 348, 338, 339, 340, 341, 342, 343, 344, 345, 346, 347, 348, 361, 370, 371, 372, 362, 363, 364, 365, 366, 367, 368, 369, 370, 371, 372, 325, 334, 335, 336, 326, 327, 328, 329, 330, 331, 332, 333, 334, 335, 336, 349, 358, 359, 360, 350, 351, 352, 353, 354, 355, 356, 357, 358, 359, 360, 241, 250, 251, 252, 242, 243, 244, 245, 246, 247, 248, 249, 250, 251, 252]

oligopool_3D-S3: [1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 277, 286, 287, 288, 278, 279, 280, 281, 282, 283, 284, 285, 286, 287, 288, 493, 502, 503, 504, 494, 495, 496, 497, 498, 499, 500, 501, 502, 503, 504, 385, 394, 395, 396, 386, 387, 388, 389, 390, 391, 392, 393, 394, 395, 396, 409, 418, 419, 420, 410, 411, 412, 413, 414, 415, 416, 417, 418, 419, 420, 373, 382, 383, 384, 374, 375, 376, 377, 378, 379, 380, 381, 382, 383, 384, 397, 406, 407, 408, 398, 399, 400, 401, 402, 403, 404, 405, 406, 407, 408, 241, 250, 251, 252, 242, 243, 244, 245, 246, 247, 248, 249, 250, 251, 252]

EXAMPLE 2

Preparation of 2D DNA Nanostructures for Comparison

1. Description of the 2D DNA Nanostructures Prepared

Rectangular 2D DNA nanostructures, each with 48 dye molecules with a pairwise distance of 5 nm to the respective nearest dye molecule within the same 2D DNA nanostructure (such a 21) DNA nanostructure is for example shown in FIG. 1A of WO 2016/140727) were prepared in three variants, i.e. in variants 2D_1, 2D_2 and 2D_3:

2D DNA nanostructure variant 2D_1: red fluorescent:

A 2D_1 DNA nanostructure comprises 48 DNA staple strands with additional single-stranded sequences complementary to fluorophore adapters for red dyes (designated sequence S1), as well as 48 related fluorophore adapters which are each provided with an Atto647N dye, (oligomers SEQ_ID_NO 1259). The staple strands to be extended for fluorophore adapter binding were selected in the design program CaDNAno according to the criteria that they all are located at the same side of the rectangle and have a distance from each that is sufficient that they do not significantly interact with each other. The dye adapters are dye-modified at the 3' end. This end is selected to ensure that the dyes are located as close as possible to the surface of the rectangle and have little leeway and thus, to approach each other as little as possible. Several modifications per dye adapter would be conceivable, however, they would imply higher costs and a certain loss of control of their positioning. The 2D_1 nanostructure was provided with a T1 target adapter (oligomer SEQ_ID_NO 1266) which, according to the design, is located along the rim of the structure. The SEQ ID NOs of all staple strands used for the 2D_1 DNA nanostructure are summarized in definition oligopool2D_S1 further below. Strand p7249 (SEQ ID NO 1257) was used as scaffold strand.

2D DNA nanostructure variant 2D_2: green fluorescent:

A 2D_2 DNA nanostructure comprises 48 DNA staple strands with additional single-stranded sequences complementary to fluorophore adapters for red dyes (designated sequence S2) as well as 48 related fluorophore adapters which are each provided with an Atto565 dye (oligomers SEQ_ID_NO 1260). The staple strands to be extended for fluorophore adapter binding were selected in the design program CaDNAno according to the criteria that they all are located at the same side of the rectangle and have a distance from each that is sufficient that they do not significantly interact with each other. The dye adapters are dye-modified at the 3' end. This end is selected to ensure that the dyes are located as close as possible to the inner surface of the rectangle and have little leeway and thus, to approach each other as little as possible. Several modifications per dye adapter would be conceivable, however, they would imply higher costs and a certain loss of control of their positioning. The 2D_2 DNA nanostructure was provided with a T2 target adapter (oligomer SEQ_ID_NO 1267) which, according to the design, is located along the rim of the structure. SEQ ID NOs of all staple strands used are summarized in definition oligopool2D_S2 further below. Strand p7249 (SEQ ID NO 1257) was used as scaffold strand.

2D DNA nanostructure variant 2D_3: blue fluorescent:

A 2D_3 DNA nanostructure comprises 48 DNA staple strands with additional single-stranded sequences complementary to fluorophore adapters for red dyes (designated sequence S3) as well as 48 related fluorophore adapters which are each provided with an Atto488 dye (oligomers SEQ_ID_NO 1261). The staple strands to be extended for fluorophore adapter binding were selected in the design program CaDNAno according to the criteria that they all are located at the same side of the rectangle and have a distance from each that is sufficient that they do not significantly interact with each other. The dye adapters are dye-modified at the 3' end. This end is selected to ensure that the dyes are located as close as possible to the internal surface of the rectangle and have little leeway and thus, to approach each other as little as possible. Several modifications per dye adapter would be conceivable, however, they would imply higher costs and a certain loss of control of their positioning. The 2D_3 DNA nanostructure was provided with a T3 target adapter (oligomer SEQ_ID_NO 1268) which, according to the design, is located along the rim of the structure. SEQ ID NOs of all staple strands used are summarized in definition oligopool2D_S3 further below. Strand p7249 (SEQ ID NO 1257) was used as scaffold strand.

2. Preparation Protocol:

In the present example, the 2D DNA nanostructures 2D_1-3 were prepared according to the preparation protocol described in the following.

For the preparation of the 2D DNA nanostructures 2D_1-3, first the following components were mixed to obtain a final volume of 200 µl:

10 nM p7249 scaffold strand (SEQ ID NO 1257)

100 nM of each of the staple strands (SEQ ID NOs from oligopool2D_S1 for DNA nanostructure 2D_1, SEQ ID NOs from oligopool2D_S2 for DNA nanostructure 2D_2 and SEQ ID NOs from oligopool2D_S3 for DNA nanostructure 2D_3)

120 nM fluorescence dye modified DNA oligos (SEQ ID NO 1259 for DNA nanostructure 2D_1, SEQ ID NO 1260 for DNA nanostructure 2D_2 and SEQ ID NO 1261 for DNA nanostructure 2D_3)

400 nM target-binding DNA oligos (SEQ ID NO 1266 for DNA nanostructure 2D_1, SEQ ID NO 1267 for DNA nanostructure 2D_2 and SEQ ID NO 1268 for DNA nanostructure 2D_3) 1× buffer FB02 (buffer composition see Example 1)

In order to have the DNA nanostructures fold into their shape, the above-mentioned mixtures were first heated to melt secondary structures possibly present, then slowly cooled so that the base pairings were able to find the thermal equilibrium and accordingly the planed conformation. To this end, the following thermocycler program was used (using Mastercycler Nexus X2 by Eppendorf GmbH, Hamburg, Germany):

Maintain 15 minutes at 65° C. and cool within one minute to 60° C.

Decrease from 60° C. to 20° C. in 1 hour at constant rate cool within one minute to 4° C. and keep at 4° C.

Subsequently, correctly folded 2D DNA nanostructures were separated from single DNA oligomers or smaller DNA oligomer complexes. To this aim, the following PEG purification (purification with polyethylene glycol) was used:

Mix the liquid derived from the thermocycler with the same volume of PEGX01 (for buffer composition see below)

Centrifugation for 35 min at 13000-16000 rfc at room temperature (20-25° C.)

Resuspend in 200 μl FB01 and 200 μl FB02 (for buffer composition see Example 1).

Centrifugation for 35 min at 13000-16000 rfc at room temperature (20-25° C.)

Resuspend in 100 μl FB01

Incubate on a shaker over night in the dark, at room temperature (20-25° C.) and at 600 rpm.

Store at −20° C. (e.g. for up to 3 years) or at 4° C. (e.g. for up to 12 months) for further use (in the present case, the storage was for a few days)

Also in this case, it would in principle be possible to use the agarose gel electrophoresis-based purification mentioned in Example 1 as an alternative to the PEG-based purification.

DNA Oligo Pools Used:

For the preparation of the respective 2D DNA nanostructures, oligomers were combined based on their SEQ_ID_NOs (numbers in square brackets indicate the respective SEQ ID NOs) in the following pools:

oligopool_2D-S1: [529, 538, 539, 540, 530, 531, 532, 533, 534, 535, 536, 537, 538, 539, 540, 563, 572, 573, 574, 564, 565, 566, 567, 568, 569, 570, 571, 572, 573, 574, 623, 632, 633, 634, 624, 625, 626, 627, 628, 629, 630, 631, 632, 633, 634, 657, 666, 667, 668, 658, 659, 660, 661, 662, 663, 664, 665, 666, 667, 668, 693, 702, 703, 704, 694, 695, 696, 697, 698, 699, 700, 701, 702, 703, 704, 705, 714, 715, 716, 706, 707, 708, 709, 710, 711, 712, 713, 714, 715, 716, 787, 796, 797, 798, 788, 789, 790, 791, 792, 793, 794, 795, 796, 797, 798, 799, 808, 809, 810, 800, 801, 802, 803, 804, 805, 806, 807, 808, 809, 810, 575, 584, 585, 586, 576, 577, 578, 579, 580, 581, 582, 583, 584, 585, 586, 587, 596, 597, 598, 588, 589, 590, 591, 592, 593, 594, 595, 596, 597, 598, 669, 678, 679, 680, 670, 671, 672, 673, 674, 675, 676, 677, 678, 679, 680, 681, 690, 691, 692, 682, 683, 684, 685, 686, 687, 688, 689, 690, 691, 541, 548, 549, 550, 542, 543, 544, 545, 546, 547, 548, 549, 550, 551, 560, 561, 562, 552, 553, 554, 555, 556, 557, 558, 559, 560, 561, 562, 635, 642, 643, 644, 636, 637, 638, 639, 640, 641, 642, 643, 644, 645, 654, 655, 656, 646, 647, 648, 649, 650, 651, 652, 653, 654, 655, 656]

oligopool_2D-S2: [529, 538, 539, 540, 530, 531, 532, 533, 534, 535, 536, 537, 538, 539, 540, 563, 572, 573, 574, 564, 565, 566, 567, 568, 569, 570, 571, 572, 573, 574, 623, 632, 633, 634, 624, 625, 626, 627, 628, 629, 630, 631, 632, 633, 634, 657, 666, 667, 668, 658, 659, 660, 661, 662, 663, 664, 665, 666, 667, 668, 505, 514, 515, 516, 506, 507, 508, 510, 512, 514, 515, 516, 517, 526, 527, 528, 518, 519, 520, 522, 524, 526, 527, 528, 599, 608, 609, 610, 600, 601, 602, 604, 606, 608, 609, 610, 611, 620, 621, 622, 612, 613, 614, 616, 618, 620, 621, 622, 697, 699, 701, 709, 711, 713, 791, 793, 795, 803, 805, 807, 951, 960, 961, 962, 952, 953, 954, 955, 956, 957, 958, 959, 960, 961, 962, 963, 972, 973, 974, 964, 965, 966, 967, 968, 969, 970, 971, 972, 973, 974, 1045, 1054, 1055, 1056, 1046, 1047, 1048, 1049, 1050, 1051, 1052, 1053, 1054, 1055, 1056, 1057, 1066, 1067, 1068, 1058, 1059, 1060, 1061, 1062, 1063, 1064, 1065, 1066, 1067, 1068, 541, 548, 549, 550, 542, 543, 544, 545, 546, 547, 548, 549, 550, 551, 560, 561, 562, 552, 553, 554, 555, 556, 557, 558, 559, 560, 561, 562, 635, 642, 643, 644, 636, 637, 638, 639, 640, 641, 642, 643, 644, 645, 654, 655, 656, 646, 647, 648, 649, 650, 651, 652, 653, 654, 655, 656]

oligopool_2D-S3: [529, 538, 539, 540, 530, 531, 532, 533, 534, 535, 536, 537, 538, 539, 540, 563, 572, 573, 574, 564, 565, 566, 567, 568, 569, 570, 571, 572, 573, 574, 623, 632, 633, 634, 624, 625, 626, 627, 628, 629, 630, 631, 632, 633, 634, 657, 666, 667, 668, 658, 659, 660, 661, 662, 663, 664, 665, 666, 667, 668, 505, 514, 515, 516, 506, 507, 508, 510, 512, 514, 515, 516, 517, 526, 527, 528, 518, 519, 520, 522, 524, 526, 527, 528, 599, 608, 609, 610, 600, 601, 602, 604, 606, 608, 609, 610, 611, 620, 621, 622, 612, 613, 614, 616, 618, 620, 621, 622, 697, 699, 701, 709, 711, 713, 791, 793, 795, 803, 805, 807, 575, 584, 585, 586, 576, 577, 578, 579, 580, 581, 582, 583, 584, 585, 586, 587, 596, 597, 598, 588, 589, 590, 591, 592, 593, 594, 595, 596, 597, 598, 669, 678, 679, 680, 670, 671, 672, 673, 674, 675, 676, 677, 678, 679, 680, 681, 690, 691, 692, 682, 683, 684, 685, 686, 687, 688, 689, 690, 691, 1105, 1112, 1113, 1114, 1106, 1107, 1108, 1109, 1110, 1111, 1112, 1113, 1114, 1115, 1124, 1125, 1126, 1116, 1117, 1118, 1119, 1120, 1121, 1122, 1123, 1124, 1125, 1126, 1199, 1206, 1207, 1208, 1200, 1201, 1202, 1203, 1204, 1205, 1206, 1207, 1208, 1209, 1218, 1219, 1220, 1210, 1211, 1212, 1213, 1214, 1215, 1216, 1217, 1218, 1219, 1220]

EXAMPLE 3

Comparison of the Detection of a Target Structure With the 3D Nanostructures of Example 1 and the 2D DNA Nanostructures of Example 2

1. Outline

In order to compare how well target structures can be detected with the 2D DNA nanostructures or the 3D DNA nanostructures of the invention by means of the method of the invention in its embodiment in which the identification structure with target structures and the respective bound DNA nanostructures is bound or is being bound to the surface of a carrier (in the present case, the surface of a cover slip), in the example described herein, the same target DNA oligomers were used as target structures and were detected on the one hand, based on the binding of red, green and blue 2D DNA nanostructures of the variants 2D_1, 2D_2 and 2D_3 as described in Example 2 (2D sample), and on the other hand, based on the binding of red, green and blue 3D DNA nanostructures of the variants 3D_1, 3D_2 and 3D_3 as described in Example 1 (3D sample). In addition, a control experiment was carried out for both experiments wherein it was checked whether and to which degree a false positive detection occurs on the surface of the cover slip if a target structure is absent. The comparison shows that, due to the optimized and well-conceived positioning of the dye molecules, the 3D DNA nanostructures adhere to a much lesser extent to the surface of the microscopy cover slip.

2. Material and Methods:

For the detection of target structures (in the present case, target DNA oligomers, in short: target oligomers), these were first incubated in a hybridization reaction with the respective DNA nanostructures (i.e. 2D_1, 2D_2 and 2D_3 or 3D_1, 3D_2 and 3D_3) and a capture strand in a suited buffer so that all these components were able to bind to each other and to form the identification structure (see FIG. 1, 1k). This was carried out separately for the 2D and 3D DNA nanostructures.

For the sample with 3D DNA nanostructures, hybridisation was carried out in a solution with the following components:

4 μl mixture of DNA nanoparticles 3D_1-3 with 200 pM per DNA nanoparticle set according to Example 1

10 μl 2× buffer RX07 (composition see below)

1 μl 20 nM carrier adapter (herein also referred to as capture strand) (SEQ ID NO 1262) with biotin adapter, wherein the capture strand with biotin adapter (modified with biotin at the 5' end) was provided by the company Eurofins 1 µl 750 pM single-stranded target DNA oligomer (SEQ ID NO 1269). This oligomer has complementary regions for T1, T2 and T3 so that the 3D DNA nanostructures 3D_1, 3D_2 and 3D_3 can bind with their respective T1, 2 and 3 regions to the corresponding complementary regions of the target DNA oligomer, as well as a complementary region for the capture strand. The target structure and the respective binding regions were designed in such a way that all three 3D DNA oligomers as well as the capture strand could concomitantly bind to a target DNA oligomer. For the control experiment, this volume was replaced with $H_2O$.

4 µl $H_2O$

This was incubated for 16 hours at 30° C. in order to allow capture strands, target oligomers and 3D DNA nanostructures to bind to each other.

For the case of the sample with the 2D DNA nanostructures, hybridisation was carried out in a solution with the same components, however, 4 µl mixture of DNA nanoparticles 2D_1-3, with 200 pM per DNA nanoparticle set according to Example 2, instead of 4 µl mixture of DNA nanoparticles 3D_1-3 with 200 pM per DNA nanoparticle set according to Example 1 were used. In this case also, it was ensured that all three 2D DNA nanostructures as well as the capture strand could bind to the target oligomer. The target DNA oligomer used also had the sequence with SEQ ID NO 1269. For the 2D DNA nanostructures too, a control reaction, which did not contain a target DNA oligomer, was carried out. Thus, in total, four experiments were carried out.

For the measurement, the capture strands of each experiment were placed on a microscopy surface of a respective microscopy sample carrier. A µ-slide of type VI" from ibidi GmbH (Martinsried, Germany) was used as microscopy sample carrier. For this purpose, it was treated according to the following protocol for the preparation of microscopy slides as sample:

µ-slides VI$^{0.1}$ (ibidi GmbH, Martinsried) were rinsed with 100 µl buffer A (composition, see below)

pipetting 40 µl 1 mg/ml biotinylated BSA (Sigma-Aldrich GmbH) into a first channel end of the corresponding channel of the µ-slide, incubating for 2 min, removing the fluid via the other, second channel end of the corresponding channel of the µ-slide by pipetting, pipetting 100 µl buffer A into the above first channel end, removing the fluid via the above second channel end by pipetting.

pipetting 40 µl 0.5 mg/ml streptavidin (Thermo Scientific) in the above first channel end, incubating for 2 min, removing via the above second channel end by pipetting, pipetting 100 µl buffer A in the above first channel end and removing the fluid via the above second channel end by pipetting.

pipetting 100 µl buffer B (composition see below) into the above first channel end and removing the fluid via the above second channel end by pipetting pipetting 40 µl of the hybridized solution (solution with 2D nanostructures for the 2D sample Probe or solution with 3D DNA nanostructures for the 3D sample or corresponding control experiments without target DNA oligomer) in the above first channel end. Incubation for 15 min. During this time, the biotin of the capture strands is bound to the surface-bound streptavidin. In addition, some of the DNA nanostructures adhere unspecifically to the surface. This is unintended and occurs with 2D DNA nanostructures significantly more frequently than with 3D DNA nanostructures. Removing via the above second channel end by pipetting.

Washing out the unbound DNA nanostructures by pipetting 200 µl buffer RX07 (composition see below) into the above first channel end and removing via the above second channel end by pipetting Pipetting 50 µl buffer RX07 (composition see below) into the above first channel end With completion of the above-described steps, there were two samples, one 2D sample and one 3D sample. Moreover, there were respective controls (without target DNA) for both the 2D and 3D nanostructures. The combination of the selected concentrations of biotin-BSA, streptavidin and target structures in the above described method was selected such that the individual identification structures could be easily resolved in the subsequent analysis.

Subsequently, the identification structures in the two samples were imaged with an epifluorescence microscope. To this end, an "Elite" microscope (DeltaVision) was employed. The use of a microscope of the type "Ti Eclipse" (Nikon) would also be conceivable. The camera used was a sCMOS camera (edge 4.2 by PCO) with a pixel size of 6.5 µm. With an objective magnification of 100× and a numeric aperture of 1.4, a pixel resolution of 60 nm was given, i.e. one pixel in the image corresponds to 60 nm in reality. Thus, diffraction limited images of the DNA nanostructures were taken. The filter sets were Chroma 49914 for red, Chroma 49008 for green, Chroma 49020 for blue excitation.

10 images were taken per color for both the 2D sample and the 3D sample as well as for the two controls without target DNA. The colors were imaged sequentially. Each of these images was taken at a specific section of the sample which did not overlap with the sections of the other images and which was located in the mean half along the channel width.

The 10 images of each related sample were analysed. The objective of the analysis presented herein is to compare the number of detected spots in the respective sample with target DNA and the respective sample without target DNA and to specify the number of the single-colored in comparison to multi-colored spots. The analysis was carried out manually. To this end, the images were opened with the image processing program FIJI (www.fiji.sc) and the number of single-colored, three-colored as well as the total number of fluorescent spots were counted. For 2D DNA nanostructures and 3D DNA nanostructures, mean value and standard deviation of different parameters of the respective 10 images were determined and plotted in FIG. 4.

Even though it was not applied in the present example, it is possible to use specifically programmed analysis software instead of manual analysis. In the present example, the programmed analysis software is python-based. The python-based analysis software loads the measurement data, determines local maximum values in image boxes of 9-15 pixel size (depending on magnification and numeric aperture of the objective) and calculates the cumulative absolute value of the gradient as noise-independent measurement value of the signal. In order to distinguish between image boxes with and without DNA nanostructures DBSCAN (density based spatial clustering of applications with noise) (published in Ester, Martin; Kriegel, Hans-Peter; Sander, Jorg; Xu, Xiaowei "A density-based algorithm for discovering clusters in large spatial databases with noise", Proceedings of the Second International Conference on Knowledge Discovery and Data Mining (KDD-96) AAAI Press. pp. 226-231

(1996)) is used. Optionally, the image boxes are partitioned into groups of different values of the cumulative absolute value of the gradient, which corresponds to a classification according to different numbers of fluorophores. Based on their transversal (x, y) positions, the image boxes with DNA nanostructures of each color channel are compared with all image boxes with DNA nanostructures of other color channels in order to recognize multi-colored spots in the image. The aim of the analysis using python-based software as presented herein is also to compare the number of the detected spots in experiments with and without target DNA oligomers and/or to specify the number of single-colored spots in comparison to multi-colored spots. The software stores the determined values for the number of single-colored spots as well as their location in the image and the values for the number of multi-colored spots as well as their location in the image for further use.

3. Results and Discussion:

To evaluate the suitability of the DNA nanostructures for the method described, it was measured how many DNA nanostructures were found in the respective control (without target DNA oligomer) in comparison to the corresponding sample with target DNA oligomer (top of FIG. 4). This allowed conclusions which proportion of the DNA nanostructures measured in the sample in the presence of the target structure was due to unspecific nanostructures bound to the surface. It was found that the 3D DNA nanostructures show a significantly lower degree (1.2% for 3D compared to 4.0% for 2D) of unspecific adherence to the microscopy surface of the microscopy sample carrier. The error bar (standard deviation) for the 3D DNA nanostructures crosses the zero line and thus indicates that with 3D DNA nanostructures, the rate of unspecific binding is below the limit of resolution of the measurement series.

It was further measured how many three-colored spots, i.e. data points which could be interpreted as target molecules, can be found in the control in comparison to the sample with target DNA oligomer, again for the 2D sample in comparison to the 2D control and for the 3D sample in comparison to the 3D control. This provides information regarding the false-positive recognized target structures in the case of the 2D DNA nanostructures and in the case of the 3D DNA nanostructures. The presence of three-colored measuring points in the control could be caused by the interaction of outwardly exposed dyes of different DNA nanostructures. This was avoided by the design of the 3D DNA nanostructures with inwardly disposed dyes. FIG. 4 (middle) shows the result of 0.7% for the 2D DNA nanostructures and 0.0% for the 3D DNA nanostructures. In the 3D case, not a single false-positive measurement was made. Thus, the result shows that due to the use of a plurality of DNA nanostructures binding to a target structure a very low rate of false-positive signals is measured. The result further shows that the 3D DNA nanostructures with inwardly disposed fluorescence dye molecules of the invention interact less with the carrier surface used in the example. This is due to their position inside the 3D structure.

Another parameter is the percentage of three-colored measuring points in the total number of measuring points with target DNA oligomers. It was calculated for both the 2D sample and the 3D sample based on the results of the image analysis and is represented in FIG. 4 (bottom). Due to the reaction kinetics, it is to be expected that identification structures are only partially hybridized under certain circumstances. This may for example be the case if the concentration of the DNA nanostructures is not sufficiently high for saturation of the reaction within the duration of the hybridization reaction. If the reaction is not saturated at the time of measurement, absolute quantification of an internal standard or based on empirical data is possible. The internal standard preferably indicates a reference value with known concentration, whereas empirical data preferably allow a comparison between unsaturated and saturated measurement. However, for relative measurements (as carried out herein), this is not relevant, because the ratio of partially hybridized identification structures to target structures does not depend on the target structure and the embodiments of the 3D DNA nanostructures and, thus, the relative frequencies of the completely hybridized identification structures among these are the same as the relative frequencies of the target structures among the latter. Yet, in this respect 2D and 3D nanostructures are comparable due the similar size. However, DNA nanostructures that are bound to each other as well as DNA nanostructures that are unspecifically bound to the surface may alter the result drastically. This is clear in FIG. 4 (bottom) where only 6.8% of the measuring points on the surface may be considered recognizable structures for 2D DNA nanostructures whereas 25.7% can be considered such for 3D DNA nanostructures. Thus, the microscopy surface can be used more efficiently with 3D DNA nanostructures than with 2D DNA nanostructures.

In summary, it can be noted that the 3D DNA nanostructures of the invention have a more than three-times lower tendency to unspecifically adhere to the microscopy surface of the microscopy sample carrier and a drastic and unquantifiable lower tendency to adhere to each other compared to the 2D DNA nanostructures. The area use efficiency of 3D DNA nanostructures is almost four times higher.

The method of the invention uses multiple binding of DNA nanostructures to increase the specificity, i.e. it reduces the false-positive identification rate. With the measurement method with only one DNA nanostructure binding, this rate would be as high as shown in FIG. 4 (top), i.e. 4.0% (2D) and 1.2% (3D), while it is 0.7% (2D) and 0% (3D).

Buffers Used
RX07buffer
4×SSC (saline sodium citrate buffer consisting of an aqueous solution of 150 mM sodium chloride and 15 mM trisodium citrate which is adjusted to pH 7.0 with HCl)
5% dextrane sulfate
0.1% Tween20
5×Denhardts
Buffer A
10 mM Tris-HCl at pH 7.5
100 mM NaCl
0.05% Tween 20
Buffer B
10 mM Tris-HCl at pH 8.0
10 mM $MgCl_2$
1 mM EDTA
0.05% Tween 20

EXAMPLE 4

Gene Expression Analysis Based on Tissue Samples

Here, a tissue sample, e.g. of a breast tumor, is to be analyzed with respect to the expression of the number of marker genes, e.g. 100 genes such as Her2/neu, estrogen receptor, progesterone receptor, TFRC, GAPDH, etc.

The tissue sample can first be dissolved into a suspension of single cells, e.g. enzymatically and/or by shearing forces.

Subsequently, the cells may be disrupted, e.g. mechanically, by lysis buffer, enzymatically and/or chemically or by light.

The lysate can be further processed, e.g. RNA can be extracted, components can be filtered, nucleic acids can be isolated for example by ethanol precipitation. Alternatively, the lysate can be directly subject to further use.

Lysate, the at least two nanoreporters (designed for the respective mRNA sequences which correspond to the genes to be analyzed), in some applications also substrate-binding adapters (target adapters) and reaction buffers are mixed and incubated for a sufficient time period, e.g. 12 h, wherein complexes (identification structures) are formed.

Subsequently, the complexes are detected, in some applications on a surface or in solution.

It is possible to determine relative gene expression by counting the individual mRNA sequences detected and identified, e.g. if mRNA 1 is detected 200 times and mRNA 2 is detected 300 times, gene expression of gene 2 is 3/2 higher than that of gene 1.

In addition, it is possible to add nucleic acids which bind to defined nanoreporter (exactly comparable with an mRNA sequence) in known concentrations as reference in the incubation step. This allows the normalization and absolute qualification of the other detected mRNA sequences. If this reference is e.g. identified 100 times with an initial concentration of 100 pM, the concentration of mRNA 1 can be determined to be 200 pM.

EXAMPLE 5

Protein Detection

Detection and identification of protein target molecules can be carried out in a way similar to the detection and identification of nucleic acid target molecules in a microfluidic-based, flow-based or FCS-based detection.

Precondition is that the protein target molecule possesses at least two distinguishable epitopes which can be bound by corresponding binders (antibodies, aptameres, nanobodies, adhirons).

These adapters can be specifically bound to nanoreporters which identify them. To this end, protein-based binders (antibodies, adhirons, nanobodies) can be modified with a specific, short (15-35 nt) DNA sequence (via SNAP tags, HALO tags, click chemistry, SMCC linker, NHS/amino reactions or the like), the reverse complement of which is attached to the corresponding DNA nanostructures (nanoreporters) and, thus, becomes an adapter. Nucleic acid-based binders (RNA or DNA aptameres) can be elongated with a corresponding sequence into an adapter, wherein their reverse complement is attached to the corresponding DNA nanostructures.

By admixing protein target molecules and adapters at DNA nanostructures and with sufficient reaction time, detectable complexes consisting of target protein and at least two adapters which are each coupled at a DNA nanostructure form.

The complexes can be identified by simultaneous detection of the at least two DNA nanostructures.

Example of the detection of two protein targets:

Protein target 1 with epitope A and epitope B which bind to antibody A and antibody B, respectively.

Protein target 2 with epitope C and epitope D which bind to antibody C and antibody D, respectively.

Antibody A is coupled to a DNA nanostructure which is labeled with red fluorescence dyes.

Antibody B is coupled to a DNA nanostructure which is labeled with green fluorescence dyes.

Antibody C is coupled to a DNA nanostructure which is labeled with yellow fluorescence dyes.

Antibody D is coupled to a DNA nanostructure which is labeled with blue fluorescence dyes.

Admixing the protein targets and the coupled antibody/DNA nanostructures and reaction for a sufficient time period, e.g. 12 hours.

Measurement of the complexes in flow detection. The reaction solution is diluted such that only in extremely rare cases, more than one complex is detected. Simultaneous detection of red/green identifies one single protein target 1, simultaneous detection of yellow/blue identifies one single protein target 2. After previous calibration, it is possible to quantify protein targets 1 and 2 by counting the different detections.

With the same method, it is possible to identify clusters of proteins, wherein, in this case, different antibodies identify different proteins (instead of different epitopes) in the target cluster.

The invention claimed is:

1. A method for the detection of a target structure, comprising:
   a) forming an identification structure, comprising:
      (i) the target structure, and
      (ii) at least two 3D DNA nanostructures, wherein the at least two 3D DNA nanostructures are separate and independent from each other, wherein each of the 3D DNA nanostructures comprises one or more inwardly disposed fluorescence dye molecules, wherein each of the 3D DNA nanostructures specifically binds to a different portion of the target structure, and wherein the 3D DNA nanostructures are bound to regions of the target structure that are pairwise different; and
   b) detecting the target structure by measuring at least one fluorescence signal, wherein the 3D DNA nanostructures and parameters of fluorescence measurement are selected such that the at least one measured fluorescence signal of the identification structure a) is distinguishable from the fluorescence signal of each of the at least two isolated 3D DNA nanostructures, when these are not bound in the identification structure.

2. The method of claim 1, wherein the identification structure is bound to a carrier or wherein the method further comprises the step of binding the formed identification structure to a carrier.

3. The method of claim 2, wherein a bond or the binding of the identification structure to the carrier is mediated or is being mediated via the target structure.

4. The method of claim 3, wherein the target structure is bound or is being bound to the carrier, wherein the bond or binding is mediated by a carrier adapter that specifically binds or is bound to the target structure.

5. The method of claim 1, wherein the specific binding of at least one of the 3D DNA nanostructures is mediated by a target adapter assigned to a corresponding 3D DNA nanostructure, wherein the target adapter or each of the target adapters is designed to bind to the respective DNA nanostructure and to the respective region(s) of the target structure.

6. The method of claim 1, wherein the method is further additionally suited for the detection of one or more further target structures that are different from each other, wherein the different target structures are pairwise different, and wherein the method further comprises:
   c) for each of the one or more further target structures that are different from each other: forming a respectively assigned identification structure, wherein each of the further identification structures comprises:
      (i) the further target structure that was assigned, and
      (ii) at least two 3D DNA nanostructures, wherein each of the at least two 3D DNA nanostructures comprises one or more inwardly disposed fluorescence dye molecules and wherein each of the at least two 3D DNA nanostructures is specifically bound to the respective further target structure, and wherein the at least two 3D DNA nanostructures are bound to regions of the respective target structure that are pairwise different;
   and wherein step b) further comprises:
   d) detecting the one or more further target structures by measuring the at least one fluorescence signal, wherein all 3D DNA nanostructures and the parameters of fluorescence measurement are selected such that the at least one measured fluorescence signal of the identification structures formed in a) and c) is distinguishable from the fluorescence signal of all isolated 3D DNA nanostructures, when these are not bound in one of the identification structures, and that the measured fluorescence signals of all formed identification structures are pairwise distinguishable from each other.

7. The method of claim 6, wherein each of the different target structures is present multiple times and the method comprises the multiple detection of one or more of the different target structures.

8. The method of claim 6, wherein measuring at least one fluorescence signal comprises:
   e) creating a data set, which contains data of fluorescence signals emitted by a section of a sample by using a fluorescence microscope;
   and wherein the detection of the target structure comprises:
   f) identifying one or more of the datums contained in the data set, which represents the fluorescence signal of the identification structure.

9. The method of claim 8, wherein the fluorescence signals of the identification structures formed for the individual different target structures differ from the fluorescence signal of all isolated 3D DNA nanostructures, when these are not bound in one of the identification structures, and the fluorescence signals of the identification structures which were formed for the individual different target structures are pairwise different, in that the corresponding fluorescence signals comprise a distinguishably different combination of color and/or intensity information.

10. The method of claim 9, wherein in the 3D DNA nanostructures k intensity levels distinguishable from each other and/or m color levels distinguishable from each other are used, wherein the respective overlap of adjacent distributions is lower than 30%, and wherein k>2 and m>2.

11. The method of claim 10, wherein each of the k intensity levels is formed by intensity distribution and wherein the k intensity distributions are distinguishable from each other.

12. The method of claim 10, wherein each of the k intensity levels is formed by intensity distribution and wherein the k intensity distributions are statistically distinguishable from each other.

13. The method of claim 10, wherein the m color distributions are distinguishable from each other.

14. The method of claim 10, wherein the m color distributions are statistically distinguishable from each other.

15. The method of claim 8, wherein the identifying in step f) comprises the following steps:
   f1) reading out a color and/or an intensity information of a datum and/or image element; and
   f2) comparing the color and/or intensity information of the datum and/or image element with a color and/or intensity information, being representative for the identification structure.

16. The method of claim 8, wherein using a fluorescence microscope comprises using a fluorescence microscope in epifluorescence, TIRF, lightsheet and/or confocal microscopy.

17. The method of claim 1, wherein measuring at least one fluorescence signal comprises:
   e) creating a data set, which contains data of fluorescence signals emitted by a section of a sample by using a fluorescence microscope;

and wherein the detection of the target structure comprises:
f) identifying one or more of the datums contained in the data set, which represent(s) the fluorescence signal of the identification structures.

18. The method of claim 17, wherein the identifying in step f) comprises the following steps:
f1) reading out a color and/or an intensity information of a datum and/or image element; and
f2) comparing the color and/or intensity information of the datum and/or image element with a color and/or intensity information, being representative for the identification structure.

19. The method of claim 17, wherein using a fluorescence microscope comprises using a fluorescence microscope in epifluorescence, TIRF, lightsheet and/or confocal microscopy.

* * * * *